United States Patent
Jain et al.

(10) Patent No.: US 11,453,677 B2
(45) Date of Patent: *Sep. 27, 2022

(54) TRICYCLIC COMPOUNDS USEFUL TO TREAT ORTHOMYXOVIRUS INFECTIONS

(71) Applicant: Novartis AG, Basel (CH)

(72) Inventors: Rama Jain, Fremont, CA (US); Dennis Christofer Koester, Emeryville, CA (US); James R. Manning, Pleasant Hill, CA (US); James Clifford Sutton, Pleasanton, CA (US); Benjamin Robert Taft, Lafayette, CA (US); Lifeng Wan, Union City, CA (US); Qian Zhao, Louisville, CO (US)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/933,000

(22) Filed: Jul. 20, 2020

(65) Prior Publication Data

US 2020/0347072 A1 Nov. 5, 2020

Related U.S. Application Data

(63) Continuation of application No. 16/083,089, filed as application No. PCT/IB2017/051338 on Mar. 7, 2017, now Pat. No. 10,858,366.

(60) Provisional application No. 62/305,392, filed on Mar. 8, 2016.

(51) Int. Cl.
| | | |
|---|---|---|
| C07D 487/14 | (2006.01) | |
| C07D 471/14 | (2006.01) | |
| C07D 491/22 | (2006.01) | |
| C07D 498/14 | (2006.01) | |
| A61P 31/16 | (2006.01) | |
| C07D 513/14 | (2006.01) | |

(52) U.S. Cl.
CPC .......... C07D 487/14 (2013.01); A61P 31/16 (2018.01); C07D 471/14 (2013.01); C07D 491/22 (2013.01); C07D 498/14 (2013.01); C07D 513/14 (2013.01)

(58) Field of Classification Search
CPC .................................................. C07D 487/14
See application file for complete search history.

(56) References Cited

U.S. PATENT DOCUMENTS

| | | |
|---|---|---|
| 7,211,572 B2 | 5/2007 | Miyazaki et al. |
| 8,927,710 B2 | 1/2015 | Akiyama et al. |
| 8,987,441 B2 | 3/2015 | Takahashi et al. |
| 9,469,638 B2 | 10/2016 | Akiyama et al. |
| 10,160,764 B2 | 12/2018 | Jain et al. |
| 10,858,366 B2 * | 12/2020 | Jain ..................... C07D 498/14 |
| 2011/0190254 A1 | 8/2011 | Nishitani et al. |
| 2011/0245236 A1 | 10/2011 | Ali et al. |
| 2012/0022251 A1 | 1/2012 | Sumino et al. |
| 2012/0195857 A1 | 8/2012 | Belema et al. |
| 2013/0197219 A1 | 8/2013 | Takahashi et al. |
| 2014/0256937 A1 | 9/2014 | Akiyama |
| 2015/0031876 A1 | 1/2015 | Sumino et al. |
| 2015/0072982 A1 | 3/2015 | Hendricks et al. |
| 2015/0202208 A1 | 7/2015 | Kiyama et al. |
| 2016/0002227 A1 | 1/2016 | Schulz-Gasch et al. |
| 2019/0367517 A1 | 12/2019 | Chen et al. |

FOREIGN PATENT DOCUMENTS

| | | |
|---|---|---|
| CN | 102803260 A | 11/2012 |
| EP | 2774928 B1 | 8/2017 |
| EP | 2444400 B1 | 3/2018 |
| EP | 2620436 B1 | 5/2018 |
| GB | 2158440 A1 | 11/1985 |
| JP | A-S61-167687 A | 7/1986 |
| KR | 20200118062 A | 10/2020 |
| WO | 200316275 A1 | 2/2003 |
| WO | 2004078163 A2 | 9/2004 |
| WO | 200561490 A1 | 7/2005 |
| WO | 2005087766 A1 | 9/2005 |

(Continued)

OTHER PUBLICATIONS

Chen "Computation-Guided Discovery of Influenza Endonuclease Inhibitors" ACS Med. Chem. Letters, vol. 5, (2014), pp. 61-64.

Rodriguez et al. "Palau'chlor: A Practical and Reactive Chlorinating Reagent" J Am. Chem. Soc., vol. 136, No. 19, (2014), pp. 6908-6911.

Zhang, "Discovery of Novel Trisubstituted Asymmetric Derivatives of (2S,4R,5R)-2-benzhydryl-5-benzylaminotetrahydropyran-4-ol, Exhibiting High Affinity for Serotonin and Norepinephrine Transporters in a Stereospecific Manner," J. Med. Chem., vol. 48, (2005), pp. 4962-4971.

(Continued)

*Primary Examiner* — John S Kenyon
(74) *Attorney, Agent, or Firm* — McNeill Baur PLLC

(57) ABSTRACT

The present invention provides a compound of Formula (I) including pharmaceutically acceptable salts thereof: (I) and therapeutic uses of these compounds. The invention further provides pharmaceutical compositions comprising these compounds, compositions comprising these compounds with a therapeutic co-agent, and methods of using the compounds and compositions to treat viral infections.

(I)

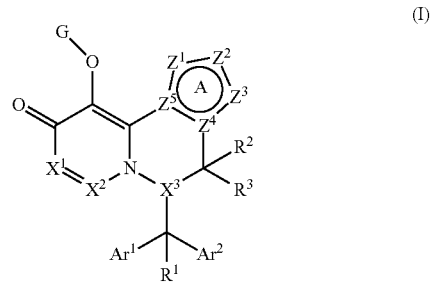

14 Claims, No Drawings

(56) References Cited

FOREIGN PATENT DOCUMENTS

| | | |
|---|---|---|
| WO | 2007138081 A1 | 12/2007 |
| WO | WO-2007138081 A * | 12/2007 ............ A61P 25/00 |
| WO | 2010110231 A1 | 9/2010 |
| WO | 2010110409 A1 | 9/2010 |
| WO | 2010147068 A1 | 12/2010 |
| WO | 2012151567 A1 | 11/2012 |
| WO | 2014046441 A1 | 3/2014 |
| WO | 2014108406 A1 | 7/2014 |
| WO | 2015026792 A1 | 2/2015 |
| WO | 2015038655 A1 | 3/2015 |
| WO | 2015038660 A1 | 3/2015 |
| WO | 2015038665 A1 | 3/2015 |
| WO | 2016145103 A1 | 9/2016 |
| WO | 2017153919 A1 | 9/2017 |
| WO | 2018030463 A1 | 2/2018 |
| WO | 2018042303 A1 | 3/2018 |
| WO | 2019166950 A1 | 9/2019 |

OTHER PUBLICATIONS

Baughman et al., "Identification of Influenza Endonuclease Inhibitors Using a Novel Flourescence Polarization Assay," ACS Med. Checm. Bio., vol. 7, No. 3, 2012, 526-534.

Liu et al., "Total Synthesis of the Securinega Alkaloid (-)-Secu'amamine A" J. Am. Chem. Soc. 130:7562-7563, 2008.

International Search Report, issued in PCT/IB2017/055137, dated Oct. 30, 2017.

International Search Report, issued in PCT/IB2017/051338, dated May 10, 2017.

International Search Report, issued in PCT/IB2019/051549, dated May 21, 2019.

* cited by examiner

TRICYCLIC COMPOUNDS USEFUL TO TREAT ORTHOMYXOVIRUS INFECTIONS

CROSS-REFERENCE TO RELATED APPLICATIONS

This application is a continuation of U.S. application Ser. No. 16/083,089, filed Sep. 7, 2018, which is a National Stage application of International Application No. PCT/IB2017/051338, filed Mar. 7, 2017, which claims the benefit of U.S. Provisional Application No. 62/305,392, filed Mar. 8, 2016, the contents of which are incorporated herein by reference.

FIELD OF THE INVENTION

The invention provides compounds that inhibit orthomyxovirus replication, and are accordingly useful for treatment of viral infections caused by orthomyxoviruses. The invention further provides pharmaceutical compositions containing these compounds and methods of using these compounds to treat or prevent viral infections caused by orthomyxovirus.

BACKGROUND

Orthomyxoviruses have negative-sense single stranded RNA genomes, and replicate in the nucleus of infected cells, as they lack the machinery to generate the cap structure to produce their own mRNA. Members of the Orthomyxovirus Family have an RNA-dependent RNA polymerase with endonuclease activity that cleaves a section of the capped 5'-end of cellular mRNA; the RNA polymerase then uses the cleavage product as a primer for synthesis of viral mRNA. This process is known as cap-snatching. This endonuclease has been recognized as a promising target for development of antivirals effective against orthomyxoviruses. *ACS Med. Chem. Letters* 2014, vol. 5, 61-64. Inhibitors of this endonuclease have been disclosed, for example, in WO2015/038660 and US2015/0072982, WO2010/147068, and US2013/0197219, which report that such inhibitors are useful to treat influenza infections in mammals.

The orthomyxovirus family includes influenza A, influenza B and influenza C, all of which can infect humans, as well as several other genera of viruses that generally do not infect humans. Influenza A is the most virulent of these pathogens in humans, often accounting for the majority of serious cases of influenza during a typical flu season. It is estimated that influenza kills as many as 40,000 people per year in the U.S., in spite of the widespread use of vaccines to reduce the incidence of influenza; thus there is a great need for antiviral therapeutics effective to treat influenza, especially influenza A. The present invention provides compounds that inhibit replication of orthomyxoviruses, including influenza A, influenza B and influenza C. Without being bound by theory, it is believed these compounds achieve their antiviral effects by inhibiting the endonuclease function of the viral polymerase. Because this endonuclease is highly conserved across influenza A viruses (id.), the compounds are especially useful for treatment of influenza A.

SUMMARY OF THE INVENTION

In one aspect, the invention provides a compound of the formula (I):

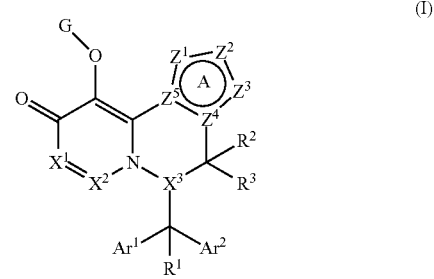

(I)

or a pharmaceutically acceptable salt thereof, wherein:
G is H or a group selected from —C(O)R, —C(O)—OR, —C($R^G$)$_2$—O—C(O)R, —C($R^G$)$_2$—O—C(O)—OR, —C(O)—NR$_2$, and —C($R^G$)$_2$—O—C(O)NR$_2$, where each R is independently $C_1$-$C_4$ alkyl, phenyl, pyridyl, $C_3$-$C_7$ cycloalkyl, or a 3-6 membered heterocyclic ring containing one or two heteroatoms selected from N, O and S as ring members; and each R is optionally substituted with one or two groups selected from halo, CN, —OH, amino, $C_{1-4}$ alkyl, phenyl, $C_{1-4}$ alkoxy, $C_{1-4}$ haloalkyl, and $C_{1-4}$ haloalkoxy;

and each $R^G$ is independently selected from H and $C_{1-4}$ alkyl;

$X^1$ is $CR^{X1}$ or N, where $R^{X1}$ is H, halo, $C_{1-6}$ alkyl, $C_{1-4}$ haloalkyl, CN, COOH, or a 5-6 membered heteroaryl ring containing 1-4 heteroatoms selected from N, O and S as ring members and optionally substituted by 1-2 groups selected from halo, hydroxy, amino, $C_{1-3}$ alkyl, $C_{1-3}$ haloalkyl, and $C_{1-3}$ alkoxy;

$X^2$ is $CR^{X2}$ or N, where $R^{X2}$ is H, halo, $C_{1-6}$ alkyl or $C_{1-4}$ haloalkyl;

$X^3$ is $CR^{X3}$ or N, where $R^{X3}$ is H, $C_{1-4}$ alkyl or $C_{1-4}$ haloalkyl;

provided that $X^2$ is $CR^{x2}$ if either or both of $X^1$ and $X^3$ represent N;

$R^1$ is H, halo, hydroxy, $C_{1-4}$ alkyl, $C_{1-4}$ haloalkyl, or $C_{1-4}$ alkoxy;

$R^2$ and $R^3$ are independently H, $C_{1-4}$ alkyl or $C_{3-5}$ cycloalkyl, wherein each $C_{1-4}$ alkyl and $C_{3-5}$ cycloalkyl is optionally substituted with one or two groups selected from halo, CN, —OH, $C_{1-4}$ alkoxy, $C_{1-4}$ haloalkyl, and $C_{1-4}$ haloalkoxy;

or $R^2$ and $R^3$ taken together with the carbon atom to which both are attached can form a 3-5 membered cycloalkyl ring or a 3-5 membered cyclic ether ring having one oxygen as a ring member;

Ring A is a five-membered heteroaryl ring containing at least one carbon ring atom and up to four heteroatoms selected from N, O and S as ring members, wherein
$Z^1$ is N, O or S;
$Z^2$ and $Z^3$ are independently $CR^z$, N, $NR^z$, O or S; and
$Z^4$ and $Z^5$ each independently represent C or N,
provided $Z^4$ and $Z^5$ are not both simultaneously N,
where each $R^z$ is independently selected from H, halo, $C_{1-4}$ alkyl, $C_{3-6}$ cycloalkyl, phenyl, 5-6 membered heteroaryl containing one or two heteroatoms selected from N, O and S as ring members, $C_{1-4}$ alkoxy, CN, CON($R^4$)$_2$ and $C_{1-4}$ haloalkyl, wherein the $C_{1-4}$ alkyl is optionally substituted with one or two groups selected from —OR$^4$, —N(R$^4$)$_2$, COOR$^4$, CON(R$^4$)$_2$, and a 5-6 membered heterocyclic ring containing one or two heteroatoms selected from N, O and S as ring members;

R$^4$ at each occurrence is independently selected from H, C$_{1-4}$ alkyl, C$_{1-4}$ haloalkyl, C$_{3-6}$ cycloalkyl, phenyl, a 5-6 membered heterocyclic ring containing one or two heteroatoms selected from N, O and S as ring members, wherein the C$_{1-4}$ alkyl, C$_{3-6}$ cycloalkyl, phenyl, and 5-6 membered heterocyclic ring containing one or two heteroatoms selected from N, O and S as ring members are each optionally substituted with one or two groups independently selected from halo, —OH, C$_{1-2}$ alkyl, and —O(C$_{1-2}$ alkyl);

and two R$^4$ groups directly attached to the same nitrogen atom can optionally be taken together to form a 4-6 membered heterocycle optionally containing an additional heteroatom selected from N, O and S as a ring member and optionally substituted with one or two groups selected from halo, —OH, C$_{1-2}$ alkyl, and —O(C$_{1-2}$ alkyl);

Ar$^1$ and Ar$^2$ each represent phenyl or a 5-6 membered heteroaryl ring containing 1-3 heteroatoms selected from N, O and S as ring members, and are each independently substituted with up to three groups selected from halo, C$_{1-4}$ alkyl, C$_{1-4}$ haloalkyl, C$_{1-4}$ alkoxy, C$_{1-4}$ haloalkoxy, C$_{2-4}$ alkyne, —S(C$_{1-3}$ alkyl), —SO$_2$(C$_{1-3}$ alkyl), and CN;

and Ar$^1$ and Ar$^2$ are optionally linked together by a bridge of the formula —C(R$^L$)$_2$-L- to form a tricyclic ring system wherein each Ar$^1$ and Ar$^2$ is optionally substituted by up to two groups independently selected from halo, C$_{1-4}$ alkyl, C$_{1-4}$ haloalkyl, C$_{1-4}$ alkoxy, C$_{1-4}$ haloalkoxy, C$_{2-4}$ alkyne, —S(C$_{1-3}$ alkyl), —SO$_2$(C$_{1-3}$ alkyl), and CN, where L is selected from S, S=O, SO$_2$, O, C(R$^L$)$_2$ and CF$_2$, and each R$^L$ is independently H or C$_{1-2}$ alkyl;

which are further described herein.

The compounds of Formula (I) are inhibitors of the endonuclease function of influenza viruses as shown by the data provided herein, and they inhibit replication of influenza viruses. Accordingly, these compounds are useful to treat or prevent orthomyxovirus infections in mammals susceptible to such infections, and are particularly useful to treat influenza virus infections in humans. They are also useful to inhibit replication of orthomyxoviruses, including influenza viruses, in cells.

In another aspect, the invention provides pharmaceutical compositions comprising a compound of Formula (I) admixed with at least one pharmaceutically acceptable carrier or excipient, optionally admixed with two or more pharmaceutically acceptable carriers or excipients.

In another aspect, the invention provides a method to treat a subject infected with influenza A, B or C, which comprises administering to a subject in need of such treatment an effective amount of a compound of Formula (I) or any subgenus or species thereof as described herein, or a pharmaceutical composition comprising such compound. The subject can be a mammal, and is preferably a human, although the compounds and methods of the invention are suitable for treatment of other species that contract Influenza A, Influenza B, or influenza C, as well as other orthomyxoviruses. The invention includes compounds of Formula (I) and the subgenera of Formula (I) described herein, and all stereoisomers (including diastereoisomers and enantiomers) except where a specific isomer is expressly described, as well as tautomers and isotopically enriched versions thereof (including deuterium substitutions) as well as pharmaceutically acceptable salts of these compounds. Compounds of the present invention also comprise polymorphs of compounds of formula I (or subformulae thereof) and salts thereof.

DETAILED DESCRIPTION

The following definitions apply unless otherwise expressly provided:

As used herein, the term "halogen" or halo refers to fluorine, bromine, chlorine or iodine, in particular it refers to fluorine or chlorine when attached to an alkyl group, and further includes bromine or iodine when on an aryl or heteroaryl group.

As used herein, unless otherwise specified, the term "heteroatoms" refers to nitrogen (N), oxygen (O) or sulfur (S) atoms.

As used herein, the term "alkyl" refers to a fully saturated branched or unbranched hydrocarbon moiety having up to 10 carbon atoms. Unless otherwise provided, alkyl refers to hydrocarbon moieties having 1 to 6 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more substituents in place of hydrogen, such as one, two, or three substituents, up to the number of hydrogens present on the unsubstituted alkyl group. Suitable substituents for alkyl groups, if not otherwise specified, may be selected from halogen, CN, oxo, hydroxy, C$_{1-4}$ alkoxy, substituted or unsubstituted C$_{3-6}$ cycloalkyl, substituted or unsubstituted phenyl, amino, (C$_{1-4}$ alkyl)amino, di(C$_{1-4}$ alkyl)amino, C$_{1-4}$ alkylthio, C$_{1-4}$ alkylsulfonyl, —C(=O)—C$_{1-4}$ alkyl, COOH, COO(C$_{1-4}$ alkyl), —O(C=O)—C$_{1-4}$ alkyl, —NHC(=O)C$_{1-4}$ alkyl and —NHC(=O)OC$_{1-4}$ alkyl groups, where substituents for the substituted cycloalkyl or phenyl are up to three groups selected from Me, Et, —OMe, —OEt, CF$_3$, halo, CN, OH, and NH$_2$.

As used herein, the term "alkylene" refers to a divalent alkyl group having 1 to 10 carbon atoms, and two open valences to attach to other features. Unless otherwise provided, alkylene refers to moieties having 1 to 6 carbon atoms. Representative examples of alkylene include, but are not limited to, methylene, ethylene, n-propylene, iso-propylene, n-butylene, sec-butylene, iso-butylene, tert-butylene, n-pentylene, isopentylene, neopentylene, n-hexylene, 2,2-dimethylbutylene, and the like. A substituted alkylene is an alkylene group containing one or more, such as one, two or three substituents; unless otherwise specified, suitable substituents for an alkylene group are selected from the substituents listed above for alkyl groups.

As used herein, the term "haloalkyl" refers to an alkyl as defined herein, which is substituted by one or more halo groups. The haloalkyl can be monohaloalkyl, dihaloalkyl, trihaloalkyl, or polyhaloalkyl including perhaloalkyl. A monohaloalkyl can have one chloro or fluoro within the alkyl group. Chloro and fluoro are commonly present as substituents on alkyl or cycloalkyl groups; fluoro, chloro and bromo are often present on aryl or heteroaryl groups. Dihaloalkyl and polyhaloalkyl groups can have two or more of the same halo atoms or a combination of different halo groups on the alkyl. Typically the polyhaloalkyl contains up to 12, or 10, or 8, or 6, or 4, or 3, or 2 halo groups. Non-limiting examples of haloalkyl include fluoromethyl, difluoromethyl, trifluoromethyl, chloromethyl, dichloromethyl, trichloromethyl, 2,2,2-trifluoroethyl, pentafluoroethyl, heptafluoropropyl, difluorochloromethyl, dichlorofluoromethyl, difluoroethyl, difluoropropyl, dichloroethyl and dichloropropyl. A perhalo-alkyl refers to an alkyl having all hydrogen atoms replaced with halo atoms, e.g., trifluoromethyl.

As used herein, the term "alkoxy" refers to alkyl-O—, wherein alkyl is defined above. Representative examples of alkoxy include, but are not limited to, methoxy, ethoxy, propoxy, 2-propoxy, butoxy, tert-butoxy, pentyloxy, hexyloxy, and the like. Typically, alkoxy groups have 1-6 carbons, more commonly 1-4 carbon atoms.

A "substituted alkoxy" is an alkoxy group containing one or more, such as one, two or three substituents on the alkyl portion of the alkoxy. Unless otherwise specified, suitable substituents are selected from the substituents listed above for alkyl groups, except that hydroxyl and amino are not normally present on the carbon that is directly attached to the oxygen of the substituted 'alkyl-0' group.

Similarly, each alkyl part of other groups like "alkylaminocarbonyl", "alkoxyalkyl", "alkoxycarbonyl", "alkoxycarbonylalkyl", "alkylsulfonyl", "alkylsulfoxyl", "alkylamino", "haloalkyl" shall have the same meaning as described in the above-mentioned definition of "alkyl". When used in this way, unless otherwise indicated, the alkyl group is often a 1-4 carbon alkyl and is not further substituted by groups other than the component named. When such alkyl groups are substituted, suitable substituents are those named above for alkyl groups unless, otherwise specified.

As used herein, the term "haloalkoxy" refers to haloalkyl-O—, wherein haloalkyl is defined above. Representative examples of haloalkoxy include, but are not limited to, fluoromethoxy, difluoromethoxy, trifluoromethoxy, trichloromethoxy, 2-chloroethoxy, 2,2,2-trifluoroethoxy, 1,1,1,3,3,3-hexafluoro-2-propoxy, and the like. Typically, haloalkyl groups have 1-4 carbon atoms.

As used herein, the term "cycloalkyl" refers to saturated or unsaturated non-aromatic monocyclic, bicyclic, tricyclic or spirocyclic hydrocarbon groups of 3-12 carbon atoms: the cycloalkyl group may be unsaturated, and may be fused to another ring that can be saturated, unsaturated or aromatic, provided the ring atom of the cycloalkyl group that is connected to the molecular formula of interest is not an aromatic ring carbon. Unless otherwise provided, cycloalkyl refers to cyclic hydrocarbon groups having between 3 and 9 ring carbon atoms or between 3 and 7 ring carbon atoms. Preferably, cycloalkyl groups are saturated monocyclic rings having 3-7 ring atoms, such as cyclopropyl, cyclobutyl, cyclopentyl and cyclohexyl, unless otherwise specified.

A substituted cycloalkyl is a cycloalkyl group substituted by one, or two, or three, or more than three substituents, up to the number of hydrogens on the unsubstituted group. Typically, a substituted cycloalkyl will have 1-4 substituents unless otherwise specified. Suitable substituents, unless otherwise specified, are independently selected from the group consisting of halogen, hydroxyl, thiol, cyano, nitro, oxo, C1-C4-alkylimino, C1-C4-alkoximino, hydroxyimino, C1-C4-alkyl, C2-C4-alkenyl, C2-C4-alkynyl, C1-C4-alkoxy, C1-C4-thioalkyl, C2-C4-alkenyloxy, C2-C4-alkynyloxy, C1-C4-alkylcarbonyl, carboxy, C1-C4-alkoxycarbonyl, amino, C1-C4-alkylamino, di-C1-C4-alkylamino, C1-C4-alkylaminocarbonyl, di-C1-C4-alkylaminocarbonyl, C1-C4-alkylcarbonylamino, C1-C4-alkylcarbonyl(C1-C4-alkyl)amino, C1-C4-alkylsulfonyl, C1-C4-alkylsulfamoyl, and C1-C4-alkylaminosulfonyl, where each of the aforementioned hydrocarbon groups (e.g., alkyl, alkenyl, alkynyl, alkoxy residues) may be further substituted by one or more groups independently selected at each occurrence from the list of substituents for 'alkyl' groups herein. Preferred substituents for a cycloalkyl group include C1-C4 alkyl and the substituent groups listed above as suitable substituents for alkyl groups.

Exemplary monocyclic hydrocarbon groups include, but are not limited to, cyclopropyl, cyclobutyl, cyclopentyl, cyclopentenyl, cyclohexyl and cyclohexenyl and the like. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl and the like. Exemplary tricyclic hydrocarbon groups include adamantyl and the like.

Similarly, each cycloalkyl part of other groups like "cycloalkyloxy", "cycloalkoxyalkyl", "cycloalkoxycarbonyl", "cycloalkoxy-carbonylalkyl", "cycloalkylsulfonyl", "halocycloalkyl" shall have the same meaning as described in the above-mentioned definition of "cycloalkyl". When used in these terms, the cycloalkyl is typically a monocyclic 3-7 carbon ring, that is unsubstituted or substituted with 1-2 groups. When optionally substituted, the substituents are typically selected from C1-C4 alkyl and those set forth above as suitable for alkyl groups.

As used herein, the term "aryl" refers to an aromatic hydrocarbon group having 6-14 carbon atoms in the ring portion. Typically, aryl is monocyclic, bicyclic or tricyclic aryl having 6-14 carbon atoms, often 6-10 carbon atoms, e.g., phenyl or naphthyl. Furthermore, the term "aryl" as used herein, refers to an aromatic substituent which can be a single aromatic ring, or multiple aromatic rings that are fused together. Non-limiting examples include phenyl, naphthyl and 1,2,3,4-tetrahydronaphthyl, provided the tetrahydronaphthyl is connected to the formula being described through a carbon of the aromatic ring of the tetrahydronaphthyl group. Unless otherwise indicated, a preferred aryl group is phenyl.

A substituted aryl is an aryl group substituted by 1-5 (such as one, or two, or three) substituents independently selected from the group consisting of hydroxyl, thiol, cyano, nitro, C1-C4-alkyl, C2-C4-alkenyl, C2-C4-alkynyl, C1-C4-alkoxy, C1-C4-thioalkyl, C2-C4-alkenyloxy, C2-C4-alkynyloxy, halogen, C1-C4-alkylcarbonyl, carboxy, C1-C4-alkoxycarbonyl, amino, C1-C4-alkylamino, di-C1-C4-alkylamino, C1-C4-alkylaminocarbonyl, di-C1-C4-alkylaminocarbonyl, C1-C4-alkylcarbonylamino, C1-C4-alkylcarbonyl(C1-C4-alkyl)amino, C1-C4-alkylsulfonyl, sulfamoyl, C1-C4-alkylsulfamoyl, and C1-C4-alkylaminosulfonyl where each of the aforementioned hydrocarbon groups (e.g., alkyl, alkenyl, alkynyl, alkoxy residues) may be further substituted by one or more groups independently selected at each occurrence from the groups listed above as suitable substituents for alkyl groups. Preferred substituents for a substituted aryl group are $C_{1-4}$ alkyl and those groups named above as suitable substituents for alkyl groups, excluding divalent groups such as oxo.

Similarly, each aryl part of other groups like "aryloxy", "aryloxyalkyl", "aryloxycarbonyl", "aryloxy-carbonylalkyl" shall have the same meaning as described in the above-mentioned definition of "aryl".

As used herein, the term "heterocyclyl" refers to a heterocyclic radical that is saturated or partially unsaturated but not aromatic, and can be a monocyclic or a polycyclic ring (in case of a polycyclic ring particularly a bicyclic, tricyclic or spirocyclic ring); and has 3 to 14, more commonly 4 to 10, and most preferably 5 or 6 ring atoms; wherein one or more, preferably one to four, especially one or two ring atoms are heteroatoms independently selected from O, S and N (the remaining ring atoms therefore being carbon). Even if it is described as, e.g., a C5-6 atom ring, a heterocycle contains at least one heteroatom as a ring atom with the other ring atoms being carbon, and has the number of ring atoms stated, e.g. 5-6 in this example. Preferably, a heterocyclyl group has one or two such heteroatoms as ring atoms, and preferably the heteroatoms are not directly connected to each other. The bonding ring (i.e. the ring connecting to the Formula of interest) preferably has 4 to 12, especially 5 to 7 ring atoms unless otherwise specified. The heterocyclic group can be fused to an aromatic ring, provided the atom of the heterocyclic group attached to the Formula of interest is not aromatic. The heterocyclic group can be attached to the Formula of interest via a heteroatom (typically nitrogen) or a carbon atom of the heterocyclic group. The heterocyclyl can include fused or bridged rings as well as spirocyclic rings, and only one ring of a polycyclic heterocyclic group needs to contain a heteroatom as a ring atom. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

A substituted heterocyclyl is a heterocyclyl group independently substituted by 1-5 (such as one, or two, or three) substituents selected from the substituents described above for a cycloalkyl group.

Similarly, each heterocyclyl part of other groups like "heterocyclyloxy", "heterocyclyloxyalkyl", "heterocyclyloxycarbonyl" shall have the same meaning as described in the above-mentioned definition of "heterocyclyl".

As used herein, the term "heteroaryl" refers to a 5-14 membered monocyclic- or bicyclic- or tricyclic-aromatic ring system, having 1 to 8 heteroatoms as ring members, with the remaining ring atoms being carbon, and the heteroatoms are selected from N, O and S. Typically, the heteroaryl is a 5-10 membered ring system, especially a 5-6 membered monocyclic or an 8-10 membered bicyclic group. Typical heteroaryl groups include 2- or 3-thienyl, 2- or 3-furyl, 2- or 3-pyrrolyl, 2-, 4-, or 5-imidazolyl, 1-, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2, 3-triazolyl, 1- or 2-tetrazolyl, 2-, 3-, or 4-pyridyl, 3- or 4-pyridazinyl, 3-, 4-, or 5-pyrazinyl, 2-pyrazinyl, and 2-, 4-, or 5-pyrimidinyl.

The term "heteroaryl" also refers to a group in which a heteroaromatic ring is fused to one or more aryl, cycloalkyl, or heterocyclyl rings. Non-limiting examples include 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

A substituted heteroaryl is a heteroaryl group containing one or more substituents, typically one or two substituents, selected from the substituents described above as suitable for an aryl group.

Similarly, each heteroaryl part of other groups like "heteroaryloxy", "heteroaryloxyalkyl", "heteroaryloxycarbonyl" shall have the same meaning as described in the above-mentioned definition of "heteroaryl".

Various embodiments of the invention are described herein. It will be recognized that features specified in each embodiment may be combined with other specified features to provide further embodiments of the present invention.

In a first embodiment (Embodiment 1), the invention provides a compound of the formula (I):

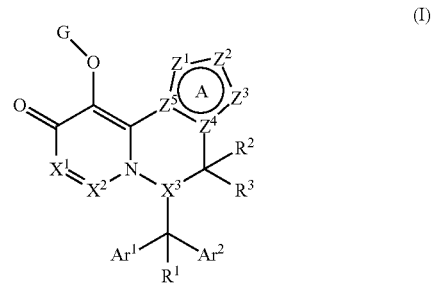

(I)

or a pharmaceutically acceptable salt thereof, wherein:

G is H or a group selected from —C(O)R, —C(O)—OR, —C(R$^G$)$_2$—O—C(O)R, —C(R$^G$)$_2$—O—C(O)—OR, —C(O)—NR$_2$, and —C(R$^G$)$_2$—O—C(O)NR$_2$, where each R is H or a group independently selected from C$_1$-C$_4$ alkyl, phenyl, pyridyl, C$_3$-C$_7$ cycloalkyl, and a 3-6 membered heterocyclic ring containing one or two heteroatoms selected from N, O and S as ring members; and each R that is not H is optionally substituted with one or two groups selected from halo, CN, —OH, amino, C$_{1-4}$ alkyl, phenyl, C$_{1-4}$ alkoxy, C$_{1-4}$ haloalkyl, and C$_{1-4}$ haloalkoxy;

and each R$^G$ is independently selected from H and C$_{1-4}$ alkyl;

X$^1$ is CR$^{X1}$ or N, where R$^{X1}$ is H, halo, C$_{1-6}$ alkyl, C$_{1-4}$ haloalkyl, CN, COOH, or a 5-6 membered heteroaryl ring containing 1-4 heteroatoms selected from N, O and S as ring members and optionally substituted by 1-2 groups selected from halo, hydroxy, amino, C$_{1-3}$ alkyl, C$_{1-3}$ haloalkyl, and C$_{1-3}$ alkoxy;

X$^2$ is CR$^{X2}$ or N, where R$^{X2}$ is H, halo, C$_{1-6}$ alkyl or C$_{1-4}$ haloalkyl;

X$^3$ is CR$^{X3}$ or N, where R$^{X3}$ is H, C$_{1-4}$ alkyl or C$_{1-4}$ haloalkyl;

provided that X$^2$ is CR$^{X2}$ if either or both of X$^1$ and X$^3$ represent N;

R$^1$ is H, halo, hydroxy, C$_{1-4}$ alkyl, C$_{1-4}$ haloalkyl, or C$_{1-4}$ alkoxy;

R$^2$ and R$^3$ are independently H, C$_{1-4}$ alkyl or C$_{3-5}$ cycloalkyl, wherein each C$_{1-4}$ alkyl and C$_{3-5}$ cycloalkyl is optionally substituted with one or two groups selected from halo, CN, —OH, C$_{1-4}$ alkoxy, C$_{1-4}$ haloalkyl, and C$_{1-4}$ haloalkoxy;

or R$^2$ and R$^3$ taken together with the carbon atom to which both are attached can form a 3-5 membered cycloalkyl ring or a 3-5 membered cyclic ether ring having one oxygen as a ring member;

Ring A is a five-membered heteroaryl ring containing at least one carbon ring atom and up to four heteroatoms selected from N, O and S as ring members, wherein Z$^1$ is N, O or S;

Z$^2$ and Z$^3$ are independently CR$^z$, N, NR$^z$, O or S; and

Z$^4$ and Z$^5$ each independently represent C or N, provided Z$^4$ and Z$^5$ are not both simultaneously N, where each R$^z$ is independently selected from H, halo, C$_{1-4}$ alkyl, C$_{3-6}$ cycloalkyl, phenyl, 5-6 membered heteroaryl containing one or two heteroatoms selected from N, O and S as ring members, C$_{1-4}$ alkoxy, CN, CON(R$^4$)$_2$ and C$_{1-4}$ haloalkyl, wherein the C$_{1-4}$ alkyl is optionally substituted with one or two groups selected from —OR$^4$, —N(R$^4$)$_2$, COOR$^4$, CON(R$^4$)$_2$, and a 5-6 membered heterocyclic ring containing one or two heteroatoms selected from N, O and S as ring members;

R$^4$ at each occurrence is independently selected from H, C$_{1-4}$ alkyl, C$_{1-4}$ haloalkyl, C$_{3-6}$ cycloalkyl, phenyl, a 5-6 membered heterocyclic ring containing one or two heteroatoms selected from N, O and S as ring members, wherein the C$_{1-4}$ alkyl, C$_{3-6}$ cycloalkyl, phenyl, and 5-6 membered heterocyclic ring containing one or two heteroatoms selected from N, O and S as ring members are each optionally substituted with one or two groups independently selected from halo, —OH, C$_{1-2}$ alkyl, and —O(C$_{1-2}$ alkyl);

and two R$^4$ groups directly attached to the same nitrogen atom can optionally be taken together to form a 4-6 membered heterocycle optionally containing an additional heteroatom selected from N, O and S as a ring member and optionally substituted with one or two groups selected from halo, —OH, C$_{1-2}$ alkyl, and —O(C$_{1-2}$ alkyl);

Ar$^1$ and Ar$^e$ each represent phenyl or a 5-6 membered heteroaryl ring containing 1-3 heteroatoms selected from N, O and S as ring members, and are each independently substituted with up to three groups selected from halo, C$_{1-4}$ alkyl, C$_{1-4}$ haloalkyl, C$_{1-4}$ alkoxy, C$_{1-4}$ haloalkoxy, C$_{2-4}$ alkyne, —S(C$_{1-3}$ alkyl), —SO$_2$(C$_{1-3}$ alkyl), and CN;

and Ar$^1$ and Ar$^2$ are optionally linked together by a bridge of the formula C(R$^L$)$_2$-L- to form a tricyclic ring system wherein each Ar$^1$ and Ar$^2$ is optionally substituted by up to two groups independently selected from halo, C$_{1-4}$ alkyl, C$_1$ haloalkyl, C$_{1-4}$ alkoxy, C$_{1-4}$ haloalkoxy, C$_{2-4}$ alkyne, —S(C$_{1-3}$ alkyl), —SO$_2$(C$_{1-3}$ alkyl), and CN, where L is selected from S, S=O, SO$_2$, O, C(R$^L$)$_2$ and CF$_2$, and each R$^L$ is independently H or C$_{1-2}$ alkyl.

A particular aspect of Embodiment 1 is a compound of Embodiment 1a, which is a compound having this formula:

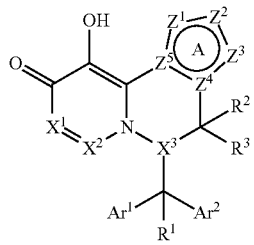

(1a)

or a pharmaceutically acceptable salt thereof, wherein:

X$^1$ is CR$^{X1}$ or N, where R$^{X1}$ is H, halo, C$_{1-6}$ alkyl, C$_{1-4}$ haloalkyl, CN, COOH, or a 5-6 membered heteroaryl ring containing 1-4 heteroatoms selected from N, O and S as ring members and optionally substituted by 1-2 groups selected from halo, hydroxy, amino, C$_{1-3}$ alkyl, C$_{1-3}$ haloalkyl, and C$_{1-3}$ alkoxy;

X$^2$ is CR$^{X2}$ or N, where R$^{X2}$ is H, halo, C$_{1-6}$ alkyl or C$_{1-4}$ haloalkyl;

X$^3$ is CR$^{X3}$ or N, where R$^{X3}$ is H, C$_{1-4}$ alkyl or C$_{1-4}$ haloalkyl;

provided that X$^2$ is CR$^{X2}$ if either or both of X$^1$ and X$^3$ represent N;

R$^1$ is H, halo, hydroxy, C$_{1-4}$ alkyl, C$_{1-4}$ haloalkyl, or C$_{1-4}$ alkoxy;

Ring A is a five-membered heteroaryl ring containing at least one carbon ring atom and up to four heteroatoms selected from N, O and S as ring members, wherein Z$^1$ is N, O or S;

Z$^2$ and Z$^3$ are independently CR$^z$, N, NR$^z$ O or S; and

Z$^4$ and Z$^5$ each independently represent C or N, provided Z$^4$ and Z$^5$ are not both simultaneously N, where each R$^z$ is independently selected from H, halo, C$_{1-4}$ alkyl, C$_{3-6}$ cycloalkyl, C$_{1-4}$ alkoxy, and C$_{1-4}$ haloalkyl;

R$^2$ and R$^3$ are independently H or C$_{1-4}$ alkyl;

Ar$^1$ and Ar$^2$ each represent phenyl or a 5-6 membered heteroaryl ring containing 1-3 heteroatoms selected from N, O and S as ring members, and are each independently substituted with up to three groups selected from halo, C$_{1-4}$ alkyl, C$_{1-4}$ haloalkyl, C$_{1-4}$ alkoxy, C$_{1-4}$ haloalkoxy, C$_{2-4}$ alkyne, and CN;

and Ar$^1$ and Ar$^2$ are optionally linked together by a bridge of the formula —C(R$^L$)$_2$-L- to form a tricyclic ring system wherein each Ar$^1$ and Ar$^2$ is optionally substituted by up to two groups independently selected from halo, C$_{1-4}$ alkyl, C$_{1-4}$ haloalkyl, C$_{1-4}$ alkoxy, C$_{1-4}$ haloalkoxy, C$_{2-4}$ alkyne, and CN, where L is selected from S, S=O, SO$_2$, O, C(R$^L$)$_2$ and CF$_2$, and each R$^L$ is independently H or C$_{1-2}$ alkyl.

Embodiment 2

A compound according to embodiment 1 or 1a, or a pharmaceutically acceptable salt thereof, wherein X$^1$ is CH.

Embodiment 3

A compound according to embodiment 1 or 1a or embodiment, 2 or a pharmaceutically acceptable salt thereof, wherein X$^2$ is CH or N.

Embodiment 4

A compound according to any one of the preceding embodiments, or a pharmaceutically acceptable salt thereof, wherein X$^3$ is CH.

Embodiment 5

A compound according to any of the preceding embodiments or a pharmaceutically acceptable salt thereof, wherein R$^2$ and R$^3$ are both H.

Embodiment 6

A compound according to any of the preceding embodiments or a pharmaceutically acceptable salt thereof, wherein R$^1$ is H.

Embodiment 7

A compound according to any of the preceding embodiments or a pharmaceutically acceptable salt thereof, wherein Ring A is selected from imidazole, pyrazole, triazole, oxazole, isoxazole, thiazole, isothiazole, oxadiazole, thiadiazole, and tetrazole.

Embodiment 8

A compound according to any of the preceding embodiments or a pharmaceutically acceptable salt thereof, wherein $Z^5$ is C.

Embodiment 9

A compound according to any of the preceding embodiments or a pharmaceutically acceptable salt thereof, wherein $Z^4$ is N.

Embodiment 10

A compound according to any one of the preceding embodiments, or a pharmaceutically acceptable salt thereof, wherein $Z^3$ is $CR^z$ or N.

Embodiment 11

A compound of any of the preceding embodiments or a pharmaceutically acceptable salt thereof, wherein ring A is selected from imidazole, pyrazole, triazole and tetrazole.

Embodiment 12

A compound of any of the preceding embodiments, which is of the formula:

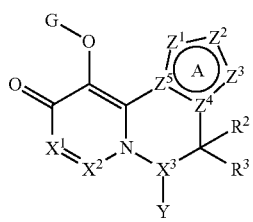

wherein Y represents a group selected from

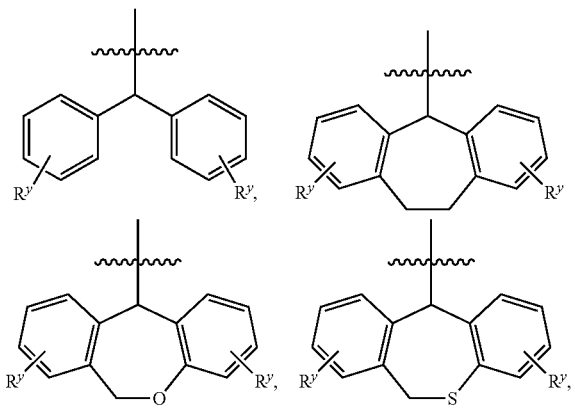

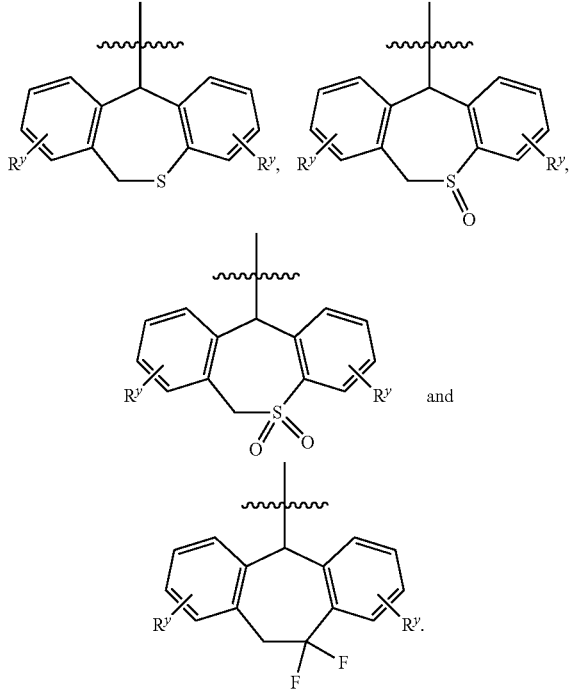

wherein each $R^y$ is independently selected from H, halo, $C_{1-4}$ alkyl, $C_{1-4}$ haloalkyl, $C_{1-4}$ alkoxy, $C_{1-4}$ haloalkoxy, $C_{2-4}$ alkyne, and CN, or a pharmaceutically acceptable salt thereof. In these embodiments, G is sometimes H. In other examples of these embodiments, G is selected from —C(O)R, —C(O)—OR, —CH$_2$—O—C(O)R, and —CH$_2$—O—C(O)—OR; wherein R is $C_1$-$C_4$ alkyl, optionally substituted with one or two groups selected from halo, CN, —OH, amino, phenyl, $C_{1-4}$ alkoxy, $C_{1-4}$ haloalkyl, and $C_{1-4}$ haloalkoxy.

Embodiment 13

A compound of embodiment 1 or 1a, which is selected from the compounds in Table 1 and the pharmaceutically acceptable salts thereof.

Embodiment 14

A pharmaceutical composition comprising a compound of any of the preceding embodiments or a pharmaceutically acceptable salt thereof and one or more pharmaceutically acceptable carriers.

Embodiment 15

A combination comprising a therapeutically effective amount of a compound according to any one of embodiments 1 to 13 or a pharmaceutically acceptable salt thereof and one or more therapeutically active co-agents.

Embodiment 16

A method of treating influenza, comprising administering to a subject in need thereof a therapeutically effective amount of a compound of any of embodiments 1-13 or a pharmaceutically acceptable salt thereof.

Embodiment 17

A compound according to any one of embodiments 1 to 13 or a pharmaceutically acceptable salt thereof, for use as a medicament.

Embodiment 18

A compound according to any one of embodiments 1 to 13 or a pharmaceutically acceptable salt thereof, for use in the treatment of influenza.

Embodiment 19

Use of a compound according to any one of embodiments 1 to 13 or a pharmaceutically acceptable salt thereof in the manufacture of a medicament for the treatment of influenza.

In some embodiments, the compound of Formula (I) is a compound of one of the following formulas (I-A) through (I-J):

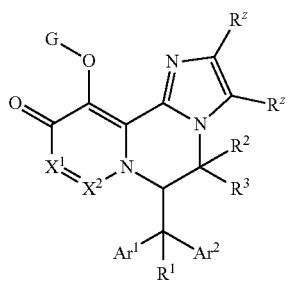
I-A

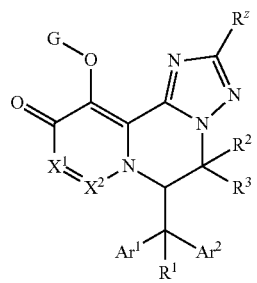
I-B

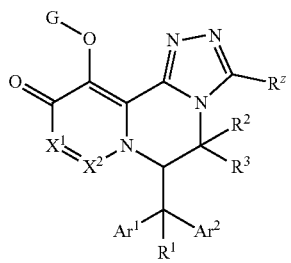
I-C

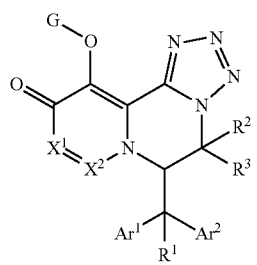
I-D

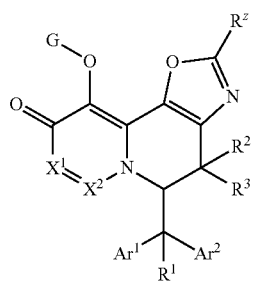
I-E

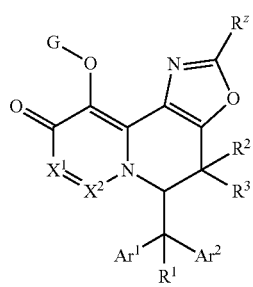
I-F

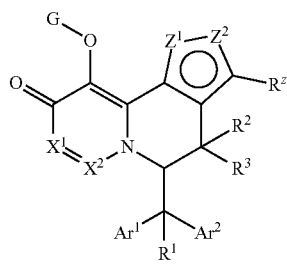
I-G

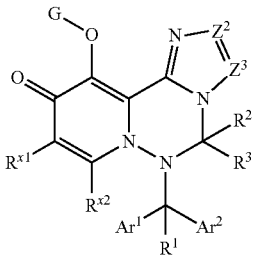
I-H

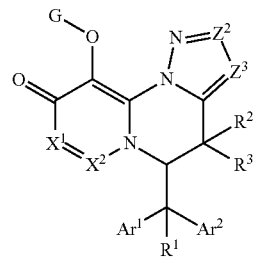
I-I

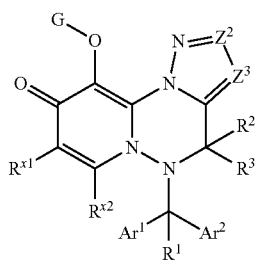
I-J

In Formula (I-G), one of $Z^1$ and $Z^2$ is N, and the other is either O or S. In Formula (I-H), $Z^2$ and $Z^3$ are independently N or $CR^z$. Other variables in Formulas (I-A) through (I-J) are as defined for Formula (I) above. In some embodiments, G in compounds of Formulas (I-A) through (I-J) is H. In other compounds of Formulas (I-A) through (I-J), G is selected from —C(O)R, —C(O)—OR, —CH$_2$—O—C(O)R, and —CH$_2$—O—C(O)—OR. The compounds of these embodiments can be used in the compositions, combinations, methods and uses of embodiments 14-19.

As used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. The term "chiral" refers to molecules which have the property of non-superimposability on their mirror image partner, while the term "achiral" refers to molecules which are superimposable on their mirror image partner. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog 'R-S' system. When a compound is a pure enantiomer, the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain compounds described herein contain one or more asymmetric centers or axes and may thus give rise to enantiomers, diastereomers, and other stereoisomeric forms that may be defined, in terms of absolute stereochemistry, as (R)- or (S)-.

Depending on the choice of the starting materials and synthesis procedures, the compounds can be present in the form of one of the possible isomers or as mixtures thereof, for example as pure optical isomers, or as isomer mixtures, such as racemates and diastereoisomer mixtures, depending on the number of asymmetric carbon atoms. The present invention is meant to include all such possible isomers, including racemic mixtures, diasteriomeric mixtures and optically pure forms. Optically active (R)- and (S)-isomers may be prepared using chiral synthons or chiral reagents, or resolved using conventional techniques. If the compound contains a double bond, the substituent may be E or Z configuration unless specified. If the compound contains a disubstituted cycloalkyl, the cycloalkyl substituent may have a cis- or trans-configuration, unless otherwise specified. All tautomeric forms are also intended to be included.

In many cases, the compounds of the present invention are capable of forming acid and/or base salts by virtue of the presence of amino and/or carboxyl groups or groups similar thereto. As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlorotheophyllinate, citrate, ethanedisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic or organic bases and can have inorganic or organic counterions.

Inorganic counterions for such base salts include, for example, ammonium salts and metals from columns I to XII of the periodic table. In certain embodiments, the counterion is selected from sodium, potassium, ammonium, alkylammonium having one to four C1-C4 alkyl groups, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Suitable organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, tetrahydrofuran, toluene, chloroform, dichloromethane, methanol, ethanol, isopropanol, or acetonitrile is desirable, where practicable.

Any formula given herein is also intended to represent unlabeled forms (i.e., compounds wherein all atoms are present at natural isotopic abundances, and not isotopically enriched) as well as isotopically enriched or labeled forms of the compounds. Isotopically enriched or labeled compounds have structures depicted by the formulas given herein except that at least one atom of the compound is replaced by an atom having an atomic mass or mass number different from the atomic mass or the atomic mass distribution that occurs naturally. Examples of isotopes that can be incorporated into enriched or labeled compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$, $^{31}F$, $^{32}P$, $^{35}S$, $^{36}Cl$, and $^{125}I$. The invention includes various isotopically labeled compounds as defined herein, for example those in which radioactive isotopes, such as $^3H$ and $^{14}C$, or those in which non-radioactive isotopes, such as $^2H$ and $^{13}C$, are present at levels significantly above the natural abundance for these isotopes. These isotopically labeled compounds are useful in metabolic studies (e.g., with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically-labeled compounds of formula (I) can generally be prepared by conventional techniques known to those skilled in the art or by processes analogous to those described in the accompanying Examples using an appropriate isotopically-labeled reagent in place of the non-labeled reagent otherwise employed.

Further, substitution with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Pharmaceutically acceptable solvates in accordance with the invention include those wherein the solvent of crystallization may be isotopically substituted, e.g. $D_2O$, $d^6$-acetone, $d^6$-DMSO, as well as solvates with non-enriched solvents.

Compounds of the invention, i.e., compounds of formula (I) that contain groups capable of acting as donors and/or acceptors for hydrogen bonds may be capable of forming co-crystals with suitable co-crystal formers. These co-crystals may be prepared from compounds of formula (I) by known co-crystal forming procedures. Such procedures include grinding, heating, co-subliming, co-melting, or contacting in solution compounds of formula (I) with the co-crystal former under crystallization conditions and isolating co-crystals thereby formed. Suitable co-crystal formers include those described in WO2004/078163. Hence the invention further provides co-crystals comprising a compound of formula (I).

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drug stabilizers, binders, excipients, disintegration agents, lubricants, sweetening agents, flavoring agents, dyes, and the like and combinations thereof, as would be known to those skilled in the art for use in a pharmaceutical composition for administration to a human subject (see, for example, Remington: The Science and Practice of Pharmacy, 22nd ed.). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response in a subject, for example, an amount sufficient to reduce of one or more symptoms, alleviate conditions, slow or delay disease progression, or prevent a disease, etc. In one non-limiting embodiment, the term "a therapeutically effective amount" refers to the amount of a compound of the present invention that, when administered to a subject, is effective to reduce one or more symptoms associated with an influenza virus infection, or to shorten the duration of the symptomatic stage of an influenza virus infection, or to slow the progression of an influenza virus infection, or to reduce or stop the exacerbation of an underlying condition by an influenza virus infection.

In another non-limiting embodiment, the term "a therapeutically effective amount" refers to the amount of the compound of the present invention that, when administered to a cell, or a tissue, or a non-cellular biological material, or a medium, is effective to cause a statistically significant reduction in rate of replication or proliferation of a strain of orthomyxovirus.

As used herein, the term "subject" refers to an animal. Typically, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess of either the (R)- or (S)-configuration; i.e., for optically active compounds, it is often preferred to use one enantiomer to the substantial exclusion of the other enantiomer, so typically an enantiomeric purity of at least 95% is preferred. Substituents at atoms with unsaturated double bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof. 'Substantially pure' or 'substantially free of other isomers' as used herein means the product contains less than 5%, and preferably less than 2%, of other isomers relative to the amount of the preferred isomer, by weight.

Resulting mixtures of isomers can typically be separated on the basis of the physicochemical differences of the constituents, into the pure or substantially pure geometric or optical isomers, diastereomers, racemates, for example, by chromatography and/or fractional crystallization.

Racemates of final products or intermediates can typically be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral stationary phase.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

In another aspect, the present invention provides a pharmaceutical composition comprising a compound of the present invention, or a pharmaceutically acceptable salt thereof, and at least one pharmaceutically acceptable carrier. In some embodiments, the pharmaceutical composition comprises at least two pharmaceutically acceptable excipients or carriers. Pharmaceutically acceptable carriers and other excipients are known to those of skill in the art, and may be selected, for example, from carriers and excipients used in approved (registered) formulated therapeutic agents that are administered via similar routes of administration. The pharmaceutical composition can be formulated for particular routes of administration such as oral administration, parenteral administration, and rectal administration, and the like. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

In one embodiment, the compounds of the invention are formulated for oral delivery. Typically, these pharmaceutical compositions are tablets or gelatin capsules comprising the active ingredient (at least one compound of Formula (I)) together with one or more excipients selected from:

a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems may pertain to an inhalation or to an intranasal application that may be suitable for use to treat influenza, for example, and may contain solubilizers, stabilizers, tonicity enhancing agents, buffers and preservatives. They may be conveniently delivered in the form of a dry powder (either alone, as a mixture, for example a dry blend with lactose, or a mixed component particle, for example with phospholipids) from a dry powder inhaler or an aerosol spray presentation from a pressurized container, pump, spray, atomizer or nebulizer, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of formula (I), in free form or in salt form, exhibit valuable pharmacological properties, e.g. they inhibit or prevent replication of orthomyxovirus, as indicated by test data provided in the next sections, and are therefore indicated for therapy or for use as research chemicals, e.g. as tool compounds such as for the study of replication of an orthomyxovirus, particularly Influenza A, Influenza B or Influenza C. Accordingly, compounds of the invention are useful in the treatment of an infection caused by an orthymyxovirus, particularly Influenza A, Influenza B or Influenza C, especially in human subjects. In some embodiments, the subject to be treated is a human having or at risk of contracting an influenza viral infection. For example, subjects having pre-existing conditions such as asthma or COPD that can be greatly exacerbated by an influenza infection may be treated with the methods or compounds of the invention before exhibiting symptoms of an influenza infection, especially if they are at risk of contracting influenza due to close proximity to persons such as family members who have or appear to have influenza. In other embodiments, the subject for treatment by the methods and compositions of the invention is one diagnosed as having symptoms consistent with an influenza infection. In other embodiments, the subject may be a human who has been tested with known diagnostic methods such as a Rapid Influenza Diagnostic Test (RIDT) or Reverse Transcriptase PCT (RT-PCR) methods to detect the presence of influenza virus, and found to be infected with influenza, regardless of the presence of typical influenza symptoms.

As a further embodiment, the present invention provides the use of a compound of formula (I) or any of the embodiments within the scope of Formula (I) as described herein, in therapy. In particular, the compounds are suitable for use to treat a subject having or at particularly high risk for an orthomyxovirus viral infection, especially Influenza A, Influenza B, or Influenza C.

In another embodiment, the invention provides a method of treating a disease which is caused by an orthomyxovirus, comprising administration of a therapeutically effective amount of a compound of formula (I) or any of the embodiments within the scope of Formula (I) as described herein to a subject in need of such treatment. In some embodiments, the compound of formula (I) is administered orally. In a further embodiment, the disease is selected from Influenza A, Influenza B, and Influenza C. The method typically comprises administering an effective amount of a compound as described herein, or a pharmaceutical composition comprising an effective amount of such compound, to a subject in need of such treatment. The compound may be administered by any suitable method such as those described herein, and the administration may be repeated at intervals which may be selected by a treating physician. In some embodiments, the compound or pharmaceutical composition is administered orally.

Thus, as a further embodiment, the present invention provides the use of a compound of formula (I) or any of the embodiments of such compounds described herein for the manufacture of a medicament. In a particular embodiment, the medicament is for treatment of an orthomyxovirus infection, especially Influenza A, Influenza B, or Influenza C.

The compound of the present invention may be administered either simultaneously with, or before or after, one or more therapeutic co-agent(s). The compound of the present invention may be administered separately, by the same or different route of administration, or together in the same pharmaceutical composition as the co-agent(s). Suitable co-agents for use with the compounds of the invention include antivirals active on influenza viruses, such as neuraminidase inhibitors including oseltamivir, peramivir, zanamivir and laninamivir, laninamivir octanoate, and adamantanes such as amantadine and rimantadine. Additional co-agents for use in these methods include an M2 protein inhibitor, a polymerase inhibitor, a PB2 inhibitor, favipiravir, fludase, ADS-8902, beraprost, Neugene®, ribavirin, CAS Reg. No. 1422050-75-6, VX-787, Flu Mist Quadrivalent®, Fluarix® Quadrivalent, Fluzone® Quadrivalent, Flucelvax® and FluBlok®.

In one embodiment, the invention provides a product comprising a compound of formula (I) and at least one other therapeutic co-agent as a combined preparation for simultaneous, separate or sequential use in therapy. In one embodiment, the therapy is the treatment of a viral infection caused by an orthomyxovirus, particularly Influenza A, Influenza B or Influenza C. Products provided as a combined preparation include a composition comprising a compound of formula (I) and at least one of the other therapeutic co-agent(s) together in the same pharmaceutical composition, or the compound of formula (I) and at least one other therapeutic co-agent(s) in separate form, e.g. in the form of a kit for use to treat a subject by the methods described herein.

In one embodiment, the invention provides a pharmaceutical composition comprising a compound of formula (I) and another therapeutic co-agent(s). Suitable co-agents include antivirals active on influenza viruses, such as neuraminidase inhibitors including oseltamivir, peramivir, zanamivir and laninamivir, and adamantanes such as amantadine and rimantadine. Optionally, the pharmaceutical composition may comprise a pharmaceutically acceptable carrier, as described above.

In one embodiment, the invention provides a kit comprising two or more separate pharmaceutical compositions, at least one of which contains a compound of formula (I). The other pharmaceutical composition may contain one of the suitable co-agents. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the therapeutic co-agent may be manufactured and/or formulated by the same or different manufacturers. Moreover, the compound of the invention and the therapeutic co-agent may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the therapeutic co-agent.

Accordingly, the invention provides the use of a compound of formula (I) for treating a viral infection caused by an orthomyxovirus, particularly influenza, which may be Influenza A, Influenza B or Influenza C, wherein the medicament is prepared for administration with a therapeutic co-agent. Typically in the methods of using the compounds of the invention, the serotype of influenza is not identified before treatment. The invention also provides the use of therapeutic co-agent for treating a disease or condition, wherein the medicament is administered with a compound of formula (I).

The invention also provides a compound of formula (I) for use in a method of treating a viral infection caused by an orthomyxovirus, particularly Influenza A, Influenza B or Influenza C, wherein the compound of formula (I) is prepared for administration with a therapeutic co-agent. The invention also provides another therapeutic co-agent for use in a method of treating a viral infection caused by an orthomyxovirus, particularly influenza, e.g., Influenza A, Influenza B or Influenza C, wherein the therapeutic co-agent is prepared for administration with a compound of formula (I). The invention also provides a compound of formula (I) for use in a method of treating a viral infection caused by an orthomyxovirus, particularly Influenza A, Influenza B or Influenza C, wherein the compound of formula (I) is administered with a therapeutic co-agent. The invention also provides a therapeutic co-agent for use in a method of treating a viral infection caused by an orthomyxovirus, particularly Influenza A, Influenza B or Influenza C, wherein the a therapeutic co-agent is administered with a compound of formula (I).

The invention also provides the use of a compound of formula (I) for treating a viral infection caused by an orthomyxovirus, particularly influenza, e.g., Influenza A, Influenza B or Influenza C, wherein the patient has previously (e.g. within 24 hours) been treated with another therapeutic agent. The invention also provides the use of another therapeutic agent for treating a viral infection caused by an orthomyxovirus, particularly Influenza A, Influenza B or Influenza C, wherein the patient has previously (e.g. within 24 hours) been treated with a compound of formula (I).

In one embodiment, the therapeutic co-agent is selected from antivirals purported to be useful for treating infections caused by influenza viruses, such as neuraminidase inhibitors including oseltamivir, peramivir, zanamivir and laninamivir, and adamantanes such as amantadine and rimantadine.

The pharmaceutical composition or combination of the present invention can be in unit dosage containing about 1-1000 mg of active ingredient(s) for a human subject of about 50-70 kg, or about 1-500 mg, or about 1-250 mg, or about 1-150 mg, or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 0.1-50 mg/kg.

The invention further includes processes to make the compounds of Formula (I) as disclosed herein, and any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

A method to synthesize compounds of Formula (I-A) is depicted in Scheme A. The first step is to generate aldehyde A-2 from ester A-1 by treatment with a reducing agent, such as DIBAL-H. A-2 then undergoes cycloaddition upon treatment with amino alcohol A-3 in the presence of ammonium acetate and a 1,2-dicarbonyl species, such as glyoxal or biacetal, to provide isoxazole A-4. The alcohol A-4 can be converted to the corresponding mesylate A-5, with subsequent one step or two step deprotection of protecting groups P1 and P2 to give A-6. Treatment of A-6 with a base, such as potassium or cesium carbonate, in an aprotic solvent, such as DMF or NMP, provides A-7. In similar fashion, an appropriately protected ester A-8 can be transformed to A-9. Alternatively, P1 and P2 can be removed together or stepwise from intermediate A-4 to provide A-10, which can be treated under Mitsunobu conditions to provide A-7 as shown.

Scheme A.

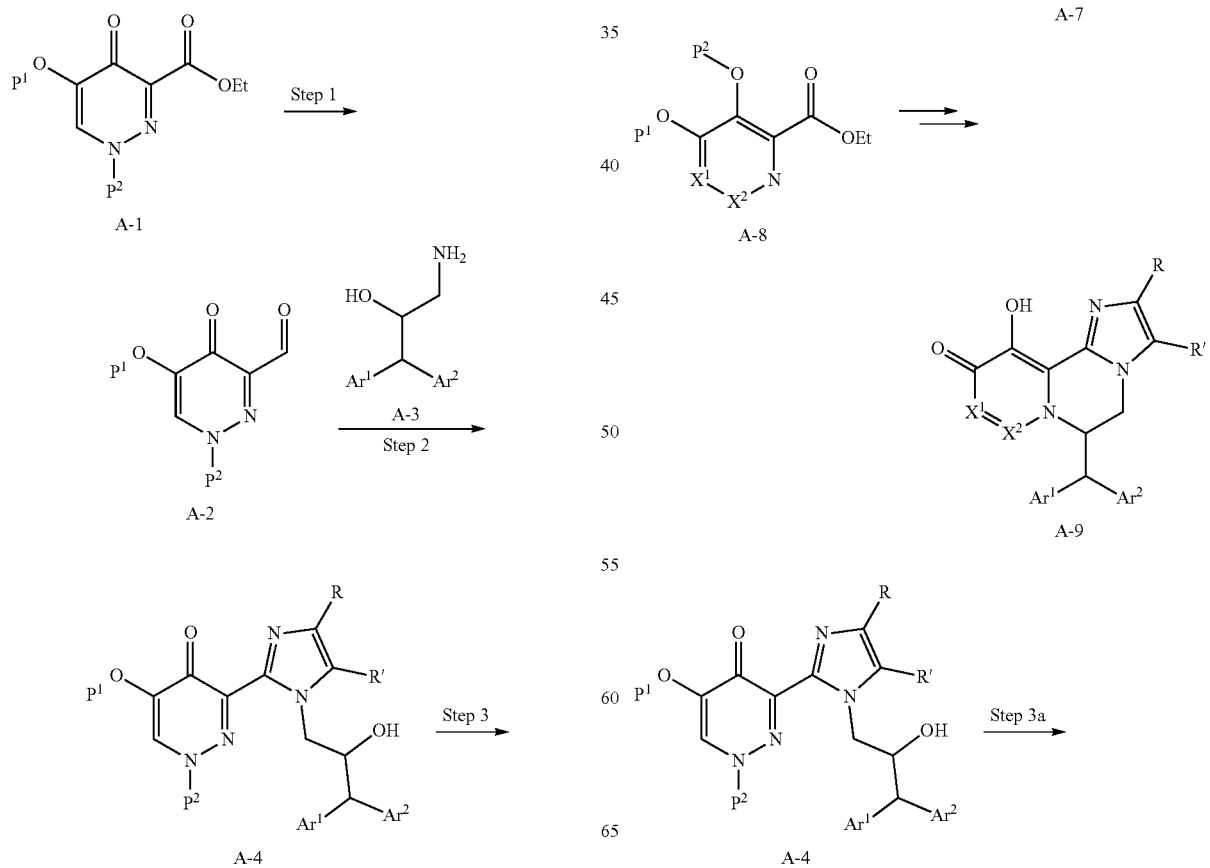

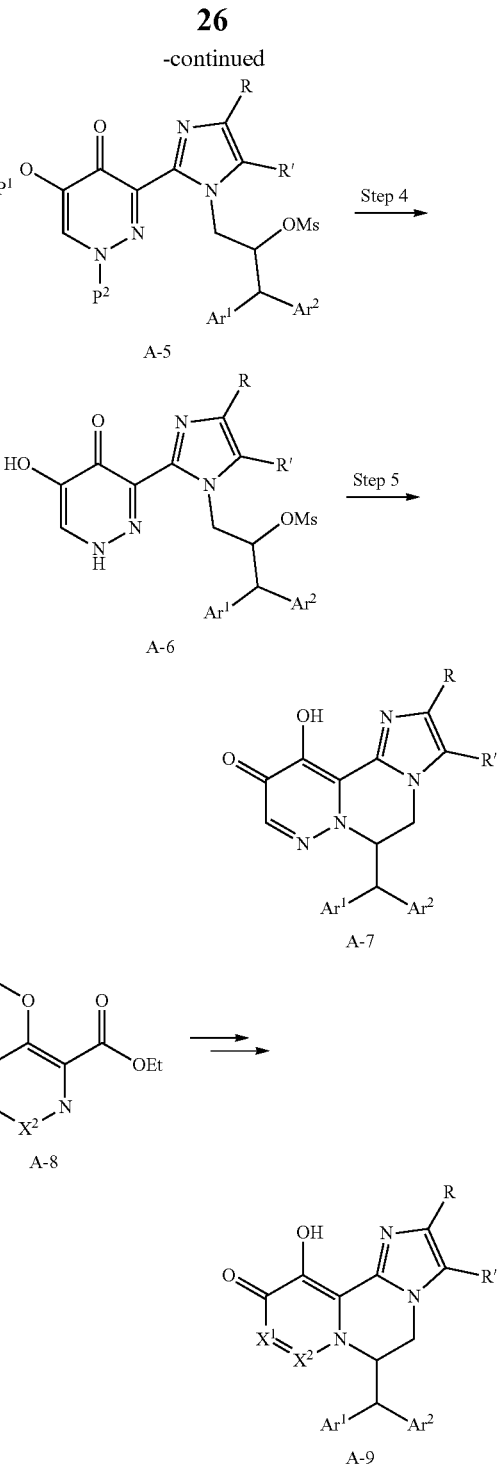

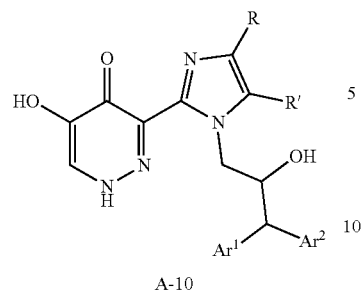

A-10

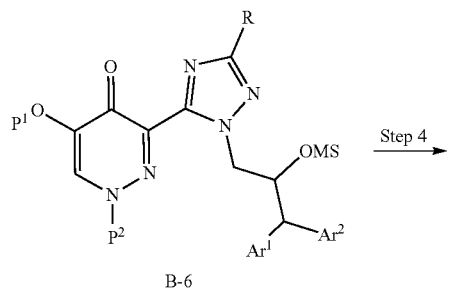

B-6

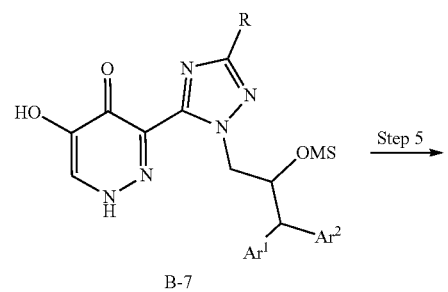

B-7

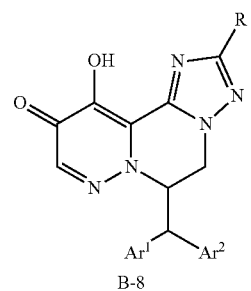

B-8

A method to synthesize compounds of Formula (I-B) is depicted in Scheme B. The first step is to condense amide B-1 with dimethyl acetal methanamine B-2 to provide B-3. Treatment of B-3 with hydrazide B-4 in a mixed solvent system consisting of, for example, water, butanol and acetic acid at elevated temperature gives B-5. The alcohol B-5 can be converted to the corresponding mesylate B-6, with subsequent one step or two step deprotection of protecting groups P1 and P2 to give B-7. Treatment of B-7 with a base, such as potassium or cesium carbonate, in an aprotic solvent, such as DMF or NMP, provides B-8. In similar fashion an appropriately protected ester B-9 can be transformed to B-10. Alternatively, P1 and P2 can be removed together or stepwise from intermediate B-5 to provide B-11 which can be treated under Mitsunobu conditions to provide B-8.

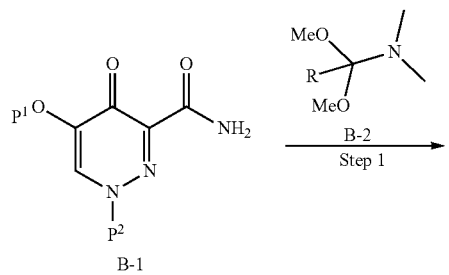

B-1

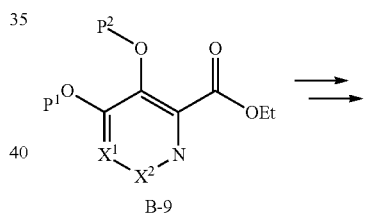

B-9

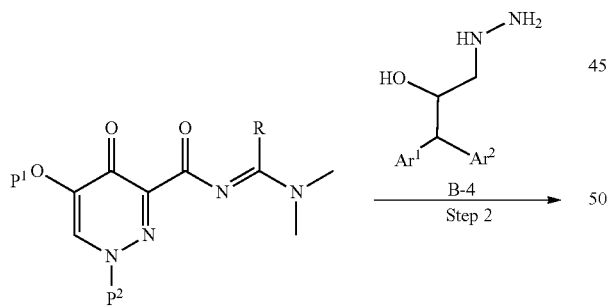

B-3

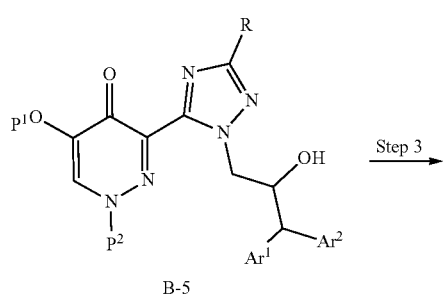

B-5

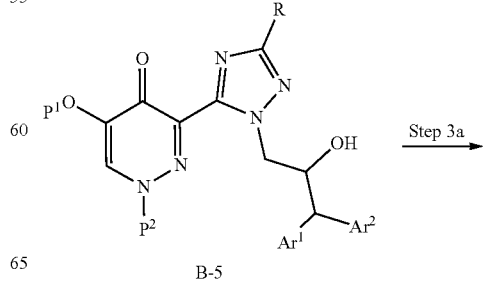

B-10

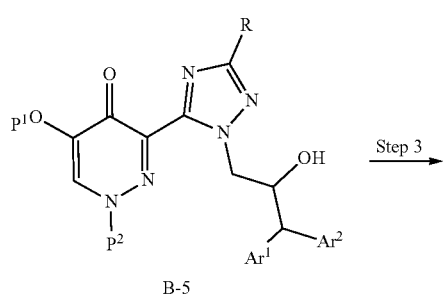

B-5

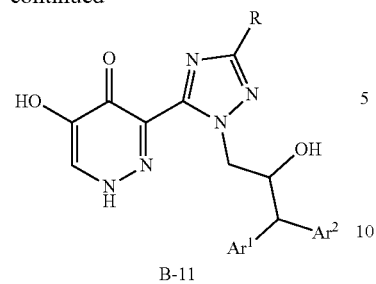

B-11

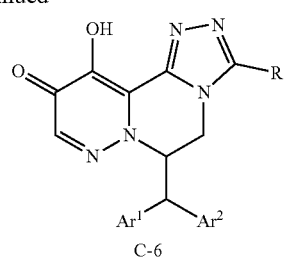

C-6

A method to synthesize compounds of Formula (I-C) is depicted in Scheme C. The first step is to couple acyl hydrazide C-1, conveniently prepared from the corresponding carboxylic acid, with dimethyl acetal methanamine C-2 to provide C-3. Treatment of C-3 with amine C-4 in a mixed solvent system consisting of, for example, acetonitrile and acetic acid at elevated temperature gives C-5. Following the previously described (Scheme A & Scheme B) three step manipulation of mesylation, deprotection and treatment with a base, such as potassium or cesium carbonate, provides C-6. In similar fashion appropriately protected intermediates C-7 can be transformed into C-8. Alternatively, as described for similar intermediates in Scheme A and Scheme B, P1 and P2 can be removed together or stepwise from intermediate C-5, and the resulting alcohol can be treated under Mitsunobu conditions to provide C-6.

C-7

C-8

A method to synthesize compounds of Formula (I-D) is depicted in Scheme D. The first step is to couple the carboxylic acid D-1 with amine D-2 to provide amide D-3. Protection of the alcohol on D-3 with a silylating agent such as, for example, TBDMS-Cl or TBDPS-Cl, provides intermediate D-4. Treatment of D-4 with PCl3 or phosgene provides D-5. Treatment with azide followed by removal of the silyl protecting group provides D-6. Following the previously described (Scheme A & Scheme B) three step manipulation of mesylation, deprotection and treatment with a base, such as potassium or cesium carbonate, provides D-7. In similar fashion appropriately protected intermediates D-8 can be transformed into D-9. Alternatively, as described for similar intermediates in Scheme A and Scheme B, P1 and P2 can be removed together or stepwise from intermediate D-6, and the resulting alcohol can be treated under Mitsunobu conditions to provide D-7.

Scheme C.

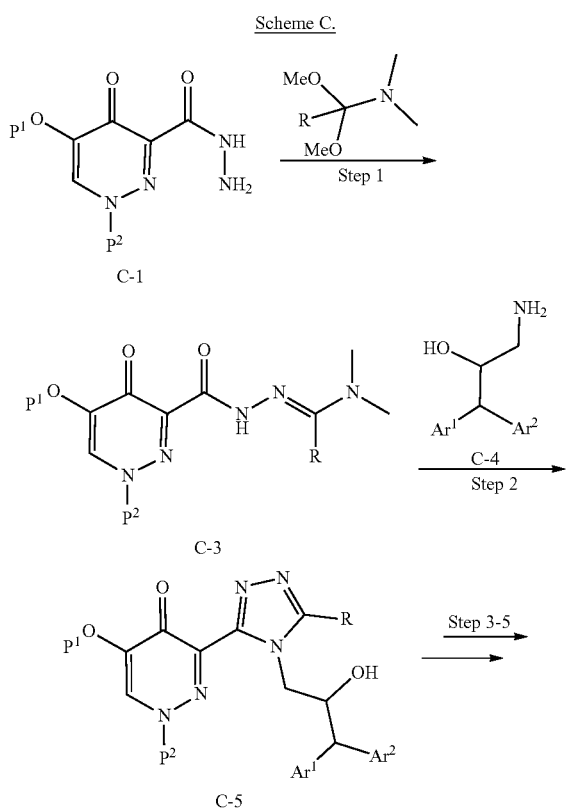

Scheme D.

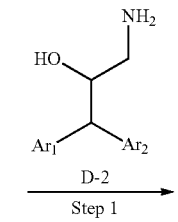

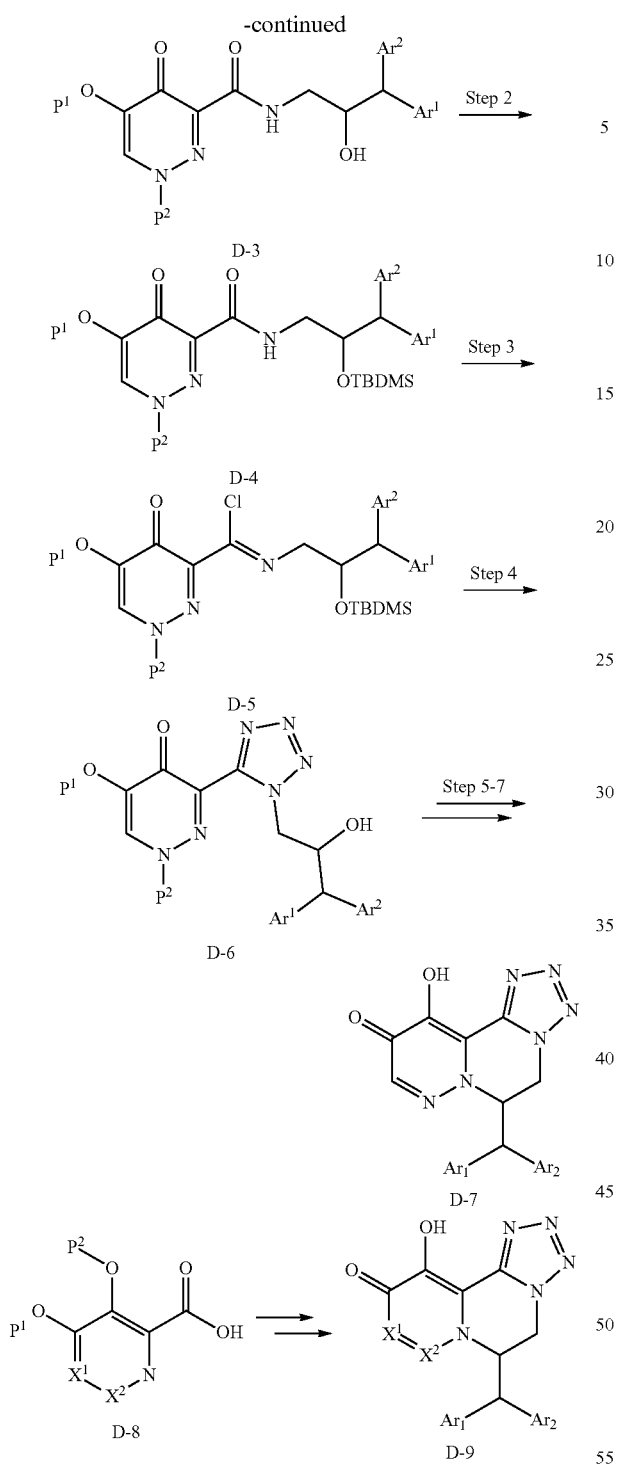

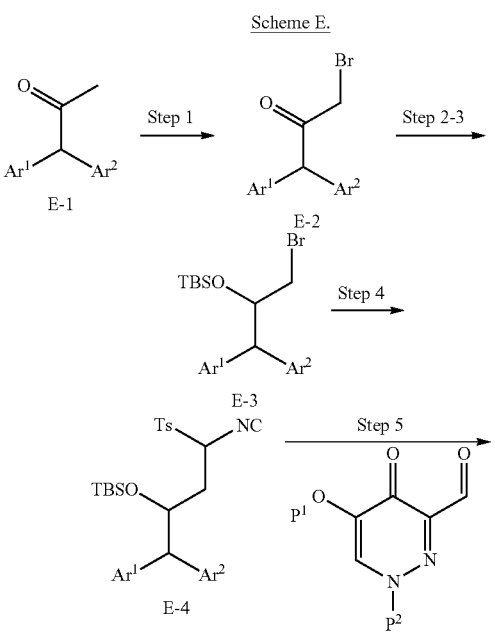

E-7. Following the previously described (Scheme A & Scheme B) three step manipulation of mesylation, deprotection and treatment with a base, such as potassium or cesium carbonate, provides E-8. In similar fashion an appropriately protected intermediate E-9 can be transformed into E-10.

Alternatively, as described for similar intermediates in Scheme A and Scheme B, P1 and P2 can be removed together or stepwise from intermediate E-7 and the resulting alcohol can be treated under Mitsunobu conditions to provide E-8.

A method to synthesize compounds of Formula (I-E) is depicted in Scheme E. The first step is to brominate ketone E-1 with a reagent such as, for example, bromine in acetic acid, to provide E-2. Reduction of the ketone followed by protection with a silylating agent such as, for example, TBS-Cl, provides E-3. Treatment of bromide E-3 with TosMIC (toluenesulfonylmethyl isocyanide) in the presence of a base such as sodium hydride provides intermediate E-4. Combining E-4 with aldehyde E-5 in the presence of a base in a solvent such as, for example, methanol provides oxazole E-6. Removal of the silyl protecting group provides alcohol

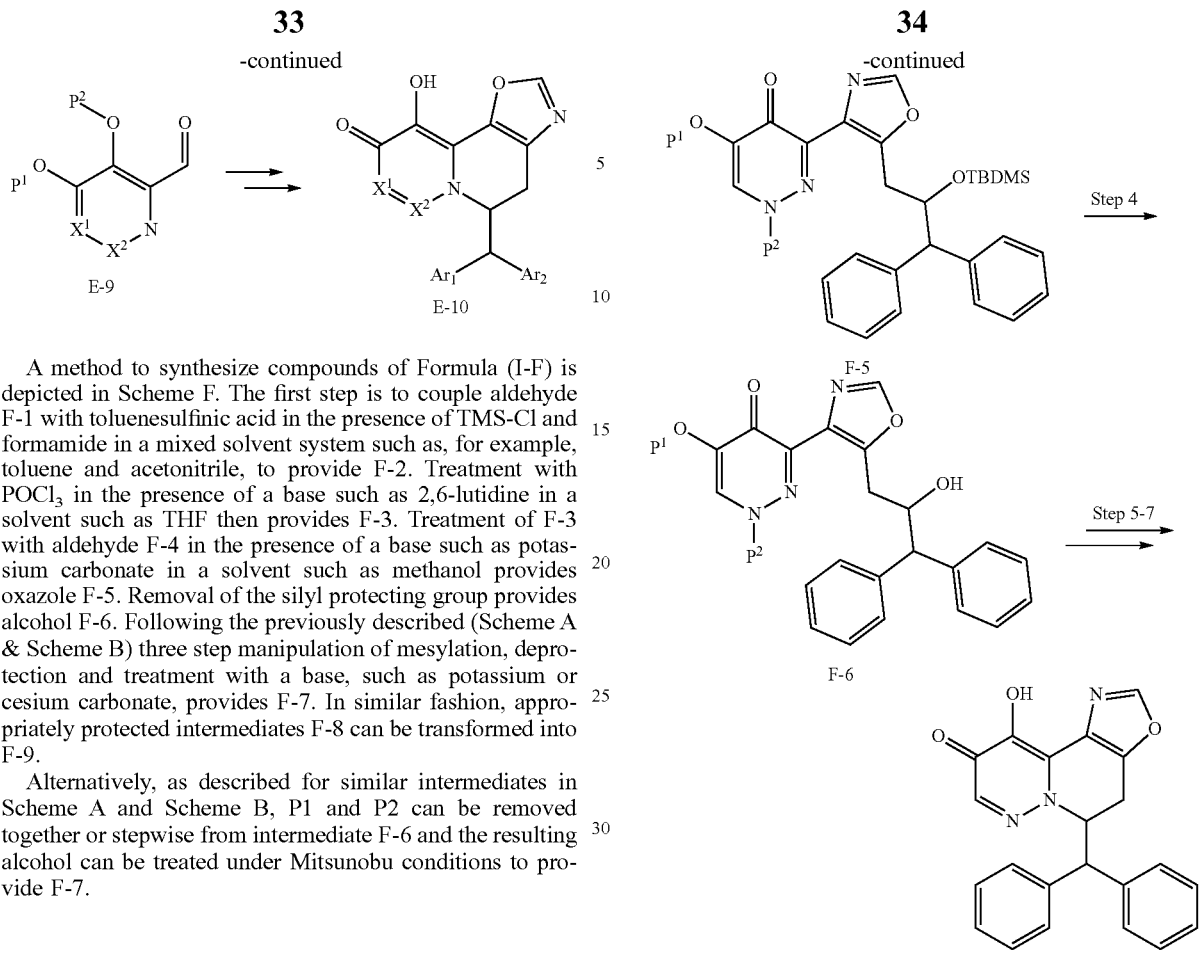

A method to synthesize compounds of Formula (I-F) is depicted in Scheme F. The first step is to couple aldehyde F-1 with toluenesulfinic acid in the presence of TMS-Cl and formamide in a mixed solvent system such as, for example, toluene and acetonitrile, to provide F-2. Treatment with $POCl_3$ in the presence of a base such as 2,6-lutidine in a solvent such as THF then provides F-3. Treatment of F-3 with aldehyde F-4 in the presence of a base such as potassium carbonate in a solvent such as methanol provides oxazole F-5. Removal of the silyl protecting group provides alcohol F-6. Following the previously described (Scheme A & Scheme B) three step manipulation of mesylation, deprotection and treatment with a base, such as potassium or cesium carbonate, provides F-7. In similar fashion, appropriately protected intermediates F-8 can be transformed into F-9.

Alternatively, as described for similar intermediates in Scheme A and Scheme B, P1 and P2 can be removed together or stepwise from intermediate F-6 and the resulting alcohol can be treated under Mitsunobu conditions to provide F-7.

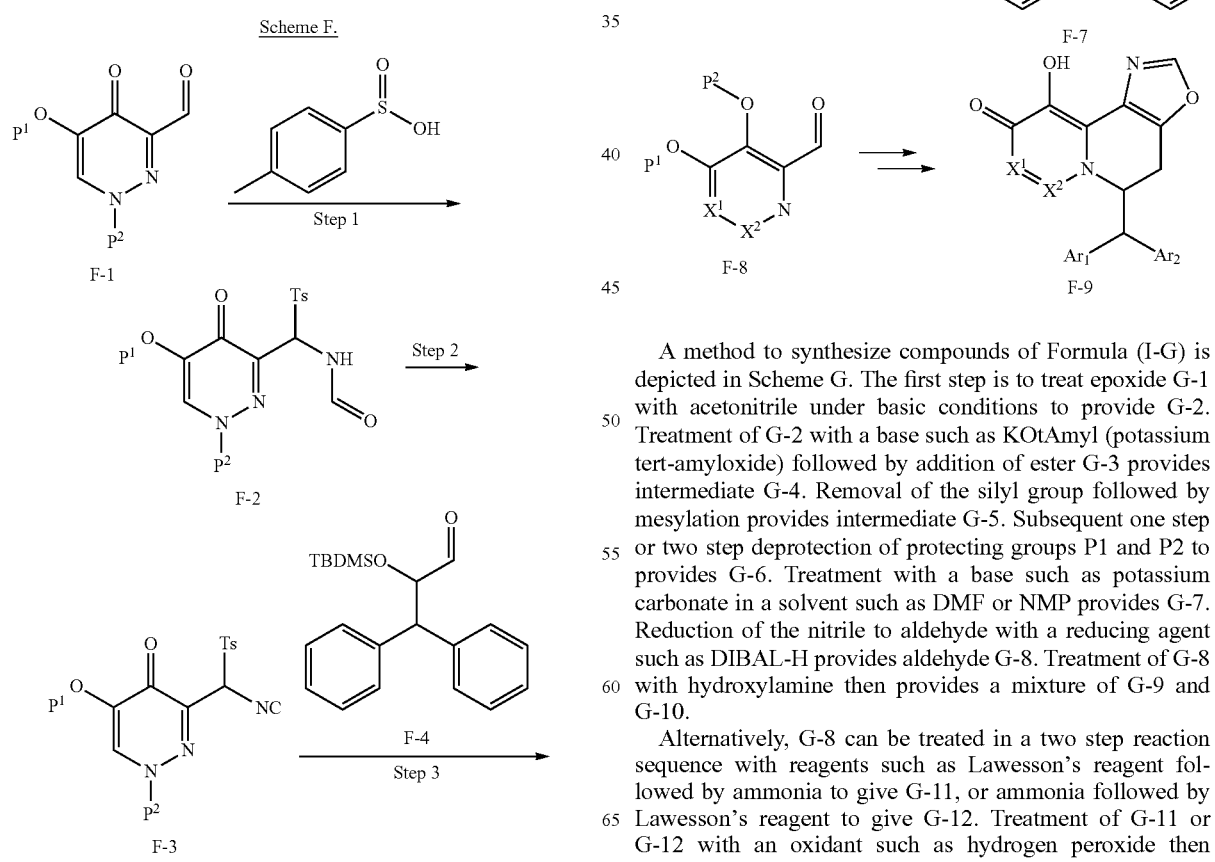

A method to synthesize compounds of Formula (I-G) is depicted in Scheme G. The first step is to treat epoxide G-1 with acetonitrile under basic conditions to provide G-2. Treatment of G-2 with a base such as KOtAmyl (potassium tert-amyloxide) followed by addition of ester G-3 provides intermediate G-4. Removal of the silyl group followed by mesylation provides intermediate G-5. Subsequent one step or two step deprotection of protecting groups P1 and P2 to provides G-6. Treatment with a base such as potassium carbonate in a solvent such as DMF or NMP provides G-7. Reduction of the nitrile to aldehyde with a reducing agent such as DIBAL-H provides aldehyde G-8. Treatment of G-8 with hydroxylamine then provides a mixture of G-9 and G-10.

Alternatively, G-8 can be treated in a two step reaction sequence with reagents such as Lawesson's reagent followed by ammonia to give G-11, or ammonia followed by Lawesson's reagent to give G-12. Treatment of G-11 or G-12 with an oxidant such as hydrogen peroxide then provides G-13 and G-14, respectively.

In similar fashion an appropriately protected intermediate G-15 can be transformed into G-16.
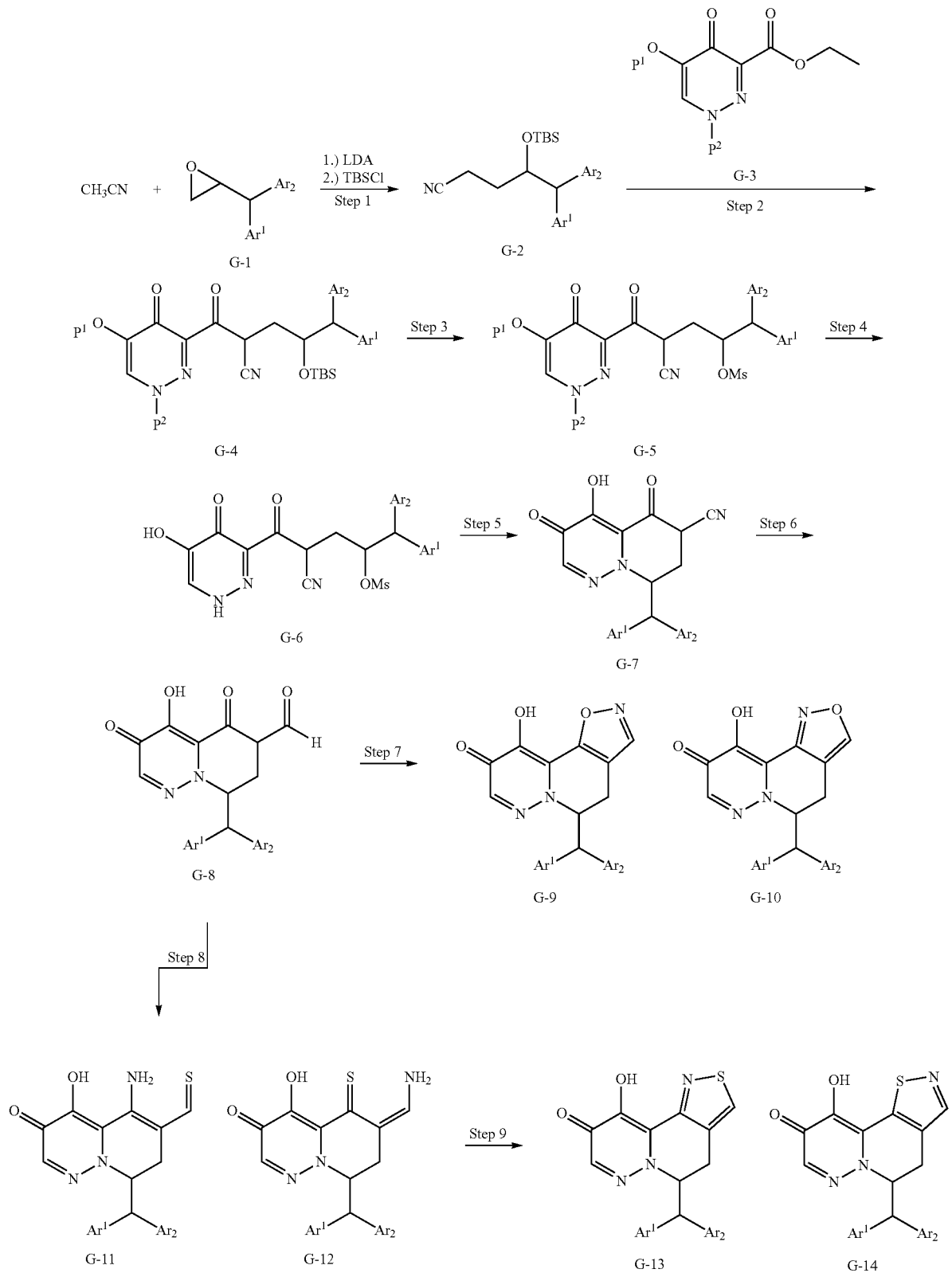
Scheme G.

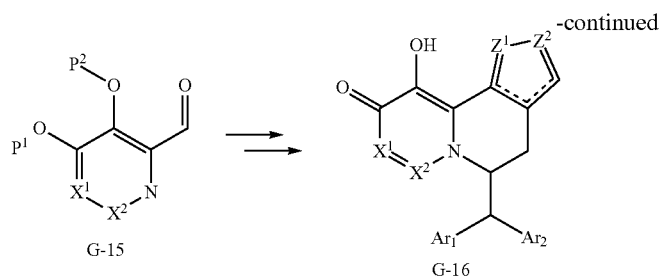

A method to synthesize compounds of Formula (I-H) is depicted in Scheme H. The first step is to brominate H-1 with a reagent such as NBS and then protect the —OH with a protecting group such as benzyl to provide H-2. Suzuki coupling with a 1,3,4-triazole boronic acid (or corresponding boronate ester) then provides H-3. A related imidazole H-6 can be prepared from ester H-4 by reduction of the ester to the aldehyde using a reducing agent such as DIBAL-H to give H-5. Subsequent treatment with an ammonia source such as ammonium carbonate in the presence of a 1,2-dicarbonyl species, such as glyoxal or biacetal, then provides H-6. A related tetrazole can be prepared from H-2 by a palladium-mediated cyanation to give H-7 followed by treatment with an azide source such as TMS-azide to give H-8.

Treatment of intermediate H-3, H-6 or H-8 with hydrazine then provides intermediates H-9. Condensation of an aldehyde or ketone with H-9 then provides intermediates H-10. Alkylation with a biaryl bromide such as H-11 then provides H-12. Alternatively, treatment of H-10 with a biaryl ketone under reductive amination conditions provides H-12.

Scheme H.

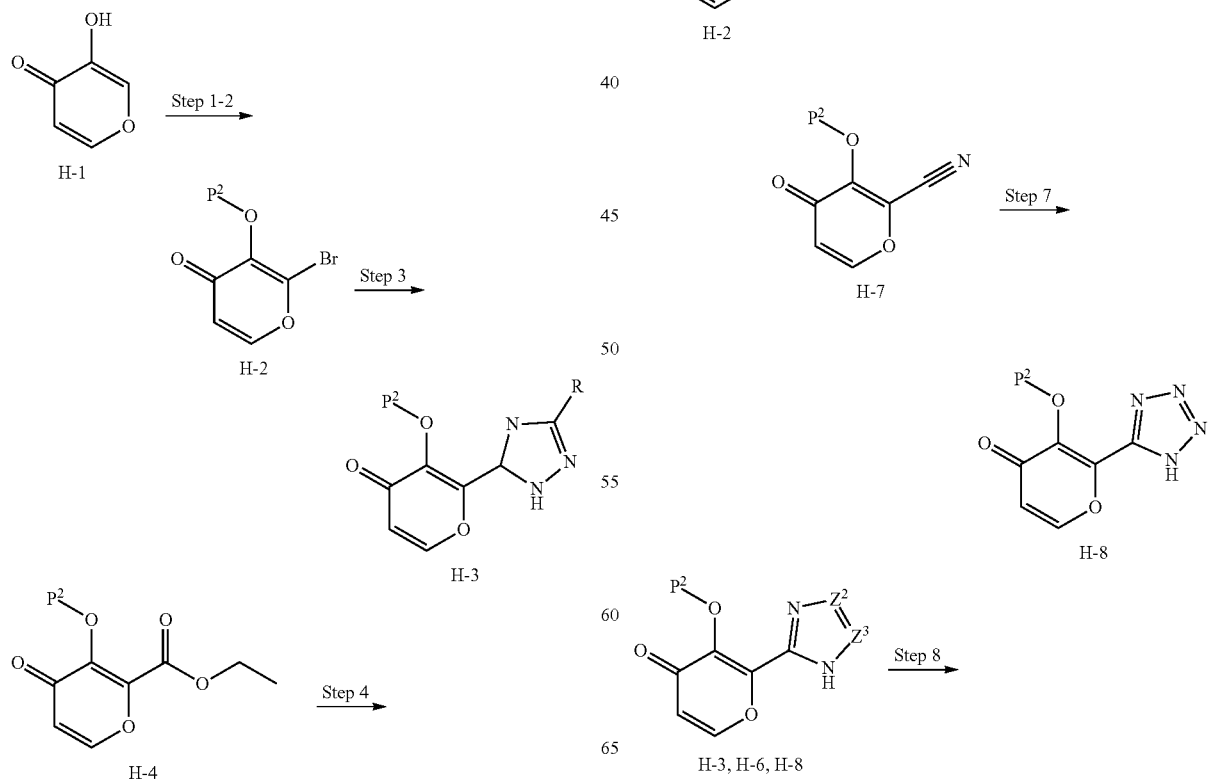

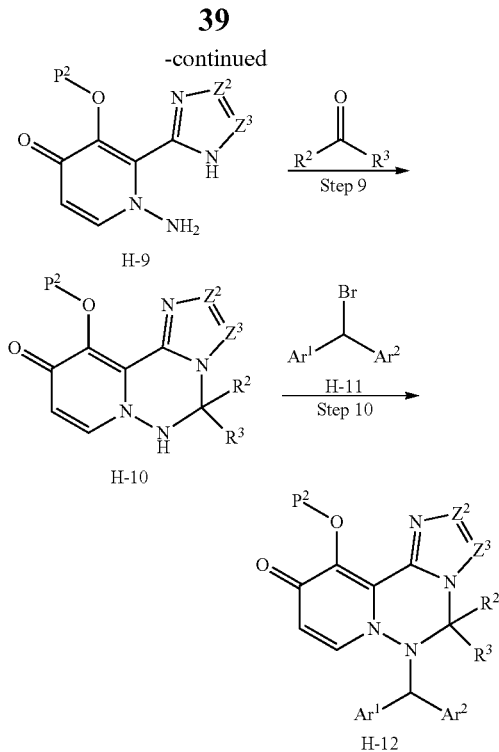

Using these synthesis schemes and the examples provided, the skilled person can prepare the compounds of Formula (I).

EXAMPLES

The following examples are intended to illustrate the invention and are not to be construed as being limitations thereon. Temperatures are given in degrees Celsius. If not mentioned otherwise, all evaporations are performed under reduced pressure, typically between about 15 mm Hg and 100 mm Hg (about 20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesize the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art in view of the following examples.

Abbreviations
ATP adenosine 5'-triphosphate
Bn benzyl
BOC tertiary butyl carboxy
br broad
BSA bovine serum albumin
d doublet
dd doublet of doublets
DCM dichloromethane
DEAD diethyl azodicarboxylate
DBAD di-tert-butyl azodicarboxylate
DIBAL-H diisobutylaluminum hydride
DIEA diethylisopropylamine
DME 1,4-dimethoxyethane
DMF N,N-dimethylformamide
DMSO dimethylsulfoxide
DTT dithiothreitol
EDTA ethylenediamine tetraacetic acid
ESI electrospray ionization
EtOAc ethyl acetate
FCC flash column chromatography
h hour(s)
HBTU 1-[bis(dimethylamino)methylene]-1H-benzotriazoliumhexafluorophosphate(1-) 3-oxide
HOBt 1-hydroxy-7-azabenzotriazole
HPLC high pressure liquid chromatography
IR infrared spectroscopy
LCMS liquid chromatography and mass spectrometry
MeOH methanol
MS mass spectrometry
MW microwave
m multiplet
min minutes
mL milliliter(s)
m/z mass to charge ratio
NBS N-bromosuccinimide
NCS N-chlorosuccinimide
NIS N-iodosuccinimide
NMP N-methyl pyrrolidinone
NMR nuclear magnetic resonance
ppm parts per million
PyBOP benzotriazol-1-yloxytripyrrolidinophosphonium hexafluorophosphate
rac racemic
rt room temperature
s singlet
SEM (2-(trimethylsilyl)ethoxy)methyl
t triplet
TBDMS t-butyldimethylsilyl
TBDPS t-butyldiphenylsilyl
TFA trifluoroacetic acid
THF tetrahydrofuran
Tris-HCl aminotris(hydroxymethyl)methane hydrochloride Example 1: 6-Benzhydryl-11-hydroxy-5H-imidazo[2',1':3,4]pyrazino[1,2-b]pyridazin-10(6H)-one Intermediate 1.1: 3-Nitro-1,1-diphenylpropan-2-ol

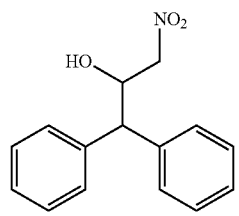 [SMILES: O=[N+]([O-])CC(O)C(c1ccccc1)c1ccccc1]

To a solution of 2,2-diphenylacetaldehyde (5.0 g, 26 mmol) in nitromethane (27 mL) was added $K_2CO_3$ (11.3 g, 82.0 mmol). The suspension was stirred at room temperature for 30 minutes. The mixture was then filtered to remove solids and the filtrate was concentrated. The residue was taken up in EtOAc (100 mL) and washed sequentially with water (100 mL), brine (2×25 mL), dried ($Na_2SO_4$), filtered and concentrated. Silica gel column chromatography (EtOAc/Heptane) provided 3-nitro-1,1-diphenylpropan-2-ol (5.6 g, colorless oil that became solid upon standing) in 85% yield. ¹H NMR (400 MHz, CDCl₃) δ 7.44-7.27 (m, 10H), 5.13 (dddd, J=9.3, 6.8, 5.2, 3.9 Hz, 1H), 4.46-4.34 (m, 2H), 3.99 (d, J=9.3 Hz, 1H), 2.33 (d, J=3.8 Hz, 1H). MS m/z 228.2 (M+1).

Intermediate 1.2: 3-Amino-1,1-diphenylpropan-2-ol

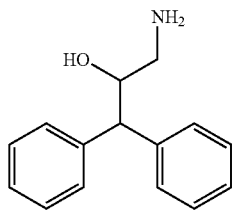 [SMILES: NCC(O)C(c1ccccc1)c1ccccc1]

To a solution of 3-nitro-1,1-diphenylpropan-2-ol (5.6 g, 22 mmol) in absolute EtOH (73 mL) under a nitrogen atmosphere was added 10% Pd/C (2.3 g). The flask was evacuated and refilled with H₂ from a balloon (three times) and then stirred vigorously at room temperature under a balloon of H₂ for 24 hours. The reaction flask was then purged with nitrogen and the mixture was filtered through celite. The filtrate was concentrated to give 3-amino-1,1-diphenylpropan-2-ol (4.9 g, colorless oil) in 100% yield. ¹H NMR (400 MHz, CDCl₃) δ 7.41-7.10 (m, 10H), 4.28 (ddd, J=9.0, 7.8, 3.1 Hz, 1H), 3.89 (d, J=9.0 Hz, 1H), 2.75 (ddd, J=12.9, 3.1, 1.7 Hz, 1H), 2.54 (ddd, J=12.9, 7.9, 1.0 Hz, 1H).

Intermediate 1.3: 5-(Benzyloxy)-4-oxo-1-((2-(trimethylsilyl)ethoxy)methyl)-1,4-dihydropyridazine-3-carbaldehyde

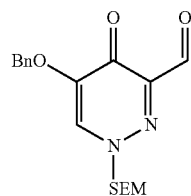

A solution of DIBAL-H (1.0 M in toluene, 4.9 mL, 4.9 mmol) was added dropwise to a solution of ethyl 5-(benzyloxy)-4-oxo-1-((2-(trimethylsilyl)ethoxy)methyl)-1,4-dihydropyridazine-3-carboxylate (1.0 g, 2.5 mmol: see US 2015/0072982 A1) in THF (25 mL) at −78° C. The reaction was stirred at −78° C. for 20 min and then quenched at the same temperature by the dropwise addition of MeOH (3 mL). The cold bath was removed and the reaction was diluted with EtOAc and a saturated aqueous solution of Rochelle's salt. The layers were separated and the aqueous layer was extracted with EtOAc. The combined organic extracts were washed with brine, dried (Na₂SO₄), filtered and concentrated. Silica gel column chromatography (EtOAc/Heptane) provided 5-(benzyloxy)-4-oxo-1-((2-(trimethylsilyl)ethoxy)methyl)-1,4-dihydropyridazine-3-carbaldehyde (0.51 g, yellow oil that solidified upon standing) in 57% yield. ¹H NMR (400 MHz, CDCl₃) δ 10.37 (s, 1H), 7.67 (s, 1H), 7.46-7.31 (m, 5H), 5.34 (s, 2H), 5.30 (s, 2H), 3.54-3.45 (m, 2H), 0.88-0.81 (m, 2H), −0.01 (d, J=7.3 Hz, 9H). MS m/z 361.3 (M+1).

Intermediate 1.4: 5-(Benzyloxy)-3-(1-(2-hydroxy-3,3-diphenylpropyl)-1H-imidazol-2-yl)-1-((2-(trimethylsilyl)ethoxy)methyl)pyridazin-4(1H)-one

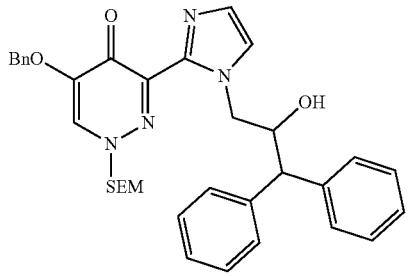 [SMILES: C[Si](C)(C)CCOCn1cc(OCc2ccccc2)c(=O)c(-c2nccn2CC(O)C(c2ccccc2)c2ccccc2)n1]

Ammonium acetate (75 mg, 0.97 mmol) and glyoxal (40% in water, 0.11 mL, 0.97 mmol) were added to a solution of 5-(benzyloxy)-4-oxo-1-((2-(trimethylsilyl)ethoxy)methyl)-1,4-dihydropyridazine-3-carbaldehyde (350 mg, 0.97 mmol) and 3-amino-1,1-diphenylpropan-2-ol (110 mg, 0.48 mmol) in MeOH (2 mL). The mixture was heated at reflux for 2 hours and then cooled to room temperature. The reaction was diluted with EtOAc and washed with dilute brine. The organic layer was dried (Na₂SO₄), filtered and concentrated to give crude 5-(benzyloxy)-3-(1-(2-hydroxy-3,3-diphenylpropyl)-1H-imidazol-2-yl)-1-((2-(trimethylsilyl)ethoxy)methyl)pyridazin-4(1H)-one which was used without further purification. MS m/z 609.3 (M+1).

Intermediate 1.5: 3-(2-(5-(Benzyloxy)-4-oxo-1-((2-(trimethylsilyl)ethoxy)methyl)-1,4-dihydropyridazin-3-yl)-1H-imidazol-1-yl)-1,1-diphenylpropan-2-yl methanesulfonate

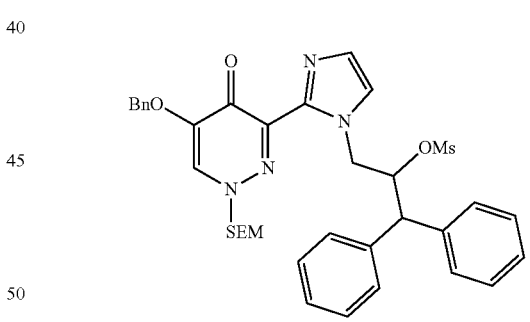

Methanesulfonyl chloride (0.094 mL, 1.2 mmol) was added dropwise to a solution of crude 5-(benzyloxy)-3-(1-(2-hydroxy-3,3-diphenylpropyl)-1H-imidazol-2-yl)-1-((2-(trimethylsilyl)ethoxy)methyl)pyridazin-4(1H)-one and Et₃N (0.20 mL, 1.5 mmol) in DCM (24 mL) at 0° C. The mixture was stirred at the same temperature for 30 min and then quenched with water. The layers were separated and the aqueous layer was extracted with DCM. The combined organic extracts were washed with brine, filtered and concentrated. Silica gel column chromatography (EtOAc/Heptane) provided 3-(2-(5-(benzyloxy)-4-oxo-1-((2-(trimethylsilyl)ethoxy)methyl)-1,4-dihydropyridazin-3-yl)-1H-imidazol-1-yl)-1,1-diphenylpropan-2-yl methanesulfonate (0.13 g, yellow oil) in 40% yield over two steps. MS m/z 687.4 (M+1).

Intermediate 1.6: 3-(2-(5-Hydroxy-4-oxo-1-((2-(trimethylsilyl)ethoxy)methyl)-1,4-dihydropyridazin-3-yl)-1H-imidazol-1-yl)-1,1-diphenylpropan-2-yl methanesulfonate

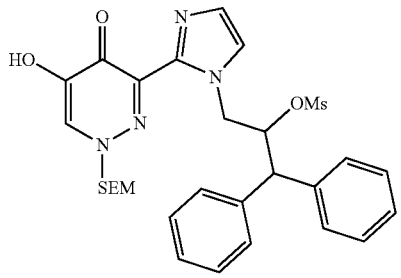 [SMILES: C[Si](C)(C)CCOCn1cc(O)c(=O)c(-c2nccn2CC(OS(C)(=O)=O)C(c2ccccc2)c2ccccc2)n1]

10% Pd/C (21 mg) was added to a solution of 3-(2-(5-(benzyloxy)-4-oxo-1-((2-(trimethylsilyl)ethoxy)methyl)-1,4-dihydropyridazin-3-yl)-1H-imidazol-1-yl)-1,1-diphenylpropan-2-yl methanesulfonate (0.13 g, 0.20 mmol) in MeOH (10 mL) under nitrogen at room temperature. The flask was then evacuated and refilled with H₂ from a balloon (three times) and then stirred vigorously under a balloon atmosphere of H₂ for 30 min. The reaction flask was then purged with nitrogen and the mixture was filtered through celite. The filtrate was concentrated to give crude 3-(2-(5-hydroxy-4-oxo-1-((2-(trimethylsilyl)ethoxy)methyl)-1,4-dihydropyridazin-3-yl)-1H-imidazol-1-yl)-1,1-diphenylpropan-2-yl methanesulfonate, which was used without further purification. MS m/z 597.2 (M+1).

Intermediate 1.7: 3-(2-(5-Hydroxy-4-oxo-1,4-dihydropyridazin-3-yl)-1H-imidazol-1-yl)-1,1-diphenylpropan-2-yl methanesulfonate

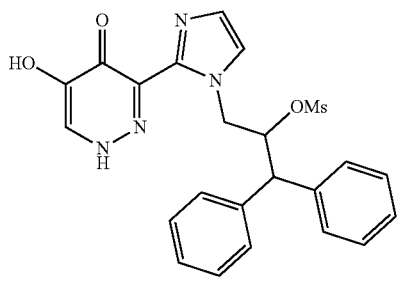 [SMILES: CS(=O)(=O)OC(Cn1ccnc1-c1n[nH]cc(O)c1=O)C(c1ccccc1)c1ccccc1]

Crude 3-(2-(5-hydroxy-4-oxo-1-((2-(trimethylsilyl)ethoxy)methyl)-1,4-dihydropyridazin-3-yl)-1H-imidazol-1-yl)-1,1-diphenylpropan-2-yl methanesulfonate was dissolved in TFA (4 mL) and stirred at room temperature for 2 hours. The reaction was then concentrated. The residue was taken up in toluene and concentrated again to give crude 3-(2-(5-hydroxy-4-oxo-1,4-dihydropyridazin-3-yl)-1H-imidazol-1-yl)-1,1-diphenylpropan-2-yl methanesulfonate, which was used without further purification. MS m/z 467.2 (M+1).

Example 1: 6-Benzhydryl-11-hydroxy-5H-imidazo[2',1':3,4]pyrazino[1,2-b]pyridazin-10(6H)-one

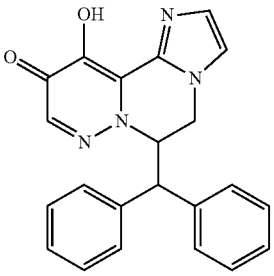 [SMILES: O=c1cnn2c(c1O)-c1nccn1CC2C(c1ccccc1)c1ccccc1]

K₂CO₃ (81 mg, 0.59 mmol) was added to a solution of crude 3-(2-(5-hydroxy-4-oxo-1,4-dihydropyridazin-3-yl)-1H-imidazol-1-yl)-1,1-diphenylpropan-2-yl methanesulfonate in DMF (2 mL). The mixture was stirred at room temperature for 12 hours and then filtered to remove solids. The filtrate was purified by reverse phase HPLC. Product fractions were combined, frozen and lyophilized to afford a TFA salt of 6-benzhydryl-11-hydroxy-5H-imidazo[2',1':3,4]pyrazino[1,2-b]pyridazin-10(6H)-one (21 mg, 0.043 mmol, white solid) in 22% yield over three steps. ¹H NMR (400 MHz, DMSO-d₆) δ 7.72-7.65 (m, 1H), 7.58 (s, 1H), 7.46 (d, J=7.3 Hz, 2H), 7.41-7.32 (m, 3H), 7.31-7.25 (m, 1H), 7.16 (dddd, J=19.6, 6.7, 5.4, 1.6 Hz, 5H), 5.89 (dd, J=11.4, 4.0 Hz, 1H), 4.73 (dd, J=14.1, 4.3 Hz, 1H), 4.35 (d, J=14.1 Hz, 1H), 4.24 (d, J=11.4 Hz, 1H). MS m/z 371.2 (M+1).

Example 2. 6-(bis(3-fluorophenyl)methyl)-11-hydroxy-5,6-dihydro-10H-imidazo[2',1':3,4]pyrazino[1,2-b]pyridazin-10-one This compound was made by the same process used to make Example 1.

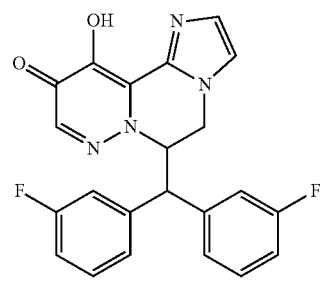 [SMILES: O=c1cnn2c(c1O)-c1nccn1CC2C(c1cccc(F)c1)c1cccc(F)c1]

MS m/z 406.9 (M+1).

Example 3. 6-benzhydryl-11-hydroxy-5,6-dihydro-10H-[1,2,4]triazolo[5',1':3,4]pyrazino[1,2-b]pyridazin-10-one

Intermediate 3.1: 5-(Benzyloxy)-4-oxo-1-((2-(trimethylsilyl)ethoxy)methyl)-1,4-dihydropyridazine-3-carboxamide

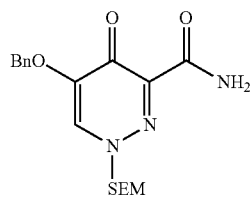 [SMILES: C[Si](C)(C)CCOCn1cc(OCc2ccccc2)c(=O)c(C(N)=O)n1]

Triethylamine (0.11 mL, 0.80 mmol) was added to a solution of 5-(benzyloxy)-4-oxo-1-((2-(trimethylsilyl)ethoxy)methyl)-1,4-dihydropyridazine-3-carboxylic acid (200 mg, 0.53 mmol: see US 2015/0072982 A1) in DMF (4 mL) at 0° C. Ethyl chloroformate (0.061 mL, 0.64 mmol) was then added and the resulting mixture was stirred at 0° C. for 20 min. A solution of aqueous NH$_4$OH (30%, 1.5 mL, 11.6 mmol) was then added dropwise. The mixture was stirred at 0° C. for 30 min and then diluted with water and extracted with EtOAc (3 times). The combined organic extracts were washed sequentially with water, brine and then dried (Na$_2$SO$_4$), filtered and concentrated to give crude 5-(benzyloxy)-4-oxo-1-((2-(trimethylsilyl)ethoxy)methyl)-1,4-dihydropyridazine-3-carboxamide which was used without further purification. MS m/z 376.3 (M+1).

Intermediate 3.2: (E)-5-(Benzyloxy)-N-((dimethylamino)methylene)-4-oxo-1-((2-(trimethylsilyl)ethoxy)methyl)-1,4-dihydropyridazine-3-carboxamide

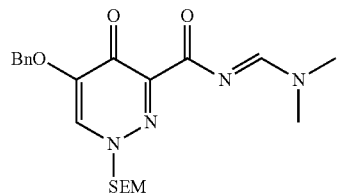 [SMILES: CN(C)/C=N/C(=O)c1nn(COCC[Si](C)(C)C)cc(OCc2ccccc2)c1=O]

A mixture of crude 5-(benzyloxy)-4-oxo-1-((2-(trimethylsilyl)ethoxy)methyl)-1,4-dihydropyridazine-3-carboxamide (0.2 g, 0.53 mmol) in N,N-dimethylformamide dimethyl acetal (10 mL) was heated at 100° C. for 1.5 hours. The solution was then cooled to room temperature and concentrated to give crude (E)-5-(benzyloxy)-N-((dimethylamino)methylene)-4-oxo-1-((2-(trimethylsilyl)ethoxy)methyl)-1,4-dihydropyridazine-3-carboxamide which was used without further purification.

Intermediate 3.3: 3-Hydrazinyl-1,1-diphenylpropan-2-ol

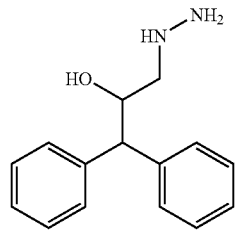 [SMILES: NNCC(O)C(c1ccccc1)c1ccccc1]

Hydrazine (0.33 mL, 10.5 mmol) was added to a solution of 2-benzhydryloxirane (220 mg, 1.05 mmol: see Zhang, S.; Zhen, J.; Reith, Maarten E. A.; Dutta, A. K. *J. Med. Chem.* 2005, 48, 4962-4971) in ethanol (10.5 mL) in a microwave vial. The vial was capped and the mixture was heated in the microwave at 100° C. for 10 minutes. The reaction mixture was concentrated and the residue was taken up in EtOAc and washed sequentially with water and brine. The organic layer was then dried (Na$_2$SO$_4$), filtered and concentrated to give crude 3-hydrazinyl-1,1-diphenylpropan-2-ol which was used without further purification. MS m/z 243.3 (M+1).

Intermediate 3.4: 5-(Benzyloxy)-3-(1-(2-hydroxy-3,3-diphenylpropyl)-1H-1,2,4-triazol-5-yl)-1-(2-(trimethylsilyl)ethoxy)methyl)pyridazin-4(1H)-one

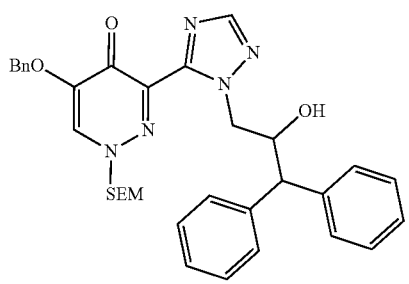

A solution of crude 3-hydrazinyl-1,1-diphenylpropan-2-ol (257 mg, 1.06 mmol) in acetic acid (15 mL) was added to crude (E)-5-(benzyloxy)-N-((dimethylamino)methylene)-4-oxo-1-((2-(trimethylsilyl)ethoxy)methyl)-1,4-dihydropyridazine-3-carboxamide (229 mg, 0.531 mmol). The mixture was heated to 90° C. for 5 minutes and then cooled to room temperature. EtOAc was added and the mixture was washed sequentially with water, saturated aqueous NaHCO$_3$, and brine. The organic layer was dried (Na$_2$SO$_4$), filtered and concentrated. Silica gel column chromatography (0-10% MeOH in EtOAc) provided 5-(benzyloxy)-3-(1-(2-hydroxy-3,3-diphenylpropyl)-1H-1,2,4-triazol-5-yl)-1-(2-(trimethylsilyl)ethoxy)methyl)pyridazin-4(1H)-one (220 mg, colorless oil) in 68% yield. MS m/z 610.4 (M+1).

Intermediate 3.5: 3-(5-(5-(Benzyloxy)-4-oxo-14(2-(trimethylsilyl)ethoxy)methyl)-1,4-dihydropyridazin-3-yl)-1H-1,2,4-triazol-1-yl)-1,1-diphenylpropan-2-yl methanesulfonate

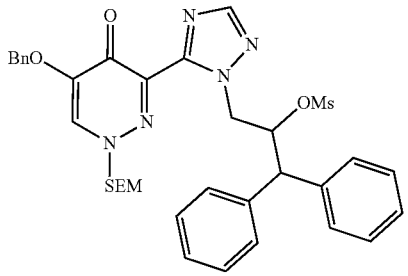 [SMILES: C[Si](C)(C)CCOCn1cc(OCc2ccccc2)c(=O)c(-c2ncnn2CC(O)C(c2ccccc2)c2ccccc2)n1]

Methanesulfonyl chloride (0.042 mL, 0.54 mmol) was added dropwise to a solution of 5-(benzyloxy)-3-(1-(2-hydroxy-3,3-diphenylpropyl)-1H-1,2,4-triazol-5-yl)-1-((2-(trimethylsilyl)ethoxy)methyl)pyridazin-4(1H)-one (220 mg, 0.36 mmol) and triethylamine (0.10 mL, 0.72 mmol) in DCM (24 mL) at 0° C. The mixture was stirred at 0° C. for 30 min and the reaction was then quenched with water. The layers were separated and the aqueous layer was extracted with DCM. The combined DCM layers were washed with brine, dried (Na$_2$SO$_4$), filtered and concentrated to give crude 3-(5-(5-(benzyloxy)-4-oxo-1-((2-(trimethylsilyl)ethoxy)methyl)-1,4-dihydropyridazin-3-yl)-1H-1,2,4-triazol-1-yl)-1,1-diphenylpropan-2-yl methanesulfonate which was used without further purification. MS m/z 688.3 (M+1).

Intermediate 3.6: 3-(5-(5-Hydroxy-4-oxo-1-((2-(trimethylsilyl)ethoxy)methyl)-1,4-dihydropyridazin-3-yl)-1H-1,2,4-triazol-1-yl)-1,1-diphenylpropan-2-yl methanesulfonate

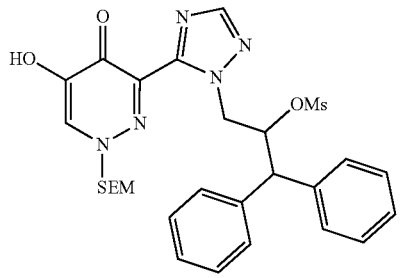

10% Pd/C (38 mg) was added to a solution of crude 3-(5-(5-(benzyloxy)-4-oxo-1-((2-(trimethylsilyl)ethoxy)methyl)-1,4-dihydropyridazin-3-yl)-1H-1,2,4-triazol-1-yl)-1,1-diphenylpropan-2-yl methanesulfonate (0.25 g, 0.36 mmol) in MeOH (36 mL) under nitrogen at room temperature. The flask was then evacuated and refilled with H$_2$ from a balloon (three times) and then stirred vigorously under a balloon atmosphere of H$_2$ for 30 min. The reaction flask was then purged with nitrogen and the mixture was filtered through celite. The filtrate was concentrated to give crude 3-(5-(5-hydroxy-4-oxo-1-((2-(trimethylsilyl)ethoxy)methyl)-1,4-dihydropyridazin-3-yl)-1H-1,2,4-triazol-1-yl)-1,1-diphenylpropan-2-yl methanesulfonate, which was used without further purification. MS m/z 598.3 (M+1).

Intermediate 3.7: 3-(5-(5-Hydroxy-4-oxo-1,4-dihydropyridazin-3-yl)-1H-1,2,4-triazol-1-yl)-1,1-diphenylpropan-2-yl methanesulfonate

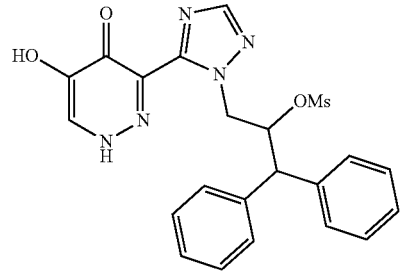 [SMILES: CS(=O)(=O)OC(Cn1ncnc1-c1n[nH]cc(O)c1=O)C(c1ccccc1)c1ccccc1]

Crude 3-(5-(5-hydroxy-4-oxo-1-((2-(trimethylsilyl)ethoxy)methyl)-1,4-dihydropyridazin-3-yl)-1H-1,2,4-triazol-1-yl)-1,1-diphenylpropan-2-yl methanesulfonate (0.22 g, 0.36 mmol) was dissolved in TFA (4 mL) and stirred at 40° C. for 30 min. The reaction was then concentrated. The residue was taken up in toluene and concentrated again to give crude 3-(5-(5-hydroxy-4-oxo-1,4-dihydropyridazin-3-yl)-1H-1,2,4-triazol-1-yl)-1,1-diphenylpropan-2-yl methanesulfonate, which was used without further purification. MS m/z 468.2 (M+1).

Example 3: Preparation of 6-benzhydryl-11-hydroxy-5,6-dihydro-10H-[1,2,4]triazolo[5',1':3,4]pyrazino[1,2-b]pyridazin-10-one

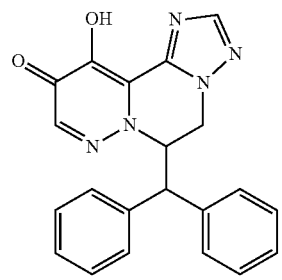

K$_2$CO$_3$ (150 mg, 1.08 mmol) was added to a solution of crude 3-(5-(5-hydroxy-4-oxo-1,4-dihydropyridazin-3-yl)-1H-1,2,4-triazol-1-yl)-1,1-diphenylpropan-2-yl methanesulfonate (169 mg, 0.36 mmol) in DMF (3.6 mL). The mixture was stirred at room temperature for 12 hours and then filtered to remove solids. The filtrate was purified by reverse phase HPLC. Product fractions were combined, frozen and lyophilized to afford a TFA salt of 6-benzhydryl-11-hydroxy-5,6-dihydro-10H-[1,2,4]triazolo[5',1':3,4]pyrazino[1,2-b]pyridazin-10-one (34 mg, 0.069 mmol, yellow solid) in 19% yield over four steps. $^1$H NMR (400 MHz, DMSO-d$_6$) δ 8.31 (s, 1H), 7.46-7.41 (m, 2H), 7.39-7.25 (m, 4H), 7.23-7.09 (m, 5H), 5.92 (ddd, J=11.8, 4.3, 1.2 Hz, 1H), 4.91 (dd, J=13.9, 4.3 Hz, 1H), 4.26-4.20 (m, 1H), 3.95 (d, J=11.6 Hz, 1H). MS m/z 372.3 (M+1).

Example 4: Preparation of (S)-6-Benzhydryl-11-hydroxy-5H-imidazo[1,2-a]pyrido[2,1-c]pyrazin-10(6H)-one

Intermediate 4.1: (S)-tert-Butyl (3-(2-(3-(benzyloxy)-4-oxo-4H-pyran-2-yl)-1H-imidazol-1-yl)-1,1-diphenylpropan-2-yl)carbamate

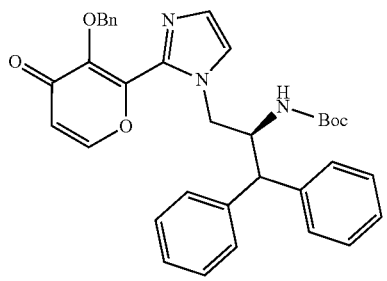 [SMILES: CC(C)(C)OC(=O)N[C@H](Cn1ccnc1-c1occc(=O)c1OCc1ccccc1)C(c1ccccc1)c1ccccc1]

Ammonium acetate (189 mg, 2.45 mmol) and a solution of glyoxal (40% in water, 0.28 mL, 2.45 mmol) were added to a solution of 3-(benzyloxy)-4-oxo-4H-pyran-2-carbaldehyde (564 mg, 2.45 mmol: US 2015/0202208 A1) and (S)-tert-butyl (3-amino-1,1-diphenylpropan-2-yl)carbamate (400 mg, 1.23 mmol: US 2012/0022251 A1) in MeOH (6 mL). The mixture was then heated at reflux for 1 hour. Additional ammonium acetate (95 mg, 1.2 mmol) and glyoxal (40% in water, 0.14 mL, 1.2 mmol) were added and the solution was heated at reflux for another 30 min. The mixture was then cooled to room temperature and diluted with EtOAc and water. The layers were separated and the aqueous layer was extracted with EtOAc. The combined organic layers were washed with brine, dried ($Na_2SO_4$), filtered and concentrated. Silica gel column chromatography (0-10% MeOH in EtOAc) provided (S)-tert-butyl (3-(2-(3-(benzyloxy)-4-oxo-4H-pyran-2-yl)-1H-imidazol-1-yl)-1,1-diphenylpropan-2-yl)carbamate (270 mg, yellow oil) in 38% yield. MS m/z 578.4 (M+1).

Intermediate 4.2: (S)-2-(1-(2-amino-3,3-diphenylpropyl)-1H-imidazol-2-yl)-3-(benzyloxy)-4H-pyran-4-one

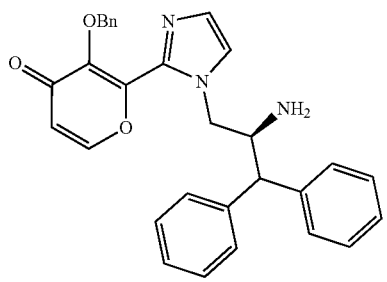 [SMILES: N[C@H](Cn1ccnc1-c1occc(=O)c1OCc1ccccc1)C(c1ccccc1)c1ccccc1]

TFA (3.6 mL) was added to a solution of (S)-tert-butyl (3-(2-(3-(benzyloxy)-4-oxo-4H-pyran-2-yl)-1H-imidazol-1-yl)-1,1-diphenylpropan-2-yl)carbamate (270 mg, 0.47 mmol) in DCM (12 mL) at room temperature. The solution was stirred for 1 hour and then concentrated in vacuo to give crude (S)-2-(1-(2-amino-3,3-diphenylpropyl)-1H-imidazol-2-yl)-3-(benzyloxy)-4H-pyran-4-one which was used without further purification. MS m/z 478.3 (M+1).

Intermediate 4.3: (S)-6-benzhydryl-11-(benzyloxy)-5H-imidazo[1,2-a]pyrido[2,1-c]pyrazin-10(6H)-one

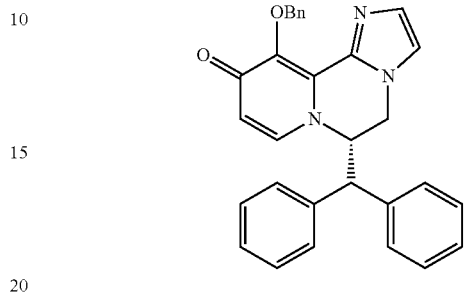

Acetic acid (12 mL) was added to a solution of crude (S)-2-(1-(2-amino-3,3-diphenylpropyl)-1H-imidazol-2-yl)-3-(benzyloxy)-4H-pyran-4-one (223 mg, 0.47 mmol) in ethanol (24 mL). The mixture was heated at 80° C. for 1 hour. The reaction was cooled to room temperature and concentrated to give crude (S)-6-benzhydryl-11-(benzyloxy)-5H-imidazo[1,2-a]pyrido[2,1-c]pyrazin-10(6H)-one which was used without further purification. MS m/z 460.3 (M+1).

Example 4: (S)-6-Benzhydryl-11-hydroxy-5H-imidazo[1,2-a]pyrido[2,1-c]pyrazin-10(6H)-one

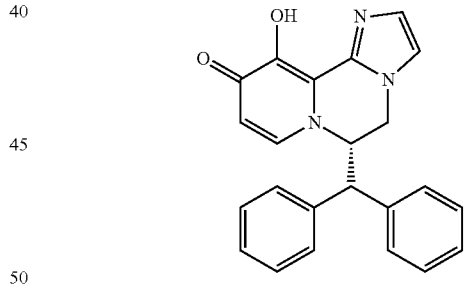

TFA (10 mL) was added to crude (S)-6-benzhydryl-11-(benzyloxy)-5H-imidazo[1,2-a]pyrido[2,1-c]pyrazin-10(6H)-one (215 mg, 0.47 mmol) in a microwave vial. The vial was capped and heated in the microwave at 90° C. for 10 min. The reaction was then concentrated. The residue was taken up in DMSO and purified by reverse phase HPLC. Product fractions were combined, frozen and lyophilized to afford a TFA salt of (S)-6-benzhydryl-11-hydroxy-5H-imidazo[1,2-a]pyrido[2,1-c]pyrazin-10(6H)-one (63 mg, 0.13 mmol, yellow solid) in 28% yield over three steps. $^1$H NMR (400 MHz, DMSO-$d_6$) δ 7.72 (d, J=1.7 Hz, 1H), 7.62 (d, J=1.8 Hz, 1H), 7.51-7.45 (m, 2H), 7.44-7.36 (m, 2H), 7.35-7.10 (m, 7H), 5.92 (d, J=7.2 Hz, 1H), 5.82 (dd, J=11.4, 3.7 Hz, 1H), 4.66 (dd, J=14.0, 4.1 Hz, 1H), 4.34-4.27 (m, 1H), 4.19 (d, J=11.8 Hz, 1H). MS m/z 370.3 (M+1).

Example 5: Preparation of (S)-6-Benzhydryl-3-chloro-11-hydroxy-5,6-dihydro-10H-imidazo[1,2-a]pyrido[2,1-c]pyrazin-10-one Intermediate 5.1: (S)-6-Benzhydryl-11-(benzyloxy)-3-chloro-5,6-dihydro-10H-imidazo[1,2-a]pyrido[2,1-c]pyrazin-10-one

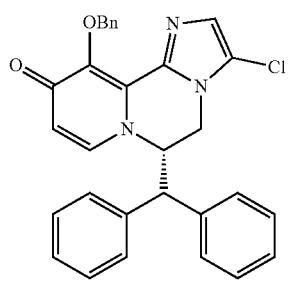 [SMILES: O=c1ccn2c(c1OCc1ccccc1)-c1ncc(Cl)n1C[C@@H]2C(c1ccccc1)c1ccccc1]

Palau'Chlor (24 mg, 0.11 mmol: Baran, et al., *J. Am. Chem. Soc.* 136(19), 6908-11 (2014)) was added to a solution of crude Intermediate 4.3 (43 mg, 0.094 mmol) in chloroform (0.9 mL) at RT. The mixture was stirred at RT for 20 min and then concentrated in vacuo. Silica gel chromatography (0-10% MeOH in EtOAc) provided (S)-6-benzhydryl-11-(benzyloxy)-3-chloro-5,6-dihydro-10H-imidazo[1,2-a]pyrido [2,1-c]pyrazin-10-one (18 mg, yellow oil) in 39% yield. $^1$H NMR (400 MHz, CDCl3) δ 7.69-7.64 (m, 2H), 7.40-7.27 (m, 7H), 7.20 (s, 1H), 7.12 (dt, J=7.5, 2.5 Hz, 5H), 6.93-6.86 (m, 2H), 6.48 (d, J=7.6 Hz, 1H), 5.81 (d, J=7.5 Hz, 1H), 5.50 (d, J=10.4 Hz, 1H), 5.37 (d, J=10.5 Hz, 1H), 4.61 (ddd, J=11.4, 3.6, 1.4 Hz, 1H), 4.10-4.05 (m, 1H), 3.75 (s, 4H), 3.52 (d, J=11.3 Hz, 1H). MS m/z 494.3 (M+1).

Example 5: (S)-6-Benzhydryl-3-chloro-11-hydroxy-5,6-dihydro-10H-imidazo[1,2-a]pyrido [2,1-c]pyrazin-10-one

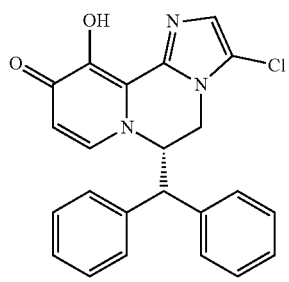

A solution of (S)-6-benzhydryl-11-(benzyloxy)-3-chloro-5,6-dihydro-10H-imidazo[1,2-a]pyrido[2,1-c]pyrazin-10-one (18 mg, 0.036 mmol) in trifluoroacetic acid (3 mL) was heated in the microwave at 90° C. for 10 min. The reaction was then concentrated. The residue was taken up in DMSO and purified by reverse phase HPLC. Product fractions were combined, frozen and lyophilized to afford a TFA salt of (S)-6-benzhydryl-3-chloro-11-hydroxy-5,6-dihydro-10H-imidazo[1,2-a]pyrido[2,1-c]pyrazin-10-one (7 mg, 0.013 mmol, yellow solid) in 37% yield. $^1$H NMR (400 MHz, DMSO-d6) δ 7.51 (s, 1H), 7.49-7.44 (m, 2H), 7.44-7.36 (m, 2H), 7.35-7.25 (m, 4H), 7.24-7.13 (m, 3H), 5.94 (d, J=7.3 Hz, 1H), 5.86 (dd, J=11.7, 3.6 Hz, 1H), 4.51 (dd, J=13.6, 3.8 Hz, 1H), 4.02 (d, J=11.6 Hz, 1H), 3.95 (dd, J=13.7, 1.2 Hz, 1H). MS m/z 404.2 (M+1).

Example 6. 6-benzhydryl-11-hydroxy-5H-imidazo[1,2-d]pyrido[2,1-f][1,2,4]triazin-10(6H)-one

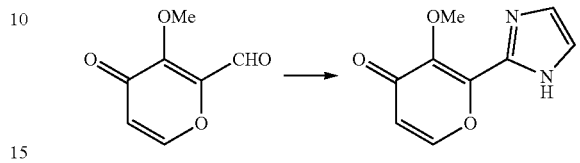

Intermediate 6.1: 2-(1H-imidazol-2-yl)-3-methoxy-4H-pyran-4-one

To 3-methoxy-4-oxo-4H-pyran-2-carbaldehyde (5.0 g, 32.4 mmol) in MeOH (50 mL) was added oxalaldehyde (40%, 9.41 mL, 64.9 mmol) and NH$_4$OAc (10.00 g, 130 mmol). The reaction was sealed and heated at 80° C. for 1 hr. The mixture was cooled and concentrated. The residue was purified on SiO$_2$ (EtOAc in heptane 10% to 100%) to give product (3.21 g, 51%). MS m/z 193.1 (M+1).

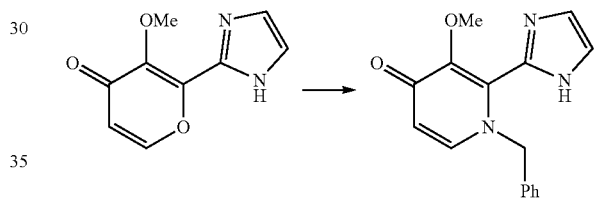

Intermediate 6.2: 1-benzyl-2-(1H-imidazol-2-yl)-3-methoxypyridin-4(1H)-one

To 2-(1H-imidazol-2-yl)-3-methoxy-4H-pyran-4-one (3.1 g, 16.13 mmol) in EtOH (30 mL) was added HOAc (4 mL) and phenylmethanamine (8.64 g, 81 mmol). The reaction was sealed and heated at 100° C. for 20 min. The mixture was cooled and concentrated. The residue was purified on SiO$_2$ (EtOAc in heptane 10% to 100%) to give product (3.88 g, 86%). MS m/z 282.3 (M+1).

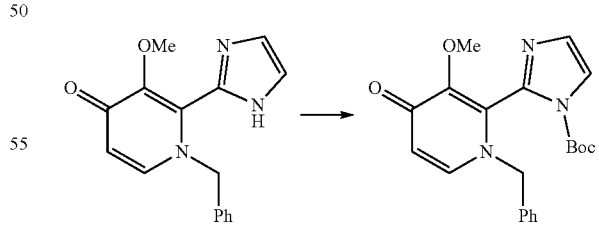

Intermediate 6.3: tert-butyl 2-(1-benzyl-3-methoxy-4-oxo-1,4-dihydropyridin-2-yl)-1H-imidazole-1-carboxylate To 1-benzyl-2-(1H-imidazol-2-yl)-3-methoxypyridin-4 (1H)-one (3.2 g, 11.38 mmol) in ACN (30 mL) was added Cs$_2$CO$_3$ (7.41 g, 22.75 mmol) and di-tert-butyl dicarbonate (4.97 g, 22.75 mmol). The reaction was sealed and heated at 60° C. for three hours. The mixture was cooled and diluted with EtOAC (100 mL). The mixture was then washed with water (50 mL) and brine (50 mL). The organic was then dried (Na$_2$SO$_4$) and concentrated. The residue was purified on SiO$_2$ (EtOAc in heptane 10% to 100%) to give product (3.68 g, 85%). MS m/z 382.3 (M+1).

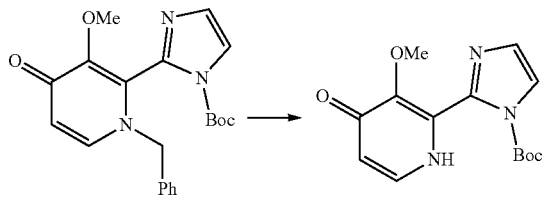 [SMILES: COc1c(-c2nccn2C(=O)OC(C)(C)C)n(Cc2ccccc2)ccc1=O ; COc1c(-c2nccn2C(=O)OC(C)(C)C)[nH]ccc1=O]

Intermediate 6.4: tert-butyl 2-(3-methoxy-4-oxo-1,4-dihydropyridin-2-yl)-1H-imidazole-1-carboxylate To tert-butyl 2-(1-benzyl-3-methoxy-4-oxo-1,4-dihydropyridin-2-yl)-1H-imidazole-1-carboxylate (400 mg, 1.049 mmol) in MeOH (10 mL) was added palladium on carbon (10%, 400 mg, 0.376 mmol). The reaction was purged with hydrogen and stirred under hydrogen for six hours. The mixture was then purged with nitrogen and filtered through celite and washed with MeOH. The filtrate was concentrated to give crude product. MS m/z 282.3 (M+1).

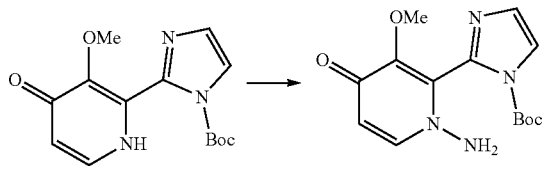 [SMILES: COc1c(-c2nccn2C(=O)OC(C)(C)C)[nH]ccc1=O ; COc1c(-c2nccn2C(=O)OC(C)(C)C)n(N)ccc1=O]

Intermediate 6.5: tert-butyl 2-(1-amino-3-methoxy-4-oxo-1,4-dihydropyridin-2-yl)-1H-imidazole-1-carboxylate To tert-butyl 2-(3-methoxy-4-oxo-1,4-dihydropyridin-2-yl)-1H-imidazole-1-carboxylate (300 mg, 1.030 mmol) in DMF (3 mL) was added Cs$_2$CO$_3$ (403 mg, 1.236 mmol). The mixture was stirred for 15 minutes and O-(2,4-dinitrophenyl)hydroxylamine (246 mg, 1.236 mmol) was then added. The reaction was stirred for one hour. The mixture was then diluted with water (20 mL) and extracted with IPA in DCM (15%, 3×30 mL). The organic was then dried (Na$_2$SO$_4$) and concentrated to give crude product. MS m/z 307.2 (M+1).

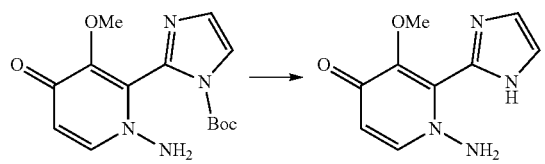 [SMILES: COc1c(-c2nccn2C(=O)OC(C)(C)C)n(N)ccc1=O ; COc1c(-c2ncc[nH]2)n(N)ccc1=O]

Intermediate 6.6: 1-amino-2-(1H-imidazol-2-yl)-3-methoxypyridin-4(1H)-one

To tert-butyl 2-(1-amino-3-methoxy-4-oxo-1,4-dihydropyridin-2-yl)-1H-imidazole-1-carboxylate (300 mg, 0.979 mmol) in DCM (3 mL) was added TFA (4 mL). The reaction was stirred for 20 minutes and then concentrated to give crude product. MS m/z 207.2 (M+1).

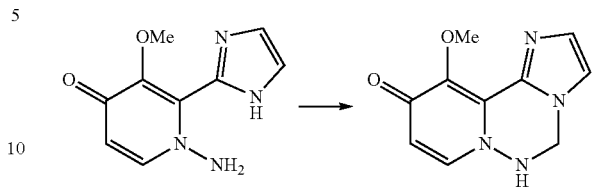

Intermediate 6.7: 11-methoxy-5H-imidazo[1,2-d]pyrido[2,1-f][1,2,4]triazin-10(6H)-one To 1-amino-2-(1H-imidazol-2-yl)-3-methoxypyridin-4(1H)-one (200 mg, 0.970 mmol) in MeOH (3 mL) was added aqueous formaldehyde (30%, 291 mg, 2.91 mmol). The reaction was sealed and heated at 55° C. for two hours. The mixture was cooled and concentrated. The residue was purified on SiO2 (MeOH in DCM 0% to 10%) to give product (156 mg, 73%). MS m/z 219.3 (M+1).

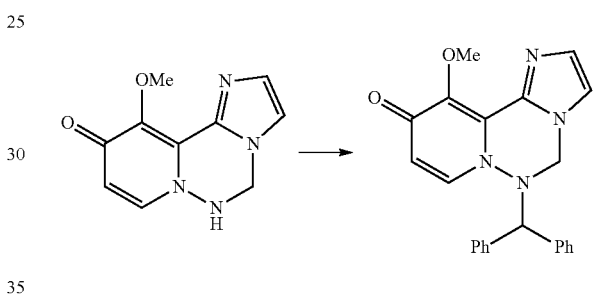

Intermediate 6.8: 6-benzhydryl-11-methoxy-5H-imidazo[1,2-d]pyrido[2,1-f][1,2,4]triazin-10(6H)-one To 11-methoxy-5H-imidazo[1,2-d]pyrido[2,1-f][1,2,4]triazin-10(6H)-one (25 mg, 0.115 mmol) in DMF (1 mL) was added (bromomethylene)dibenzene (56.6 mg, 0.229 mmol) and sodium hydride (60%, 9.16 mg, 0.229 mmol). The reaction was stirred for 20 minutes. The mixture was diluted with water (5 mL) and extracted with IPA in DCM (15%, 3×10 mL). The organic was dried (Na$_2$SO$_4$) and concentrated. The residue was purified on SiO$_2$ (MeOH in DCM 0% to 10%) to give product (30 mg, 68%). MS m/z 385.2 (M+1).

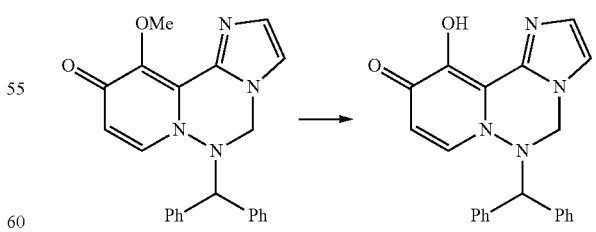

Example 6. 6-benzhydryl-11-hydroxy-5H-imidazo[1,2-d]pyrido[2,1-f][1,2,4-]triazin-10(6H)-one To 6-benzhydryl-11-methoxy-5H-imidazo[1,2-d]pyrido[2,1-f][1,2,4]triazin-10(6H)-one (20 mg, 0.052 mmol) in DMF (2 mL) was added BF$_3$-Et$_2$O (1 M in DCM, 0.156 mL, 0.156 mmol) and LiBr (45.2 mg, 0.520 mmol). The reaction was sealed and heated at 100° C. for 60 minutes. The mixture was cooled and purified by HPLC to give product (11 mg, 56%). MS m/z 371.3 (M+1).

$^1$H NMR (500 MHz, DMSO-d6) δ ppm 7.7 (s, 1H), 7.59 (s, 1H), 7.57 (m, 2H), 7.52 (d, J=7.6 Hz, 1H), 7.46 (m, 2H), 7.4 (m, 1H), 7.23-7.3 (m, 5H), 5.88 (d, J=7.6 Hz, 1H), 5.66 (dd, J=10 Hz, 2H), 5.14 (s, 1H).

Example 7. (S)-6-benzhydryl-3-bromo-11-hydroxy-5H-imidazo[1,2-a]pyrido[2,1-c]pyrazin-10(6H)-one

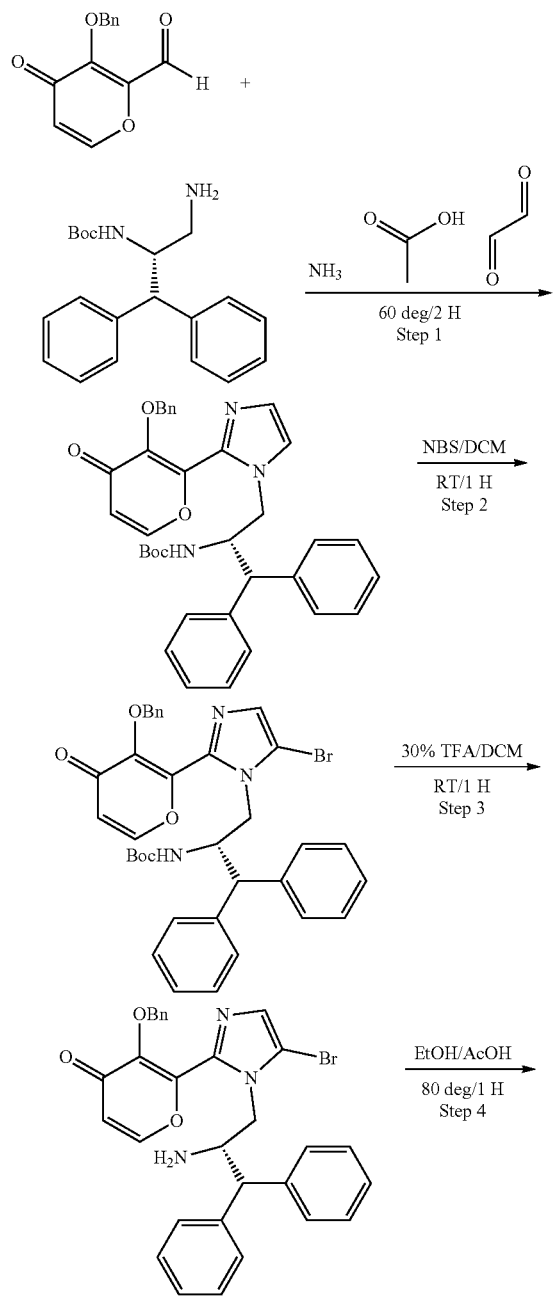

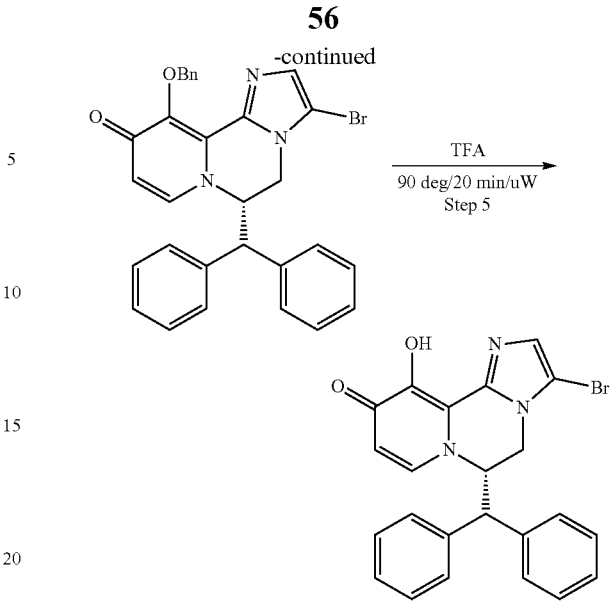

Step 1: (S)-tert-butyl (3-(2-(3-(benzyloxy)-4-oxo-4H-pyran-2-yl)-1H-imidazol-1-yl)-1,1-diphenylpropan-2-yl)carbamate Added ammonium acetate (224 mg, 2.91 mmol) to a solution of 3-(benzyloxy)-4-oxo-4H-pyran-2-carbaldehyde (670 mg, 2.91 mmol), (S)-tert-butyl (3-amino-1,1-diphenylpropan-2-yl) carbamate (500 mg, 1.455 mmol) (US 2012/0022251 A1)) and glyoxal (0.332 mL, 2.91 mmol) in MeOH (Volume: 9 mL) at RT. The mixture was then heated at reflux for 1H in heating block. LC-MS shows formation of desired product beside some side product. Still saw unreacted amine. Added again 1 eq each of ammonium acetate and glyoxal and continue heating for another 1-2H. Reaction was complete by LC-MS. The reaction was cooled to RT and diluted with EtOAc and water. The layers were separated and the aqueous layer was extracted with EtOAc. The combined organic extracts were washed with brine, dried over Na2SO4, filtered and concentrated in vacuo. The crude was purified by silica gel chromatography using 0-100% EtOAc (contains 10% MeOH)/Heptane to give (S)-tert-butyl (3-(2-(3-(benzyloxy)-4-oxo-4H-pyran-2-yl)-1H-imidazol-1-yl)-1,1-diphenylpropan-2-yl)carbamate as a light yellow foamy solid.

(840 mg, 1.454 mmol, 50.0% yield). LCMS: MH$^+$ 578.2, 0.81 min.

Step 2: (S)-tert-butyl (3-(2-(3-(benzyloxy)-4-oxo-4H-pyran-2-yl)-5-bromo-1H-imidazol-1-yl)-1,1-diphenylpropan-2-yl)carbamate To a solution of (S)-tert-butyl (3-(2-(3-(benzyloxy)-4-oxo-4H-pyran-2-yl)-1H-imidazol-1-yl)-1,1-diphenylpropan-2-yl)carbamate (430 mg, 0.744 mmol) in DCM (Volume: 10 mL) was added NBS (159 mg, 0.893 mmol) and stirred at RT/1H. Reaction was complete by LC-MS. Reaction mixture was partitioned between DCM and water. The DCM layer was separated, washed with brine, dried over sodium sulfate, filtered and evaporated. The crude was purified by silica gel chromatography using 0-100% EtOAc (contains 10% MeOH)/Heptane to give (S)-tert-butyl (3-(2-(3-(benzyloxy)-4-oxo-4H-pyran-2-yl)-5-bromo-1H-imidazol-1-yl)-1,1-diphenylpropan-2-yl)carbamate as a yellow foamy solid, (360 mg, 0.548 mmol, 73.7% yield). LCMS: MH+ 655.9, 0.98 min.

Step 3: (S)-2-(1-(2-amino-3,3-diphenylpropyl)-5-bromo-1H-imidazol-2-yl)-3-(benzyloxy)-4H-pyran-4-one To (S)-tert-butyl (3-(2-(3-(benzyloxy)-4-oxo-4H-pyran-2-yl)-5-bromo-1H-imidazol-1-yl)-1,1-diphenylpropan-2-yl)carbamate (360 mg, 0.548 mmol) in DCM (1 ml) was added 40% TFA/DCM (4 mL, 20.77 mmol) solution. Stirred at RT for 1 h. The reaction was complete by LC-MS. The reaction mixture was concentrated in vacuo and azeotrope with toluene to obtain crude (S)-2-(1-(2-amino-3,3-diphenylpropyl)-5-bromo-1H-imidazol-2-yl)-3-(benzyloxy)-4H-pyran-4-one, (305 mg, 0.548 mmol, 100% yield). LCMS: MH+ 556.0, 0.78 min.

Proceed to the next step without further purification.

Step 4: (S)-6-benzhydryl-11-(benzyloxy)-3-bromo-5H-imidazo[1,2-a]pyrido[2,1-c]pyrazin-10(6H)-one The crude (S)-2-(1-(2-amino-3,3-diphenylpropyl)-5-bromo-1H-imidazol-2-yl)-3-(benzyloxy)-4H-pyran-4-one (305 mg, 0.548 mmol) from step 3 was taken in Ethanol (6 ml) and acetic acid (3 ml). The mixture was then heated at 80° C. for 1H in heating block. The reaction was complete by LC-MS. The reaction mixture was concentrated in vacuo and the crude was purified by silica gel chromatography using 0-100% EtOAc (contains 10% MeOH)/Heptane to give (S)-6-benzhydryl-11-(benzyloxy)-3-bromo-5H-imidazo[1,2-a]pyrido[2,1-c]pyrazin-10(6H)-one as a light yellow solid, (205 mg, 0.381 mmol, 69.4% yield). LCMS: MH+ 538.0, 0.81 min.

Step 5: (S)-6-benzhydryl-3-bromo-11-hydroxy-5H-imidazo[1,2-a]pyrido[2,1-c]pyrazin-10(6H)-one To (S)-6-benzhydryl-11-(benzyloxy)-3-bromo-5H-imidazo[1,2-a]pyrido[2,1-c]pyrazin-10(6H)-one (8 mg, 0.015 mmol) was added trifluoroacetic acid (0.5 ml). The solution was then heated at 90° C. for 15 min in microwave. The reaction was complete by LC-MS. The reaction was concentrated in vacuo and azeotrope with toluene. The crude was purified by Prep HPLC to obtain (S)-6-benzhydryl-3-bromo-11-hydroxy-5H-imidazo[1,2-a]pyrido[2,1-c]pyrazin-10(6H)-one as a TFA salt, (5.8 mg, 10.31 µmol, 69.4% yield). LCMS (m/z): 448.0 (MH+), 0.71 min, 1H NMR (400 MHz, CD3OD) δ ppm 7.46 (s, 1H) 7.43 (d, J=4.35 Hz, 3H) 7.35 (dq, J=8.76, 4.17 Hz, 1H) 7.30 (d, J=7.24 Hz, 1H) 7.17-7.26 (m, 4H) 6.18 (d, J=7.14 Hz, 1H) 5.71 (dd, J=11.52, 2.91 Hz, 1H) 4.45 (dd, J=13.79, 3.86 Hz, 1H) 4.28 (d, J=12.91 Hz, 1H) 4.04 (d, J=11.54 Hz, 1H).

Example 8: (S)-6-benzhydryl-3-cyclopropyl-11-hydroxy-5H-imidazo[1,2-a]pyrido[2,1-c]pyrazin-10(6H)-one

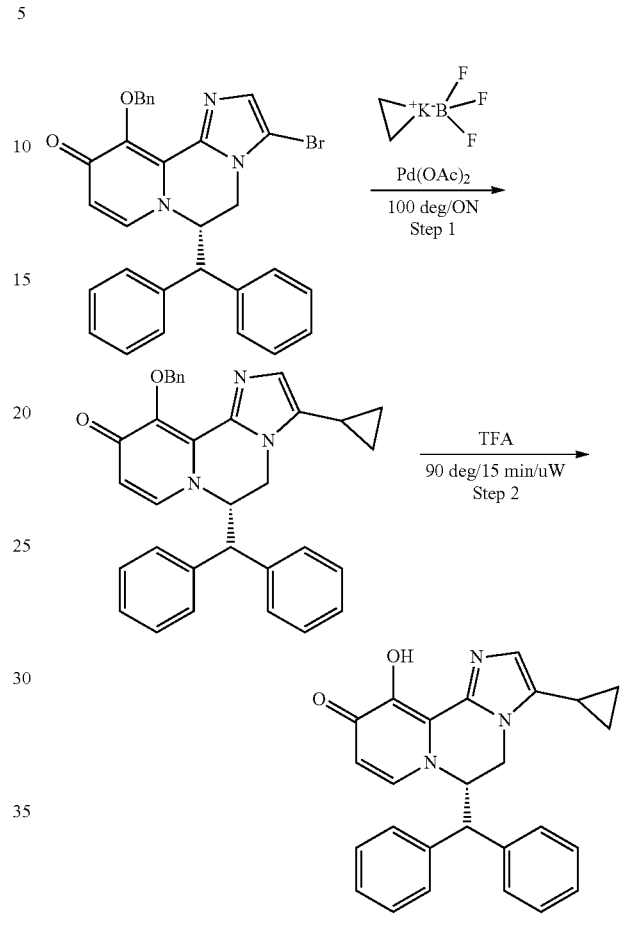

Step 1: (S)-6-benzhydryl-11-(benzyloxy)-3-cyclopropyl-5H-imidazo[1,2-a]pyrido[2,1-c]pyrazin-10(6H)-one To (S)-6-benzhydryl-11-(benzyloxy)-3-bromo-5H-imidazo[1,2-a]pyrido[2,1-c]pyrazin-10(6H)-one (40 mg, 0.074 mmol) (see example 7 step 4 for synthesis) in Toluene (Volume: 1, Ratio: 10.00) and Water (Volume: 0.1 mL, Ratio: 1.000) was added potassium cyclopropyltrifluoroborate (33.0 mg, 0.223 mmol), Di(1-adamantyl)-n-butylphosphine (5.33 mg, 0.015 mmol), cesium carbonate (121 mg, 0.371 mmol) and palladium(II) acetate (1.668 mg, 7.43 µmol). The reaction mixture was heated in heating block at 100° C./ON. The reaction was 80% complete by LC-MS. The reaction was stopped and concentrated on rotovap. The crude was partitioned between EtOAc and water. The layers were separated and the aqueous layer was extracted with EtOAc. The combined organic extracts were washed with brine, dried over Na2SO4, filtered and concentrated in vacuo. The crude was purified by silica gel chromatography using 0-10% MeOH/DCM to give (S)-6-benzhydryl-11-(benzyloxy)-3-cyclopropyl-5H-imidazo[1,2-a]pyrido[2,1-c]pyrazin-10(6H)-one, (23 mg, 0.046 mmol, 62.0% yield). LCMS: MH+ 500.3, 0.74 min.

Step 2: (S)-6-benzhydryl-3-cyclopropyl-11-hydroxy-5H-imidazo[1,2-a]pyrido[2,1-c]pyrazin-10(6H)-one To (S)-6-benzhydryl-11-(benzyloxy)-3-cyclopropyl-5H-imidazo[1,2-a]pyrido[2,1-c]pyrazin-10(6H)-one (23 mg, 0.046 mmol) was added trifluoroacetic acid (1 ml). The solution was then heated at 90° C. for 15 min in microwave. The reaction was complete by LC-MS. The reaction was concentrated in vacuo and azeotrope with toluene. The crude was purified by Prep HPLC to obtain (S)-6-benzhydryl-3-cyclopropyl-11-hydroxy-5H-imidazo[1,2-a]pyrido[2,1-c]pyrazin-10(6H)-one as a TFA salt, (6.5 mg, 0.012 mmol, 26.7% yield). LCMS (m/z): 410.3 (MH$^+$), 0.66 min, 1H NMR (400 MHz, CD3OD) δ ppm 7.40-7.56 (m, 4H) 7.29-7.40 (m, 2H) 7.13-7.26 (m, 5H) 6.03 (d, J=7.24 Hz, 1H) 5.58-5.81 (m, 1H) 4.45-4.70 (m, 2H) 4.12 (d, J=11.69 Hz, 1H) 1.33-1.56 (m, 1H) 0.75-0.98 (m, 2H) 0.60-0.71 (m, 1H) 0.32-0.43 (m, 1H)

Example 9: (S)-6-benzhydryl-3-ethyl-11-hydroxy-5H-imidazo[1,2-a]pyrido[2,1-c]pyrazin-10(6H)-one

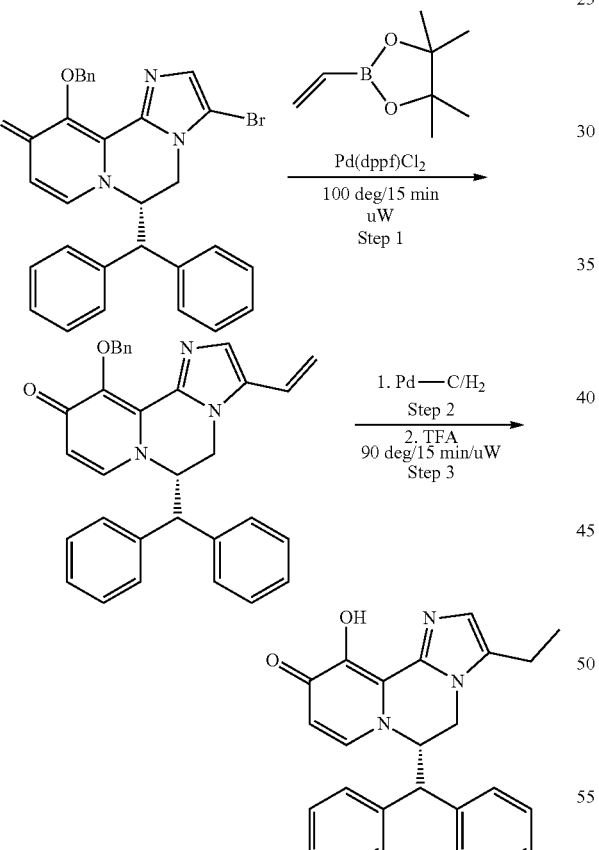

Step 1: (S)-6-benzhydryl-11-(benzyloxy)-3-vinyl-5H-imidazo[1,2-a]pyrido[2,1-c]pyrazin-10(6H)-one To (S)-6-benzhydryl-11-(benzyloxy)-3-bromo-5H-imidazo[1,2-a]pyrido[2,1-c]pyrazin-10(6H)-one (30 mg, 0.056 mmol) (see example #1 for synthesis) and 4,4,5,5-tetramethyl-2-vinyl-1,3,2-dioxaborolane (17.16 mg, 0.111 mmol) in DME (Volume: 1.5 mL) and sodium carbonate (200 μL, 0.400 mmol) was added PdCl2(dppf). CH2Cl2 adduct (4.55 mg, 5.57 μmol). Reaction mixture was heated in microwave at 110° C./15 min. Reaction was complete by LC-MS with major mass observed due to desired product. Reaction mixture was partitioned between EtOAc and water. The organic layer was separated, dried over sodium sulfate, filtered and evaporated to give crude (S)-6-benzhydryl-11-(benzyloxy)-3-vinyl-5H-imidazo[1,2-a]pyrido[2,1-c]pyrazin-10(6H)-one, (27 mg, 0.056 mmol, 100% yield). LCMS: MH$^+$ 486.3, 0.75 min.

Proceed for next step without purification.

Step 2: (S)-6-benzhydryl-11-(benzyloxy)-3-ethyl-5H-imidazo[1,2-a]pyrido[2,1-c]pyrazin-10(6H)-one Added 10% Pd—C (10.96 mg, 10.30 μmol) to a solution of crude (S)-6-benzhydryl-11-(benzyloxy)-3-vinyl-5H-imidazo[1,2-a]pyrido[2,1-c]pyrazin-10(6H)-one, (25 mg, 0.051 mmol) in MeOH (Volume: 5 mL) at RT under a nitrogen atmosphere. The flask was then evacuated and refilled with hydrogen from a balloon (3 times) and stirred under a balloon of hydrogen for 1 hour. LCMS showed complete reaction.

The reaction was filtered through a plug of celite (washed with MeOH) and the filtrate was concentrated in vacuo to give crude (S)-6-benzhydryl-11-(benzyloxy)-3-ethyl-5H-imidazo[1,2-a]pyrido[2,1-c]pyrazin-10(6H)-one, LCMS: MW 488.3, 0.72 min.

Step 3: (S)-6-benzhydryl-3-ethyl-11-hydroxy-5H-imidazo[1,2-a]pyrido[2,1-c]pyrazin-10(6H)-one To crude (S)-6-benzhydryl-11-(benzyloxy)-3-ethyl-5H-imidazo[1,2-a]pyrido[2,1-c]pyrazin-10(6H)-one (25 mg, 0.051 mmol) was added trifluoroacetic acid (1 ml). The solution was then heated at 90° C. for 15 min in microwave. The reaction was concentrated in vacuo and azeotrope with toluene. The crude was purified by Prep HPLC to obtain (S)-6-benzhydryl-3-ethyl-11-hydroxy-5H-imidazo[1,2-a]pyrido[2,1-c]pyrazin-10(6H)-one as a TFA salt, (1.25 mg, 2.23 μmol I, 4.5% yield). LCMS (m/z): 398.3 (MW), 0.64 min, 1H NMR (400 MHz, CD3OD) δ ppm 7.40-7.48 (m, 5H) 7.36 (td, J=8.57, 4.28 Hz, 2H) 7.16-7.24 (m, 5H) 6.03 (d, J=7.19 Hz, 1H) 5.63-5.75 (m, 1H) 4.52 (dd, J=14.01, 3.89 Hz, 1H) 4.32 (d, J=14.57 Hz, 1H) 4.09 (d, J=11.54 Hz, 1H) 2.24-2.48 (m, 3H) 1.04-1.16 (m, 3H)

Example 10. 6-(bis(4-chlorophenyl)methyl)-11-hydroxy-5H-imidazo[2',1':3,4]pyrazino[1,2-b]pyridazin-10(6H)-one

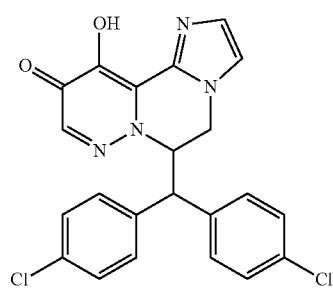 [SMILES: O=c1cnn2c(c1O)-c1nccn1CC2C(c1ccc(Cl)cc1)c1ccc(Cl)cc1]

Synthesized by the method of Example 1. LCMS (m/z): 439.3 (MH+), 0.75 min, 1H NMR (400 MHz, CD3OD) δ ppm 7.58 (d, J=1.47 Hz, 1H) 7.54 (d, J=1.47 Hz, 1H) 7.50 (s, 1H) 7.40 (s, 4H) 7.12-7.21 (m, 4H) 5.81 (dd, J=11.15, 3.37 Hz, 1H) 4.75 (dd, J=14.26, 4.28 Hz, 1H) 4.50 (d, J=13.79 Hz, 1H) 4.28 (d, J=11.20 Hz, 1H)

Example 11. 6-(bis(3-chlorophenyl)methyl)-11-hydroxy-5H-imidazo[2',1':3,4]pyrazino[1,2-b]pyridazin-10(6H)-one

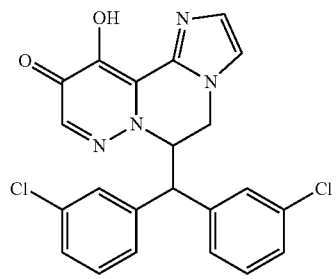 [SMILES: O=c1cnn2c(c1O)-c1nccn1CC2C(c1cccc(Cl)c1)c1cccc(Cl)c1]

Synthesized by the method of Example 1. LCMS (m/z): 439.3 (MH+), 0.74 min, 1H NMR (400 MHz, CD3OD) δ ppm 7.65 (d, J=1.66 Hz, 1H) 7.61 (d, J=1.61 Hz, 1H) 7.52 (s, 1H) 7.48 (s, 1H) 7.32-7.44 (m, 3H) 7.14-7.24 (m, 3H) 7.07-7.13 (m, 1H) 5.89 (dd, J=11.05, 3.37 Hz, 1H) 4.79 (dd, J=14.35, 4.28 Hz, 1H) 4.57 (d, J=13.69 Hz, 1H) 4.36 (d, J=11.10 Hz, 1H)

Example 12. 6-(bis(4-fluorophenyl)methyl)-11-hydroxy-5H-imidazo[2',1':3,4]pyrazino[1,2-b]pyridazin-10(6H)-one

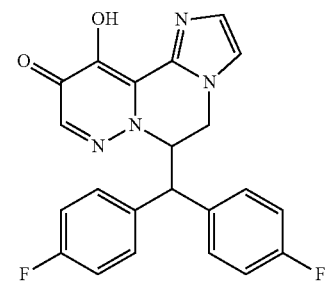 [SMILES: O=c1cnn2c(c1O)-c1nccn1CC2C(c1ccc(F)cc1)c1ccc(F)cc1]

Synthesized by the method of Example 1. LCMS (m/z): 407.3 (MH+), 0.63 min, 1H NMR (400 MHz, CD3OD) δ ppm 7.61 (d, J=1.52 Hz, 1H) 7.55-7.58 (m, 1H) 7.48-7.52 (m, 1H) 7.38-7.48 (m, 2H) 7.07-7.24 (m, 4H) 6.83-6.98 (m, 2H) 5.74-5.97 (m, 1H) 4.72-4.80 (m, 1H) 4.52 (d, J=13.69 Hz, 1H) 4.29 (d, J=11.15 Hz, 1H)

Example 13. (S)-6-benzhydryl-11-hydroxy-3-methyl-5H-imidazo[1,2-a]pyrido[2,1-c]pyrazin-10(6H)-one

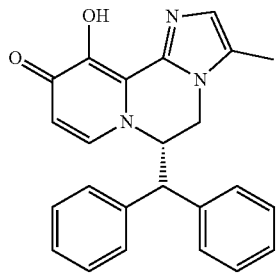 [SMILES: Cc1cnc2n1C[C@H](C(c1ccccc1)c1ccccc1)n1ccc(=O)c(O)c1-2]

Synthesized by the method of Example 7, except using 2-oxopropanal instead of glyoxal. LCMS (m/z): 384.3 (MH+), 0.61 min, 1H NMR (400 MHz, CD3OD) δ ppm 7.40-7.47 (m, 5H) 7.35-7.40 (m, 1H) 7.16-7.30 (m, 6H) 6.04 (d, J=7.19 Hz, 1H) 5.66 (dd, J=11.42, 2.96 Hz, 1H) 4.47 (dd, J=14.06, 3.84 Hz, 1H) 4.26 (d, J=13.30 Hz, 1H) 4.07 (d, J=11.44 Hz, 1H) 2.02 (d, J=0.73 Hz, 3H)

Example 14. (S)-6-benzhydryl-11-hydroxy-2,3-dimethyl-5H-imidazo[1,2-a]pyrido[2,1-c]pyrazin-10(6H)-one

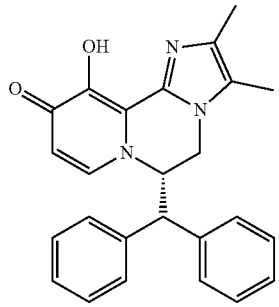 [SMILES: Cc1nc2n(c1C)C[C@H](C(c1ccccc1)c1ccccc1)n1ccc(=O)c(O)c1-2]

Synthesized by the method of Example 7, except using 2,3-butanedione instead of glyoxal. LCMS (m/z): 398.3 (MH+), 0.62 min, 1H NMR (400 MHz, CD3OD) δ ppm 7.44 (d, J=4.35 Hz, 4H) 7.37 (dq, J=8.69, 4.20 Hz, 1H) 7.16-7.30 (m, 6H) 6.03 (d, J=7.29 Hz, 1H) 5.64 (dd, J=11.40, 3.03 Hz, 1H) 4.47 (dd, J=14.13, 3.86 Hz, 1H) 4.24 (d, J=13.74 Hz, 1H) 4.09 (d, J=11.44 Hz, 1H) 2.42 (s, 3H) 1.90-2.01 (m, 3H)

Example 15. (S)-6-(bis(3-chlorophenyl)methyl)-11-hydroxy-5H-imidazo [2',1':3,4] pyrazino [1,2-b] pyridazin-10(6H)-one

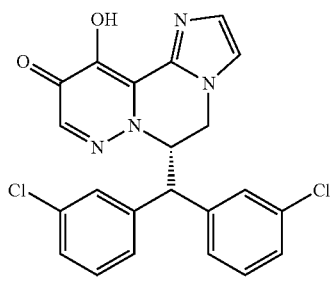 [SMILES: O=c1cnn2c(c1O)-c1nccn1C[C@@H]2C(c1cccc(Cl)c1)c1cccc(Cl)c1]

Synthesized by the method of Example 1 except the enantiomers of the corresponding intermediate 15.5 were separated by chiral HPLC. LCMS (m/z): 439.3 (MH+), 0.74 min, 1H NMR (400 MHz, CD3OD) δ ppm 7.61 (dd, J=13.11, 1.52 Hz, 2H) 7.51 (s, 1H) 7.48 (s, 1H) 7.33-7.44 (m, 3H) 7.14-7.24 (m, 3H) 7.07-7.12 (m, 1H) 5.89 (dd, J=11.05, 3.37 Hz, 1H) 4.78 (dd, J=14.31, 4.33 Hz, 1H) 4.55 (d, J=13.94 Hz, 1H) 4.34 (d, J=11.10 Hz, 1H)

Example 16. (R)-6-(bis(3-chlorophenyl)methyl)-11-hydroxy-5H-imidazo[2',1':3,4] pyrazino [1,2-b] pyridazin-10(6H)-one

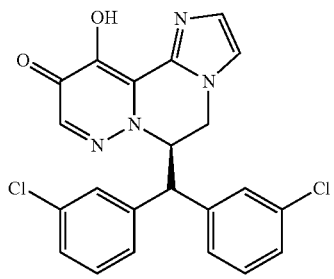 [SMILES: O=c1cnn2c(c1O)-c1nccn1C[C@H]2C(c1cccc(Cl)c1)c1cccc(Cl)c1]

Synthesized by the method of Example 1 except the enantiomers of the corresponding intermediate 16.5 were separated by chiral HPLC. LCMS (m/z): 439.3 (MH+), 0.73 min, 1H NMR (400 MHz, CD3OD) δ ppm 7.62 (dd, J=12.74, 1.59 Hz, 2H) 7.51 (s, 1H) 7.48 (s, 1H) 7.33-7.44 (m, 3H) 7.14-7.24 (m, 3H) 7.07-7.12 (m, 1H) 5.89 (dd, J=11.05, 3.37 Hz, 1H) 4.78 (dd, J=14.38, 4.35 Hz, 1H) 4.56 (d, J=14.33 Hz, 1H) 4.35 (d, J=11.10 Hz, 1H)

General Synthesis of Chiral Amino Alcohols

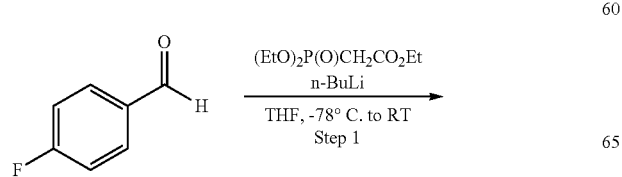

-continued

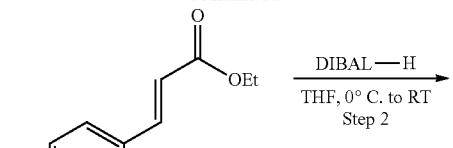

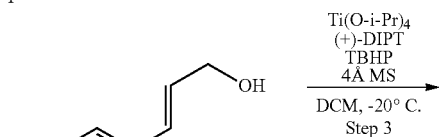

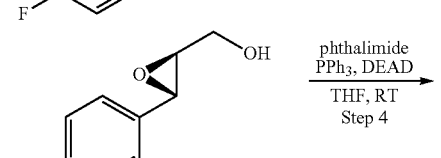

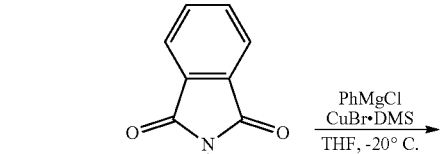

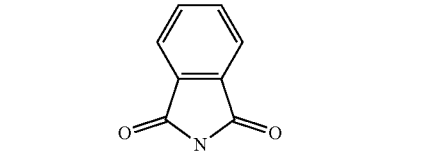

AA-1

Step 1: ethyl (E)-3-(4-fluorophenyl)acrylate

Added a solution of n-butyllithium (2.5 M in hexane, 17.60 ml, 44.0 mmol) dropwise to a solution of triethyl phosphonoacetate (8.01 ml, 40.0 mmol) in THF (Volume: 40 ml) at −78° C. After 5 minutes, 4-fluorobenzaldehyde (4.29 ml, 40 mmol) was added dropwise. The solution was then stirred for 10 minutes at −78° C. and RT for 2 hours. The reaction was quenched with brine, diluted with diethyl ether and then washed 3 times with brine. The organic layer was dried ($Na_2SO_4$), filtered and concentrated to give crude ethyl (E)-3-(4-fluorophenyl)acrylate which was used without further purification. MS m/z 195.1 (M+1).

Step 2: (E)-3-(4-fluorophenyl)prop-2-en-1-ol

Added a solution of DIBAL-H (1.0 M in toluene, 120 ml, 120 mmol) slowly to a solution of crude ethyl (E)-3-(4-fluorophenyl)acrylate (7.77 g, 40 mmol) in THF (Volume: 40 ml) at 0° C. After the addition was complete, the mixture was stirred at RT for 2 hours. The reaction was quenched by the addition of saturated aqueous potassium-sodium tartrate (100 mL). The resulting solution was stirred at 40° C. and solid potassium-sodium tartrate (~30 grams) was added. The mixture was then cooled to RT and diluted with diethyl ether (600 mL), washed with saturated aqueous potassium-sodium tartrate (3×200 mL), dried ($Na_2SO_4$), filtered and concentrated. Silica gel column chromatography (EtOAc/heptane) provided (E)-3-(4-fluorophenyl)prop-2-en-1-ol (4.12 g, white solid) in 68% yield over 2 steps. $^1$H NMR (400 MHz, Chloroform-d) δ 7.41-7.30 (m, 2H), 7.05-6.95 (m, 2H), 6.59 (dt, J=15.8, 1.5 Hz, 1H), 6.28 (dt, J=15.9, 5.7 Hz, 1H), 4.32 (dd, J=5.8, 1.6 Hz, 2H).

Step 3: ((2S,3S)-3-(4-fluorophenyl)oxiran-2-yl)methanol

Added titanium isopropoxide (0.802 ml, 2.71 mmol) and tert-butyl hydroperoxide (5.5 M in decane, 9.85 ml, 54.2 mmol) sequentially to a stirred mixture of (+)-diisopropyl L-tartrate (0.708 ml, 3.38 mmol) and 4 A molecular sieves (powdered) (1.3 g, 27.1 mmol) in DCM (Volume: 246 ml) at −20° C. (under nitrogen). The mixture was stirred at −20° C. for 1 hour, and then a solution of (E)-3-(4-fluorophenyl) prop-2-en-1-ol (4.12 g, 27.1 mmol) in DCM (7 mL) was added dropwise over 30 min. The mixture was stirred at −20° C. for 3 hours. The reaction was quenched at −20° C. with a 10% aqueous NaOH solution saturated with NaCl (2.7 mL). Then, diethyl ether (40 mL) was added and the cold bath was allowed to warm to 10° C. while $MgSO_4$ (2.7 grams) and celite (677 mg) were added. After another 15 minutes of stirring, the mixture was allowed to settle and then filtered through a pad of celite (washed with diethyl ether). The filtrate was concentrated. Silica gel column chromatography (EtOAc/heptane) provided ((2S,3S)-3-(4-fluorophenyl)oxiran-2-yl)methanol (3.47 g, colorless oil) in 76% yield. $^1$H NMR (400 MHz, Chloroform-d) δ 7.30-7.21 (m, 2H), 7.09-7.00 (m, 2H), 4.04 (ddd, J=12.8, 5.2, 2.4 Hz, 1H), 3.92 (d, J=2.2 Hz, 1H), 3.81 (ddd, J=12.7, 7.8, 3.7 Hz, 1H), 3.19 (dt, J=4.2, 2.3 Hz, 1H), 1.87-1.77 (m, 1H).

Step 4: 2-(((2S,3S)-3-(4-fluorophenyl)oxiran-2-yl)methyl)isoindoline-1,3-dione Added DEAD (1.22 ml, 7.73 mmol) dropwise to a solution of ((2S,3S)-3-(4-fluorophenyl)oxiran-2-yl)methanol (1 g, 5.95 mmol), phthalimide (0.962 g, 6.54 mmol), and triphenylphosphine (2.028 g, 7.73 mmol) in THF (Volume: 19.8 ml) at RT. The yellow solution was stirred for 30 minutes, by which time LCMS showed reaction complete. The reaction mixture was concentrated. Silica gel column chromatography (EtOAc/heptane) provided 2-(((2S,3S)-3-(4-fluorophenyl)oxiran-2-yl)methyl)isoindoline-1,3-dione (1.6 g, white solid) in 91% yield. MS m/z 298.1 (M+1). $^1$H NMR (400 MHz, Chloroform-d) δ 7.88 (dt, J=5.1, 2.5 Hz, 2H), 7.75 (ddd, J=8.6, 5.4, 3.1 Hz, 2H), 7.25-7.18 (m, 2H), 7.07-6.95 (m, 2H), 4.14 (dd, J=14.3, 4.6 Hz, 1H), 3.90-3.79 (m, 2H), 3.21 (ddd, J=5.6, 4.6, 2.0 Hz, 1H).

Step 5: 2-((2R,3R)-3-(4-fluorophenyl)-2-hydroxy-3-phenylpropyl)isoindoline-1,3-dione Added THF (Volume: 23.5 mL) to copper(I) bromide-dimethyl sulfide complex (484 mg, 2.35 mmol) and ((2S,3S)-3-(4-fluorophenyl)oxiran-2-yl)methanol (700 mg, 2.35 mmol) at RT. Cooled to −20° C. in an acetone bath with periodic dry ice additions. A solution of phenylmagnesium chloride (2.0 M in THF, 4.47 mL, 8.95 mmol) was added dropwise. The reaction was quenched with saturated aqueous $NH_4Cl$ solution and extracted with diethyl ether (2 times). The combined organic extracts were dried over $MgSO_4$, filtered and concentrated. Silica gel column chromatography (EtOAc/heptane) provided 2-((2R,3R)-3-(4-fluorophenyl)-2-hydroxy-3-phenylpropyl)isoindoline-1,3-dione (0.463 g, white solid) in 52% yield. MS m/z 376.3 (M+1).

Step 6: (1R,2R)-3-amino-1-(4-fluorophenyl)-1-phenylpropan-2-ol

Added hydrazine (0.581 mL, 18.5 mmol) to a solution of 2-(2R,3R)-3-(4-fluorophenyl)-2-hydroxy-3-phenylpropyl) isoindoline-1,3-dione (463 mg, 1.233 mmol) in ethanol (Volume: 10 mL) at RT. The mixture was heated at 65° C. for 1 hour, by which time LCMS showed reaction complete. The reaction was cooled to RT and concentrated on the rotovap. The residue was triturated with DCM and then filtered to remove solids. The filtrate was concentrated to give crude (1R,2R)-3-amino-1-(4-fluorophenyl)-1-phenyl-propan-2-ol (254 mg, yellow foam) in 84% yield that was used without further purification. MS m/z 246.2 (M+1).

The intermediates in the following table were prepared by a method similar to intermediate AA-1.

| Intermediate No. | Structure | Name | Materials | LCMS |
|---|---|---|---|---|
| AA-2 | 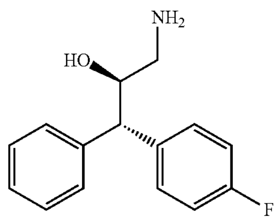 [SMILES: NC[C@H](O)[C@@H](c1ccccc1)c1ccc(F)cc1] | (1S,2R)-3-amino-1-(4-fluorophenyl)-1-phenylpropan-2-ol | Step 1: benzaldehyde<br>Step 5: 4-fluorophenylmagnesium bromide | 246.2 |
| AA-3 | 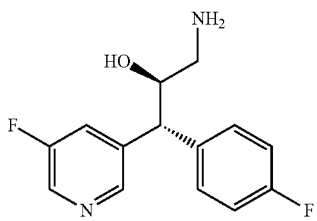 [SMILES: NC[C@H](O)[C@H](c1ccc(F)cc1)c1cncc(F)c1] | (1R,2R)-3-amino-1-(4-fluorophenyl)-1-(5-fluoropyridin-3-yl)propan-2-ol | Step 1: 5-fluoronicotinaldehyde<br>Step 5: 4-fluorophenylmagnesium bromide | 265.2 |
| AA-4 | 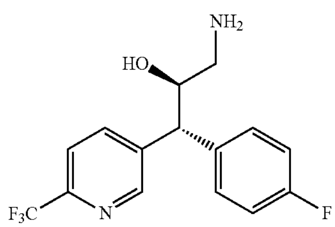 [SMILES: NC[C@H](O)[C@H](c1ccc(F)cc1)c1ccc(C(F)(F)F)nc1] | (1R,2R)-3-amino-1-(4-fluorophenyl)-1-(6-(trifluoromethyl)pyridin-3-yl)propan-2-ol | Step 1: 6-(trifluoromethyl)nicotinaldehyde<br>Step 5: 4-fluorophenylmagnesium bromide | 315.3 |
| AA-5 | 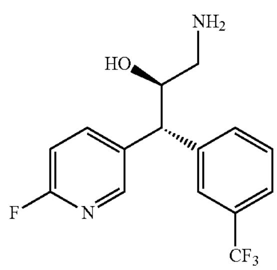 [SMILES: NC[C@H](O)[C@@H](c1ccc(F)nc1)c1cccc(C(F)(F)F)c1] | (1S,2R)-3-amino-1-(4-fluorophenyl)-1-(3-(trifluoromethyl)phenyl)propan-2-ol | Step 1: 4-fluorobenzaldehyde<br>Step 5: (3-(trifluoromethyl)phenyl)magnesium bromide | 314.2 |
| AA-6 | 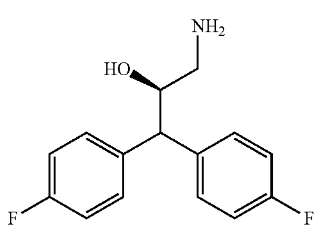 [SMILES: NC[C@H](O)C(c1ccc(F)cc1)c1ccc(F)cc1] | (R)-3-amino-1,1-bis(4-fluorophenyl)propan-2-ol | Step 1: 4-fluorobenzaldehyde<br>Step 5: 4-fluorophenylmagnesium bromide | 264.2 |
| AA-7 | 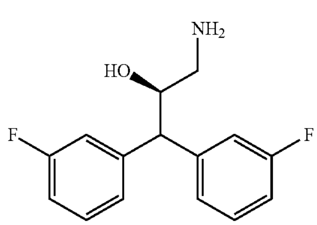 [SMILES: NC[C@H](O)C(c1cccc(F)c1)c1cccc(F)c1] | (R)-3-amino-1,1-bis(3-fluorophenyl)propan-2-ol | Step 1: 3-fluorobenzaldehyde<br>Step 5: 3-fluorophenylmagnesium bromide | 264.4 |

-continued

| Intermediate No. | Structure | Name | Materials | LCMS |
|---|---|---|---|---|
| AA-8 | 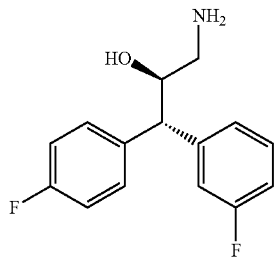 [SMILES: NC[C@H](O)[C@@H](c1ccc(F)cc1)c1cccc(F)c1] | (1S,2R)-3-amino-1-(3-fluorophenyl)-1-(4-fluorophenyl)propan-2-ol | Step 1: 4-fluorobenzaldehyde Step 5: 3-fluorophenylmagnesium bromide | 264.3 |
| AA-9 | 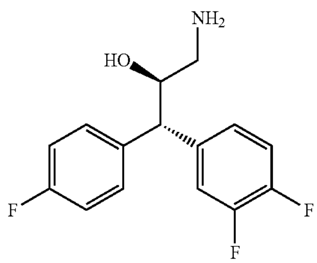 [SMILES: NC[C@H](O)[C@@H](c1ccc(F)cc1)c1ccc(F)c(F)c1] | (1S,2R)-3-amino-1-(3,4-difluorophenyl)-1-(4-fluorophenyl)propan-2-ol | Step 1: 4-fluorobenzaldehyde Step 5: 3,4-difluorophenylmagnesium bromide | 282.2 |
| AA-10 | 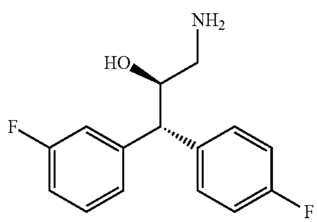 [SMILES: NC[C@H](O)[C@H](c1ccc(F)cc1)c1cccc(F)c1] | (1R,2R)-3-amino-1-(3-fluorophenyl)-1-(4-fluorophenyl)propan-2-ol | Step 1: 3-fluorobenzaldehyde Step 5: 4-fluorophenylmagnesium bromide | 264.2 |
| AA-11 | 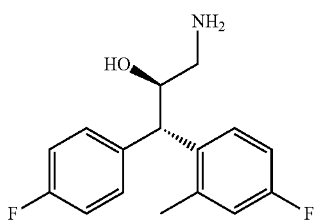 [SMILES: Cc1cc(F)ccc1[C@H](c1ccc(F)cc1)[C@@H](O)CN] | (1S,2R)-3-amino-1-(4-fluoro-2-methylphenyl)-1-(4-fluorophenyl)propan-2-ol | Step 1: 4-fluorobenzaldehyde Step 5: (4-fluoro-2-methylphenyl)magnesium bromide | 278.2 |
| AA-12 | 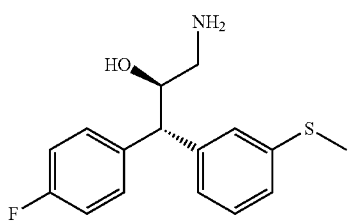 [SMILES: CSc1cccc([C@H](c2ccc(F)cc2)[C@@H](O)CN)c1] | (1S,2R)-3-amino-1-(4-fluorophenyl)-1-(3-(methylthio)phenyl)propan-2-ol | Step 1: 4-fluorobenzaldehyde Step 5: (3-(methylthio)phenyl)magnesium bromide | 292.2 |
| AA-13 | 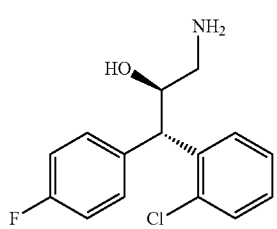 [SMILES: NC[C@H](O)[C@@H](c1ccc(F)cc1)c1ccccc1Cl] | (1S,2R)-3-amino-1-(2-chlorophenyl)-1-(4-fluorophenyl)propan-2-ol | Step 1: 4-fluorobenzaldehyde Step 5: (2-chlorophenyl)magnesium bromide | 280.2 |

| Intermediate No. | Structure | Name | Materials | LCMS |
|---|---|---|---|---|
| AA-14 | 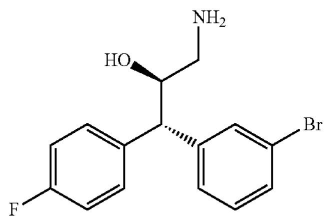 [SMILES: NC[C@H](O)[C@@H](c1ccc(F)cc1)c1cccc(Br)c1] | (1S,2R)-3-amino-1-(3-bromophenyl)-1-(4-fluorophenyl)propan-2-ol | Step 1: 4-fluorobenzaldehyde<br>Step 5: (3-bromophenyl)magnesium bromide | 324.1 |
| AA-15 | 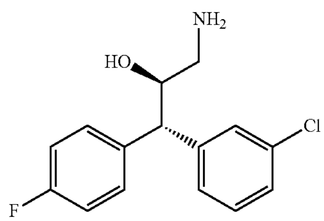 [SMILES: NC[C@H](O)[C@@H](c1ccc(F)cc1)c1cccc(Cl)c1] | (1S,2R)-3-amino-1-(3-chlorophenyl)-1-(4-fluorophenyl)propan-2-ol | Step 1: 4-fluorobenzaldehyde<br>Step 5: (3-chlorophenyl)magnesium bromide | 280.1 |
| AA-16 | 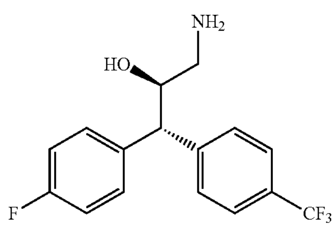 [SMILES: NC[C@H](O)[C@@H](c1ccc(F)cc1)c1ccc(C(F)(F)F)cc1] | (1R,2R)-3-amino-1-(4-fluorophenyl)-1-(4-(trifluoromethyl)phenyl)propan-2-ol | Step 1: 4-fluorobenzaldehyde<br>Step 5: (4-trifluoromethylphenyl)magnesium bromide | 314.2 |
| AA-17 | 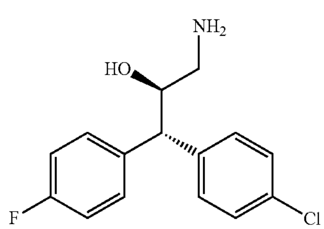 [SMILES: NC[C@H](O)[C@@H](c1ccc(F)cc1)c1ccc(Cl)cc1] | (1S,2R)-3-amino-1-(4-chlorophenyl)-1-(4-fluorophenyl)propan-2-ol | Step 1: 4-fluorobenzaldehyde<br>Step 5: (4-chlorophenyl)magnesium bromide | 280.1 |
| AA-18 | 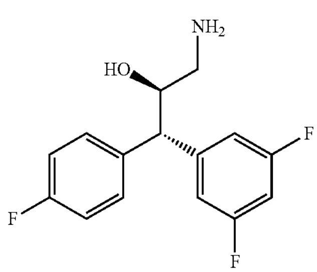 [SMILES: NC[C@H](O)[C@@H](c1ccc(F)cc1)c1cc(F)cc(F)c1] | (1S,2R)-3-amino-1-(3,5-difluorophenyl)-1-(4-fluorophenyl)propan-2-ol | Step 1: 4-fluorobenzaldehyde<br>Step 5: (3,5-difluorophenyl)magnesium bromide | 282.1 |
| AA-19 | 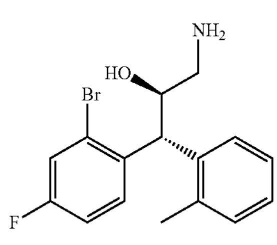 [SMILES: Cc1ccccc1[C@H](c1ccc(F)cc1Br)[C@@H](O)CN] | (1R,2R)-3-amino-1-(2-bromo-4-fluorophenyl)-1-(o-tolyl)propan-2-ol | Step 1: 2-bromo-4-fluorobenzaldehyde<br>Step 5: (2-methylphenyl)magnesium bromide | 338.2 |

-continued

| Intermediate No. | Structure | Name | Materials | LCMS |
|---|---|---|---|---|
| AA-20 | 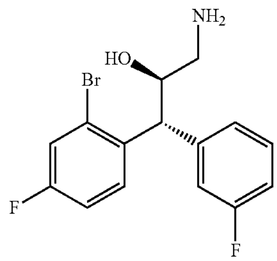 [SMILES: NC[C@H](O)[C@H](c1cccc(F)c1)c1ccc(F)cc1Br] | (1R,2R)-3-amino-1-(2-bromo-4-fluorophenyl)-1-(3-fluorophenyl)propan-2-ol | Step 1: 2-bromo-4-fluorobenzaldehyde Step 5: (3-fluorophenyl)magnesium bromide | 342.2 |
| AA-21 | 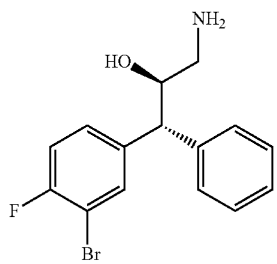 [SMILES: NC[C@H](O)[C@H](c1ccccc1)c1ccc(F)c(Br)c1] | (1R,2R)-3-amino-1-(3-bromo-4-fluorophenyl)-1-phenylpropan-2-ol | Step 1: 3-bromo-4-fluorobenzaldehyde Step 5: phenylmagnesium chloride | 324.1 |
| AA-22 | 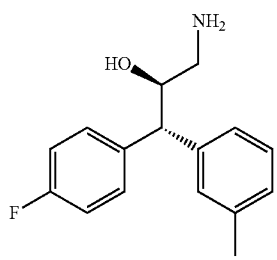 [SMILES: Cc1cccc([C@H](c2ccc(F)cc2)[C@@H](O)CN)c1] | (1S,2R)-3-amino-1-(4-fluorophenyl)-1-(m-tolyl)propan-2-ol | Step 1: 4-fluorobenzaldehyde Step 5: (3-methylphenyl)magnesium bromide | 260.2 |
| AA-23 | 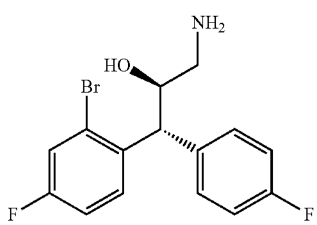 [SMILES: NC[C@H](O)[C@H](c1ccc(F)cc1)c1ccc(F)cc1Br] | (1R,2R)-3-amino-1-(2-bromo-4-fluorophenyl)-1-(4-fluorophenyl)propan-2-ol | Step 1: 2-bromo-4-fluorobenzaldehyde Step 5: (4-fluorophenyl)magnesium bromide | 342.1 |
| AA-24 | 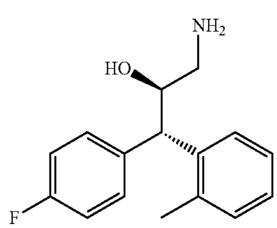 [SMILES: Cc1ccccc1[C@H](c1ccc(F)cc1)[C@@H](O)CN] | (1S,2R)-3-amino-1-(4-fluorophenyl)-1-(o-tolyl)propan-2-ol | Step 1: 4-fluorobenzaldehyde Step 5: (2-methylphenyl)magnesium bromide | 260.2 |
| AA-25 | 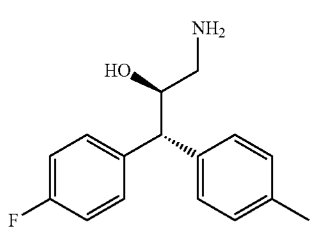 [SMILES: Cc1ccc([C@H](c2ccc(F)cc2)[C@@H](O)CN)cc1] | (1R,2R)-3-amino-1-(4-fluorophenyl)-1-(p-tolyl)propan-2-ol | Step 1: 4-fluorobenzaldehyde Step 5: (4-methylphenyl)magnesium bromide | 260.2 |

Synthesis of Intermediate AA-26

(1S,2R)-3-amino-1-(4-fluorophenyl)-1-(3-(methylsulfonyl)phenyl)propan-2-ol

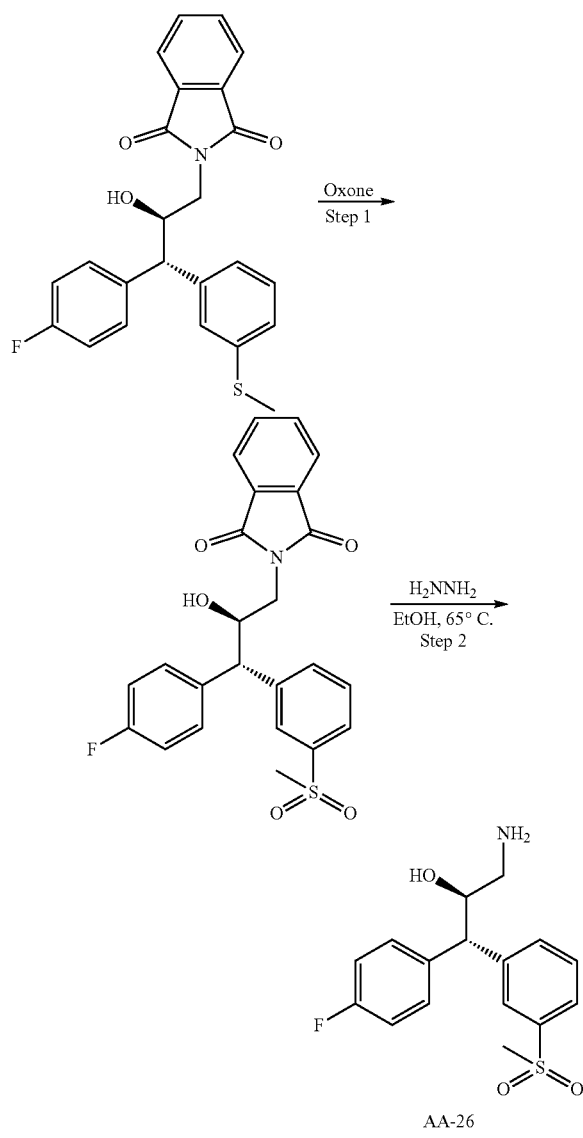

AA-26

Step 1: 2-(2R,3S)-3-(4-fluorophenyl)-2-hydroxy-3-(3-(methylsulfonyl) phenyl) propyl) isoindoline-1,3-dione Added a solution of OXONE (175 mg, 0.285 mmol) in water (Volume: 3.00 mL to 2-((2R,3S)-3-(4-fluorophenyl)-2-hydroxy-3-(3-(methylthio)phenyl)propyl)isoindoline-1,3-dione (60 mg, 0.142 mmol, Synthesis: see intermediate AA-12, steps 1-5) in THF (Volume: 3 mL) at 0° C. Reaction mixture was stirred in ice bath for 3H. LC-MS at this point showed major desired product. The reaction was quenched with saturated sodium thiosulfate solution and was extracted with EtOAc (twice). The combined organic extracts were washed with brine, dried over Na$_2$SO$_4$, filtered and concentrated in vacuo to provide crude 2-((2R,3S)-3-(4-fluorophe- nyl)-2-hydroxy-3-(3-(methylsulfonyl) phenyl) propyl)isoindoline-1,3-dione (65.0 mg, 0.142 mmol, 100% yield). LCMS: MH$^+$ 454.3, 0.91 min.

Proceed for next step without further purification.

Step 2: (1S,2R)-3-amino-1-(4-fluorophenyl)-1-(3-(methylsulfonyl)phenyl)propan-2-ol Prepared from 2-((2R,3S)-3-(4-fluorophenyl)-2-hydroxy-3-(3-(methylsulfonyl) phenyl) propyl)isoindoline-1,3-dione by the method of intermediate AA-1, step 6. LCMS: MH$^+$ 324.3, 0.67 min.

Synthesis of Intermediate AA-27

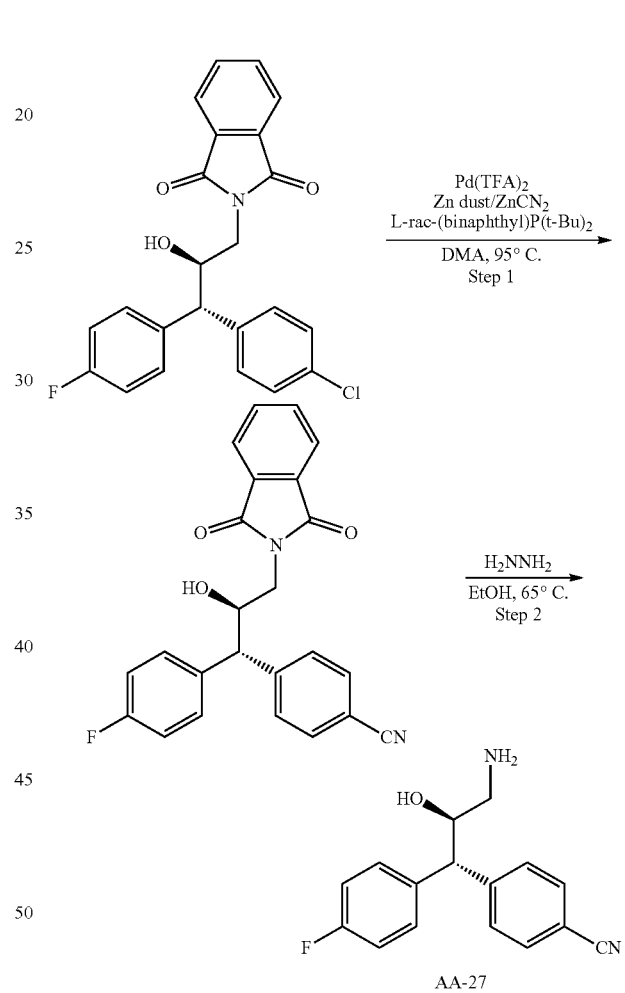

AA-27

Step 1: 4-((1R,2R)-3-(1,3-dioxoisoindolin-2-yl)-1-(4-fluorophenyl)-2-hydroxypropyl)benzonitrile Added 24(2R,3S)-3-(4-chlorophenyl)-3-(4-fluorophenyl)-2-hydroxypropyl)isoindoline-1,3-dione (250 mg, 0.610 mmol, Synthesis: see intermediate AA-17, steps 1-5), zinc powder (39.9 mg, 0.610 mmol), zinc cyanide (143 mg, 1.22 mmol), rac-2-(di-t-butylphosphino)-1,1'-binaphthyl (48.6 mg, 0.122 mmol) and bis(2,2,2-trifluoroacetyl)palladium (18 mg, 0.061 mmol) at RT to a microwave vial equipped with a stir bar. Cap was sealed and N2 was passed through for 5 min. Then added DMA (Volume: 5 mL) through the syringe and N2 was passed through for an additional 5 min. The microwave vial was placed in a heating block and heated at 95° C. for 1 hour. LC-MS showed complete reaction. Reaction mixture was diluted with DCM and filtered through celite. Washed with DCM and solvent was evaporated. The crude material was purified by silica gel chromatography using 0-40% EtOAc heptane to give 4-((1R,2R)-3-(1,3-dioxoisoindolin-2-yl)-1-(4-fluorophenyl)-2-hydroxypropyl)benzonitrile, (195 mg, 0.463 mmol, 76% yield). LCMS: MH+401.3, 0.79 min. 1H NMR (400 MHz, CDCl3) δ ppm 7.79-7.86 (m, 2H) 7.68-7.76 (m, 2H) 7.55-7.61 (m, 2H) 7.45-7.51 (m, 2H) 7.29-7.36 (m, 2H) 7.01 (t, J=8.58 Hz, 2H) 4.62-4.79 (m, 1H) 4.05-4.14 (m, 1H) 3.68-3.87 (m, 2H) 2.46 (d, J=5.23 Hz, 1H).

Step 2: 4-((1R,2R)-3-amino-1-(4-fluorophenyl)-2-hydroxypropyl)benzonitrile

Prepared from 4-((1R,2R)-3-(1,3-dioxoisoindolin-2-yl)-1-(4-fluorophenyl)-2-hydroxypropyl)benzonitrile by the method of intermediate AA-1, step 6. LCMS: MH+ 271.3, 0.63 min.

The intermediates in the following table were prepared by a method similar to intermediate AA-27.

| Intermediate No. | Structure | Name | Starting Material | LCMS |
|---|---|---|---|---|
| AA-28 | 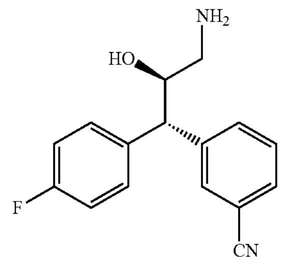 [SMILES: N#Cc1cccc([C@H](c2ccc(F)cc2)[C@@H](O)CN)c1] | 3-((1S,2R)-3-amino-1-(4-fluorophenyl)-2-hydroxypropyl)benzonitrile | Step 1: 2-((2R,3S)-3-(3-chlorophenyl)-3-(4-fluorophenyl)-2-hydroxypropyl)isoindoline-1,3-dione | 271.1 |
| AA-29 | 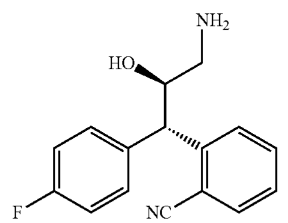 [SMILES: N#Cc1ccccc1[C@H](c1ccc(F)cc1)[C@@H](O)CN] | 2-((1S,2R)-3-amino-1-(4-fluorophenyl)-2-hydroxypropyl)benzonitrile | Step 1: 2-((2R,3S)-3-(2-chlorophenyl)-3-(4-fluorophenyl)-2-hydroxypropyl)isoindoline-1,3-dione | 271.2 |
| AA-30 | 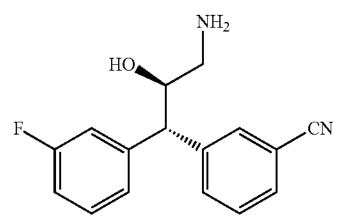 [SMILES: N#Cc1cccc([C@H](c2cccc(F)c2)[C@@H](O)CN)c1] | 3-((1R,2R)-3-amino-1-(3-fluorophenyl)-2-hydroxypropyl)benzonitrile | Step 1: 2-((2R,3S)-3-(3-chlorophenyl)-3-(3-fluorophenyl)-2-hydroxypropyl)isoindoline-1,3-dione | 271.2 |

Example 17. (S)-6-((R)-(4-fluorophenyl)(phenyl)methyl)-11-hydroxy-5,6-dihydro-10H-imidazo[2',1':3,4]pyrazino[1,2-b]pyridazin-10-one

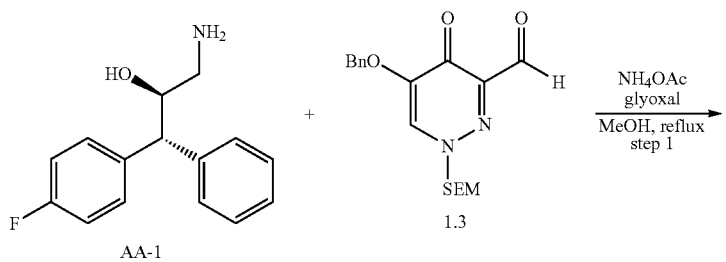

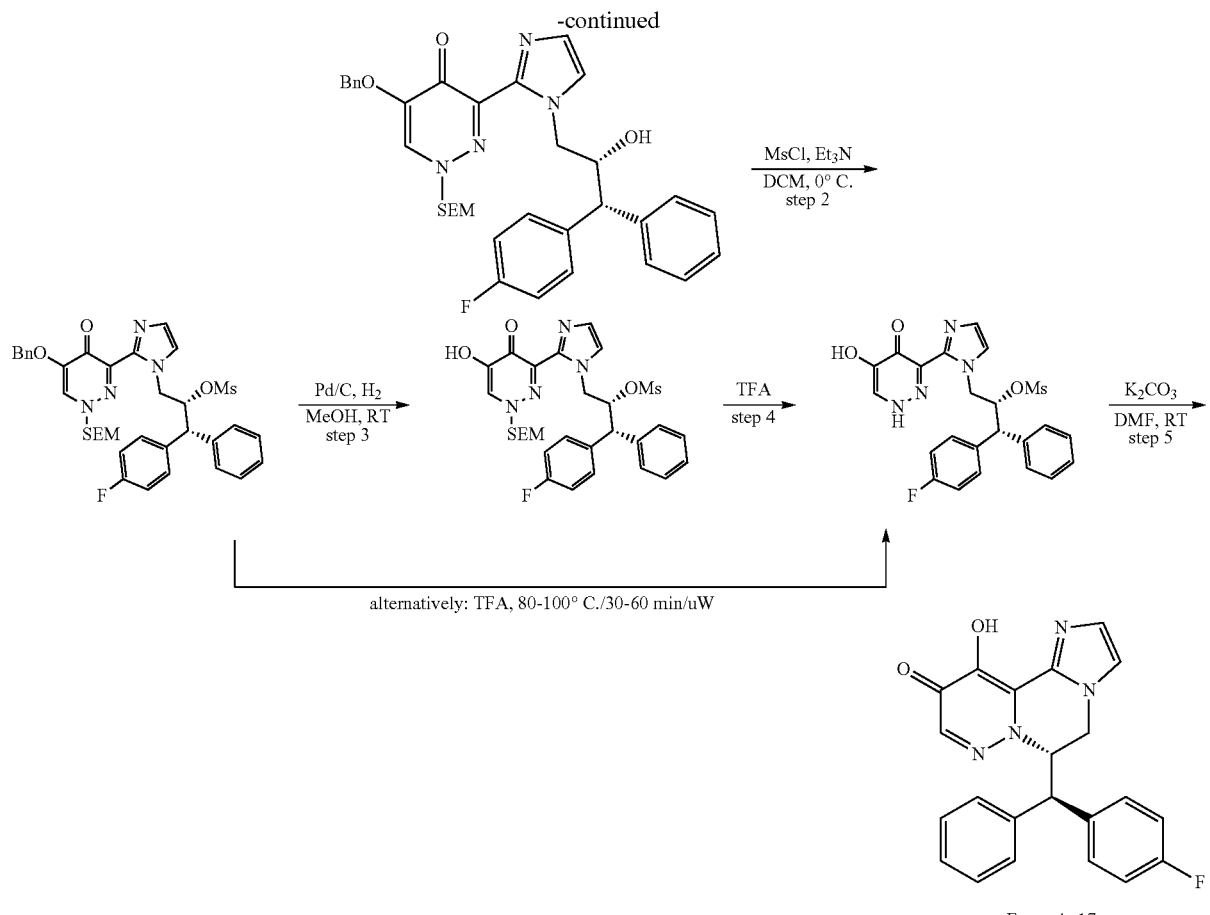

Example 17

Step 1: 5-(benzyloxy)-3-(1-((2R,3R)-3-(4-fluorophenyl)-2-hydroxy-3-phenylpropyl)-1H-imidazol-2-yl)-1-((2-(trimethylsilyl)ethoxy)methyl)pyridazin-4(1H)-one Ammonium acetate (118 mg, 1.53 mmol) and glyoxal (40% in water, 0.18 mL, 1.53 mmol) were added to a solution of 5-(benzyloxy)-4-oxo-1-((2-(trimethylsilyl)ethoxy)methyl)-1,4-dihydropyridazine-3-carbaldehyde (551 mg, 1.53 mmol) and (1R,2R)-3-amino-1-(4-fluorophenyl)-1-phenylpropan-2-ol (250 mg, 1.02 mmol) in MeOH (5 mL). The mixture was heated at reflux for 2 hours and then cooled to room temperature. The reaction was diluted with EtOAc and washed with dilute brine. The organic layer was dried (Na$_2$SO$_4$), filtered and concentrated. Silica gel column chromatography (EtOAc/heptane/MeOH) provided 5-(benzyloxy)-3-(1-((2R,3R)-3-(4-fluorophenyl)-2-hydroxy-3-phenylpropyl)-1H-imidazol-2-yl)-1-((2-(trimethylsilyl)ethoxy)methyl)pyridazin-4(1H)-one (0.143 g, yellow oil) in 22% yield. MS m/z 627.4 (M+1).

Step 2: (1R,2R)-3-(2-(5-(benzyloxy)-4-oxo-1-((2-(trimethylsilyl)ethoxy)methyl)-1,4-dihydropyridazin-3-yl)-1H-imidazol-1-yl)-1-(4-fluorophenyl)-1-phenylpropan-2-yl methanesulfonate Methanesulfonyl chloride (0.036 mL, 0.46 mmol) was added dropwise to a solution of 5-(benzyloxy)-3-(1-((2R,3R)-3-(4-fluorophenyl)-2-hydroxy-3-phenylpropyl)-1H-imidazol-2-yl)-1-((2-(trimethylsilyl)ethoxy)methyl)pyridazin-4(1H)-one (143 mg, 0.228 mmol) and Et$_3$N (0.095 mL, 0.68 mmol) in DCM (4.5 mL) at 0° C. The mixture was stirred at the same temperature for 30 min and then quenched with water. The layers were separated and the aqueous layer was extracted with DCM. The combined organic extracts were washed with brine, filtered and concentrated. Silica gel column chromatography (EtOAc/Heptane/MeOH) provided (1R,2R)-3-(2-(5-(benzyloxy)-4-oxo-1-((2-(trimethylsilyl)ethoxy)methyl)-1,4-dihydropyridazin-3-yl)-1H-imidazol-1-yl)-1-(4-fluorophenyl)-1-phenylpropan-2-yl methanesulfonate (100 mg, yellow oil) in 62% yield. MS m/z 705.3 (M+1).

Step 3: (1R,2R)-1-(4-fluorophenyl)-3-(2-(5-hydroxy-4-oxo-1-((2-(trimethylsilyl)ethoxy)methyl)-1,4-dihydropyridazin-3-yl)-1H-imidazol-1-yl)-1-phenylpropan-2-yl methanesulfonate 10% Pd/C (15 mg) was added to a solution of (1R,2R)-3-(2-(5-(benzyloxy)-4-oxo-1-((2-(trimethylsilyl)ethoxy)methyl)-1,4-dihydropyridazin-3-yl)-1H-imidazol-1-yl)-1-(4-fluorophenyl)-1-phenylpropan-2-yl methanesulfonate (100 mg, 0.142 mmol) in MeOH (10 mL) under nitrogen at room temperature. The flask was then evacuated and refilled with H$_2$ from a balloon (three times) and then stirred vigorously under a balloon atmosphere of H$_2$ for 30 min. The reaction flask was then purged with nitrogen and the mixture was filtered through celite. The filtrate was concentrated to give crude (1R,2R)-1-(4-fluorophenyl)-3-(2-(5-hydroxy-4-oxo-1-(2-(trimethylsilyl)ethoxy)methyl)-1,4-dihydropyridazin-3-yl)-1H-imidazol-1-yl)-1-phenylpropan-2-yl methanesulfonate, which was used without further purification. MS m/z 615.3 (M+1).

Step 4: (1R,2R)-1-(4-fluorophenyl)-3-(2-(5-hydroxy-4-oxo-1,4-dihydropyridazin-3-yl)-1H-imidazol-1-yl)-1-phenylpropan-2-yl methanesulfonate Crude (1R,2R)-1-(4-fluorophenyl)-3-(2-(5-hydroxy-4-oxo-1-((2-(trimethylsilyl)ethoxy)methyl)-1,4-dihydropyridazin-3-yl)-1H-imidazol-1-yl)-1-phenylpropan-2-yl methanesulfonate was dissolved in TFA (5 mL) and stirred at room temperature for 2 hours. The reaction was then concentrated. The residue was taken up in toluene and concentrated again to give crude (1R,2R)-1-(4-fluorophenyl)-3-(2-(5-hydroxy-4-oxo-1,4-dihydropyridazin-3-yl)-1H-imidazol-1-yl)-1-phenylpropan-2-yl methanesulfonate, which was used without further purification. MS m/z 485.2 (M+1).

Step 5: (S)-6-((R)-(4-fluorophenyl)(phenyl)methyl)-11-hydroxy-5,6-dihydro-10H-imidazo[2',1':3,4]pyrazino[1,2-b]pyridazin-10-one $K_2CO_3$ (59 mg, 0.43 mmol) was added to a solution of crude (1R,2R)-1-(4-fluorophenyl)-3-(2-(5-hydroxy-4-oxo-1,4-dihydropyridazin-3-yl)-1H-imidazol-1-yl)-1-phenylpropan-2-yl methanesulfonate in DMF (2 mL). The mixture was stirred at room temperature for 3 hours and then filtered to remove solids. The filtrate was purified by reverse phase HPLC. Product fractions were combined, frozen and lyophilized to afford a TFA salt of 6-benzhydryl-11-hydroxy-5H-imidazo[2',1':3,4]pyrazino[1,2-b]pyridazin-10(6H)-one (26 mg, 0.051 mmol, white solid) in 36% yield over three steps. $^1$H NMR (400 MHz, DMSO-$d_6$) δ 7.67 (d, J=1.6 Hz, 1H), 7.56 (s, 1H), 7.54-7.46 (m, 2H), 7.35 (s, 1H), 7.25-7.08 (m, 7H), 5.88 (dd, J=11.2, 4.0 Hz, 1H), 4.71 (dd, J=14.1, 4.2 Hz, 1H), 4.36 (d, J=14.2 Hz, 1H), 4.28 (d, J=11.4 Hz, 1H). MS m/z 389.3 (M+1).

The compounds in the following table were prepared by a method similar to Example 17. In some cases steps 3 & 4 were replaced with microwave heating in neat TFA at 80-100° C. for 30-60 min.

| Example No. | Starting Material | Structure | Mass M + H | 1H NMR |
|---|---|---|---|---|
| 18 | AA-2 | 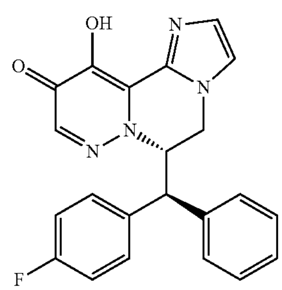 [SMILES: O=c1cnn2c(c1O)-c1nccn1C[C@@H]2[C@@H](c1ccccc1)c1ccc(F)cc1] | 389.3 | (400 MHz, DMSO-d6) δ 7.69 (d, J = 1.7 Hz, 1H), 7.69 (d, J = 1.6 Hz, 1H), 7.47 (d, J = 7.3 Hz, 2H), 7.42 (s, 1H), 7.38 (t, J = 7.5 Hz, 2H), 7.33-7.20 (m, 3H), 6.99 (t, J = 8.8 Hz, 2H), 5.93-5.84 (m, 1H), 4.73 (dd, J = 14.1, 4.3 Hz, 1H), 4.32 (dd, J = 12.8, 10.0 Hz, 2H). |
| 19 | AA-3 | 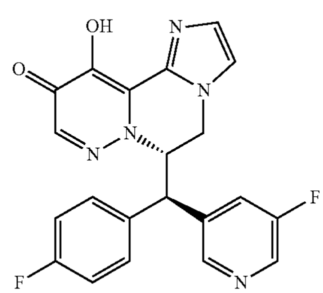 | 408.3 | (400 MHz, DMSO-d6) δ 8.54 (d, J = 2.7 Hz, 1H), 8.50 (t, J = 1.7 Hz, 1H), 8.07 (dt, J = 10.1, 2.3 Hz, 1H), 7.72-7.60 (m, 2H), 7.47-7.41 (m, 1H), 7.33-7.24 (m, 2H), 7.04 (t, J = 8.8 Hz, 2H), 5.96 (dd, J = 11.3, 3.9 Hz, 1H), 4.75 (dd, J = 14.3, 4.1 Hz, 1H), 4.60-4.53 (m, 1H), 4.46 (d, J = 14.2 Hz, 1H). |
| 20 | AA-4 | 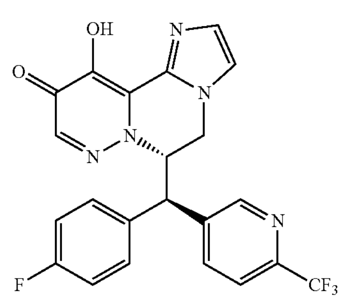 [SMILES: O=c1cnn2c(c1O)-c1nccn1C[C@@H]2[C@H](c1ccc(F)cc1)c1ccc(C(F)(F)F)nc1] | 458.4 | (400 MHz, DMSO-d6) δ 8.87 (s, 1H), 8.30 (dd, J = 7.9, 2.2 Hz, 1H), 7.95 (d, J = 8.2 Hz, 1H), 7.60 (s, 1H), 7.52 (d, J = 1.9 Hz, 1H), 7.37 (s, 1H), 7.33-7.22 (m, 2H), 7.04 (t, J = 8.8 Hz, 2H), 6.05-5.95 (m, 1H), 4.73 (dd, J = 14.3, 3.9 Hz, 1H), 4.62-4.54 (m, 1H), 4.41 (d, J = 14.2 Hz, 1H). |

-continued

| Example No. | Starting Material | Structure | Mass M + H | 1H NMR |
|---|---|---|---|---|
| 21 | AA-5 | (structure: tricyclic imidazo-pyrazine core with OH and =O; substituent is CH linked to 3-CF3-phenyl and 4-F-phenyl) | 457.3 | (400 MHz, MeOD) δ ppm 4.49 (d, J = 11.30 Hz, 1 H) 4.57 (d, J = 14.33 Hz, 1 H) 4.80 (dd, J = 14.33, 4.25 Hz, 1 H) 5.91 (dd, J = 11.25, 3.91 Hz, 1 H) 7.17 (t, J = 8.66 Hz, 2 H) 7.36-7.42 (m, 1 H) 7.44 (s, 1 H) 7.46-7.58 (m, 5 H) 7.64 (d, J = 1.37 Hz, 1 H) 7.68 (s, 1 H) |
| 22 | AA-6 | (structure: core with CH linked to two 4-F-phenyl groups) | 407.3 | (400 MHz, MeOD) δppm 7.40 (s, 4 H) 7.35 (s, 1 H) 7.07-7.23 (m, 4 H) 6.88 (t, J = 8.68 Hz, 2 H) 5.70 (br d, J = 11.30 Hz, 1 H) 4.67 (brdd, J = 13.99, 3.96 Hz, 1 H) 4.38 (br d, J = 13.99, 1 H) 4.16 (br d, J = 11.35 Hz, 1 H) |
| 23 | AA-7 | (structure: core with CH linked to two 3-F-phenyl groups) | 407.3 | (400 MHz, MeOD) δ ppm 7.52-7.63 (m, 2 H) 7.40-7.51 (m, 2 H) 7.15-7.28 (m, 3 H) 6.99-7.11 (m, 2 H) 6.87-6.97 (m, 2 H) 5.86 (dd, J = 11.20, 3.52 Hz, 1 H) 4.76 (dd, J = 14.28, 4.21 Hz, 1 H) 4.52 (d, J = 14.18 Hz, 1 H) 4.34 (d, J = 11.25 Hz, 1 H) |
| 24 | AA-8 | (structure: core with CH linked to 3-F-phenyl and 4-F-phenyl) | 407.3 | (400 MHz, MeOD) δ ppm 4.36 (d, J = 11.20 Hz, 1 H) 4.55 (d, J = 14.33 Hz, 1 H) 4.78 (dd, J = 14.33, 4.35 Hz, 1 H) 5.86 (dd, J = 11.10, 3.86 Hz, 1 H) 6.85-6.97 (m, 2 H) 7.01 (br d, J = 10.17 Hz, 1 H) 7.08-7.22 (m, 3 H) 7.45 (dd, J = 8.61, 5.23 Hz, 2 H) 7.52 (s, 1 H) 7.62 (d, J = 1.32 Hz, 1 H) 7.66 (d, J = 1.37 Hz, 1 H) |
| 25 | AA-9 | (structure: core with CH linked to 3,4-diF-phenyl and 4-F-phenyl) | 425.3 | (400 MHz, MeOD) δ ppm 4.35 (d, J = 11.35 Hz, 1 H) 4.53 (d, J = 14.33 Hz, 1 H) 4.77 (dd, J = 14.33, 4.30 Hz, 1 H) 5.84 (dd, J = 11.30, 3.81 Hz, 1 H) 6.93-6.99 (m, 1 H) 7.07 (dt, J = 10.27, 8.44 Hz, 1 H) 7.12-7.28 (m, 3 H) 7.45 (dd, J = 8.61, 5.23 Hz, 2 H) 7.57 (s, 1 H) 7.62 (s, 1 H) 7.67 (s, 1 H) |

-continued

| Example No. | Starting Material | Structure | Mass M + H | 1H NMR |
|---|---|---|---|---|
| 26 | AA-10 | (structure) | 407.3 | (400 MHz, MeOD) δ ppm 4.34 (d, J = 11.25 Hz, 1 H) 4.51-4.61 (m, 1 H) 4.79 (dd, J = 14.31, 4.28 Hz, 1 H) 5.86 (dd, J = 11.20, 3.81 Hz, 1H) 6.92 (t, J = 8.71 Hz, 2 H) 7.02-7.12 (m, 1 H) 7.14-7.30 (m, 4 H) 7.36-7.46 (m, 1 H) 7.47-7.54 (m, 1 H) 7.64 (dd, J = 12.28, 1.47 Hz, 2 H) |
| 27 | AA-11 | (structure) | 421.3 | (400 MHz, MeOD) δ ppm 1.90-2.12 (m, 3 H) 4.46 (d, J = 10.71 Hz, 1 H) 4.55 (d, J = 13.55 Hz, 1 H) 4.77 (dd, J = 14.26, 4.23 Hz, 1 H) 5.90 (dd, J = 10.64, 3.01 Hz, 1 H) 6.74 (dd, J = 9.81, 2.67 Hz, 1 H) 6.86-6.98 (m, 1 H) 6.86-6.98 (m, 1 H) 7.11 (t, J = 8.68 Hz, 2 H) 7.37 (dd, J = 8.66, 5.18 Hz, 2 H) 7.57 (s, 2 H) 7.59 (s, 1 H) 7.63 (dd, J = 8.73, 5.70 Hz, 1 H) |
| 28 | AA-12 | (structure) | 435.3 | (400 MHz, MeOD) δ ppm 2.27-2.42 (m, 3 H) 4.29 (d, J = 10.96 Hz, 1 H) 4.56 (d, J = 14.23 Hz, 1 H) 4.78 (dd, J = 14.26, 4.28 Hz, 1 H) 5.82 (dd, J = 10.91, 3.81 Hz, 1 H) 6.84-7.01 (m, 2 H) 7.02-7.22 (m, 4 H) 7.46 (dd, J = 8.61, 5.23 Hz, 2 H) 7.50 (s, 1 H) 7.62 (d, J = 10.71 Hz, 2 H) |
| 29 | AA-13 | (structure) | 423.3 | (400 MHz, MeOD) δ ppm 4.58 (d, J = 14.13 Hz, 1 H) 4.81 (dd, J = 14.23, 4.06 Hz, 1 H) 4.90 (br s, 1 H) 4.95-4.95 (m, 1 H) 5.91 (dd, J = 11.44, 3.23 Hz, 1 H) 7.10-7.23 (m, 4 H) 7.23-7.33 (m, 1 H) 7.40-7.52 (m, 3 H) 7.61 (d, J = 8.85 Hz, 2 H) 7.68 (d, J = 7.78 Hz, 1 H) |
| 30 | AA-14 | (structure) | 467.2 | (400 MHz, MeOD) δ ppm 7.65 (d, J = 1.42 Hz, 1 H) 7.61 (d, J = 1.42 Hz, 1 H) 7.53 (s, 1 H) 7.45 (dd, J = 8.66, 5.23 Hz, 2 H) 7.30-7.36 (m, 2 H) 7.07-7.19 (m, 4 H) 5.84 (dd, J = 11.00, 3.67 Hz, 1 H) 4.78 (dd, J = 14.33, 4.35 Hz, 1 H) 4.55 (d, J = 14.33 Hz, 1 H) 4.34 (d, J = 11.10 Hz, 1 H) |

-continued

| Example No. | Starting Material | Structure | Mass M + H | 1H NMR |
|---|---|---|---|---|
| 31 | AA-15 | 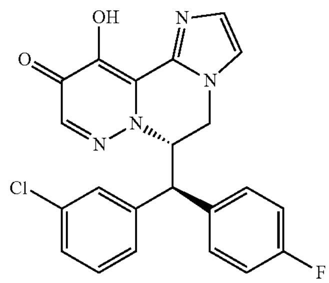 [SMILES: O=c1cnn2c(c1O)-c1nccn1C[C@@H]2[C@@H](c1ccc(F)cc1)c1cccc(Cl)c1] | 423.1 | (400 MHz, MeOD) δ ppm 7.63 (d, J = 1.47 Hz, 1 H) 7.59 (d, J = 1.42 Hz, 1 H) 7.52 (s, 1 H) 7.45 (dd, J = 8.63, 5.21 Hz, 2 H) 7.21 (s, 1 H) 7.12-7.20 (m, 4 H) 7.06-7.11 (m, 1 H) 5.84 (dd, J = 11.10, 3.67 Hz, 1 H) 4.77 (dd, J = 14.28, 4.30 Hz, 1 H) 4.54 (d, J = 14.33 Hz, 1 H) 4.33 (d, J = 11.10 Hz, 1 H) |
| 32 | AA-16 | 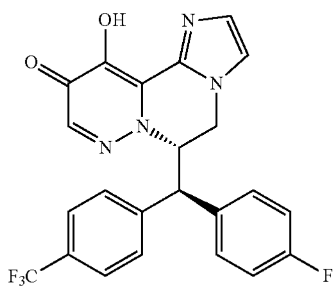 [SMILES: O=c1cnn2c(c1O)-c1nccn1C[C@@H]2[C@@H](c1ccc(F)cc1)c1ccc(C(F)(F)F)cc1] | 457.3 | (400 MHz, MeOD) δ ppm 4.46 (d, J = 11.25 Hz, 1 H) 4.57 (d, J = 14.28 Hz, 1 H) 4.80 (dd, J = 14.31, 4.33 Hz, 1 H) 5.92 (dd, J = 11.18, 3.79 Hz, 1 H) 7.15 (t, J = 8.68 Hz, 2 H) 7.37-7.53 (m, 6 H) 7.63 (s, 1 H) 7.67 (d, J = 1.17 Hz, 1 H) |
| 33 | AA-17 | 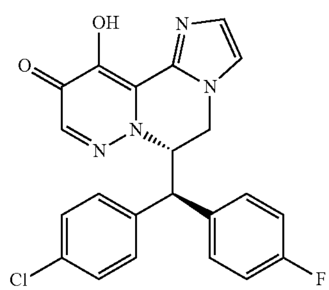 [SMILES: O=c1cnn2c(c1O)-c1nccn1C[C@@H]2[C@@H](c1ccc(F)cc1)c1ccc(Cl)cc1] | 423.3 | (400 MHz, MeOD) δ ppm 7.63 (d, J = 1.42 Hz, 1 H) 7.61-7.66 (m, 1 H) 7.59 (d, J = 1.42 Hz, 1 H) 7.53 (s, 1 H) 7.43 (dd, J = 8.66, 5.23 Hz, 2 H) 7.10-7.22 (m, 6 H) 5.83 (dd, J = 11.18, 3.69 Hz, 1 H) 4.77 (dd, J = 14.31, 4.33 Hz, 1 H) 4.53 (d, J = 14.23 Hz, 1 H) 4.31 (d, J = 11.20 Hz, 1 H) |
| 34 | AA-18 | 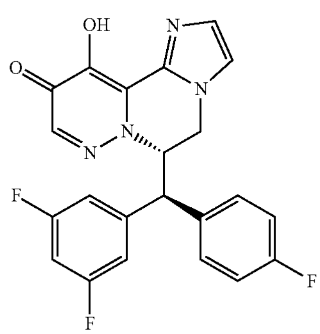 [SMILES: O=c1cnn2c(c1O)-c1nccn1C[C@@H]2[C@@H](c1ccc(F)cc1)c1cc(F)cc(F)c1] | 425.3 | (400 MHz, MeOD) δ ppm 4.34 (br d, J = 14.18 Hz, 1 H) 4.48 (br d, J = 11.59 Hz, 1 H) 4.71 (br dd, J = 14.23, 4.16 Hz, 1 H) 5.94 (dd, J = 11.62, 3.64 Hz, 1 H) 6.96-7.13 (m, 3 H) 7.22 (t, J = 8.78 Hz, 2 H) 7.41-7.58 (m, 3 H) 7.65 (d, J = 1.13 Hz, 1 H) 7.70 (d, J = 1.17 Hz, 1 H) |
| 35 | AA-19 | 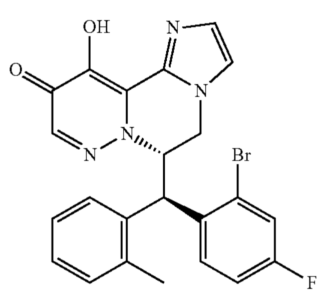 [SMILES: Cc1ccccc1[C@H](c1ccc(F)cc1Br)[C@H]1Cn2ccnc2-c2c(O)c(=O)cnn21] | 481.2 | (500 MHz, CD3OD) δ 7.11 (dd, J = 9.0, 5.8 Hz, 1H), 6.83-6.73 (m, 4H), 6.64 (dd, J = 8.3, 2.6 Hz, 1H), 6.53-6.45 (m, 1H), 6.41 (t, J = 7.8 Hz, 1H), 6.35-6.30 (m, 1H), 6.22 (d, J = 7.6 Hz, 1H), 5.09 (d, J = 9.7 Hz, 1H), 4.27 (d, J = 9.7 Hz, 1H), 4.04-4.01 (m, 1H), 3.96-3.86 (m, 1H), 1.24 (s, 3H). |

-continued

| Example No. | Starting Material | Structure | Mass M + H | 1H NMR |
|---|---|---|---|---|
| 36 | AA-20 | (structure) | 487.2 | (500 MHz, CD3OD) δ 7.21 (dd, J = 8.8, 5.7 Hz, 1H), 6.88-6.83 (m, 2H), 6.73-6.66 (m, 2H), 6.57 (td, J = 8.3, 2.6 Hz, 1H), 6.45-6.38 (m, 1H), 6.26-6.20 (m, 1H), 6.15 (t, J = 8.8 Hz, 2H), 5.12 (dd, J = 11.2, 3.8 Hz, 1H), 4.01 (dd, J = 14.5, 4.1 Hz, 1H), 3.96 (d, J = 11.2 Hz, 1H), 3.74 (d, J = 14.4 Hz, 1H). |
| 37 | AA-21 | (structure) | 469.2 | (500 MHz, CD3OD) δ 6.94 (d, J = 6.4 Hz, 1H), 6.89-6.84 (m, 2H), 6.69 (d, J = 2.0 Hz, 2H), 6.46 (t, J = 8.5 Hz, 1H), 6.40 (dd, J = 5.5, 1.7 Hz, 3H), 6.35 (d, J = 6.1 Hz, 2H), 5.09 (d, J = 9.7 Hz, 1H), 4.03-3.98 (m, 1H), 3.83 (d, J = 14.3 Hz, 1H), 3.56 (d, J = 11.0 Hz, 1H). |
| 38 | AA-22 | (structure) | 403.3 | (500 MHz, CD3OD) δ 6.80 (t, J = 10.1 Hz, 3H), 6.74 (d, J = 2.1 Hz, 1H), 6.62-6.55 (m, 2H), 6.39 (t, J = 7.5 Hz, 1H), 6.34-6.26 (m, 3H), 6.19 (d, J = 7.5 Hz, 1H), 5.13 (d, J = 10.9 Hz, 1H), 4.00 (d, J = 15.3 Hz, 1H), 3.79 (d, J = 14.0 Hz, 1H), 3.72 (d, J = 10.4 Hz, 1H), 1.19 (s, 3H). |
| 39 | AA-23 | (structure) | 487.0 | (500 MHz, CD3OD) δ 7.27-7.17 (m, 1H), 6.89-6.84 (m, 2H), 6.71 (d, J = 2.6 Hz, 1H), 6.67 (dt, J = 8.4, 2.7 Hz, 1H), 6.56 (td, J = 8.3, 2.8 Hz, 1H), 6.40 (ddd, J = 8.2, 5.1, 2.5 Hz, 2H), 6.14 (td, J = 9.0, 2.5 Hz, 2H), 5.10 (dd, J = 11.4, 3.7 Hz, 1H), 4.04-3.98 (m, 1H), 3.93 (dd, J = 11.4, 2.4 Hz, 1H), 3.75 (d, J = 14.2 Hz, 1H). |
| 40 | AA-24 | (structure) | 403.4 | (500 MHz, CD3OD) δ 6.80 (t, J = 10.1 Hz, 3H), 6.74 (d, J = 2.1 Hz, 1H), 6.59 (dd, J = 8.5, 5.2 Hz, 2H), 6.39 (t, J = 7.5 Hz, 1H), 6.30 (dt, J = 18.7, 7.9 Hz, 3H), 6.19 (d, J = 7.9 Hz, 1H), 5.13 (d, J = 10.9 Hz, 1H), 4.00 (d, J = 13.0 Hz, 1H), 3.80 (d, J = 14.5 Hz, 1H), 3.72 (d, J = 10.5 Hz, 1H), 1.19 (s, 3H). |

-continued

| Example No. | Starting Material | Structure | Mass M + H | 1H NMR |
|---|---|---|---|---|
| 41 | AA-25 | 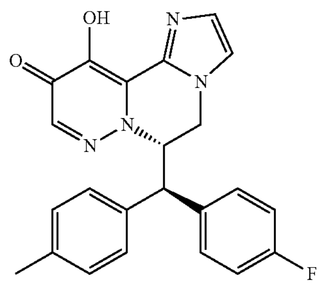 [SMILES: Cc1ccc([C@H](c2ccc(F)cc2)[C@H]2Cn3ccnc3-c3c(O)c(=O)cnn32)cc1] | 403.3 | (500 MHz, CD3OD) δ 6.84 (d, J = 1.6 Hz, 1H), 6.81 (t, J = 1.7 Hz, 1H), 6.71 (d, J = 2.4 Hz, 1H), 6.63 (dd, J = 8.6, 5.3 Hz, 2H), 6.36-6.31 (m, 2H), 6.25-6.18 (m, 4H), 5.07-4.98 (m, 1H), 3.98 (dd, J = 14.4, 4.3 Hz, 1H), 3.77 (d, J = 14.1 Hz, 1H), 3.45 (d, J = 10.9 Hz, 1H), 1.45 (d, J = 2.5 Hz, 3H). |
| 42 | AA-26 | 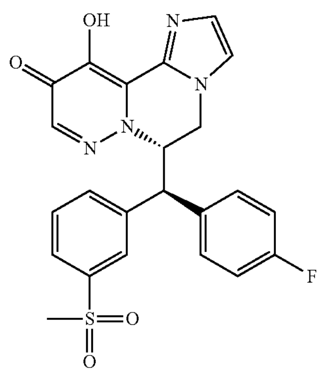 [SMILES: CS(=O)(=O)c1cccc([C@H](c2ccc(F)cc2)[C@H]2Cn3ccnc3-c3c(O)c(=O)cnn32)c1] | 467.1 | (400 MHz, MeOD) δ ppm 3.03 (s, 3 H) 4.48-4.60 (m, 2 H) 4.79 (br dd, J = 14.23, 4.21 Hz, 1 H) 5.92 (dd, J = 11.30, 3.86 Hz, 1 H) 7.18 (t, J = 8.66 Hz, 2 H) 7.42-7.55 (m, 4 H) 7.56-7.63 (m, 2 H) 7.65 (s, 1 H) 7.71-7.82 (m, 2 H) |
| 43 | AA-28 | 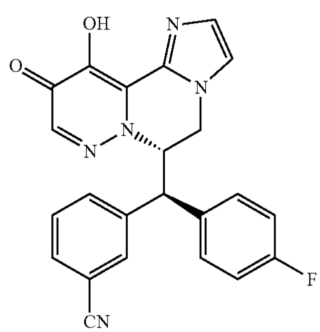 [SMILES: N#Cc1cccc([C@H](c2ccc(F)cc2)[C@H]2Cn3ccnc3-c3c(O)c(=O)cnn32)c1] | 414.3 | (400 MHz, MeOD) δ ppm 4.45 (d, J = 11.40 Hz, 1 H) 4.56 (d, J = 14.43 Hz, 1 H) 4.79 (dd, J = 14.33, 4.30 Hz, 1 H) 5.93 (dd, J = 11.32, 3.74 Hz, 1 H) 7.17 (t, J = 8.66 Hz, 2 H) 7.34-7.42 (m, 1 H) 7.43-7.52 (m, 3 H) 7.52-7.58 (m, 2 H) 7.63-7.68 (m, 2 H) 7.68-7.71 (m, 1 H) |
| 44 | AA-29 | 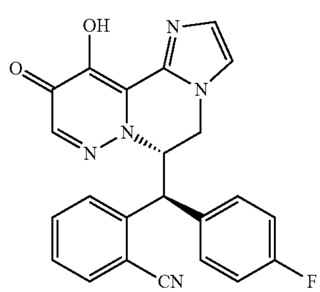 [SMILES: N#Cc1ccccc1[C@H](c1ccc(F)cc1)[C@H]1Cn2ccnc2-c2c(O)c(=O)cnn21] | 414.3 | (400 MHz, MeOD) δ ppm 4.57-4.71 (m, 2 H) 4.76-4.84 (m, 1 H) 5.98 (br dd, J = 11.66, 3.01 Hz, 1 H) 7.12-7.26 (m, 3 H) 7.34-7.40 (m, 1 H) 7.41 (s, 1 H) 7.47-7.56 (m, 3 H) 7.59-7.68 (m, 3 H) 7.84 (d, J = 8.12 Hz, 1 H) |
| 45 | AA-27 | 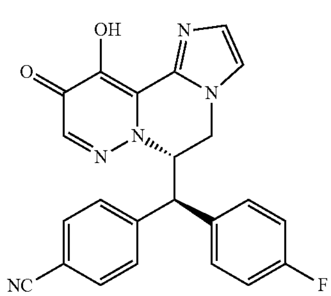 [SMILES: N#Cc1ccc([C@H](c2ccc(F)cc2)[C@H]2Cn3ccnc3-c3c(O)c(=O)cnn32)cc1] | 414.3 | (400 MHz, MeOD) δ ppm 7.67 (d, J = 1.56 Hz, 1 H) 7.62 (d, J = 1.47 Hz, 1 H) 7.56 (d, J = 8.31 Hz, 2 H) 7.51 (s, 1 H) 7.40-7.49 (m, 4 H) 7.12-7.21 (m, 2 H) 5.92 (dd, J = 11.20, 3.62 Hz, 1 H) 4.79 (dd, J = 14.35, 4.33 Hz, 1 H) 4.55 (d, J = 14.38 Hz, 1 H) 4.46 (d, J = 11.35 Hz, 1 H) |

| Example No. | Starting Material | Structure | Mass M + H | 1H NMR |
|---|---|---|---|---|
| 46 | AA-30 | (structure shown) | 414.3 | (400 MHz, MeOD) δ ppm 4.47 (d, J = 11.44 Hz, 1 H) 4.57 (d, J = 14.28 Hz, 1 H) 4.81 (dd, J = 14.38, 4.25 Hz, 1 H) 5.91-6.02 (m, 1 H) 7.06-7.20 (m, 1 H) 7.24-7.32 (m, 2 H) 7.34-7.52 (m, 3 H) 7.57 (d, J = 8.02 Hz, 2 H) 7.60-7.73 (m, 3 H) |

Example 47. (S)-6-(bis(4-fluorophenyl)methyl)-2,3-dibromo-11-hydroxy-5,6-dihydro-10H-imidazo[2',1':3,4]pyrazino[1,2-b]pyridazin-10-one

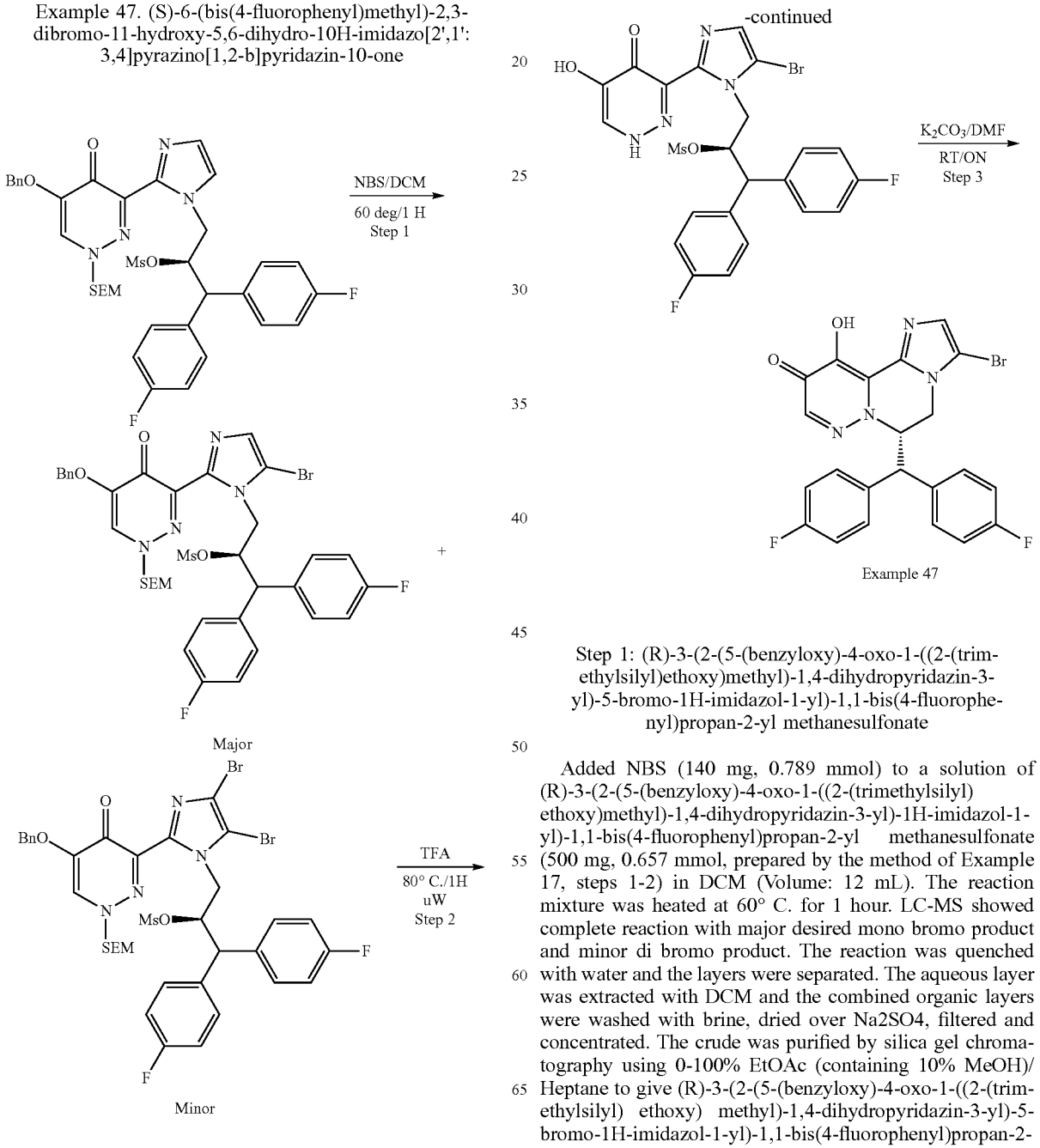

Step 1: (R)-3-(2-(5-(benzyloxy)-4-oxo-1-((2-(trimethylsilyl)ethoxy)methyl)-1,4-dihydropyridazin-3-yl)-5-bromo-1H-imidazol-1-yl)-1,1-bis(4-fluorophenyl)propan-2-yl methanesulfonate Added NBS (140 mg, 0.789 mmol) to a solution of (R)-3-(2-(5-(benzyloxy)-4-oxo-1-((2-(trimethylsilyl)ethoxy)methyl)-1,4-dihydropyridazin-3-yl)-1H-imidazol-1-yl)-1,1-bis(4-fluorophenyl)propan-2-yl methanesulfonate (500 mg, 0.657 mmol, prepared by the method of Example 17, steps 1-2) in DCM (Volume: 12 mL). The reaction mixture was heated at 60° C. for 1 hour. LC-MS showed complete reaction with major desired mono bromo product and minor di bromo product. The reaction was quenched with water and the layers were separated. The aqueous layer was extracted with DCM and the combined organic layers were washed with brine, dried over Na2SO4, filtered and concentrated. The crude was purified by silica gel chromatography using 0-100% EtOAc (containing 10% MeOH)/Heptane to give (R)-3-(2-(5-(benzyloxy)-4-oxo-1-((2-(trimethylsilyl) ethoxy) methyl)-1,4-dihydropyridazin-3-yl)-5-bromo-1H-imidazol-1-yl)-1,1-bis(4-fluorophenyl)propan-2- yl methanesulfonate as a yellow solid, (350 mg, 0.437 mmol, 66.4% yield). LCMS: MH+ 801.4, 1.17 min.

Step 2: (R)-3-(5-bromo-2-(5-hydroxy-4-oxo-1,4-dihydropyridazin-3-yl)-1H-imidazol-1-yl)-1,1-bis(4-fluorophenyl)propan-2-yl methanesulfonate Added TFA (1 mL, 13 mmol) to (R)-3-(2-(5-(benzyloxy)-4-oxo-1-((2-(trimethylsilyl) ethoxy) methyl)-1, 4-dihydro-pyridazin-3-yl)-5-bromo-1H-imidazol-1-yl)-1,1-bis(4-fluorophenyl)propan-2-yl methanesulfonate (55 mg, 0.069 mmol). Heated in microwave at 80° C. for 60 min. LC-MS showed complete reaction. Solvent was evaporated and azeotroped with toluene. LCMS: MH+ 581.2, 0.80 min. Proceed to next step without further purification.

Step 3: (S)-6-(bis(4-fluorophenyl)methyl)-3-bromo-11-hydroxy-5,6-dihydro-10H-imidazo [2',1':3,4] pyrazino[1,2-b]pyridazin-10-one To (R)-3-(5-bromo-2-(5-hydroxy-4-oxo-1,4-dihydro-pyridazin-3-yl)-1H-imidazol-1-yl)-1,1-bis(4-fluorophenyl) propan-2-yl methanesulfonate (14.0 mg, 0.024 mmol) in DMF (Volume: 1 mL) was added potassium carbonate (11.6 mg, 0.0.084 mmol) at RT. Reaction mixture was stirred at RT overnight. LC-MS showed complete reaction. The reaction mixture was filtered and the crude solution was purified by prep HPLC to obtain (S)-6-(bis(4-fluorophenyl)methyl)-3-bromo-11-hydroxy-5,6-dihydro-10H-imidazo[2',1':3,4] pyrazino[1,2-b]pyridazin-10-one as a TFA salt, (4.2 mg, 6.87 μmol, 28.3% yield). LCMS (m/z): 485.3 (MH+), 0.85 min, 1H NMR (400 MHz, CD₃OD) δ ppm 4.19 (d, J=11.35 Hz, 1H) 4.27 (d, J=13.89 Hz, 1H) 4.54 (dd, J=13.96, 4.08 Hz, 1H) 5.81 (dd, J=11.27, 3.50 Hz, 1H) 6.89-6.97 (m, 2H) 7.15 (t, J=8.68 Hz, 2H) 7.23 (dd, J=8.61, 5.23 Hz, 2H) 7.44 (dd, J=8.58, 5.26 Hz, 2H) 7.50 (s, 1H) 7.53 (s, 1H).

Example 48. (S)-6-(bis(4-fluorophenyl)methyl)-2,3-dibromo-11-hydroxy-5,6-dihydro-10H-imidazo[2',1':3,4]pyrazino[1,2-b]pyridazin-10-one

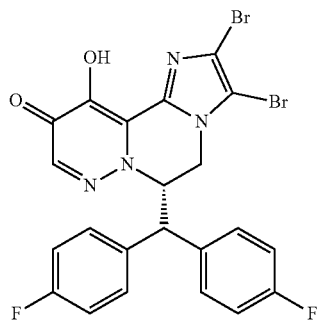 [SMILES: O=c1cnn2c(c1O)-c1nc(Br)c(Br)n1C[C@@H]2C(c1ccc(F)cc1)c1ccc(F)cc1]

Prepared by the method of Example 47.

LCMS (m/z): 563.3 (MH+), 0.97 min, 1H NMR (400 MHz, CD3OD) δ ppm 4.13-4.30 (m, 2H) 4.50-4.64 (m, 1H) 5.76 (br dd, J=11.18, 2.91 Hz, 1H) 6.91 (t, J=8.63 Hz, 2H) 7.14 (t, J=8.66 Hz, 2H) 7.22 (dd, J=8.49, 5.31 Hz, 2H) 7.38-7.53 (m, 3H).

Example 49. (S)-6-(bis(4-fluorophenyl)methyl)-11-hydroxy-10-oxo-5,6-dihydro-10H-imidazo[2',1':3,4]pyrazino[1,2-b]pyridazine-3-carbonitrile

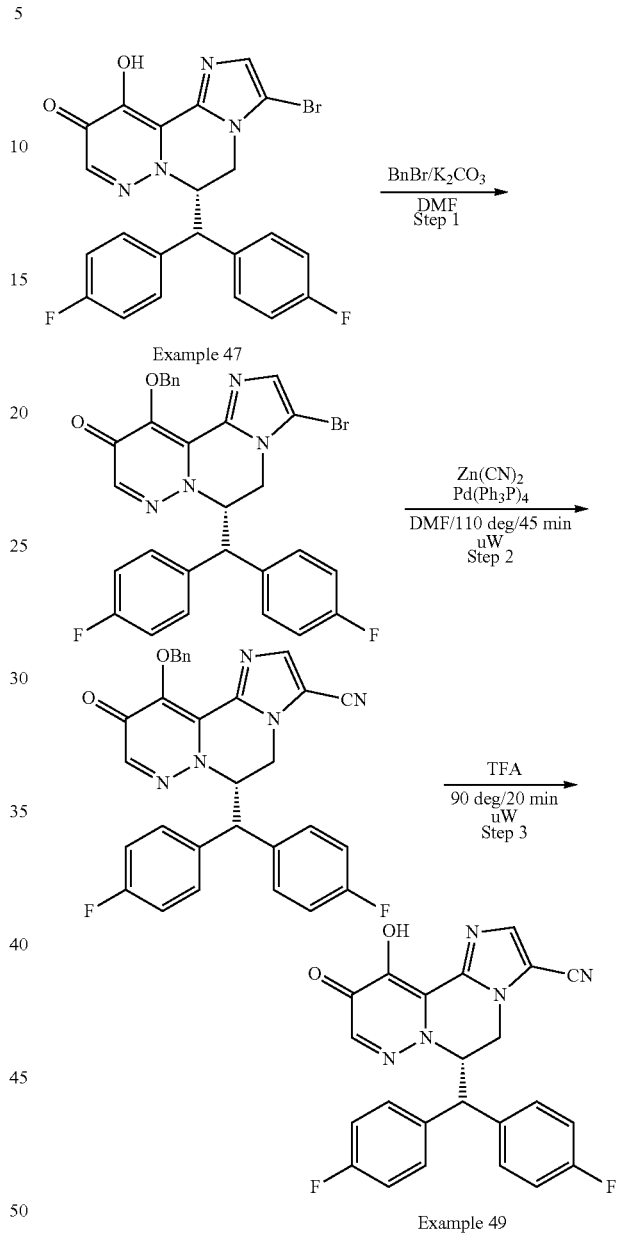

Example 49

Step 1: (S)-11-(benzyloxy)-6-(bis(4-fluorophenyl) methyl)-3-bromo-5H-imidazo [2',1':3,4] pyrazino[1,2-b]pyridazin-10(6H)-one To crude (S)-6-(bis(4-fluorophenyl)methyl)-3-bromo-11-hydroxy-5,6-dihydro-10H-imidazo [2',1':3,4]pyrazino[1,2-b]pyridazin-10-one (Example 47, 209 mg, 0.431 mmol) in DMF (Volume: 5 mL) was added potassium carbonate (208 mg, 1.507 mmol) and benzyl bromide (0.128 mL, 1.077 mmol) at RT. Reaction mixture was stirred at RT overnight. LC-MS showed complete reaction. The reaction mixture was partitioned between EtOAc/water. The EtOAc layer was separated and washed with brine. Dried over sodium sulfate, filtered and evaporated. The crude was purified by silica gel chromatography using 0-100% EtOAc (contains 10% MeOH)/Heptane to give (S)-11-(benzyloxy)-6-(bis(4-fluorophenyl)methyl)-3-bromo-5H-imidazo [2',1':3,4] pyrazino[1,2-b]pyridazin-10(6H)-one, (190 mg, 0.297 mmol, 69% yield). LCMS: MH+ 575.2, 1.12 min.

Step 2: (S)-11-(benzyloxy)-6-(bis(4-fluorophenyl)methyl)-10-oxo-6,10-dihydro-5H-imidazo [2',1':3,4]pyrazino[1,2-b]pyridazine-3-carbonitrile To (S)-11-(benzyloxy)-6-(bis(4-fluorophenyl)methyl)-3-bromo-5H-imidazo [2',1':3,4] pyrazino[1,2-b]pyridazin-10 (6H)-one (20 mg, 0.035 mmol) in DMF (Volume: 1 mL) was added Zn(CN)2 (12.24 mg, 0.104 mmol) and Pd(Ph3P)4 (6.02 mg, 5.21 μmol). Purged with N2 and reaction mixture was heated in microwave at 100° C. for 60 min. LC-MS showed major desired product and minor SM. Reaction was stopped. The reaction mixture was partitioned between EtOAc/water. The EtOAc layer was separated and washed with brine. Dried over sodium sulfate, filtered and evaporated. The crude (S)-11-(benzyloxy)-6-(bis(4-fluorophenyl)methyl)-10-oxo-6,10-dihydro-5H-imidazo[2',1':3,4]pyrazino[1,2-b]pyridazine-3-carbonitrile was used in the next step. LCMS: MH+ 522.2, 1.06 min.

Step 3: (S)-6-(bis(4-fluorophenyl)methyl)-11-hydroxy-10-oxo-5,6-dihydro-10H-imidazo [2',1':3,4] pyrazino[1,2-b]pyridazine-3-carbonitrile To crude (S)-11-(benzyloxy)-6-(bis(4-fluorophenyl)methyl)-10-oxo-6,10-dihydro-5H-imidazo[2',1':3,4]pyrazino[1,2-b]pyridazine-3-carbonitrile was added TFA (1 mL). Reaction mixture was heated at 90° C./20 min in microwave. LC-MS showed complete reaction. The solvent was evaporated and azeotroped with toluene. The crude was dissolved in DMSO and purified through prep-HPLC using ACN/Water/0.1% TFA to obtain (S)-6-(bis(4-fluorophenyl)methyl)-11-hydroxy-10-oxo-5,6-dihydro-10H-imidazo [2',1':3,4]pyrazino[1,2-b]pyridazine-3-carbonitrile as a TFA salt, (3.5 mg, 6.22 μmol, 18% yield). LCMS (m/z): 432.2 (MH+), 0.92 min, 1H NMR (400 MHz, CD3OD) δ ppm 4.16 (br d, J=11.25 Hz, 1H) 4.27 (br d, J=13.94 Hz, 1H) 4.72 (br dd, J=14.06, 3.69 Hz, 1H) 5.81 (br dd, J=11.27, 3.20 Hz, 1H) 6.92 (br t, J=8.68 Hz, 2H) 7.13-7.27 (m, 4H) 7.37-7.55 (m, 3H) 8.08 (s, 1H).

Example 50: (S)-6-(bis(4-fluorophenyl)methyl)-11-hydroxy-3-(hydroxymethyl)-5,6-dihydro-10H-imidazo[2',1:3,4]pyrazino[1,2-b]pyridazin-10-one

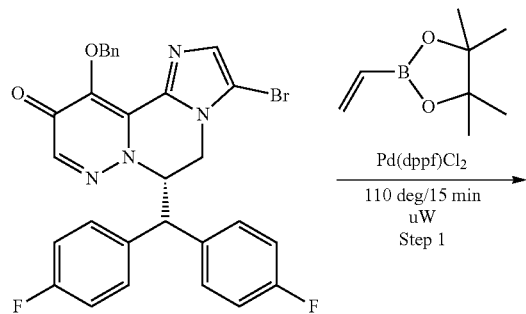

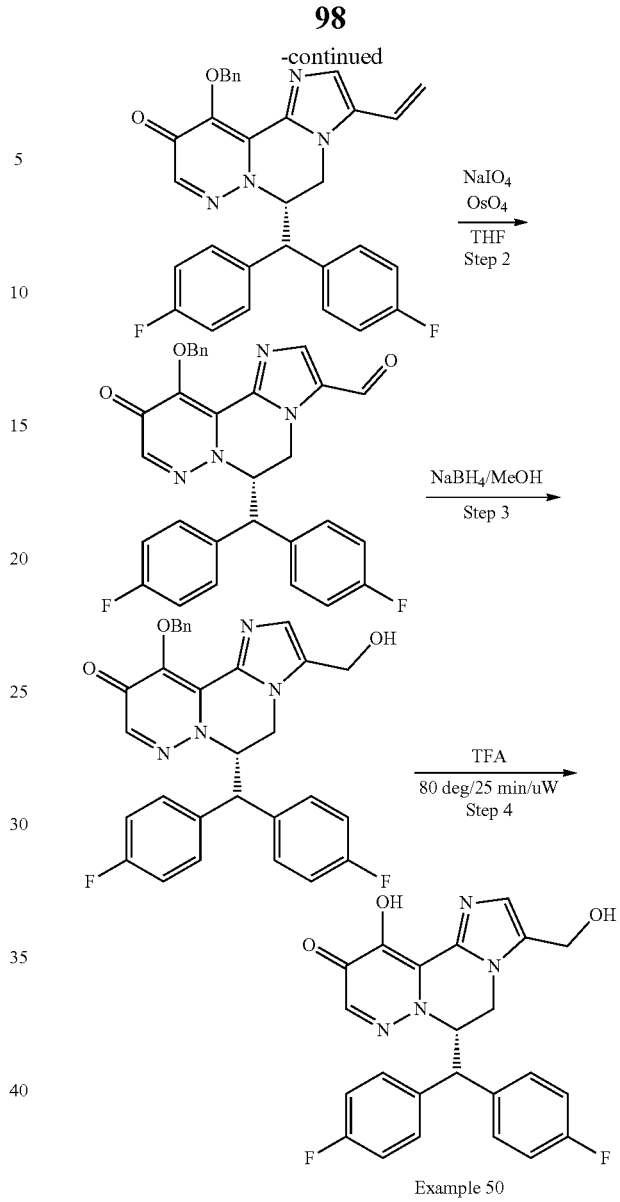

Example 50

Step 1: (S)-11-(benzyloxy)-6-(bis(4-fluorophenyl)methyl)-3-vinyl-5H-imidazo [2',1':3,4] pyrazino[1,2-b]pyridazin-10(6H)-one To (S)-11-(benzyloxy)-6-(bis(4-fluorophenyl)methyl)-3-bromo-5H-imidazo [2',1':3,4] pyrazino[1,2-b]pyridazin-10 (6H)-one (For synthesis see Example 49 Step 1, 90 mg, 0.156 mmol) and 4,4,5,5-tetramethyl-2-vinyl-1,3,2-dioxaborolane (48.2 mg, 0.312 mmol) in DME (Volume: 2 mL) and aqueous sodium carbonate (1 M, 400 μL, 0.400 mmol) was added PdCl2(dppf).CH2Cl2 adduct (12.8 mg, 0.0156 mmol). Reaction mixture was heated in microwave at 110° C. for 15 min. LC-MS showed complete reaction. Reaction mixture was partitioned between EtOAc and water. The organic layer was separated, dried over sodium sulfate, filtered and concentrated. The crude was purified by silica gel chromatography using 0-100% EtOAc (contains 10% MeOH)/Heptane to give (S)-11-(benzyloxy)-6-(bis(4-fluorophenyl)methyl)-3-vinyl-5H-imidazo [2',1':3,4] pyrazino [1,2-b]pyridazin-10(6H)-one, (52 mg, 0.100 mmol, 64% yield) as a light brown solid. LCMS: MH+ 523.3, 0.93 min.

Step 2: (S)-11-(benzyloxy)-6-(bis(4-fluorophenyl) methyl)-10-oxo-6,10-dihydro-5H-imidazo [2',1':3,4] pyrazino[1,2-b]pyridazine-3-carbaldehyde To (S)-11-(benzyloxy)-6-(bis(4-fluorophenyl)methyl)-3-vinyl-5H-imidazo [2',1':3,4] pyrazino [1,2-b]pyridazin-10 (6H)-one (52 mg, 0.100 mmol) in THF (Volume: 2 mL) was added sodium periodate (53.2 mg, 0.249 mmol) and osmium tetroxide (0.117 mL, 0.015 mmol) (4% solution in water). Reaction mixture was stirred at RT for 2H. Added 1 eq more of sodium periodate and stirred further 30 min. LCMS showed complete reaction. The ppt was filtered off, washed with methanol and the filtrate was concentrated. The residue was partitioned between EtOAc and saturated NaHCO₃ solution. The organic layer was separated, dried over sodium sulfate, filtered and concentrated to give crude (S)-11-(benzyloxy)-6-(bis(4-fluorophenyl)methyl)-10-oxo-6,10-dihydro-5H-imidazo [2',1':3,4]pyrazino[1,2-b]pyridazine-3-carbaldehyde, LCMS: MH+ 525.3, 1.07 min.

Step 3: (S)-11-(benzyloxy)-6-(bis(4-fluorophenyl) methyl)-3-(hydroxymethyl)-5H-imidazo [2',1':3,4] pyrazino[1,2-b]pyridazin-10(6H)-one The crude (S)-11-(benzyloxy)-6-(bis (4-fluorophenyl) methyl)-10-oxo-6,10-dihydro-5H-imidazo [2',1':3,4] pyrazino[1,2-b]pyridazine-3-carbaldehyde (52 mg, 0.100 mmol) from step 2 was taken up in MeOH (Volume: 3 mL). The reaction mixture was cooled in ice bath then added sodium borohydride (5.27 mg, 0.139 mmol). The reaction was stirred at ice bath temperature for 30 min. LC-MS showed complete reaction. The solvent was evaporated. The crude reaction mixture was partitioned between EtOAc and saturated NaHCO₃ solution. The organic layer was separated, dried over sodium sulfate, filtered and evaporated to give crude (S)-11-(benzyloxy)-6-(bis(4-fluorophenyl) methyl)-3-(hydroxymethyl)-5H-imidazo [2',1':3,4]pyrazino [1,2-b]pyridazin-10(6H)-one, LCMS: MH+ 527.3, 0.89 min.

Step 4: (S)-6-(bis(4-fluorophenyl)methyl)-11-hydroxy-3-(hydroxymethyl)-5H-imidazo [2',1':3,4] pyrazino[1,2-b]pyridazin-10(6H)-one To crude (S)-11-(benzyloxy)-6-(bis(4-fluorophenyl) methyl)-3-(hydroxymethyl)-5H-imidazo [2',1':3,4]pyrazino [1,2-b]pyridazin-10(6H)-one from step 3 (52 mg, 0.100 mmol) was added trifluoroacetic acid (1 ml, 13 mmol). The solution was then heated at 80° C. for 25 min in microwave. The reaction was concentrated in vacuo and azeotroped with toluene. The crude was purified by prep HPLC to obtain (S)-6-(bis (4-fluorophenyl) methyl)-11-hydroxy-3-(hydroxymethyl)-5H-imidazo [2',1':3,4] pyrazino[1,2-b] pyridazin-10(6H)-one as a TFA salt, (5.2 mg, 9.26 μmol, 18.7% yield). LCMS (m/z): 437.3 (MH+), 0.76 min, 1H NMR (400 MHz, CD3OD) δ ppm 4.29 (d, J=11.05 Hz, 1H) 4.39 (d, J=13.84 Hz, 1H) 4.52-4.62 (m, 2H) 4.63-4.73 (m, 1H) 5.81 (dd, J=11.00, 3.52 Hz, 1H) 6.91 (t, J=8.71 Hz, 2H) 7.07-7.26 (m, 4H) 7.46 (dd, J=8.58, 5.26 Hz, 2H) 7.53 (d, J=5.62 Hz, 2H).

Example 51: (S)-6-((S)-(4-fluorophenyl)(o-tolyl) methyl)-11-hydroxy-3-(hydroxymethyl)-5,6-dihydro-10H-imidazo[2',1':3,4]pyrazino[1,2-b] pyridazin-10-one

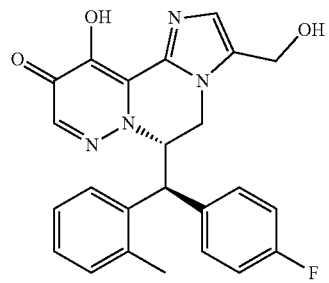 [SMILES: Cc1ccccc1[C@H](c1ccc(F)cc1)[C@H]1Cn2c(CO)cnc2-c2c(O)c(=O)cnn21]

Prepared by the method of Example 50. LCMS (m/z): 433.3 (MH+), 0.76 min, 1H NMR (400 MHz, CD3OD) δ ppm 1.97 (s, 3H) 4.38 (d, J=13.74 Hz, 1H) 4.49 (s, 1H) 4.50-4.54 (m, 1H) 4.57 (s, 1H) 4.60 (s, 1H) 4.66 (br dd, J=14.18, 4.16 Hz, 1H) 5.89 (br dd, J=10.69, 3.30 Hz, 1H) 6.96 (br d, J=7.58 Hz, 1H) 7.02-7.13 (m, 3H) 7.17 (br t, J=7.78 Hz, 1H) 7.35-7.45 (m, 3H) 7.48 (s, 1H) 7.66 (br d, J=7.83 Hz, 1H).

Example 52: (S)-6-benzhydryl-11-hydroxy-3-(1H-pyrazol-4-yl)-5,6-dihydro-10H-imidazo[1,2-a]pyrido[2,1-c]pyrazin-10-one

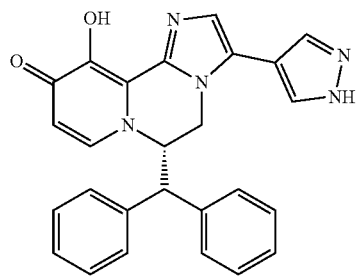 [SMILES: O=c1ccn2c(c1O)-c1ncc(-c3cn[nH]c3)n1C[C@@H]2C(c1ccccc1)c1ccccc1]

Prepared by the method of Example 9, steps 1 and 3 using tert-butyl 4-(4,4,5,5-tetra methyl-1,3,2-dioxaborolan-2-yl)-1H-pyrazole-1-carboxylate LCMS (m/z): 436.3 (MH+), 0.58 min, 1H NMR (400 MHz, CD3OD) δ ppm 7.68 (s, 1H) 7.21-7.47 (m, 14H) 6.18 (d, J=7.14 Hz, 1H) 5.73 (br dd, J=11.47, 2.71 Hz, 1H) 4.58 (dd, J=14.01, 3.74 Hz, 1H) 4.41 (d, J=13.74 Hz, 1H) 4.15 (d, J=11.54 Hz, 1H).

Example 53: (S)-6-benzhydryl-11-hydroxy-3-phenyl-5H-imidazo [1,2-a] pyrido[2,1-c]pyrazin-10(6H)-one

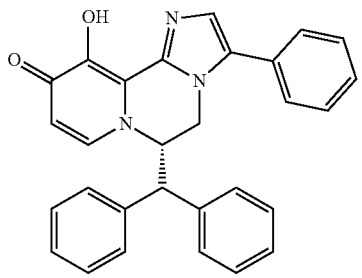 [SMILES: O=c1ccn2c(c1O)-c1ncc(-c3ccccc3)n1C[C@@H]2C(c1ccccc1)c1ccccc1]

Prepared by the method of Example 9, steps 1 and 3 using 4,4,5,5-tetramethyl-2-phenyl-1,3,2-dioxaborolane. LCMS (m/z): 446.3 (MH+), 0.73 min, 1H NMR (400 MHz, CD3OD) δ ppm 7.65 (s, 1H) 7.36-7.44 (m, 3H) 7.30-7.36 (m, 3H) 7.26-7.29 (m, 1H) 7.19-7.26 (m, 5H) 7.05-7.15 (m, 2H) 6.15 (d, J=7.14 Hz, 1H) 5.69 (br dd, J=11.64, 2.69 Hz, 1H) 4.59 (br dd, J=13.94, 3.72 Hz, 1H) 4.40 (br d, J=13.89 Hz, 1H) 4.18 (d, J=11.59 Hz, 1H).

Example 54: (S)-6-benzhydryl-11-hydroxy-3-(hydroxymethyl)-5, 6-dihydro-10H-imidazo [1,2-a] pyrido[2,1-c]pyrazin-10-one

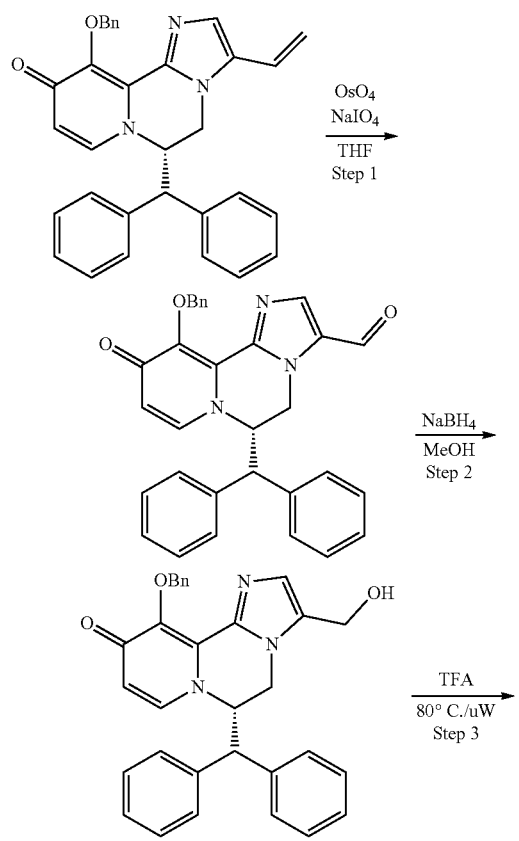

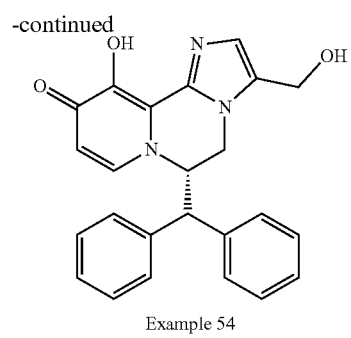

Example 54

Step 1: (S)-6-benzhydryl-11-(benzyloxy)-10-oxo-6,10-dihydro-5H-imidazo[1,2-a]pyrido[2,1-c]pyrazine-3-carbaldehyde To (S)-6-benzhydryl-11-(benzyloxy)-3-vinyl-5H-imidazo [1, 2-a]pyrido [2,1-c]pyrazin-10(6H)-one (50 mg, 0.103 mmol) in THF (Volume: 3 mL) was added sodium periodate (55.1 mg, 0.257 mmol) and osmium tetroxide (0.121 mL, 0.015 mmol) (4% solution in water). Reaction mixture was stirred at RT/2H. Added 1 eq more of sodium periodate and stirred further 30 min. LCMS showed complete reaction. The ppt was filtered off, washed with methanol and evaporated. The residue was partitioned between EtOAc/Satd. NaHCO₃ solution. The organic layer was separated, dried over sodium sulfate, filtered and evaporated to give crude (S)-6-benzhydryl-11-(benzyloxy)-10-oxo-6,10-dihydro-5H-imidazo[1,2-a]pyrido[2,1-c]pyrazine-3-carbaldehyde, LCMS: MH+ 488.3, 0.83 min.

Step 2: (S)-6-benzhydryl-11-(benzyloxy)-3-(hydroxymethyl)-5H-imidazo [1,2-a]pyrido[2,1-c]pyrazin-10(6H)-one The crude (S)-6-benzhydryl-11-(benzyloxy)-10-oxo-6,10-dihydro-5H-imidazo[1,2-a]pyrido[2,1-c]pyrazine-3-carbaldehyde (50 mg, 0.103 mmol) from step 2 was taken in MeOH (Volume: 3.00 mL). The reaction mixture was cooled in ice bath then added sodium borohydride (5.45 mg, 0.144 mmol). RM was stirred in ice bath 30 min. LC-MS showed complete reaction. The solvent was evaporated. The crude reaction mixture was partitioned between EtOAc/Satd. NaHCO₃ solution. The organic layer was separated, dried over sodium sulfate, filtered and evaporated to give crude (S)-6-benzhydryl-11-(benzyloxy)-3-(hydroxymethyl)-5H-imidazo [1,2-a]pyrido[2,1-c]pyrazin-10(6H)-one, LCMS: MH+ 490.3, 0.76 min.

Step 3: (S)-6-benzhydryl-11-(benzyloxy)-3-(hydroxymethyl)-5H-imidazo [1,2-a]pyrido[2,1-c]pyrazin-10(6H)-one To crude (S)-6-benzhydryl-11-(benzyloxy)-3-(hydroxymethyl)-5H-imidazo [1,2-a]pyrido[2,1-c]pyrazin-10(6H)-one from step 3 (25 mg, 0.036 mmol) was added trifluoroacetic acid (1 ml, 12.98 mmol). The solution was then heated at 80° C. for 25 min in microwave. The reaction was concentrated in vacuo and azeotrope with toluene. The crude was purified by Prep HPLC to obtain (S)-6-benzhydryl-11-(benzyloxy)-3-(hydroxymethyl)-5H-imidazo [1,2-a]pyrido[2,1-c] pyrazin-10(6H)-one as a TFA salt, (3.2 mg, 5.98 μmol, 16.7% yield). LCMS (m/z): 400.3 (MH+), 0.59 min, 1H NMR (400 MHz, CD3OD) δ ppm 3.34 (s, 1H) 4.12 (d, J=11.54 Hz, 1H) 4.23 (d, J=13.89 Hz, 1H) 4.49-4.53 (m, 1H) 4.53-4.63 (m, 2H) 5.70 (br d, J=13.45 Hz, 1H) 6.10 (d, J=7.19 Hz, 1H) 7.21 (s, 4H) 7.26 (d, J=7.24 Hz, 1H) 7.33-7.39 (m, 1H) 7.39-7.48 (m, 4H) 7.56 (s, 1H).

Example 55: (6S)-6-benzhydryl-11-hydroxy-3-(1-hydroxyethyl)-5H-imidazo [1,2-a]pyrido[2,1-c]pyrazin-10(6H)-one

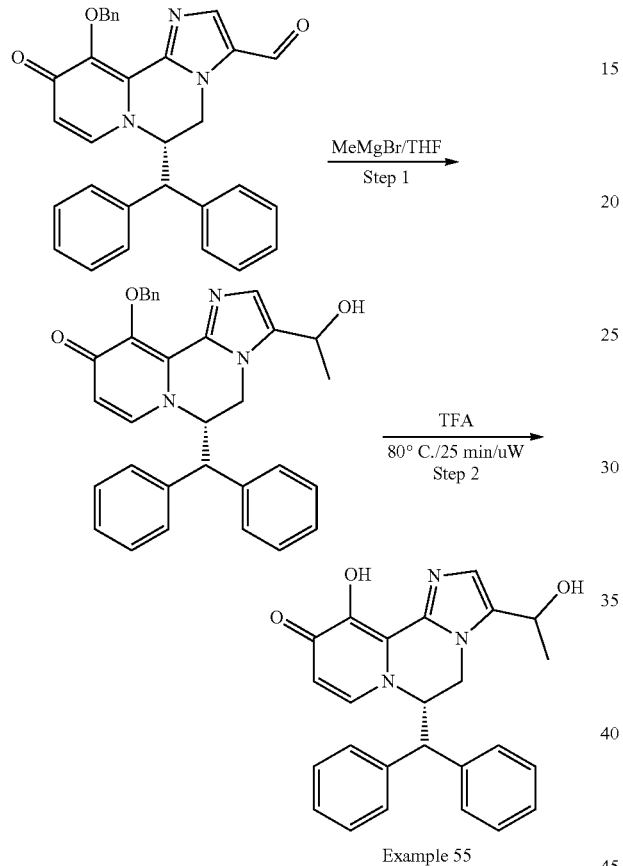

Example 55

Step 1: (6S)-6-benzhydryl-11-(benzyloxy)-3-(1-hydroxyethyl)-5H-imidazo [1,2-a]pyrido[2,1-c]pyrazin-10(6H)-one To pure (S)-6-benzhydryl-11-(benzyloxy)-10-oxo-6, 10-dihydro-5H-imidazo [1,2-a]pyrido[2,1-c]pyrazine-3-carbaldehyde (Example 54, step 1) (30 mg, 0.062 mmol) in THF (Volume: 2 mL) was added at −78° C. dropwise methylmagnesium bromide (0.110 mL, 0.154 mmol). Reaction mixture was stirred at this temperature for 30 min then slowly warmed to RT. Stirred 1H at RT. The reaction was quenched with Satd. NH4Cl and extracted with ethyl acetate twice. The combined organic extract was washed with brine, dried over sodium sulfate, filtered and evaporated to give crude (6S)-6-benzhydryl-11-(benzyloxy)-3-(1-hydroxyethyl)-5H-imidazo[1,2-a]pyrido[2,1-c]pyrazin-10(6H)-one, LCMS: MH+ 504.2, 0.86 min.

Step 2: (6S)-6-benzhydryl-11-hydroxy-3-(1-hydroxyethyl)-5H-imidazo[1,2-a]pyrido[2,1-c]pyrazin-10(6H)-one For synthesis see Example 54, step 3.
LCMS (m/z): 414.3 (MH+), 0.64 min, 1H NMR (400 MHz, CD3OD) δ ppm 1.47 (d, J=6.50 Hz, 3H) 4.10 (d, J=11.54 Hz, 1H) 4.39 (q, J=6.55 Hz, 1H) 4.58 (d, J=2.20 Hz, 2H) 5.67 (brd, J=11.44 Hz, 1H) 6.09 (d, J=7.19 Hz, 1H) 7.17-7.27 (m, 5H) 7.33-7.38 (m, 1H) 7.40-7.48 (m, 4H) 7.50-7.53 (m, 1H).

Example 56: (S)-6-benzhydryl-11-hydroxy-3-(methoxymethyl)-5H-imidazo [1,2-a]pyrido[2,1-c]pyrazin-10(6H)-one

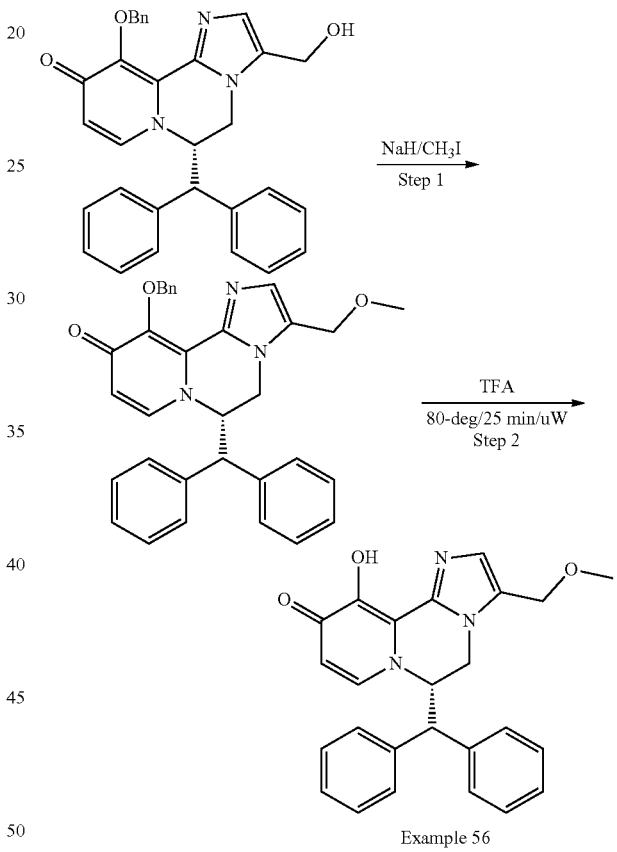

Example 56

Step 1: (S)-6-benzhydryl-11-(benzyloxy)-3-(methoxymethyl)-5H-imidazo [1,2-a]pyrido[2,1-c]pyrazin-10(6H)-one To crude (S)-6-benzhydryl-11-(benzyloxy)-3-(hydroxymethyl)-5H-imidazo [1, 2-a] pyrido [2, 1-c] pyrazin-10(6H)-one (Example 54, step 2) (40 mg, 0.074 mmol) in DMF (Volume: 1 mL) was added in ice bath, NaH (5.88 mg, 0.147 mmol). The reaction mixture was stirred 5-10 min followed by the addition of iodomethane (0.074 mL, 0.147 mmol). The RM was warm to RT and stirred for 30 min. LC-MS showed complete reaction. The reaction mixture was partitioned between EtOAc/water. The organic layer was separated, dried over sodium sulfate, filtered and evaporated to give crude (S)-6-benzhydryl-11-(benzyloxy)-3-(methoxymethyl)-5H-imidazo [1,2-a]pyrido[2,1-c]pyrazin-10(6H)-one, LCMS: MH+ 504.2, 0.78 min.

Step 2: (S)-6-benzhydryl-11-hydroxy-3-(methoxymethyl)-5H-imidazo [1, 2-a]pyrido[2,1-c]pyrazin-10 (6H)-one For synthesis see Example 54, step 3. LCMS (m/z): 414.3 (MH+), 0.69 min, 1H NMR (400 MHz, CD3OD) δ ppm 3.04-3.12 (m, 3H) 4.05-4.23 (m, 2H) 4.40 (d, J=13.11 Hz, 1H) 4.46-4.58 (m, 2H) 5.67 (dd, J=11.52, 2.23 Hz, 1H) 6.06 (d, J=7.19 Hz, 1H) 7.13-7.28 (m, 6H) 7.32-7.39 (m, 1H) 7.40-7.49 (m, 4H) 7.56 (s, 1H).

Example 57: (S)-6-benzhydryl-3-(difluoromethyl)-11-hydroxy-5H-imidazo[1,2-a]pyrido[2,1-c]pyrazin-10(6H)-one

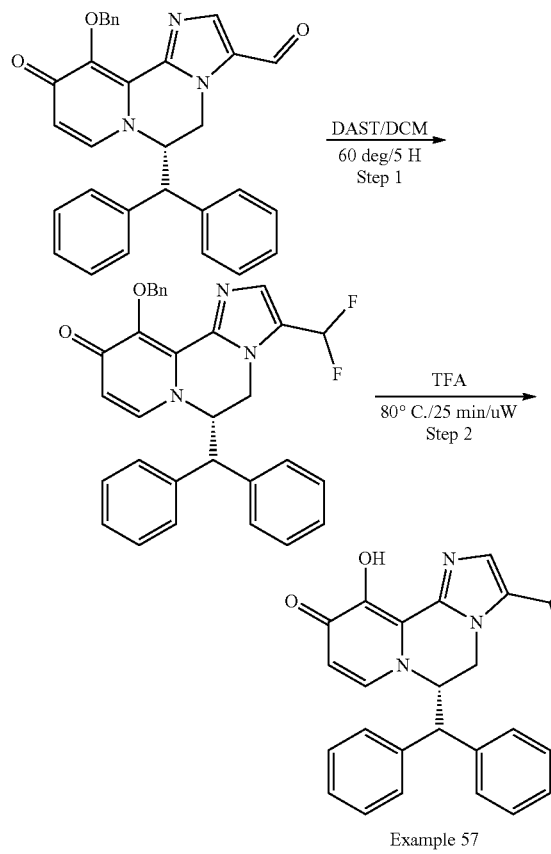

Example 57

Step 1: (S)-6-benzhydryl-11-(benzyloxy)-3-(difluoromethyl)-5H-imidazo[1,2-a]pyrido[2,1-c]pyrazin-10(6H)-one To pure (S)-6-benzhydryl-11-(benzyloxy)-10-oxo-6,10-dihydro-5H-imidazo [1,2-a]pyrido[2,1-c]pyrazine-3-carbaldehyde (Example 54, step 1) (25 mg, 0.046 mmol) in DCM (Volume: 1 mL) was added DAST (0.030 ml, 0.231 mmol) at RT. Reaction mixture was then heated at 60° C./5H in heating block. LC-MS showed complete reaction. The reaction mixture was partitioned between DCM/Satd. NaHCO₃ solution. The organic layer was separated, dried over sodium sulfate, filtered and evaporated to give (S)-6-benzhydryl-11-(benzyloxy)-3-(difluoromethyl)-5H-imidazo [1,2-a]pyrido[2,1-c]pyrazin-10(6H)-one, LCMS: MH+ 510.2, 0.89 min.

Step 2: (S)-6-benzhydryl-3-(difluoromethyl)-11-hydroxy-5H-imidazo [1, 2-a] pyrido [2, 1-c] pyrazin-10(6H)-one For synthesis see Example 54, step 3. LCMS (m/z): 420.3 (MH+), 0.77 min, 1H NMR (400 MHz, CD3OD) δ ppm 4.15 (d, J=11.69 Hz, 1H) 4.53 (d, J=13.89 Hz, 1H) 4.69 (dd, J=13.91, 3.94 Hz, 1H) 5.72 (dd, J=11.64, 3.42 Hz, 1H) 6.19 (d, J=7.19 Hz, 1H) 6.75-7.05 (m, 1H) 7.10-7.26 (m, 5H) 7.28-7.50 (m, 6H) 7.71 (t, J=2.35 Hz, 1H).

Example 58: (S)-6-benzhydryl-11-hydroxy-3-(trifluoromethyl)-5H-imidazo[1,2-a]pyrido[2,1-c]pyrazin-10(6H)-one

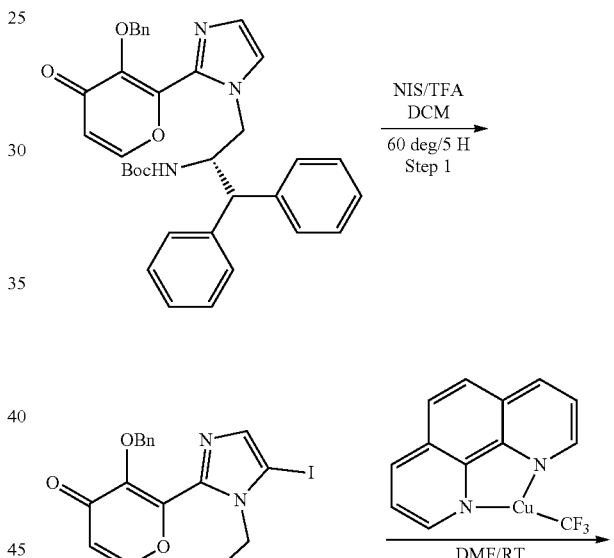

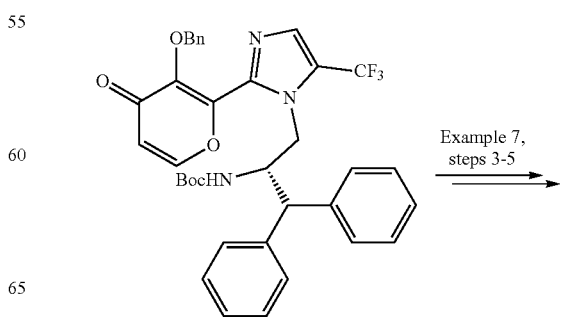

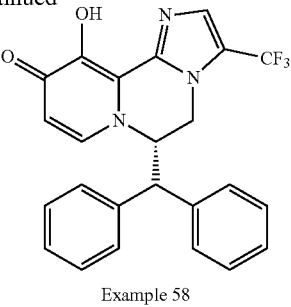

Example 58

Step 1: (S)-tert-butyl (3-(2-(3-(benzyloxy)-4-oxo-4H-pyran-2-yl)-5-iodo-1H-imidazol-1-yl)-1,1-diphenylpropan-2-yl)carbamate To a solution of (S)-tert-butyl (3-(2-(3-(benzyloxy)-4-oxo-4H-pyran-2-yl)-1H-imidazol-1-yl)-1,1-diphenylpropan-2-yl)carbamate (150 mg, 0.259 mmol) (Intermediate 4.1) in DCM (Volume: 6 mL) was added TFA (5.7 µl, 0.075 mmol) and NIS (117 mg, 0.518 mmol). Reaction mixture was heated at 60° C./5H. LC-MS showed major desired product. Reaction mixture was partitioned between DCM and water. The DCM layer was separated, washed with brine, dried over sodium sulfate, filtered and evaporated. The crude was purified by silica gel chromatography using 0-100% EtOAc (contains 10% MeOH)/Heptane to give (S)-tert-butyl (3-(2-(3-(benzyloxy)-4-oxo-4H-pyran-2-yl)-5-iodo-1H-imidazol-1-yl)-1,1-diphenylpropan-2-yl)carbamate as a light brown foamy solid, (80 mg, 0.114 mmol, 43.8% yield). LCMS: MH+ 703.3, 1.10 min.

Step 2: (S)-tert-butyl (3-(2-(3-(benzyloxy)-4-oxo-4H-pyran-2-yl)-5-(trifluoromethyl)-1H-imidazol-1-yl)-1,1-diphenylpropan-2-yl)carbamate To (S)-tert-butyl (3-(2-(3-(benzyloxy)-4-oxo-4H-pyran-2-yl)-5-iodo-1H-imidazol-1-yl)-1,1-diphenylpropan-2-yl)carbamate (80 mg, 0.114 mmol) in DMF (Volume: 2 mL) was added (1,10-Phenanthroline)(trifluoromethyl)copper(I), (35.6 mg, 0.114 mmol). Stirred at RT/1H. LCMS showed only 10-15% conversion to product. LC-MS shows no change in % product after 5H. Added again (1,10-Phenanthroline)(trifluoromethyl)copper(I), (35.6 mg, 0.114 mmol) and reaction was left stirred at RT/ON. Still desired product was present in minor amount. Reaction mixture was diluted with EtOAc and filtered to remove solid. The EtOAc layer was washed with brine, dried over sodium sulfate, filtered and evaporated to provide crude mixture containing starting material and 10-15% of (S)-tert-butyl (3-(2-(3-(benzyloxy)-4-oxo-4H-pyran-2-yl)-5-(trifluoromethyl)-1H-imidazol-1-yl)-1,1-diphenylpropan-2-yl)carbamate. LCMS: MH+ 646.3, 1.21 min. Proceed for next step.

Example 58: (S)-6-benzhydryl-11-hydroxy-3-(trifluoromethyl)-5H-imidazo[1,2-a]pyrido[2,1-c]pyrazin-10(6H)-one Prepared from (S)-tert-butyl (3-(2-(3-(benzyloxy)-4-oxo-4H-pyran-2-yl)-5-(trifluoromethyl)-1H-imidazol-1-yl)-1,1-diphenylpropan-2-yl)carbamate by the method of Example 7, steps 3-5. LCMS (m/z): 438.3 (MH+), 0.90 min, 1H NMR (400 MHz, CD3OD) δ ppm 3.99-4.20 (m, 1H) 4.38 (br d, J=12.91 Hz, 1H) 4.69 (br d, J=12.67 Hz, 1H) 5.68 (br s, 1H) 6.05 (br d, J=18.44 Hz, 1H) 7.03-7.72 (m, 12H) 7.81-7.92 (m, 1H).

Example 59: (S)-6-benzhydryl-11-hydroxy-10-oxo-5,6-dihydro-10H-imidazo[1,2-a]pyrido[2,1-c]pyrazine-3-carbonitrile

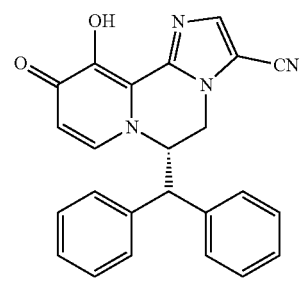 [SMILES: N#Cc1cnc2n1C[C@H](C(c1ccccc1)c1ccccc1)n1ccc(=O)c(O)c1-2]

Prepared from (S)-6-benzhydryl-11-(benzyloxy)-3-bromo-5,6-dihydro-10H-imidazo[1,2-a]pyrido[2,1-c]pyrazin-10-one (see Example 7, step 4) by the method of Example 49, steps 2-3. LCMS (m/z): 395.2 (MH+), 1H NMR (500 MHz, MeOD-d4) δ 8.08 (s, 1H), 7.47-7.41 (m, 4H), 7.39-7.33 (m, 2H), 7.22 (s, 5H), 6.19 (d, J=7.1 Hz, 1H), 5.73 (dd, J=11.2, 3.8 Hz, 1H), 4.64 (dd, J=13.8, 3.8 Hz, 1H), 4.29 (d, J=13.8 Hz, 1H), 4.05 (d, J=11.2 Hz, 1H).

Example 60: (S)-6-benzhydryl-11-hydroxy-3-(pyrrolidin-1-ylmethyl)-5H-imidazo[1,2-a]pyrido[2,1-c]pyrazin-10(6H)-one

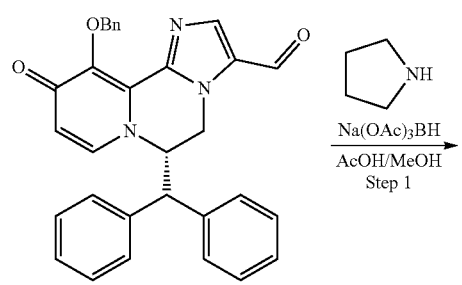

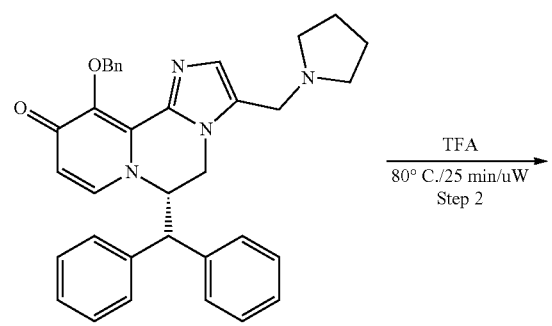

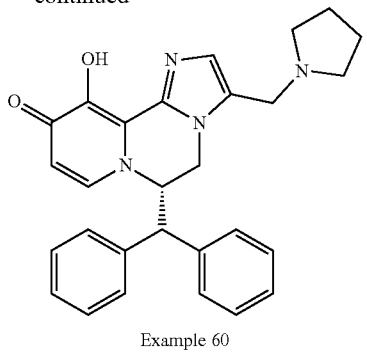

Example 60

Step 1: (S)-6-benzhydryl-11-(benzyloxy)-3-(pyrrolidin-1-ylmethyl)-5H-imidazo[1,2-a]pyrido[2,1-c]pyrazin-10(6H)-one To pure (S)-6-benzhydryl-11-(benzyloxy)-10-oxo-6,10-dihydro-5H-imidazo [1,2-a]pyrido[2,1-c]pyrazine-3-carbaldehyde (Example 54, step 1) (25 mg, 0.046 mmol) in MeOH (Volume: 1 mL) was added acetic acid (7.93 µl, 0.138 mmol) and pyrrolidine (0.022 mL, 0.276 mmol). Stirred 5 min then added sodium triacetoxyborohydride (97.8 mg, 0.462 mmol). The reaction was quenched with satd. NH4Cl and product was extracted with ethyl acetate. The organic layer was washed with brine, dried over sodium sulfate, filtered and evaporated to give crude (S)-6-benzhydryl-11-(benzyloxy)-3-(pyrrolidin-1-ylmethyl)-5H-imidazo[1,2-a]pyrido[2,1-c]pyrazin-10(6H)-one, LCMS: MH+ 543.3, 0.87 min.

Step 2: (S)-6-benzhydryl-11-hydroxy-3-(pyrrolidin-1-ylmethyl)-5H-imidazo[1,2-a]pyrido[2,1-c]pyrazin-10(6H)-one For synthesis see example 54, step 3. LCMS (m/z): 453.3 (MH+), 0.57 min, 1H NMR (400 MHz, CD3OD) δ ppm 1.92-2.02 (m, 3H) 2.03 (s, 1H) 4.11 (d, J=11.59 Hz, 1H) 4.25 (br d, J=14.92 Hz, 1H) 4.43 (br d, J=14.87 Hz, 1H) 4.50-4.65 (m, 2H) 5.76 (br dd, J=11.59, 2.74 Hz, 1H) 6.05 (d, J=7.24 Hz, 1H) 7.08-7.16 (m, 2H) 7.17-7.22 (m, 3H) 7.33-7.53 (m, 6H) 7.65 (s, 1H).

The compounds in this table were prepared by a method similar to Example 60.

| Example No. | Structure | Mass M + H | 1H NMR |
|---|---|---|---|
| 61 | 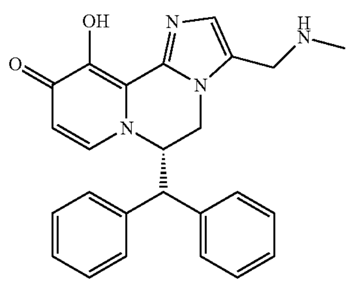 [SMILES: CNCc1cnc2n1C[C@H](C(c1ccccc1)c1ccccc1)n1ccc(=O)c(O)c1-2] | 413.3 | (400 MHz, CD3OD) δ ppm 2.60 (s, 3 H) 2.68 (s, 1 H) 3.87 (d, J = 14.87 Hz, 1 H) 3.98 (d, J = 11.49 Hz, 1 H) 4.24 (d, J = 14.92 Hz, 1 H) 4.34-4.41 (m, 1 H) 4.51 (dd, J = 13.99, 3.77 Hz, 1 H) 5.69 (br dd, J = 11.59, 3.03 Hz, 1 H) 6.01-6.02 (m, 1 H) 6.05 (d, J = 7.29 Hz, 1 H) 7.08-7.27 (m, 7H) 7.33-7.51 (m, 6 H) 7.60 (s, 1 H) |
| 62 | 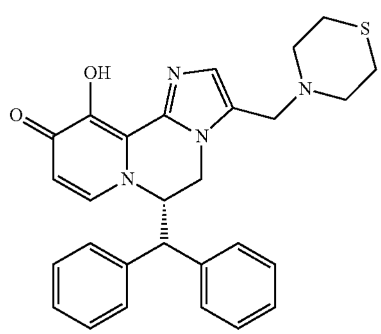 [SMILES: O=c1ccn2c(c1O)-c1ncc(CN3CCSCC3)n1C[C@@H]2C(c1ccccc1)c1ccccc1] | 485.3 | (400 MHz, CD3OD) δ ppm 2.42-2.64 (m, 4 H) 2.67-3.01 (m, 4 H) 3.63 (br d, J = 14.18 Hz, 1 H) 3.92 (br d, J = 14.87 Hz, 1 H) 4.23 (d, J = 11.64 Hz, 1 H) 4.55-4.65 (m, 1 H) 4.66-4.77 (m, 1 H) 5.76 (dd, J = 11.64, 3.57 Hz, 1 H) 6.08 (d, J = 7.19 Hz, 1 H) 7.07-7.15 (m, 2 H) 7.16-7.24 (m, 4 H) 7.34-7.40 (m, 1 H) 7.41-7.50 (m, 4 H) 7.62 (s, 1 H) |
| 63 | 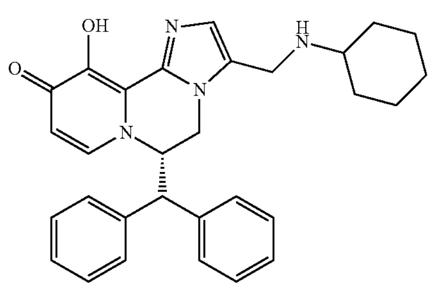 [SMILES: O=c1ccn2c(c1O)-c1ncc(CNC3CCCCC3)n1C[C@@H]2C(c1ccccc1)c1ccccc1] | 481.3 | (400 MHz, CD3OD) δ ppm 1.11-1.47 (m, 5 H) 1.72 (br d, J = 12.62 Hz, 1 H) 1.82-1.95 (m, 2 H) 2.06 (br s, 2 H) 3.03-3.20 (m, 1 H) 3.76 (d, J = 14.87 Hz, 1 H) 3.94 (d, J = 11.40 Hz, 1 H) 4.31 (dd, J = 14.45, 7.16 Hz, 2 H) 4.41-4.53 (m, 1 H) 5.67 (br dd, J = 11.35, 2.64 Hz, 1 H) 6.04 (d, J = 7.19 Hz, 1 H) 7.10-7.30 (m, 6 H) 7.31-7.50 (m, 5 H) 7.58 (s, 1 H) |

-continued

| Example No. | Structure | Mass M + H | 1H NMR |
|---|---|---|---|
| 64 | 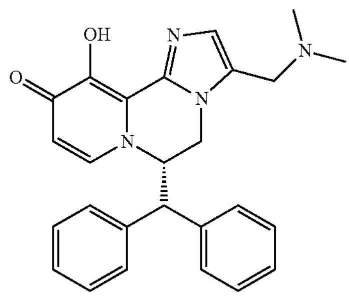 [SMILES: CN(C)Cc1cnc2n1C[C@H](C(c1ccccc1)c1ccccc1)n1ccc(=O)c(O)c1-2] | 427.3 | (400 MHz, CD3OD) δ ppm 2.59-2.78 (m, 6 H) 3.98-4.20 (m, 2 H) 4.40 (d, J = 14.82 Hz, 1 H) 4.47-4.64 (m, 2 H) 5.77 (br d, J = 11.49 Hz, 1 H) 6.00-6.15 (m, 1 H) 7.07-7.16 (m, 2 H) 7.16-7.26 (m, 3 H) 7.34-7.51 (m, 5 H) 7.67 (s, 1 H) |
| 65 | 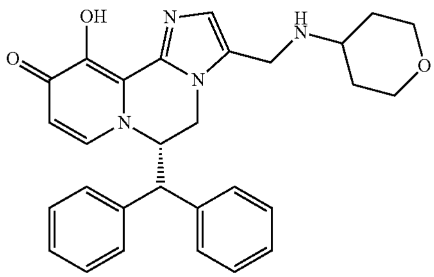 [SMILES: O=c1ccn2c(c1O)-c1ncc(CNC3CCOCC3)n1C[C@@H]2C(c1ccccc1)c1ccccc1] | 483.3 | (400 MHz, CD3OD) δ ppm 1.62 (qd, J = 11.64, 4.65 Hz, 2 H) 1.89-2.03 (m, 2 H) 3.34-3.49 (m, 3 H) 3.80 (d, J = 14.92 Hz, 1 H) 3.95 (d, J = 11.44 Hz, 1 H) 4.02 (br d, J = 11.93 Hz, 2 H) 4.28-4.40 (m, 2 H) 4.43-4.52 (m, 1 H) 5.69 (br dd, J = 11.42, 3.11 Hz, 1 H) 6.06 (d, J = 7.19 Hz, 1H) 7.09-7.29 (m, 6 H) 7.30-7.54 (m, 5 H) 7.61 (s, 1 H) |
| 66 | 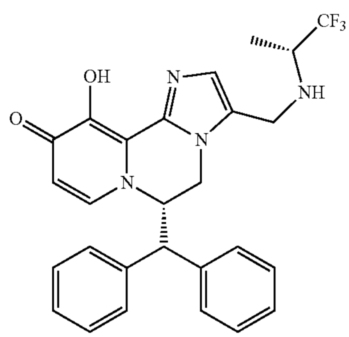 [SMILES: C[C@@H](NCc1cnc2n1C[C@H](C(c1ccccc1)c1ccccc1)n1ccc(=O)c(O)c1-2)C(F)(F)F] | 495.3 | (400 MHz, CD3OD) δ ppm 1.06 (d, J = 6.80 Hz, 3 H) 3.01 (dquin, J = 14.24, 7.16, 7.16, 7.16, 7.16 Hz, 1 H) 3.63 (d, J = 14.57 Hz, 1 H) 3.81 (d, J = 14.57 Hz, 1 H) 4.14 (d, J = 11.59 Hz, 1 H) 4.55 (dd, J = 14.23, 3.96 Hz, 1 H) 4.75 (d, J = 14.23 Hz, 1 H) 5.70 (dd, J = 11.49, 3.52 Hz, 1 H) 6.08 (d, J = 7.19 Hz, 1 H) 7.13-7.30 (m, 6 H) 7.32-7.39 (m, 1 H) 7.40-7.50 (m, 4 H) 7.54 (s, 1 H) |
| 67 | 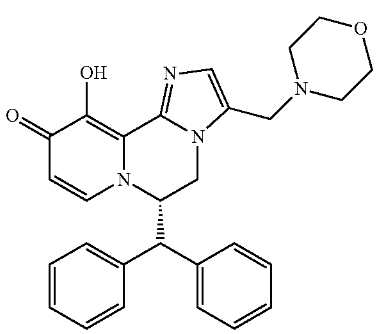 | 469.3 | (400 MHz, CD3OD) δ ppm 2.36-2.79 (m, 4 H) 3.41-3.76 (m, 5 H) 3.85-4.00 (m, 1 H) 4.23 (d, J = 11.64 Hz, 1 H) 4.63 (br dd, J = 14.16, 3.99 Hz, 1H) 4.75 (br d, J = 13.60 Hz, 1 H) 5.68-5.85 (m, 1 H) 6.03-6.19 (m, 1 H) 7.06-7.16 (m, 2 H) 7.17-7.28 (m, 4 H) 7.30-7.54 (m, 5 H) 7.65 (d, J = 2.89 Hz, 1H) |

Example 68: (S)-6-benzhydryl-11-hydroxy-N,N-dimethyl-10-oxo-5,6-dihydro-10H-imidazo[1,2-a]pyrido[2,1-c]pyrazine-3-carboxamide

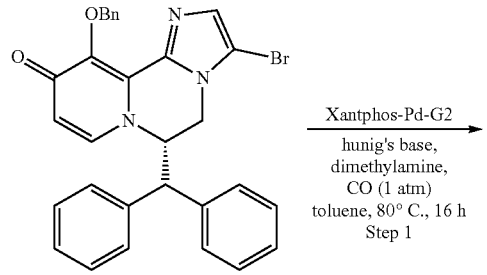

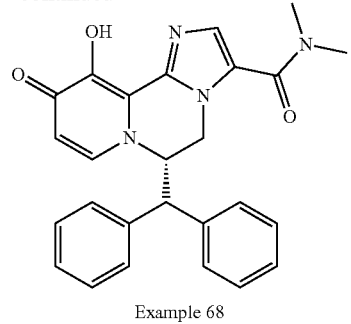

Example 68

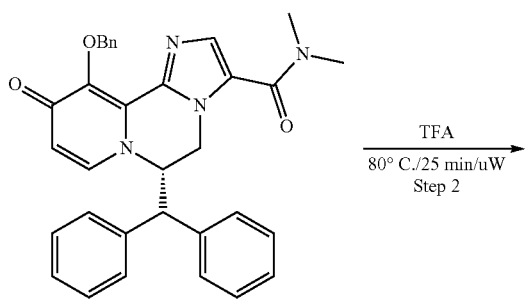

Step 1: (S)-6-benzhydryl-11-(benzyloxy)-N,N-dimethyl-10-oxo-5,6-dihydro-10H-imidazo[1,2-a]pyrido[2,1-c]pyrazine-3-carboxamide To an oven-dried 4 mL vial was added (S)-6-benzhydryl-11-(benzyloxy)-3-bromo-5,6-dihydro-10H-imidazo[1,2-a]pyrido[2,1-c]pyrazin-10-one (see Example 7, step 4) (30 mg, 0.056 mmol) and Xantphos-Pd-G2 (5.0 mg, 10 mol %). The vial was sealed with a septa-top cap and purged with vacuum/N2 via needle (×3). Toluene (0.55 mL, 0.1 M) was added and the reaction was purged with CO by bubbling through via a needle. Hunig's base (15 µl, 0.084 mmol, 1.5 eq) and the dimethylamine (0.17 mmol, 3.0 eq) were then added and the reaction was heated to 80 C and stirred under an atmosphere of CO overnight at which point the product had precipitated around the edges of the vial. The reaction was then concentrated and used in the next step without further purification.

Step 2: (S)-6-benzhydryl-11-hydroxy-N,N-dimethyl-10-oxo-5,6-dihydro-10H-imidazo[1,2-a]pyrido[2,1-c]pyrazine-3-carboxamide For synthesis see example 54, step 3. LCMS (m/z): 441.2 (MH+), 0.76 min.

The compounds in the following table were prepared by a method similar to Example 68.

| Example No. | Structure | Mass M + H | 1H NMR |
|---|---|---|---|
| 69 | ![structure] | 427.2 | (500 MHz, DMSO-d6) δ 8.55 (q, J = 4.5 Hz, 1H), 7.98 (s, 1 H), 7.45-7.14 (m, 10H), 5.92 (d, J = 7.1 Hz, 1H), 5.80 (dd, J = 11.4, 3.0 Hz, 1H), 5.07 (d, J = 14.4 Hz, 1H), 4.54 (dd, J = 14.4, 3.9 Hz, 1H), 4.04 (d, J = 11.4 Hz, 2H), 2.68 (d, J = 4.5 Hz, 3H). |
| 70 | ![structure] | 453.2 | |

| Example No. | Structure | Mass M + H | 1H NMR |
|---|---|---|---|
| 71 | 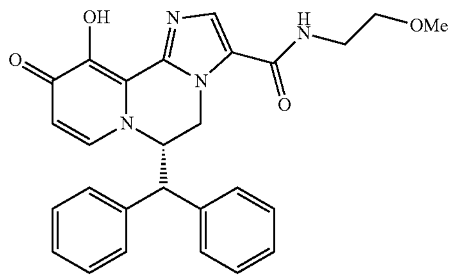 [SMILES: COCCNC(=O)c1cnc2n1C[C@H](C(c1ccccc1)c1ccccc1)n1ccc(=O)c(O)c1-2] | 471.2 | Product exists as a ~4:1 rotameric mixture, *indicates minor isomer. (500 MHz, DMSO-d6) δ 8.64 (m, 1H), 8.51* (m, 1 H), 8.02 (s, 1H), 7.73* (d, J = 6.8 Hz, 1H), 7.44-7.14 (m, 10H), 6.63* (d, J = 7.0 Hz, 1H), 6.02* (dd, J = 11.4, 3.0 Hz, 1 H), 5.81 (d, J = 7.0 Hz, 1H), 5.74 (dd, J = 11.4, 3.0 Hz, 1H), 5.05* (d, J = 14.9 Hz, 1H), 5.02 (d, J = 14.7, 1 H), 4.63* (dd, J = 14.9, 3.8 Hz, 0H), 4.51 (dd, J = 14.7, 3.8 Hz, 1H), 3.97 (d, J = 11.4 Hz, 1H), 3.86* (d, J = 11.4 Hz, 1H), 3.39-3.24 (m, 7H). |
| 72 | 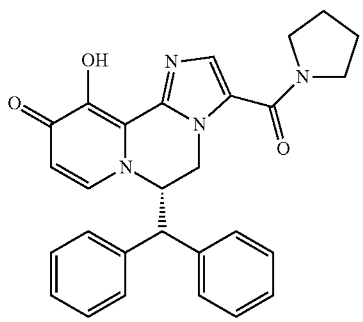 [SMILES: O=C(c1cnc2n1C[C@H](C(c1ccccc1)c1ccccc1)n1ccc(=O)c(O)c1-2)N1CCCC1] | 467.2 | Product exists as a ~6:1 rotameric mixture, *indicates minor isomer. (500 MHz, DMSO-d6) δ 7.86 (s, 1H), 7.82* (s, 1H), 7.75-7.67 (m, 10H), 6.65* (d, J = 6.5 Hz, 1H), 6.00* (dd, J = 11.9, 3.3 Hz, 0H), 5.82 (d, J = 7.3 Hz, 1H), 5.71 (dd, J = 11.3, 3.3 Hz, 1H), 4.69-4.63 (m, 1H), 4.62-4.65* (m, 1H) 4.48 (dd, J = 14.3, 3.5 Hz, 1H), 3.90 (d, J = 11.3 Hz, 1H), 3.81-3.71 (m, 4H), 2.05-1.80 (m, 4H) |

Example 73: 6-benzhydryl-5-cyclopropyl-11-hydroxy-5,6-dihydro-10H-imidazo[1,2-d]pyrido[2,1-f][1,2,4]triazin-10-one

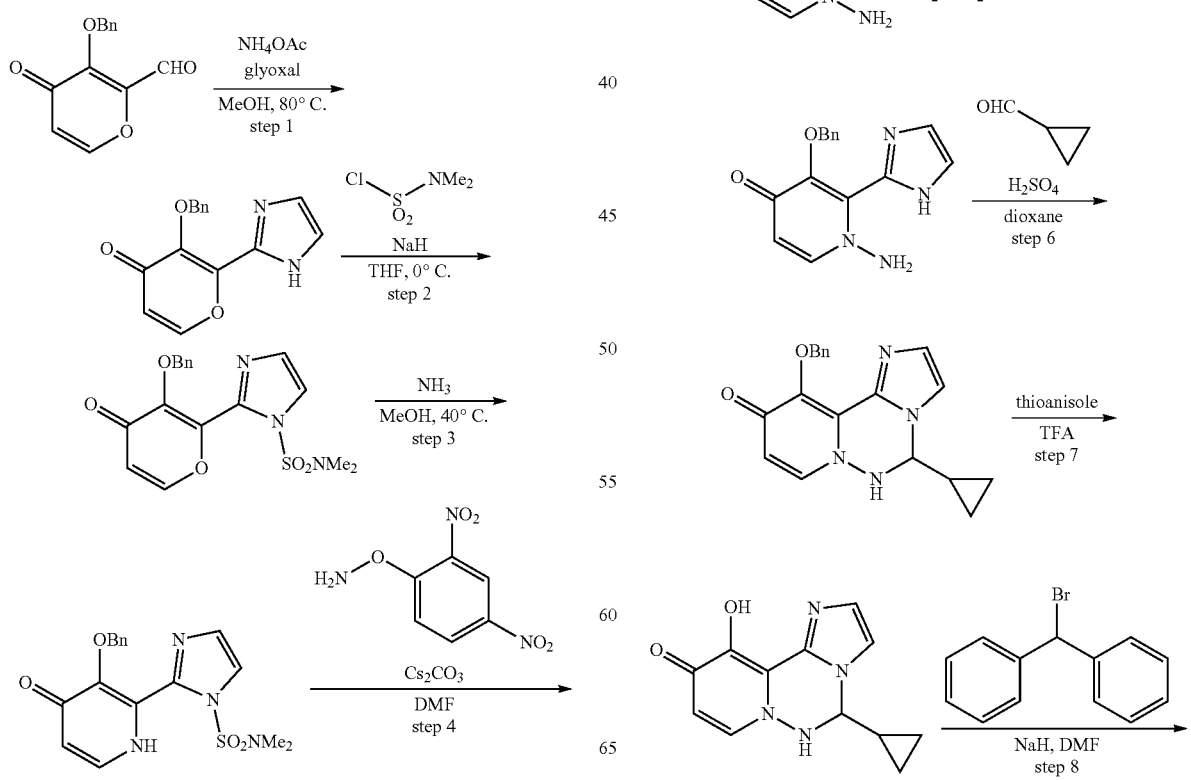

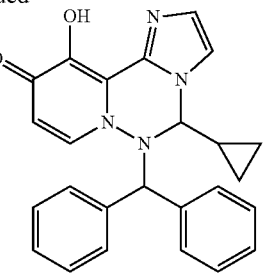

Example 73

Step 1: 3-(benzyloxy)-2-(1H-imidazol-2-yl)-4H-pyran-4-one

To 3-(benzyloxy)-4-oxo-4H-pyran-2-carbaldehyde (22.3 g, 97 mmol) in MeOH (500 mL) was added glyoxal (40% in water, 19.7 ml, 136 mmol) and ammonium acetate (22.40 g, 291 mmol). The reaction was sealed and heated at 80° C. for 1 hr. The mixture was cooled and concentrated to give crude 3-(benzyloxy)-2-(1H-imidazol-2-yl)-4H-pyran-4-one, which was used in the next step without purification. LCMS (m/z): 269.2 (MH+), 0.37 min.

Step 2: 2-(3-(benzyloxy)-4-oxo-4H-pyran-2-yl)-N,N-dimethyl-1H-imidazole-1-sulfonamide To 3-(benzyloxy)-2-(1H-imidazol-2-yl)-4H-pyran-4-one (10 g, 37.3 mmol) in DMF (200 mL) at 0° C. was added NaH (2.236 g, 55.9 mmol). The resulting mix was stirred at 0° C. for 30 min. Dimethylsulfamoyl chloride (7.99 mL, 74.6 mmol) was then added dropwise. The cold bath was removed and the reaction was stirred at rt for two hours. The mixture was diluted with EtOAc (400 mL) and washed with water (2×200 mL) and brine (100 mL). The organic layer was dried (Na2SO4) and concentrated. The residue was purified by silica gel chromatography (10-100% EtOAc in heptane, with 10% MeOH) to give 2-(3-(benzyloxy)-4-oxo-4H-pyran-2-yl)-N,N-dimethyl-1H-imidazole-1-sulfonamide (11 g, 29 mmol, 79% yield). LCMS: MH+ 376.3, 0.82 min.

Step 3: 2-(3-(benzyloxy)-4-oxo-1,4-dihydropyridin-2-yl)-N,N-dimethyl-1H-imidazole-1-sulfonamide To 2-(3-(benzyloxy)-4-oxo-4H-pyran-2-yl)-N,N-dimethyl-1H-imidazole-1-sulfonamide (10 g, 26.6 mmol) was added NH3 (7.0 M, 10 mL, 70.0 mmol) in MeOH. The reaction was sealed and heated to 40° C. The reaction was stirred for three hours, and then concentrated. The residue was purified by silica gel chromatography to give 2-(3-(benzyloxy)-4-oxo-1,4-dihydropyridin-2-yl)-N,N-dimethyl-1H-imidazole-1-sulfonamide (2.1 g, 5.6 mmol, 21% yield). LCMS: MH+375.3, 0.53 min.

Step 4: 2-(1-amino-3-(benzyloxy)-4-oxo-1,4-dihydropyridin-2-yl)-N,N-dimethyl-1H-imidazole-1-sulfonamide To 2-(3-(benzyloxy)-4-oxo-1,4-dihydropyridin-2-yl)-N,N-dimethyl-1H-imidazole-1-sulfonamide (2.1 g, 5.61 mmol) in DMF (15 mL) was added Cs2CO3 (2.74 g, 8.41 mmol). The mixture was stirred for 15 minutes and O-(2,4-dinitrophenyl)hydroxylamine (2.234 g, 11.22 mmol) was then added. The mixture was stirred for 2 hours. Most of the solvent was then removed via rotovap. The residue was diluted with DCM/MeOH (30/10 mL) and silica gel (20 g). Dry loaded onto silica gel chromatography and eluted with (10-100% EtOAc in heptane, w/10% MeOH) to give 2-(1-amino-3-(benzyloxy)-4-oxo-1,4-dihydropyridin-2-yl)-N,N-dimethyl-1H-imidazole-1-sulfonamide (1.8 g, 4.6 mmol, 82% yield). LCMS: MH+390.3, 0.55 min.

Step 5: 1-amino-3-(benzyloxy)-2-(1H-imidazol-2-yl)pyridin-4(1H)-one

To 2-(1-amino-3-(benzyloxy)-4-oxo-1,4-dihydropyridin-2-yl)-N,N-dimethyl-1H-imidazole-1-sulfonamide (1.8 g, 4.62 mmol) in dioxane (30 mL) was added 10% H2SO4 (30 mL). The reaction was stirred at rt for 5 hours. NaOH (6N) was added to adjust to pH 9. The mixture was extracted with EtOAc (5×50 mL). The organic layer was dried (Na2SO4) and concentrated. The residue was purified by silica gel chromatography (10-100% EtOAc in heptane, w/10% MeOH) to give 1-amino-3-(benzyloxy)-2-(1H-imidazol-2-yl)pyridin-4(1H)-one (1.1 g, 3.9 mmol, 84% yield). LCMS: MH+283.2, 0.29 min.

Step 6: 11-(benzyloxy)-5-cyclopropyl-5H-imidazo[1,2-d]pyrido[2,1-f][1,2,4]triazin-10(6H)-one To 1-amino-3-(benzyloxy)-2-(1H-imidazol-2-yl)pyridin-4(1H)-one (90 mg, 0.319 mmol) in dioxane (1 mL) was added sulfuric acid (1 mL, 0.400 mmol). The mixture was stirred for 10 minutes. The solvent was evaporated on the rotovap (bath temp. 50° C.) and the residue was dried under high vacuum overnight. The residue was dissolved in MeOH (2 mL) and NaOH (0.4 mL, 1M) was added to quench sulfuric acid. The mixture was dried and the residue was washed with MeOH/DCM (1:1, 10 mL). The solution was dried to give crude 11-(benzyloxy)-5-cyclopropyl-5H-imidazo[1,2-d]pyrido[2,1-f][1,2,4]triazin-10(6H)-one (100 mg). LCMS: MH+335.3, 0.51 min.

Step 7: 5-cyclopropyl-11-hydroxy-5H-imidazo[1,2-d]pyrido[2,1-f][1,2,4]triazin-10(6H)-one To crude 11-(benzyloxy)-5-cyclopropyl-5H-imidazo[1,2-d]pyrido[2,1-f][1,2,4]triazin-10(6H)-one (100 mg, 0.299 mmol) in TFA (2 mL) was added thioanisole (149 mg, 1.196 mmol). The mixture was stirred for one hour. The mixture was concentrated and dried under vacuum overnight to give crude 5-cyclopropyl-11-hydroxy-5H-imidazo[1,2-d]pyrido[2,1-f][1,2,4]triazin-10(6H)-one (73 mg). LCMS: MH+245.2, 0.32 min.

Step 8: 6-benzhydryl-5-cyclopropyl-11-hydroxy-5H-imidazo[1,2-d]pyrido[2,1-f][1,2,4]triazin-10(6H)-one To crude 5-cyclopropyl-11-hydroxy-5H-imidazo[1,2-d]pyrido[2,1-f][1,2,4]triazin-10(6H)-one (20 mg, 0.082 mmol) in DMF (1 mL) was added sodium hydride (13.1 mg, 0.328 mmol) and (bromomethylene)dibenzene (101 mg, 0.409 mmol). The mixture was stirred for 20 minutes at rt. HCl (1N, 0.4 mL) was added to quench the reaction. The resulting mixture was purified by reverse phase HPLC (MeCN/water with 0.1% TFA) to give, after lyophilization, 6-benzhydryl-5-cyclopropyl-11-hydroxy-5H-imidazo[1,2-d]pyrido[2,1-f][1,2,4]triazin-10(6H)-one (16.8 mg, 26 μmol, 32% yield). LCMS (m/z): 411.3 (MH+), 1H NMR (400 MHz, DMSO-d6) δ 7.91 (d, J=1.6 Hz, 1H), 7.71 (m, 1H), 7.7-7.5 (m, 3H), 7.45-7.30 (m, 3H), 7.30-7.10 (m, 5H), 5.78 (d, J=6.1 Hz, 1H), 5.11 (s, 1H), 4.95 (d, J=7.0 Hz, 1H), 1.31 (m, 1H), 0.85-0.65 (m, 2H), 0.5-0.3 (m, 2H).

Example 74: 6-(6,11-dihydrodibenzo[b,e]thiepin-11-yl)-11-hydroxy-5,6-dihydro-10H-imidazo[1,2-d]pyrido[2,1-f][1,2,4]triazin-10-one

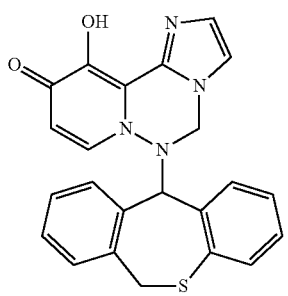 [SMILES: O=c1ccn2c(c1O)-c1nccn1CN2C1c2ccccc2CSc2ccccc21]

Prepared by the method of Example 73 using 30% aqueous formaldehyde in DCM/MeOH (2:1) in step 6 and 11-bromo-6,11-dihydrodibenzo[b,e]thiepine in step 8. LCMS (m/z): 415.2 (MH+), 1H NMR (400 MHz, DMSO-d6) δ 7.61 (m, 1H), 7.55-7.38 (m, 3H), 7.35-7.2 (m, 3H), 7.2-7.0 (m, 3H), 6.8-6.7 (m, 2H), 5.72 (d, J=6.0 Hz, 1H), 5.7-5.5 (m, 2H), 5.12 (d, J=6.0 Hz, 1H), 4.1-3.9 (m, 2H).

Example 75: 6-benzhydryl-11-hydroxy-5,5-dimethyl-5,6-dihydro-10H-imidazo[1,2-d]pyrido[2,1-f][1,2,4]triazin-10-one

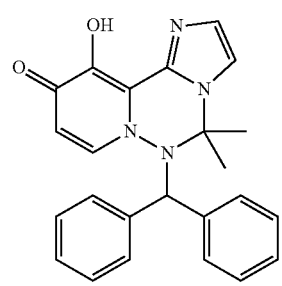 [SMILES: CC1(C)N(C(c2ccccc2)c2ccccc2)n2ccc(=O)c(O)c2-c2nccn21]

Prepared by the method of Example 73 using acetone in step 6. LCMS (m/z): 399.4 (MH+), 1H NMR (400 MHz, DMSO-d6) δ 7.97 (m, 2H), 7.8-7.6 (m, 3H), 7.5-7.4 (m, 2H), 7.30 (d, J=6 Hz, 1H), 7.2-7.0 (m, 3H), 6.8-6.7 (m, 2H), 5.92 (d, J=6.0 Hz, 1H), 5.41 (s, 1H), 1.81 (s, 3H), 1.55 (s, 3H).

Example 76: 5-cyclopropyl-6-(6,11-dihydrodibenzo[b,e]thiepin-11-yl)-11-hydroxy-5,6-dihydro-10H-imidazo[1,2-d]pyrido[2,1-f][1,2,4]triazin-10-one

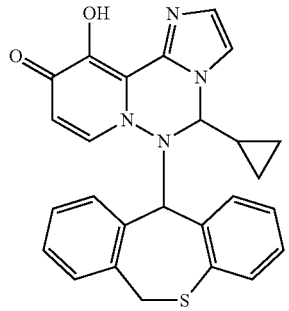 [SMILES: O=c1ccn2c(c1O)-c1nccn1C(C1CC1)N2C1c2ccccc2CSc2ccccc21]

Prepared by the method of Example 73 using 11-bromo-6,11-dihydrodibenzo[b,e]thiepine in step 8. LCMS (m/z): 455.2 (MH+).

Example 77: 6-benzhydryl-11-hydroxy-5-isopropyl-5,6-dihydro-10H-imidazo[1,2-d]pyrido[2,1-f][1,2,4]triazin-10-one

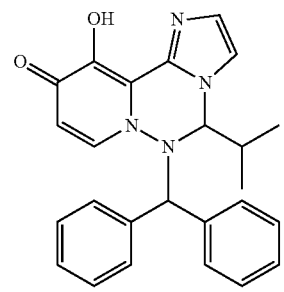 [SMILES: CC(C)C1N(C(c2ccccc2)c2ccccc2)n2ccc(=O)c(O)c2-c2nccn21]

Prepared by the method of Example 73 using isobutyraldehyde in step 6. LCMS (m/z): 413.2 (MH+), 1H NMR (400 MHz, DMSO-d6) δ 7.81 (s, 1H), 7.78-7.62 (m, 4H), 7.55-7.3 (m, 4H), 7.3-7.15 (m, 4H), 5.68 (d, J=6.0 Hz, 1H), 5.12 (d, J=6.0 Hz, 1H), 4.91 (s, 1H), 1.92 (m, 1H), 1.15 (d, J=7.0 Hz, 3H), 0.85 (d, J=7.0 Hz, 3H).

Example 78: 6-benzhydryl-5-ethyl-11-hydroxy-5,6-dihydro-10H-imidazo[1,2-d]pyrido[2,1-f][1,2,4]triazin-10-one

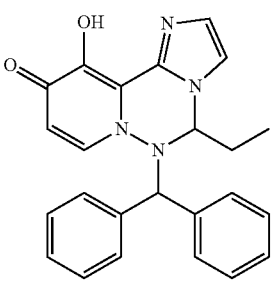 [SMILES: CCC1N(C(c2ccccc2)c2ccccc2)n2ccc(=O)c(O)c2-c2nccn21]

Prepared by the method of Example 73 using propionaldehyde in step 6. LCMS (m/z): 399.2 (MH+), 1H NMR (400

MHz, DMSO-d6) δ 7.6-7.55 (m, 4H), 7.5-7.35 (m, 4H), 7.3-7.15 (m, 4H), 6.52-6.5 (m, 1H), 5.65 (d, J=6.0 Hz, 1H), 5.53-5.1 (m, 1H), 4.96 (s, 1H), 1.72 (m, 2H), 1.05 (d, J=7.0 Hz, 3H).

Example 79: 6-benzhydryl-11-hydroxy-6H,10H-spiro[imidazo[1,2-d]pyrido[2,1-f][1,2,4]triazine-5,3'-oxetan]-10-one

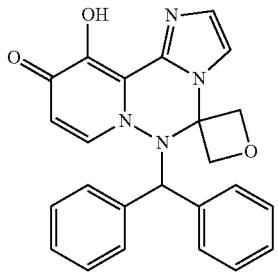 [SMILES: O=c1ccn2c(c1O)-c1nccn1C1(COC1)N2C(c1ccccc1)c1ccccc1]

Prepared by the method of Example 73 using 3-oxetanone and acetic acid in step 6 and reversing the order of steps 7 and 8. LCMS (m/z): 413.3 (MH+), 1H NMR (400 MHz, DMSO-d6) δ 7.95 (d, J=1.8 Hz, 1H), 7.82 (m, 1H), 7.7-7.5 (m, 3H), 7.5-7.38 (m, 3H), 7.34-7.10 (m, 5H), 5.72 (d, J=6.0 Hz, 1H), 5.02 (s, 1H), 4.72 (d, J=8.2 Hz, 1H), 4.42 (d, J=8.2 Hz, 1H), 4.36 (d, J=8.0 Hz, 1H), 4.05 (d, J=8.2 Hz, 1H).

Example 80: 6-(6,11-dihydrodibenzo[b,e]thiepin-11-yl)-11-hydroxy-6H,10H-spiro[imidazo[1,2-d]pyrido[2,1-f][1,2,4]triazine-5,3'-oxetan]-10-one

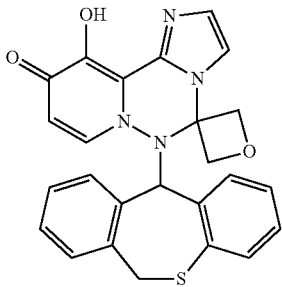 [SMILES: O=c1ccn2c(c1O)-c1nccn1C1(COC1)N2C1c2ccccc2CSc2ccccc21]

Prepared by the method of Example 73 using 3-oxetanone and acetic acid in step 6 and reversing the order of steps 7 and 8 (using 11-bromo-6,11-dihydrodibenzo[b,e]thiepine). LCMS (m/z): 457.1 (MH+), 1H NMR (400 MHz, DMSO-d6) δ 8.25 (s, 1H), 7.75 (s, 1H), 7.5-7.45 (m, 1H), 7.42-7.35 (m, 1H), 7.3-7.05 (m, 4H), 7.0-6.8 (m, 2H), 6.5 (m, 1H), 6.12 (d, J=8.0 Hz, 1H), 5.72 (d, J=6.0 Hz, 1H), 5.1 (d, J=8.0 Hz, 1H), 4.91 (s, 1H), 4.62 (d, J=8.2 Hz, 1H), 4.32 (d, J=8.2 Hz, 1H), 4.26 (d, J=8.0 Hz, 1H), 3.95 (d, J=8.2 Hz, 1H).

Example 81: 5-benzhydryl-10-hydroxy-4,5-dihydro-9H-pyrido[1,2-b]thiazolo[4,5-d]pyridazin-9-one

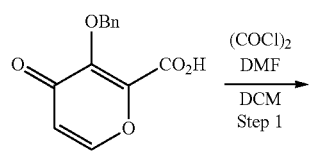

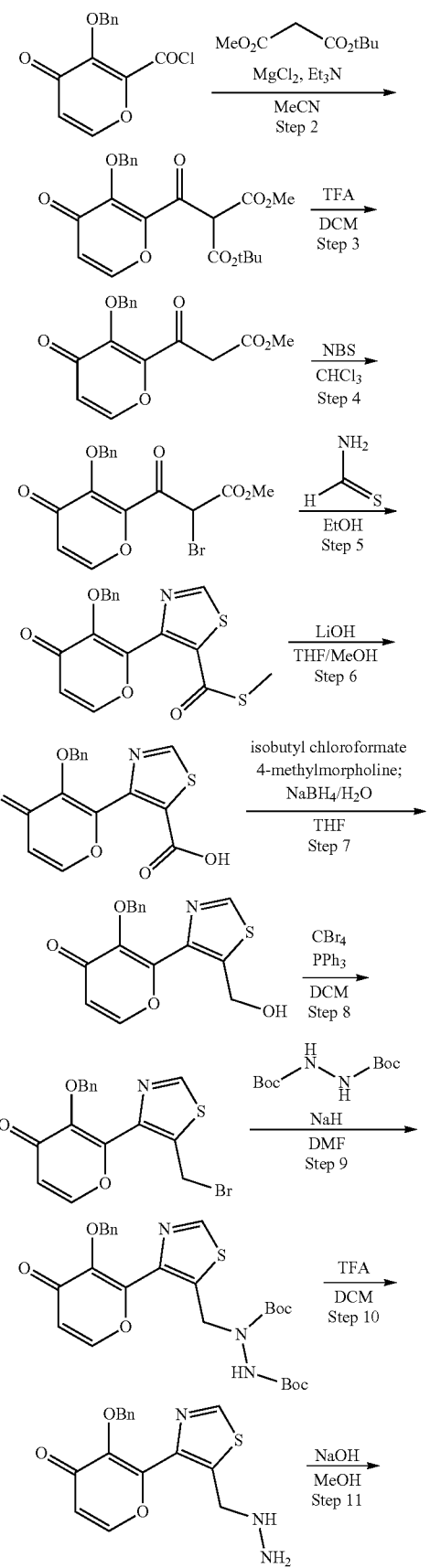

-continued

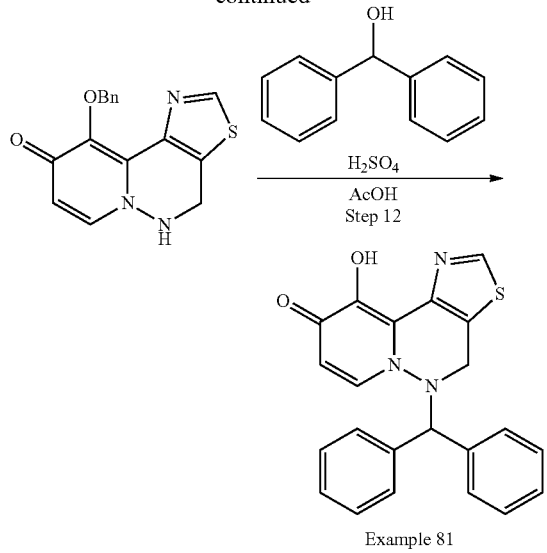

Example 81

Step 1: 3-(benzyloxy)-4-oxo-4H-pyran-2-carbonyl Chloride

To a suspension of 3-(benzyloxy)-4-oxo-4H-pyran-2-carboxylic acid (40 g, 162 mmol) in DCM (500 mL) was added 1 mL DMF, followed by dropwise addition of oxalyl chloride (15.6 mL, 179 mmol). The reaction turned clear after 30 minutes. After another 30 minutes, the reaction was then concentrated and the residue was carried to the next step directly.

Step 2: 1-(tert-butyl) 3-methyl 2-(3-(benzyloxy)-4-oxo-4H-pyran-2-carbonyl) malonate To a mixture of tert-butyl methyl malonate (31.1 g, 179 mmol) and magnesium chloride (17.02 g, 179 mmol) in 350 mL acetonitrile at 0° C. is added triethylamine (100 mL, 715 mmol). The mixture is stirred for 15 minutes at 0° C. 3-(benzyloxy)-4-oxo-4H-pyran-2-carbonyl chloride (43 g, 162 mmol) in acetonitrile (30 mL) is added dropwise. The reaction mixture is allowed to warm to room temperature and stirred for two hours. The reaction mixture is cooled to 0° C. and quenched with 30 mL 6N HCl. To the resulting mixture is added 1 L ether and the mixture is transferred to a separatory funnel. The aqueous layer is removed and the organics are washed with 2×300 mL water followed by washings with brine until the ether layer is clear. The organic layer is dried over magnesium sulphate, filtered, then concentrated to give 1-(tert-butyl) 3-methyl 2-(3-(benzyloxy)-4-oxo-4H-pyran-2-carbonyl)malonate which is used without further purification.

Step 3: methyl 3-(3-(benzyloxy)-4-oxo-4H-pyran-2-yl)-3-oxopropanoate

To 1-(tert-butyl) 3-methyl 2-(3-(benzyloxy)-4-oxo-4H-pyran-2-carbonyl)malonate (65 g, 162 mmol) in DCM (200 mL) at RT was added TFA (100 mL). The reaction was stirred for one hour and concentrated. Silica gel chromatography (0-80% EtOAc in heptane) purification provided methyl 3-(3-(benzyloxy)-4-oxo-4H-pyran-2-yl)-3-oxopropanoate (42 g, 82%). LCMS (MH+), 303.1, 0.72 min.

Step 4: Methyl 3-(3-(benzyloxy)-4-oxo-4H-pyran-2-yl)-2-bromo-3-oxopropanoate To a solution of methyl 3-(3-(benzyloxy)-4-oxo-4H-pyran-2-yl)-3-oxopropanoate (5 g, 16.54 mmol) in chloroform (Volume: 60 mL) was added NBS (2.94 g, 16.54 mmol) in 5 portions over 2 hour period of time at ambient temperature under nitrogen. The resulting mixture was stirred at 25° C. for 2 h. Reaction was quenched by adding water. The organic phase was washed with brine, dried over sodium sulfate and filtered. The filtrate was concentrated. The resulting residue was purified by silica gel chromatography (methanol in dichloromethane 0% to 5%) to give methyl 3-(3-(benzyloxy)-4-oxo-4H-pyran-2-yl)-2-bromo-3-oxopropanoate (3.4 g, 8.30 mmol, 50.2% yield). MS m/z 381/383 (M+2).

Step 5: Methyl 4-(3-(benzyloxy)-4-oxo-4H-pyran-2-yl)thiazole-5-carboxylate

To an ice cold solution of methyl 3-(3-(benzyloxy)-4-oxo-4H-pyran-2-yl)-2-bromo-3-oxopropanoate (3.4 g, 5.35 mmol) in EtOH (Volume: 20 mL) was added methanethioamide (0.687 g, 11.24 mmol). The resulting mixture was stirred at 25° C. for 16 h. The reaction mixture was concentrated and the resulting residue was purified on silica gel (ethyl acetate in heptane 0% to 60%) to give methyl 4-(3-(benzyloxy)-4-oxo-4H-pyran-2-yl)thiazole-5-carboxylate (610 mg, 32% yield). MS m/z 344 (M+1).

Step 6: 4-(3-(Benzyloxy)-4-oxo-4H-pyran-2-yl)thiazole-5-carboxylic Acid

To an ice cold solution of methyl 4-(3-(benzyloxy)-4-oxo-4H-pyran-2-yl)thiazole-5-carboxylate (270 mg, 0.78 mmol) in mix solvent of THF (Volume: 1.5 mL, Ratio: 1.000), MeOH (Volume: 1.5 mL, Ratio: 1.000) was added 1.0 M lithium hydroxide hydrate (1.02 mL, 1.02 mmol). The resulting mixture was stirred at 55° C. in an oil bath for 1 h. The reaction solution was concentrated and the residue was diluted with ethyl acetate and water. Then 1.0 M hydrogen chloride (1.02 mL, 1.02 mmol) was added dropwise into the solution. The organic phase was washed with water, brine, dried over sodium sulfate, and filtered. The filtrate was concentrated. The resulting residue was dried under high vacuum to give 4-(3-(benzyloxy)-4-oxo-4H-pyran-2-yl)thiazole-5-carboxylic acid (260 mg, 100% yield), MS m/z 330 (M+1).

Step 7: 3-(Benzyloxy)-2-(5-(hydroxymethyl)thiazol-4-yl)-4H-pyran-4-one

To a cold solution of 4-(3-(benzyloxy)-4-oxo-4H-pyran-2-yl)thiazole-5-carboxylic acid (260 mg, 0.78 mmol) in THF (Volume: 3.0 mL) at −40° C. was added isobutyl chloroformate (0.24 mL, 1.82 mmol) and followed by the addition of 4-methylmorpholine (0.20 mL, 1.82 mmol). The resulting mixture was stirred at −40° C. for 30 min. Then the solution was warmed up to 0° C. and was stirred for another 40 min. The formation of intermediate was confirmed by LCMS data. The reaction was continued for 5 h. The reaction solution was filtered through a filter funnel and the filter cake was rinsed with 10 ml THF. The combined filtrate was concentrated to half of the volume, and the residue was re-cooled to −40° C. At this point sodium borohydride (29.9 mg, 0.79 mmol) was added followed by the addition of 0.4 ml water. The resulting mixture was stirred at −35° C. for 20 min, and then was allowed to warm up to ambient temperature and was stirred for another 1 h.

The reaction mixture was diluted with ethyl acetate and water. And 1 ml HCl (1.0 M) was added dropwise into the solution to bring the pH=5. The organic phase was washed with water, saturated sodium bicarbonate solution, and brine. The organic phase was dried over sodium sulfate, and was filtered. The filtrate was concentrated. The resulting residue was dried under high vacuum to give 3-(benzyloxy)-2-(5-(hydroxymethyl)thiazol-4-yl)-4H-pyran-4-one (54 mg, 22% yield), MS m/z 316 (M+1).

Step 8: 3-(Benzyloxy)-2-(5-(bromomethyl)thiazol-4-yl)-4H-pyran-4-one

To a solution of 3-(benzyloxy)-2-(5-(hydroxymethyl)thiazol-4-yl)-4H-pyran-4-one (54 mg, 0.17 mmol) in DCM (Volume: 1 mL) was added carbon tetrabromide (108 mg, 0.32 mmol). The resulting solution was cooled in an ice bath, and followed by the addition of triphenylphosphine (90 mg, 0.34 mmol) in 1 ml DCM. After addition, the ice bath was removed away and the resulting mixture was stirred at 25° C. for 6 hr. The reaction solution was concentrated to remove solvent. The resulting residue was extracted into ether (3×10 ml), the combined ether layer was concentrated to give crude product 3-(benzyloxy)-2-(5-(bromomethyl)thiazol-4-yl)-4H-pyran-4-one (40 mg, 65% yield), which was used for next step without purification. MS m/z 378/380 (M+2).

Step 9: Di-tert-butyl 1-((4-(3-(benzyloxy)-4-oxo-4H-pyran-2-yl)thiazol-5-yl)methyl)hydrazine-1,2-dicarboxylate To an ice cold solution of 3-(benzyloxy)-2-(5-(bromomethyl)thiazol-4-yl)-4H-pyran-4-one (40 mg, 0.11 mmol) in DMF (Volume: 0.5 mL) was added a mix solution of di-tert-butyl hydrazine-1,2-dicarboxylate (34.4 mg, 0.15 mmol) and sodium hydride (5.92 mg, 0.15 mmol) in 1.0 ml DMF. The resulting mixture was stirred at 0° C. for 10 min, and then was stirred ambient temperature for 30 min. The reaction solution was diluted with ethyl acetate and water, the organic phase was washed with water, brine, dried over sodium sulfate, and was filtered. The filtrate was concentrated to give crude product di-tert-butyl 1-((4-(3-(benzyloxy)-4-oxo-4H-pyran-2-yl)thiazol-5-yl)methyl)hydrazine-1,2-dicarboxylate (35 mg, 63% yield), MS m/z 530 (M+1).

Step 10: 3-(Benzyloxy)-2-(5-(hydrazinylmethyl)thiazol-4-yl)-4H-pyran-4-one

To an ice cold solution of di-tert-butyl 1-((4-(3-(benzyloxy)-4-oxo-4H-pyran-2-yl)thiazol-5-yl)methyl)hydrazine-1,2-dicarboxylate (35 mg, 0.066 mmol) in DCM (Volume: 1 mL) was added a cold solution of TFA (3 ml, 38.9 mmol) in 1.0 ml DCM. The resulting mixture was stirred at 25° C. for 1 h. The reaction solution was concentrated. The residue was purified by reverse-phase HPLC to give 3-(benzyloxy)-2-(5-(hydrazinylmethyl)thiazol-4-yl)-4H-pyran-4-one (10 mg, 43.6% yield), MS m/z 330 (M+1).

Step 11: 10-(benzyloxy)-4,5-dihydro-9H-pyrido[1,2-b]thiazolo[4,5-d]pyridazin-9-one To a solution of 3-(benzyloxy)-2-(5-(hydrazinylmethyl)thiazol-4-yl)-4H-pyran-4-one (10 mg, 0.03 mmol) in MeOH (Volume: 0.5 mL) was added 1 N NaOH (0.09 mL, 0.09 mmol). The resulting mixture was stirred at 25° C. for 2 h. The reaction solution was concentrated to give 10-(benzyloxy)-4,5-dihydro-9H-pyrido[1,2-b]thiazolo[4,5-d]pyridazin-9-one (8.0 mg, 85% yield), MS m/z 312 (M+1).

Step 12: 5-Benzhydryl-10-hydroxy-4,5-dihydro-9H-pyrido[1,2-b]thiazolo[4,5-d]pyridazin-9-one To an ice cooled solution of 10-(benzyloxy)-4,5-dihydro-9H-pyrido[1,2-b]thiazolo[4,5-d]pyridazin-9-one (8 mg, 0.026 mmol) and diphenylmethanol (9.47 mg, 0.051 mmol) in acetic acid (Volume: 0.5 ml) was added concentrated sulfuric acid (0.014 ml, 0.25 mmol). The reaction mixture was heated to 75° C. in an oil bath for 15 min. The oil bath temperature was raised to 90° C., and the reaction mixture was heated for 30 min. Cold water (2 ml) was added to reaction mixture, and the resulting mixture was extracted with ethyl acetate (2 ml). The organic phase was concentrated. The crude product was purified by reverse-phase HPLC (MeCN/water with 0.1% TFA) to give 5-benzhydryl-10-hydroxy-4,5-dihydro-9H-pyrido[1,2-b]thiazolo[4,5-d]pyridazin-9-one (1.5 mg, 11% yield) as TFA salt. MS m/z 388.3 (M+1), 0.70 min.

Example 82: 5-benzhydryl-10-hydroxy-3-methyl-4,5-dihydroimidazo[4,5-d]pyrido[1,2-b]pyridazin-9(3H)-one

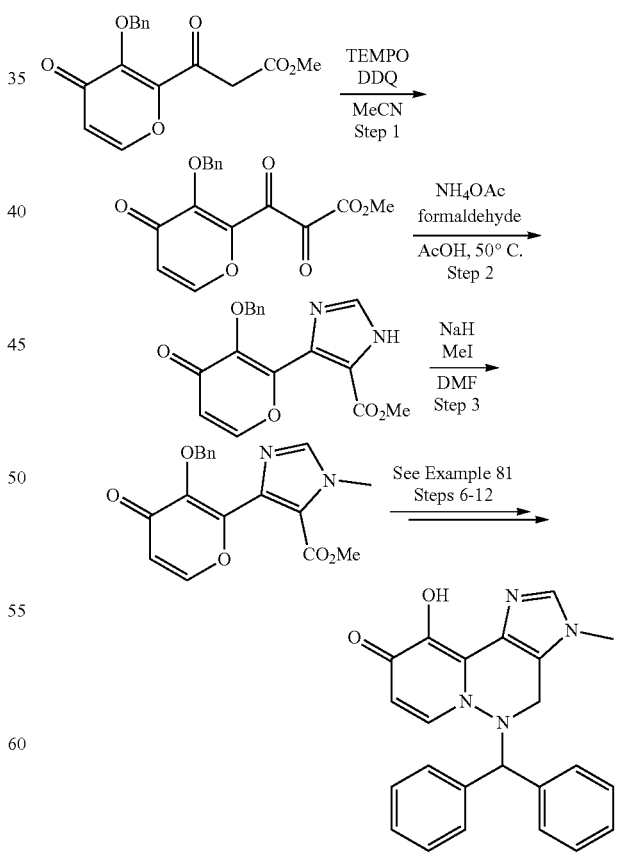

Example 82

Step 1: methyl 3-(3-(benzyloxy)-4-oxo-4H-pyran-2-yl)-2,3-dioxopropanoate

A solution of methyl 3-(3-(benzyloxy)-4-oxo-4H-pyran-2-yl)-3-oxopropanoate (6 g, 19.85 mmol) in acetonitrile (50 mL) was added to a solution of TEMPO (3.72 g, 23.82 mmol) in acetonitrile (100 mL), followed 5 minutes later by addition of DDQ (4.96 g, 21.83 mmol). Another portion of DDQ (4.7 g) was added one hour later. The reaction was stirred for 3 hours and concentrated. Silica gel chromatography (0-100% EtOAc in heptane) provided methyl 3-(3-(benzyloxy)-4-oxo-4H-pyran-2-yl)-2,3-dioxopropanoate (6 g, 96%). LCMS: (MS+H2O+1, 335.2, 0.65 min).

Step 2: methyl 4-(3-(benzyloxy)-4-oxo-4H-pyran-2-yl)-1H-imidazole-5-carboxylate To a suspension of ammonium acetate (9.75 g, 126 mmol) in HOAc (20 mL) was added methyl 3-(3-(benzyloxy)-4-oxo-4H-pyran-2-yl)-2,3-dioxopropanoate (4 g, 12.65 mmol). The mixture was stirred for 10 minutes and formaldehyde (2.53 g, 25.3 mmol) was then added. The reaction mix was then heated to 50° C. for three hours. The reaction mixture was then concentrated to remove most of the HOAc. The residue was then diluted with sat. NaHCO₃ (50 mL) and extracted with IPA/DCM (15%). The organic layer was dried (Na₂SO₄) and concentrated. Silica gel chromatography (0-100% EtOAc in heptane with 10% MeOH) provided methyl 4-(3-(benzyloxy)-4-oxo-4H-pyran-2-yl)-1H-imidazole-5-carboxylate (2.1 g, 51%). LCMS: (MS+1, 327.2, 0.44 min).

Step 3: methyl 4-(3-(benzyloxy)-4-oxo-4H-pyran-2-yl)-1-methyl-1H-imidazole-5-carboxylate To methyl 4-(3-(benzyloxy)-4-oxo-4H-pyran-2-yl)-1H-imidazole-5-carboxylate (2.1 g, 6.44 mmol) in DMF (20 mL) at 0° C. was added sodium hydride (0.386 g, 9.65 mmol). The mixture was stirred for 30 minutes and iodomethane (0.601 mL, 9.65 mmol) was then added dropwise. The mixture was stirred for another hour and then diluted with EtOAc (20 mL) and quenched with HCl (1M, 2 mL) and water (10 mL). The aqueous layer was extracted with EtOAc (2×10 mL). The combined organic was dried (Na2SO4) and concentrated. Silica gel chromatography (0-100% EtOAc in heptane with 10% MeOH) provided methyl 4-(3-(benzyloxy)-4-oxo-4H-pyran-2-yl)-1-methyl-1H-imidazole-5-carboxylate (1.45 g, 66%). LCMS: (MS+1, 341.2, 0.71 min).

Example 82: 5-benzhydryl-10-hydroxy-3-methyl-4,5-dihydroimidazo[4,5-d]pyrido[1,2-b]pyridazin-9(3H)-one Prepared from methyl 4-(3-(benzyloxy)-4-oxo-4H-pyran-2-yl)-1-methyl-1H-imidazole-5-carboxylate by the method of Example 81, steps 6-12. LCMS (m/z): 385.1 (MH+), 1H NMR (400 MHz, DMSO-d6) δ (400 MHz, DMSO-d6) δ 7.95 (s, 1H), 7.6-7.1 (s, 8H), 6.7-6.4 (m, 3H), 5.65 (d, J=6.0 Hz, 1H), 4.92 (s, 1H), 5.12 (s, 2H), 3.5 (s, 3H).

Example 83: 5-benzhydryl-10-hydroxy-4,5-dihydro-9H-oxazolo[4,5-d]pyrido[1,2-b]pyridazin-9-one

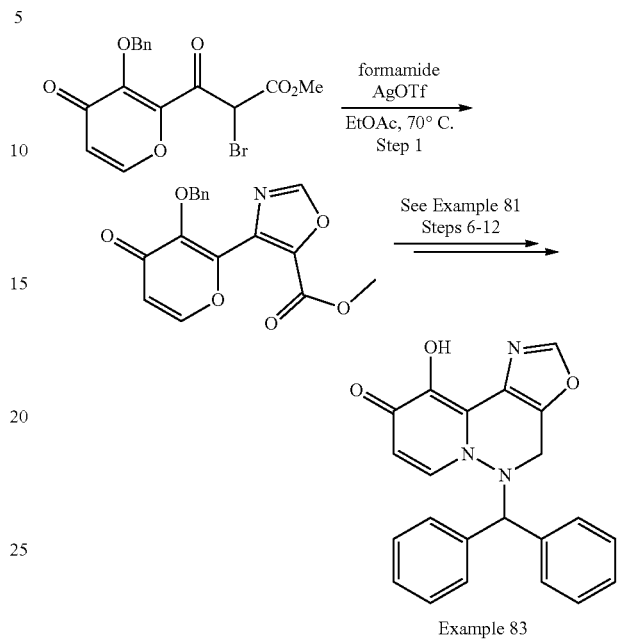

Example 83

Step 1: methyl 4-(3-(benzyloxy)-4-oxo-4H-pyran-2-yl)oxazole-5-carboxylate

To a solution of methyl 3-(3-(benzyloxy)-4-oxo-4H-pyran-2-yl)-2-bromo-3-oxopropanoate (6.46 g, 16.95 mmol) in EtOAc (Volume: 24.2 ml) were added formamide (1.013 ml, 25.4 mmol) and AgOTf (6.53 g, 25.4 mmol) and heated at 70° C. for overnight. LC/MS showed good conversion but not complete. Another 1.5 equiv. each was added and heated for another overnight. LC/MS showed the reaction complete. After the reaction mixture was cooled to rt, EtOAc (20 mL) & saturated NaCl (20 mL) were added and stirred for 2 h, the salts (Ag Br and AgCl) were filtered and the resulting biphasic solution was transferred to a separatory funnel and the layers separated. The aqueous layer was back extracted with EtOAc, and all the organics were washed with water, sat. NaHCO₃, 1N HCl and water, dried over Na2SO4, filtered and concentrated to give crude methyl 4-(3-(benzyloxy)-4-oxo-4H-pyran-2-yl)oxazole-5-carboxylate (1.46 g, 26%). LCMS: (MS+1, 328.0, 0.55 min).

Example 83: 5-benzhydryl-10-hydroxy-4,5-dihydro-9H-oxazolo[4,5-d]pyrido[1,2-b]pyridazin-9-one Prepared from methyl 4-(3-(benzyloxy)-4-oxo-4H-pyran-2-yl)oxazole-5-carboxylate by the method of Example 81, steps 6-12. LCMS (m/z): 371.9 (MH+), 1H NMR (400 MHz, DMSO-d6) δ (400 MHz, DMSO-d6) δ 8.65 (s, 1H), 7.82-7.05 (m, 11H), 5.63 (d, J=6.0 Hz, 1H), 5.05 (s, 1H), 4.78 (m, 1H), 4.2 (m, 1H).

Example 84: 5-benzhydryl-10-hydroxy-4,5-dihydro-9H-oxazolo[5,4-d]pyrido[1,2-b]pyridazin-9-one

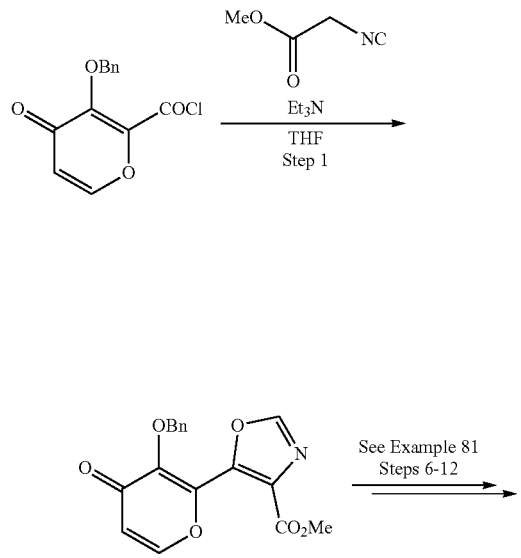

steps 6-12. LCMS (m/z): 372.1 (MH+), 1H NMR (400 MHz, DMSO-d6) δ (400 MHz, DMSO-d6) δ 8.71 (s, 1H), 7.82-7.05 (m, 11H), 5.51 (d, J=6.0 Hz, 1H), 5.18 (s, 1H), 4.2-3.7 (m, 2H).

Example 85: (S)-6-(bis(4-fluorophenyl)methyl)-10-oxo-5,6-dihydro-10H-imidazo[2',1':3,4]pyrazino[1,2-b]pyridazin-11-yl acetate

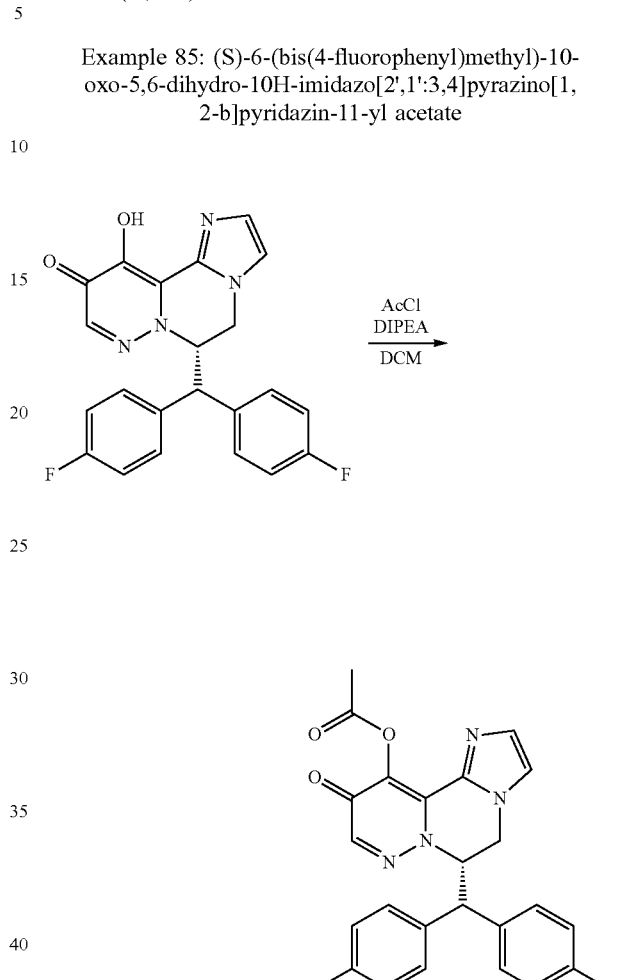

Step 1: methyl 5-(3-(benzyloxy)-4-oxo-4H-pyran-2-yl)oxazole-4-carboxylate 2-isocyanoacetate (9.01 mL, 100 mmol) was added to a solution of 3-(benzyloxy)-4-oxo-4H-pyran-2-carbonyl chloride (13.23 g, 50 mmol) (for synthesis, see example 81 step 1) and TEA (34.8 ml, 250 mmol) in THF (200 mL). The mixture was stirred overnight at RT. The solvent was then removed on a rotary evaporator. The residue was taken up in 300 mL of ethyl acetate and washed once with 100 mL of water. The organic phase was dried over Na2SO4 and the solvent was removed on a rotary evaporator. The crude was purified by silica gel chromatography (EtOAc/heptane) to give methyl 5-(3-(benzyloxy)-4-oxo-4H-pyran-2-yl)oxazole-4-carboxylate (12.3 g, 75%). LCMS: (MS+1, 328.1, 0.71 min).

Example 84: 5-benzhydryl-10-hydroxy-4,5-dihydro-9H-oxazolo[5,4-d]pyrido[1,2-b]pyridazin-9-one Prepared from methyl 5-(3-(benzyloxy)-4-oxo-4H-pyran-2-yl)oxazole-4-carboxylate by the method of Example 81, Added diisopropylethylamine (0.014 mL, 0.080 mmol) followed by acetyl chloride (3.06 μl, 0.043 mmol) to a solution of Example 22 (15 mg, 0.033 mmol) in DCM (Volume: 1 mL) at RT. Stirred at RT for 20 min, by which time LCMS showed complete conversion to product mass. Diluted with DCM and washed with dilute aqueous NaHCO3 solution. The organic layer was dried over Na2SO4, filtered and concentrated. The residue was taken up in DMSO and purified by reverse-phase prep HPLC (MeCN/water with 0.1% formic acid as eluent) to give, after lyophilization, (S)-6-(bis(4-fluorophenyl)methyl)-10-oxo-5,6-dihydro-10H-imidazo[2',1':3,4]pyrazino[1,2-b]pyridazin-11-yl acetate (13 mg, 0.026 mmol, 79% yield) as a white solid. LCMS (m/z): 449.3 (MH+), 1H NMR (400 MHz, DMSO-d6) δ (400 MHz, DMSO-d6) δ 7.55-7.47 (m, 3H), 7.45 (s, 1H), 7.34 (d, J=1.0 Hz, 1H), 7.19 (q, J=8.8 Hz, 3H), 6.98 (t, J=8.7 Hz, 2H), 6.55 (d, J=3.5 Hz, 1H), 5.79 (d, J=11.5 Hz, 1H), 4.72 (dd, J=14.0, 4.1 Hz, 1H), 4.21 (d, J=14.0 Hz, 1H), 3.95 (s, 1H), 2.33 (s, 3H).

Example 86: (S)-6-(bis(4-fluorophenyl)methyl)-10-oxo-5,6-dihydro-10H-imidazo[2',1':3,4]pyrazino[1,2-b]pyridazin-11-yl Isobutyrate

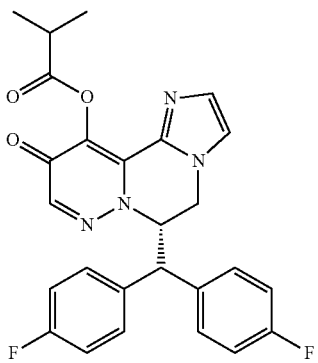 [SMILES: CC(C)C(=O)Oc1c2n(ncc1=O)[C@@H](C(c1ccc(F)cc1)c1ccc(F)cc1)Cn1ccnc1-2]

Prepared by the method of Example 85 except using isobutyryl chloride. LCMS (m/z): 477.3 (MH+), 1H NMR (400 MHz, DMSO-d6) δ 7.52 (dd, J=8.7, 5.5 Hz, 2H), 7.48 (s, 1H), 7.44 (s, 1H), 7.32 (s, 1H), 7.19 (q, J=8.6 Hz, 2H), 6.99 (t, J=8.6 Hz, 2H), 6.80 (s, 2H), 5.79 (d, J=11.6 Hz, 1H), 4.72 (dd, J=14.0, 4.0 Hz, 1H), 4.20 (d, J=13.9 Hz, 1H), 3.98 (m, 1H), 2.90 (q, J=7.1 Hz, 1H), 1.30 (t, J=6.6 Hz, 6H).

Example 87: (S)-6-(bis(4-fluorophenyl)methyl)-10-oxo-5,6-dihydro-10H-imidazo[2',1':3,4]pyrazino[1,2-b]pyridazin-11-yl 3-methylbutanoate

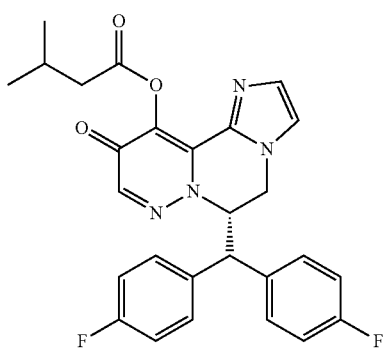 [SMILES: CC(C)CC(=O)Oc1c2n(ncc1=O)[C@@H](C(c1ccc(F)cc1)c1ccc(F)cc1)Cn1ccnc1-2]

Prepared by the method of Example 85 except using isovaleryl chloride. LCMS (m/z): 491.3 (MH+), 1H NMR (400 MHz, MeOD) δ ppm 1.01-1.17 (m, 6H) 2.24 (dt, J=13.22, 6.77 Hz, 1H) 2.61-2.70 (m, 2H) 3.97 (d, J=11.44 Hz, 1H) 4.34 (d, J=14.08 Hz, 1H) 4.60 (s, 1H) 4.71 (dd, J=14.04, 4.01 Hz, 1H) 5.55-5.79 (m, 1H) 6.90 (t, J=8.71 Hz, 2H) 7.07-7.20 (m, 4H) 7.35 (d, J=12.57 Hz, 2H) 7.42 (dd, J=8.63, 5.26 Hz, 2H) 7.49 (s, 1H).

Example 88: (S)-((6-(bis(4-fluorophenyl)methyl)-10-oxo-5,6-dihydro-10H-imidazo[2',1':3,4]pyrazino[1,2-b]pyridazin-11-yl)oxy)methyl methyl Carbonate

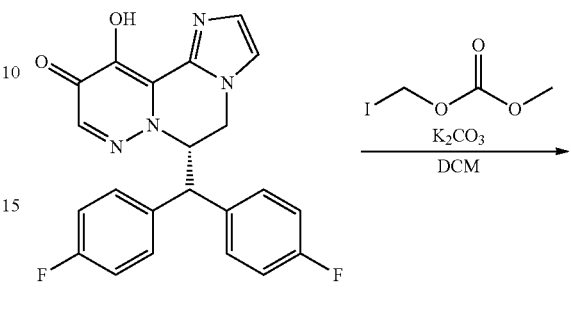

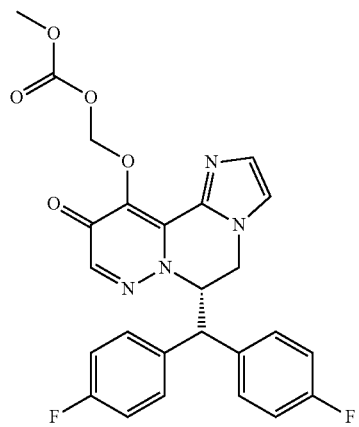

Added potassium carbonate (13.75 mg, 0.099 mmol) and iodomethyl methyl carbonate (14.3 mg, 0.066 mmol) to a solution of Example 22 (15 mg, 0.033 mmol) in DMF (Volume: 332 µl) at 0° C. Stirred at 0° C. for 1 hour and then RT for another hour, by which time LCMS showed complete conversion to product mass. The reaction was filtered to remove solids and purified by reverse-phase prep HPLC (MeCN/water with 0.1% TFA as eluent) to give, after lyophilization, (S)-((6-(bis(4-fluorophenyl)methyl)-10-oxo-5,6-dihydro-10H-imidazo[2',1':3,4]pyrazino[1,2-b]pyridazin-11-yl)oxy)methyl methyl carbonate (10 mg, 0.016 mmol, 49% yield) as a white solid. LCMS (m/z): 495.2 (MH+), 1H NMR (400 MHz, DMSO-d6) δ (400 MHz, DMSO-d6) δ 7.52-7.41 (m, 4H), 7.36 (s, 1H), 7.25-7.13 (m, 4H), 6.99 (t, J=8.8 Hz, 2H), 5.86-5.72 (m, 3H), 4.69 (dd, J=14.0, 4.0 Hz, 1H), 4.20 (d, J=14.0 Hz, 1H), 3.95-3.84 (m, 1H), 3.67 (s, 3H).

TABLE 1

Compounds of the Examples.

| Example No. | Structure | Name |
|---|---|---|
| 1 | 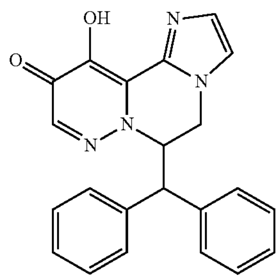 [SMILES: O=c1cnn2c(c1O)-c1nccn1CC2C(c1ccccc1)c1ccccc1] | 6-Benzhydryl-11-hydroxy-5H-imidazo[2',1',:3,4]pyrazino[1,2-b]pyridazin-10(6H)-one |
| 2 | 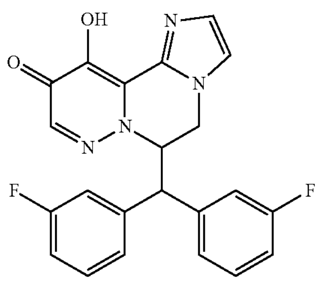 | 6-(bis(3-fluorophenyl)methyl)-11-hydroxy-5,6-dihydro-10H-imidazo[2',1':3,4]pyrazino[1,2-b]pyridazin-10-one |
| 3 | 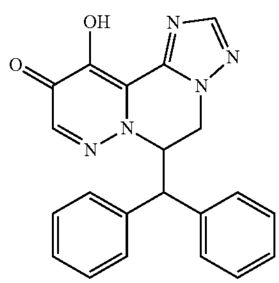 | 6-benzhydryl-11-hydroxy-5,6-dihydro-10H-[1,2,4]triazolo[5',1':3,4]pyrazino[1,2-b]pyridazin-10-one |
| 4 | 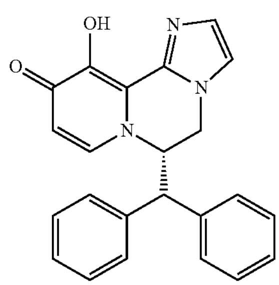 [SMILES: O=c1ccn2c(c1O)-c1nccn1C[C@@H]2C(c1ccccc1)c1ccccc1] | (S)-6-Benzhydryl-11-hydroxy-5H-imidazo[1,2-a]pyrido[2,1-c]pyrazin-10(6H)-one |
| 5 | 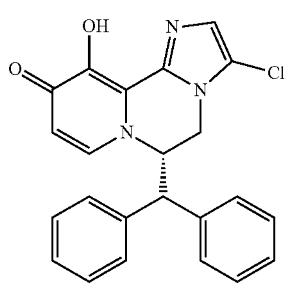 [SMILES: O=c1ccn2c(c1O)-c1ncc(Cl)n1C[C@@H]2C(c1ccccc1)c1ccccc1] | (S)-6-Benzhydryl-3-chloro-11-hydroxy-5,6-dihydro-10H-imidazo[1,2-a]pyrido[2,1-c]pyrazin-10-one |

TABLE 1-continued

Compounds of the Examples.

| Example No. | Structure | Name |
|---|---|---|
| 6 | 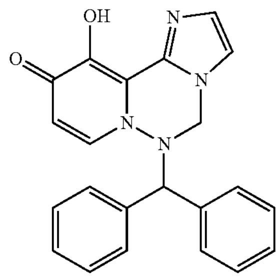 [SMILES: O=c1ccn2c(c1O)-c1nccn1CN2C(c1ccccc1)c1ccccc1] | 6-benzhydryl-11-hydroxy-5,6-dihydro-10H-imidazo[1,2-d]pyrido[2,1-f][1,2,4]triazin-10-one |
| 7 | 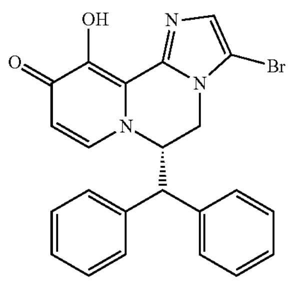 [SMILES: O=c1ccn2c(c1O)-c1ncc(Br)n1C[C@@H]2C(c1ccccc1)c1ccccc1] | (S)-6-benzhydryl-3-bromo-11-hydroxy-5H-imidazo[1,2-a]pyrido[2,1-c]pyrazin-10(6H)-one |
| 8 | 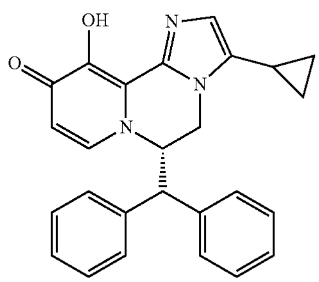 [SMILES: O=c1ccn2c(c1O)-c1ncc(C3CC3)n1C[C@@H]2C(c1ccccc1)c1ccccc1] | (S)-6-benzhydryl-3-cyclopropyl-11-hydroxy-5H-imidazo[1,2-a]pyrido[2,1-c]pyrazin-10(6H)-one |
| 9 | 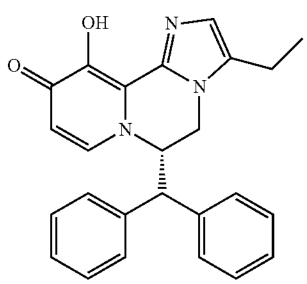 [SMILES: CCc1cnc2n1C[C@H](C(c1ccccc1)c1ccccc1)n1ccc(=O)c(O)c1-2] | (S)-6-benzhydryl-3-ethyl-11-hydroxy-5H-imidazo[1,2-a]pyrido[2,1-c]pyrazin-10(6H)-one |
| 10 | 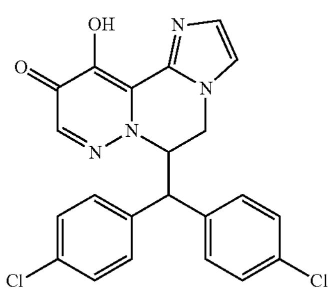 [SMILES: O=c1cnn2c(c1O)-c1nccn1CC2C(c1ccc(Cl)cc1)c1ccc(Cl)cc1] | 6-(bis(4-chlorophenyl)methyl)-11-hydroxy-5H-imidazo[2',1':3,4]pyrazino[1,2-b]pyridazin-10(6H)-one |

TABLE 1-continued

Compounds of the Examples.

| Example No. | Structure | Name |
|---|---|---|
| 11 | 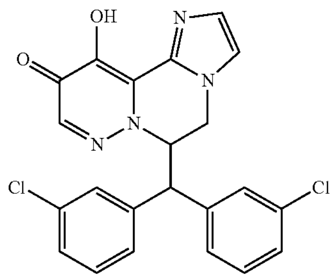 | 6-(bis(3-chlorophenyl)methyl)-11-hydroxy-5H-imidazo[2',1':3,4]pyrazino[1,2-b]pyridazin-10(6H)-one |
| 12 | 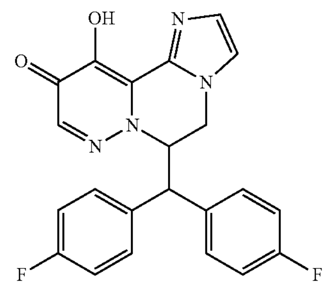 | 6-(bis(4-fluorophenyl)methyl)-11-hydroxy-5H-imidazo[2',1':3,4]pyrazino[1,2-b]pyridazin-10(6H)-one |
| 13 | 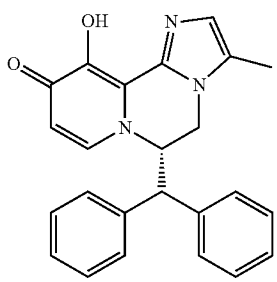 [SMILES: Cc1cnc2n1C[C@H](C(c1ccccc1)c1ccccc1)n1ccc(=O)c(O)c1-2] | (S)-6-benzhydryl-11-hydroxy-3-methyl-5H-imidazo[1,2-a]pyrido[2,1-c]pyrazin-10(6H)-one |
| 14 | 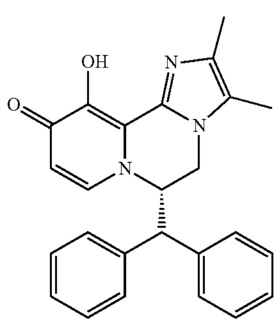 [SMILES: Cc1nc2n(c1C)C[C@H](C(c1ccccc1)c1ccccc1)n1ccc(=O)c(O)c1-2] | (S)-6-benzhydryl-11-hydroxy-2,3-dimethyl-5H-imidazo[1,2-a]pyrido[2,1-c]pyrazin-10(6H)-one |
| 15 | 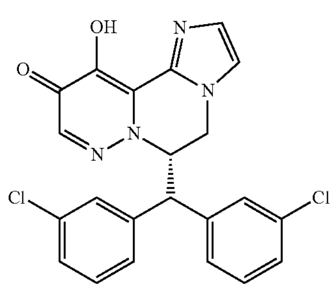 | (S)-6-(bis(3-chlorophenyl)methyl)-11-hydroxy-5H-imidazo[2',1':3,4]pyrazino[1,2-b]pyridazin-10(6H)-one |

TABLE 1-continued

Compounds of the Examples.

| Example No. | Structure | Name |
|---|---|---|
| 16 | 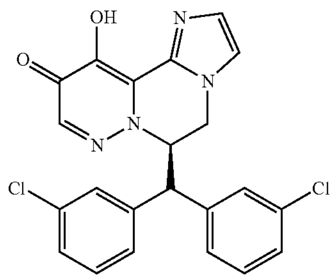 | (R)-6-(bis(3-chlorophenyl)methyl)-11-hydroxy-5H-imidazo[2',1':3,4] pyrazino [1,2-b]pyridazin-10(6H)-one |
| 17 | 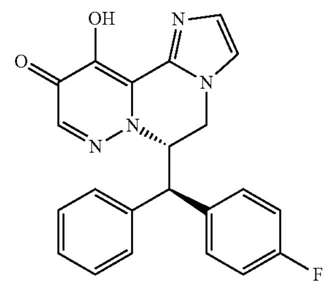 [SMILES: O=c1cnn2c(c1O)-c1nccn1C[C@@H]2[C@H](c1ccccc1)c1ccc(F)cc1] | (S)-6-((R)-(4-fluorophenyl)(phenyl)methyl)-11-hydroxy-5H-imidazo[2',1':3,4]pyrazino[1,2-b]pyridazin-10(6H)-one |
| 18 | 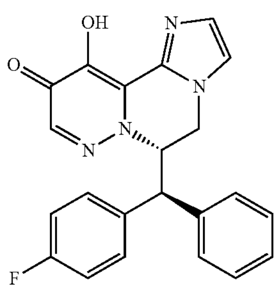 [SMILES: O=c1cnn2c(c1O)-c1nccn1C[C@@H]2[C@@H](c1ccccc1)c1ccc(F)cc1] | (S)-6-((S)-(4-fluorophenyl)(phenyl)methyl)-11-hydroxy-5,6-dihydro-10H-imidazo[2',1':3,4]pyrazino[1,2-b]pyridazin-10-one |
| 19 | 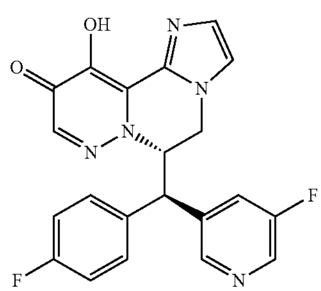 [SMILES: O=c1cnn2c(c1O)-c1nccn1C[C@@H]2[C@H](c1ccc(F)cc1)c1cncc(F)c1] | (S)-6-((R)-(4-fluorophenyl)(5-fluoropyridin-3-yl)methyl)-11-hydroxy-5,6-dihydro-10H-imidazo[2',1':3,4]pyrazino[1,2-b]pyridazin-10-one |
| 20 | 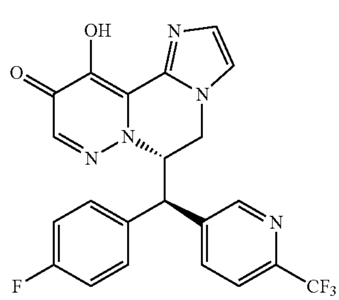 [SMILES: O=c1cnn2c(c1O)-c1nccn1C[C@@H]2[C@H](c1ccc(F)cc1)c1ccc(C(F)(F)F)nc1] | (S)-6-((R)-(4-fluorophenyl)(6-(trifluoromethyl)pyridin-3-yl)methyl)-11-hydroxy-5,6-dihydro-10H-imidazo[2',1':3,4]pyrazino[1,2-b]pyridazin-10-one |

TABLE 1-continued

Compounds of the Examples.

| Example No. | Structure | Name |
|---|---|---|
| 21 | 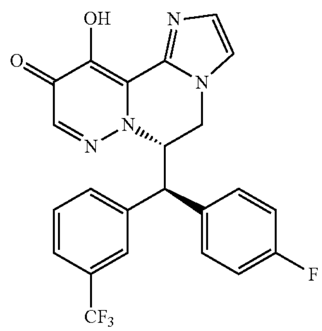 [SMILES: O=c1cnn2c(c1O)-c1nccn1C[C@@H]2[C@@H](c1ccc(F)cc1)c1cccc(C(F)(F)F)c1] | (S)-6-((S)-(4-fluorophenyl)(3-(trifluoromethyl)phenyl)methyl)-11-hydroxy-5,6-dihydro-10H-imidazo[2',1':3,4]pyrazino[1,2-b]pyridazin-10-one |
| 22 | 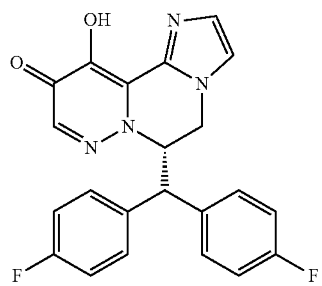 | (S)-6-(bis(4-fluorophenyl)methyl)-11-hydroxy-5,6-dihydro-10H-imidazo[2',1':3,4]pyrazino[1,2-b]pyridazin-10-one |
| 23 | 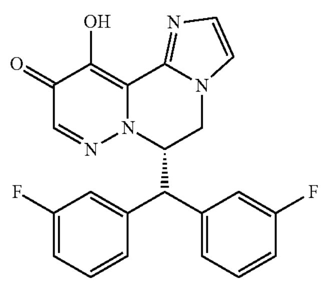 [SMILES: O=c1cnn2c(c1O)-c1nccn1C[C@@H]2C(c1cccc(F)c1)c1cccc(F)c1] | (S)-6-(bis(3-fluorophenyl)methyl)-11-hydroxy-5,6-dihydro-10H-imidazo[2',1':3,4]pyrazino[1,2-b]pyridazin-10-one |
| 24 | 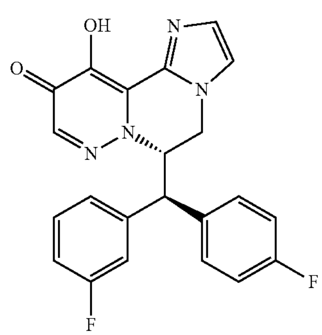 [SMILES: O=c1cnn2c(c1O)-c1nccn1C[C@@H]2[C@@H](c1ccc(F)cc1)c1cccc(F)c1] | (S)-6-((S)-(3-fluorophenyl)(4-fluorophenyl)methyl)-11-hydroxy-5,6-dihydro-10H-imidazo[2',1':3,4]pyrazino[1,2-b]pyridazin-10-one |
| 25 | 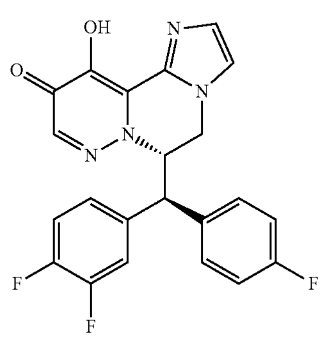 [SMILES: O=c1cnn2c(c1O)-c1nccn1C[C@@H]2[C@@H](c1ccc(F)cc1)c1ccc(F)c(F)c1] | (S)-6-((S)-(3,4-difluorophenyl)(4-fluorophenyl)methyl)-11-hydroxy-5H-imidazo[2',1':3,4]pyrazino[1,2-b]pyridazin-10(6H)-one |

TABLE 1-continued

Compounds of the Examples.

| Example No. | Structure | Name |
|---|---|---|
| 26 | 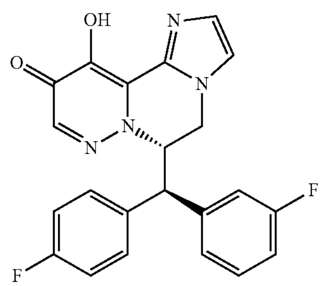 [SMILES: O=c1cnn2c(c1O)-c1nccn1C[C@@H]2[C@H](c1ccc(F)cc1)c1cccc(F)c1] | (S)-6-((R)-(3-fluorophenyl)(4-fluorophenyl)methyl)-11-hydroxy-5,6-dihydro-10H-imidazo[2',1':3,4]pyrazino[1,2-b]pyridazin-10-one |
| 27 | 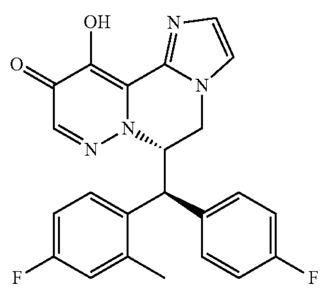 [SMILES: Cc1cc(F)ccc1[C@H](c1ccc(F)cc1)[C@H]1Cn2ccnc2-c2c(O)c(=O)cnn21] | (S)-6-((S)-(4-fluoro-2-methylphenyl)(4-fluorophenyl)methyl)-11-hydroxy-5,6-dihydro-10H-imidazo[2',1':3,4]pyrazino[1,2-b]pyridazin-10-one |
| 28 | 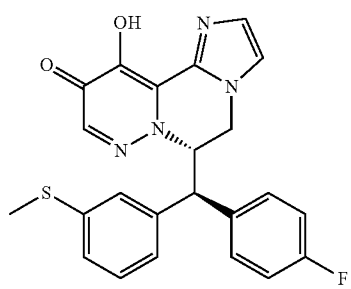 [SMILES: CSc1cccc([C@H](c2ccc(F)cc2)[C@H]2Cn3ccnc3-c3c(O)c(=O)cnn32)c1] | (S)-6-((S)-(4-fluorophenyl)(3-(methylthio)phenyl)methyl)-11-hydroxy-5,6-dihydro-10H-imidazo[2',1':3,4]pyrazino[1,2-b]pyridazin-10-one |
| 29 | 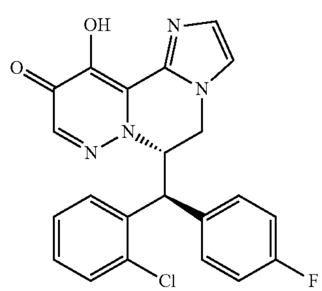 [SMILES: O=c1cnn2c(c1O)-c1nccn1C[C@@H]2[C@@H](c1ccc(F)cc1)c1ccccc1Cl] | (S)-6-((S)-(2-chlorophenyl)(4-fluorophenyl)methyl)-11-hydroxy-5,6-dihydro-10H-imidazo[2',1':3,4]pyrazino[1,2-b]pyridazin-10-one |
| 30 | 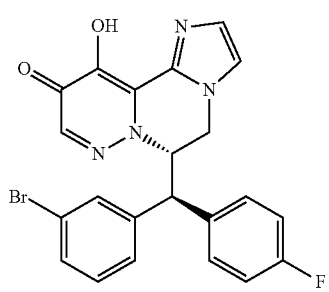 | (S)-6-((S)-(3-bromophenyl)(4-fluorophenyl)methyl)-11-hydroxy-5,6-dihydro-10H-imidazo[2',1':3,4]pyrazino[1,2-b]pyridazin-10-one |

TABLE 1-continued

Compounds of the Examples.

| Example No. | Structure | Name |
|---|---|---|
| 31 | 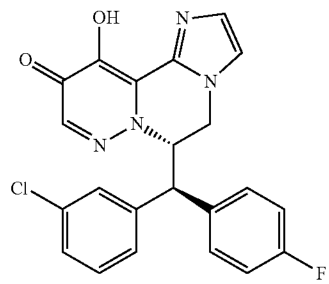 [SMILES: O=c1cnn2c(c1O)-c1nccn1C[C@@H]2[C@@H](c1ccc(F)cc1)c1cccc(Cl)c1] | (S)-6-((S)-(3-chlorophenyl)(4-fluorophenyl)methyl)-11-hydroxy-5,6-dihydro-10H-imidazo[2',1':3,4]pyrazino[1,2-b]pyridazin-10-one |
| 32 | 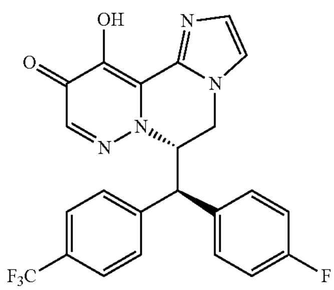 [SMILES: O=c1cnn2c(c1O)-c1nccn1C[C@@H]2[C@@H](c1ccc(F)cc1)c1ccc(C(F)(F)F)cc1] | (S)-6-((R)-(4-fluorophenyl)(4-(trifluoromethyl)phenyl)methyl)-11-hydroxy-5,6-dihydro-10H-imidazo[2',1':3,4]pyrazino[1,2-b]pyridazin-10-one |
| 33 | 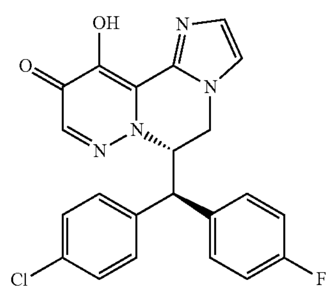 [SMILES: O=c1cnn2c(c1O)-c1nccn1C[C@@H]2[C@@H](c1ccc(F)cc1)c1ccc(Cl)cc1] | (S)-6-((S)-(4-chlorophenyl)(4-fluorophenyl)methyl)-11-hydroxy-5,6-dihydro-10H-imidazo[2',1':3,4]pyrazino[1,2-b]pyridazin-10-one |
| 34 | 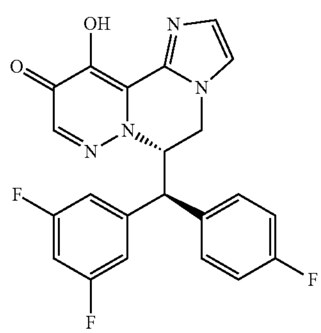 [SMILES: O=c1cnn2c(c1O)-c1nccn1C[C@@H]2[C@@H](c1ccc(F)cc1)c1cc(F)cc(F)c1] | (S)-6-((S)-(3,5-difluorophenyl)(4-fluorophenyl)methyl)-11-hydroxy-5H-imidazo[2',1':3,4]pyrazino[1,2-b]pyridazin-10(6H)-one |
| 35 | 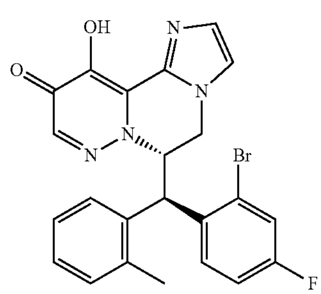 [SMILES: Cc1ccccc1[C@H](c1ccc(F)cc1Br)[C@H]1Cn2ccnc2-c2c(O)c(=O)cnn21] | (S)-6-((R)-(2-bromo-4-fluorophenyl)(o-tolyl)methyl)-11-hydroxy-5,6-dihydro-10H-imidazo[2',1':3,4]pyrazino[1,2-b]pyridazin-10-one |

TABLE 1-continued

Compounds of the Examples.

| Example No. | Structure | Name |
|---|---|---|
| 36 | 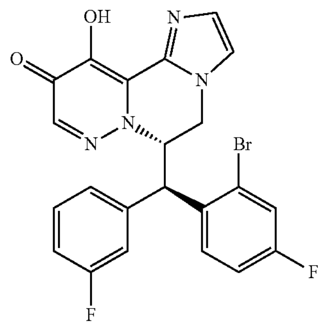 [SMILES: O=c1cnn2c(c1O)-c1nccn1C[C@@H]2[C@H](c1cccc(F)c1)c1ccc(F)cc1Br] | (S)-6-((R)-(2-bromo-4-fluorophenyl)(3-fluorophenyl)methyl)-11-hydroxy-5,6-dihydro-10H-imidazo[2',1':3,4]pyrazino[1,2-b]pyridazin-10-one |
| 37 | 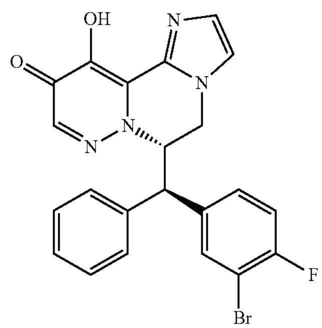 [SMILES: O=c1cnn2c(c1O)-c1nccn1C[C@@H]2[C@H](c1ccccc1)c1ccc(F)c(Br)c1] | (S)-6-((R)-(3-bromo-4-fluorophenyl)(phenyl)methyl)-11-hydroxy-5,6-dihydro-10H-imidazo[2',1':3,4]pyrazino[1,2-b]pyridazin-10-one |
| 38 | 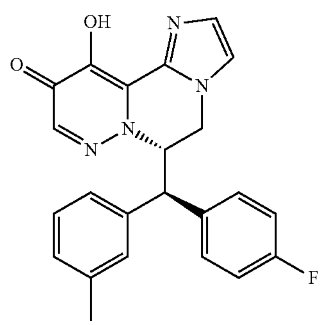 [SMILES: Cc1cccc([C@H](c2ccc(F)cc2)[C@H]2Cn3ccnc3-c3c(O)c(=O)cnn32)c1] | (S)-6-((S)-(4-fluorophenyl)(m-tolyl)methyl)-11-hydroxy-5,6-dihydro-10H-imidazo[2',1':3,4]pyrazino[1,2-b]pyridazin-10-one |
| 39 | 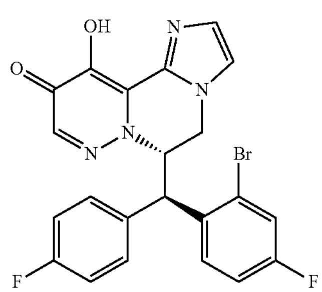 [SMILES: O=c1cnn2c(c1O)-c1nccn1C[C@@H]2[C@H](c1ccc(F)cc1)c1ccc(F)cc1Br] | (S)-6-((R)-(2-bromo-4-fluorophenyl)(4-fluorophenyl)methyl)-11-hydroxy-5,6-dihydro-10H-imidazo[2',1':3,4]pyrazino[1,2-b]pyridazin-10-one |
| 40 | 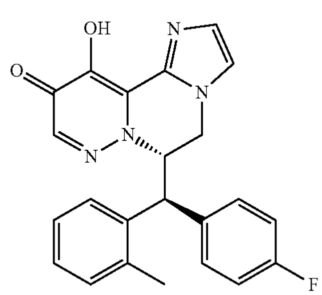 [SMILES: Cc1ccccc1[C@H](c1ccc(F)cc1)[C@H]1Cn2ccnc2-c2c(O)c(=O)cnn21] | (S)-6-((S)-(4-fluorophenyl)(o-tolyl)methyl)-11-hydroxy-5,6-dihydro-10H-imidazo[2',1':3,4]pyrazino[1,2-b]pyridazin-10-one |

TABLE 1-continued

Compounds of the Examples.

| Example No. | Structure | Name |
|---|---|---|
| 41 | 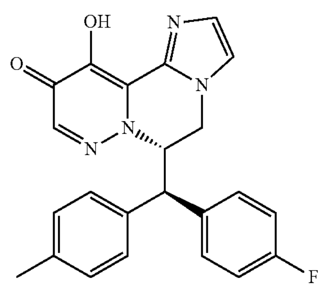 [SMILES: Cc1ccc([C@H](c2ccc(F)cc2)[C@H]2Cn3ccnc3-c3c(O)c(=O)cnn32)cc1] | (S)-6-((R)-(4-fluorophenyl)(p-tolyl)methyl)-11-hydroxy-5,6-dihydro-10H-imidazo[2',1':3,4]pyrazino[1,2-b]pyridazin-10-one |
| 42 | 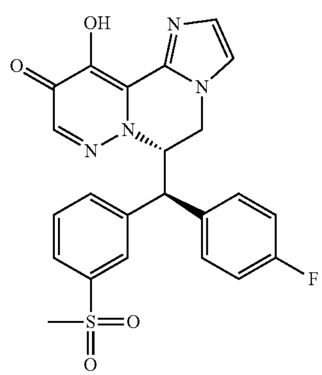 [SMILES: CS(=O)(=O)c1cccc([C@H](c2ccc(F)cc2)[C@H]2Cn3ccnc3-c3c(O)c(=O)cnn32)c1] | (S)-6-((S)-(4-fluorophenyl)(3-(methylsulfonyl)phenyl)methyl)-11-hydroxy-5,6-dihydro-10H-imidazo[2',1':3,4]pyrazino[1,2-b]pyridazin-10-one |
| 43 | 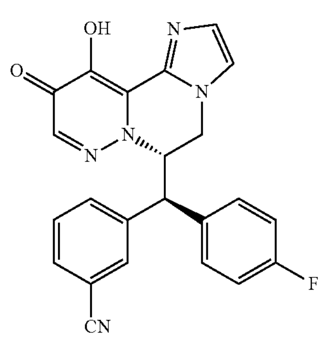 | 3-((S)-(4-fluorophenyl)((S)-11-hydroxy-10-oxo-5,6-dihydro-10H-imidazo[2',1':3,4]pyrazino[1,2-b]pyridazin-6-yl)methyl)benzonitrile |
| 44 | 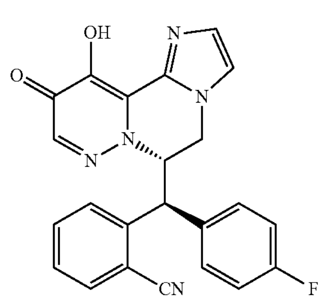 | 2-((S)-(4-fluorophenyl)((S)-11-hydroxy-10-oxo-5,6-dihydro-10H-imidazo[2',1':3,4]pyrazino[1,2-b]pyridazin-6-yl)methyl)benzonitrile |

TABLE 1-continued

Compounds of the Examples.

| Example No. | Structure | Name |
|---|---|---|
| 45 | 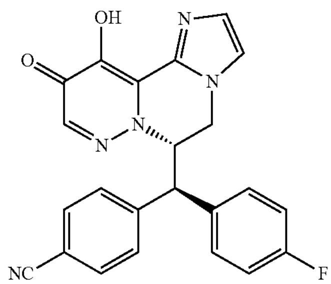 [SMILES: N#Cc1ccc([C@H](c2ccc(F)cc2)[C@H]2Cn3ccnc3-c3c(O)c(=O)cnn32)cc1] | 4-((R)-(4-fluorophenyl)((S)-11-hydroxy-10-oxo-5,6-dihydro-10H-imidazo[2',1':3,4]pyrazino[1,2-b]pyridazin-6-yl)methyl)benzonitrile |
| 46 | 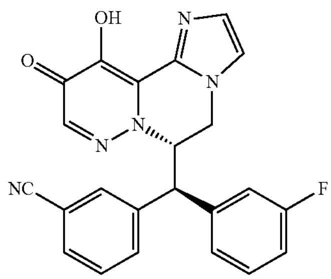 [SMILES: N#Cc1cccc([C@H](c2cccc(F)c2)[C@H]2Cn3ccnc3-c3c(O)c(=O)cnn32)c1] | 3-((R)-(3-fluorophenyl)((S)-11-hydroxy-10-oxo-5,6-dihydro-10H-imidazo[2',1':3,4]pyrazino[1,2-b]pyridazin-6-yl)methyl)benzonitrile |
| 47 | 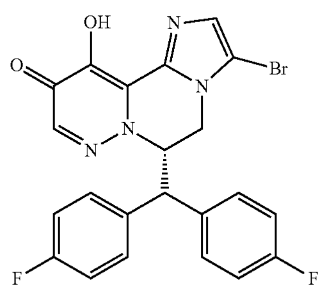 | (S)-6-(bis(4-fluorophenyl)methyl)-3-bromo-11-hydroxy-5,6-dihydro-10H-imidazo[2',1':3,4]pyrazino[1,2-b]pyridazin-10-one |
| 48 | 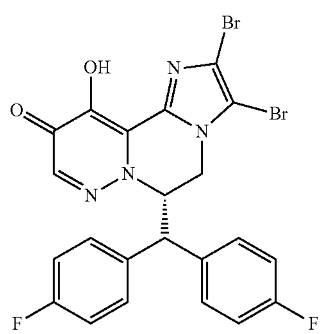 [SMILES: O=c1cnn2c(c1O)-c1nc(Br)c(Br)n1C[C@@H]2C(c1ccc(F)cc1)c1ccc(F)cc1] | (S)-6-(bis(4-fluorophenyl)methyl)-2,3-dibromo-11-hydroxy-5,6-dihydro-10H-imidazo[2',1':3,4]pyrazino[1,2-b]pyridazin-10-one |
| 49 | 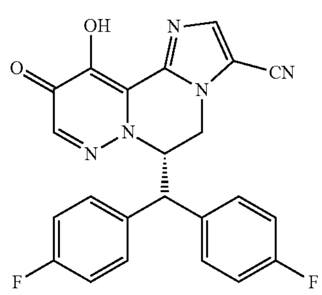 [SMILES: N#Cc1cnc2n1C[C@H](C(c1ccc(F)cc1)c1ccc(F)cc1)n1ncc(=O)c(O)c1-2] | (S)-6-(bis(4-fluorophenyl)methyl)-11-hydroxy-10-oxo-5,6-dihydro-10H-imidazo[2',1':3,4]pyrazino[1,2-b]pyridazine-3-carbonitrile |

TABLE 1-continued

Compounds of the Examples.

| Example No. | Structure | Name |
|---|---|---|
| 50 | 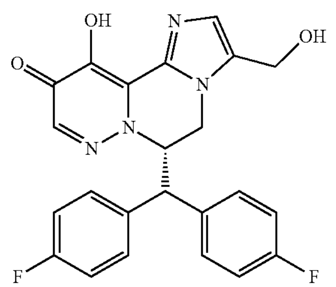 [SMILES: O=c1cnn2c(c1O)-c1ncc(CO)n1C[C@@H]2C(c1ccc(F)cc1)c1ccc(F)cc1] | (S)-6-(bis(4-fluorophenyl)methyl)-11-hydroxy-3-(hydroxymethyl)-5,6-dihydro-10H-imidazo[2',1':3,4]pyrazino[1,2-b]pyridazin-10-one |
| 51 | 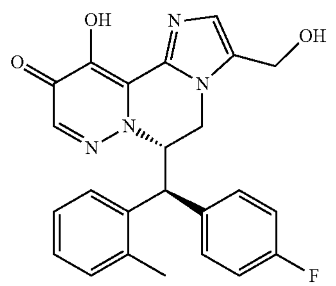 [SMILES: Cc1ccccc1[C@H](c1ccc(F)cc1)[C@H]1Cn2c(CO)cnc2-c2c(O)c(=O)cnn21] | (S)-6-((S)-(4-fluorophenyl)(o-tolyl)methyl)-11-hydroxy-3-(hydroxymethyl)-5,6-dihydro-10H-imidazo[2',1':3,4]pyrazino[1,2-b]pyridazin-10-one |
| 52 | 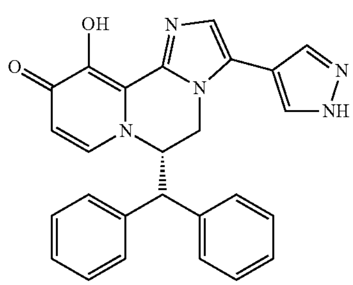 [SMILES: O=c1ccn2c(c1O)-c1ncc(-c3cn[nH]c3)n1C[C@@H]2C(c1ccccc1)c1ccccc1] | (S)-6-benzhydryl-11-hydroxy-3-(1H-pyrazol-4-yl)-5,6-dihydro-10H-imidazo[1,2-a]pyrido[2,1-c]pyrazin-10-one |
| 53 | 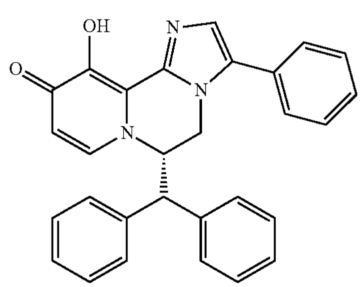 [SMILES: O=c1ccn2c(c1O)-c1ncc(-c3ccccc3)n1C[C@@H]2C(c1ccccc1)c1ccccc1] | (S)-6-benzhydryl-11-hydroxy-3-phenyl-5,6-dihydro-10H-imidazo[1,2-a]pyrido[2,1-c]pyrazin-10-one |
| 54 | 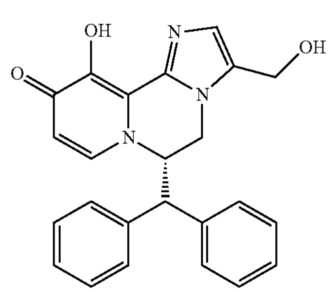 [SMILES: O=c1ccn2c(c1O)-c1ncc(CO)n1C[C@@H]2C(c1ccccc1)c1ccccc1] | (S)-6-benzhydryl-11-hydroxy-3-(hydroxymethyl)-5,6-dihydro-10H-imidazo[1,2-a]pyrido[2,1-c]pyrazin-10-one |

TABLE 1-continued

Compounds of the Examples.

| Example No. | Structure | Name |
|---|---|---|
| 55 | 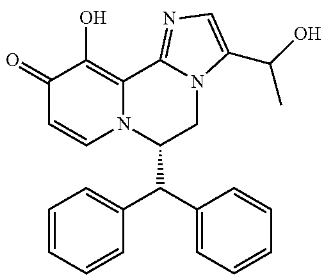 [SMILES: CC(O)c1cnc2n1C[C@H](C(c1ccccc1)c1ccccc1)n1ccc(=O)c(O)c1-2] | (6S)-6-benzhydryl-11-hydroxy-3-(1-hydroxyethyl)-5,6-dihydro-10H-imidazo[1,2-a]pyrido[2,1-c]pyrazin-10-one |
| 56 | 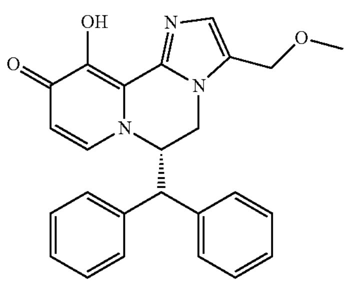 [SMILES: COCc1cnc2n1C[C@H](C(c1ccccc1)c1ccccc1)n1ccc(=O)c(O)c1-2] | (S)-6-benzhydryl-11-hydroxy-3-(methoxymethyl)-5,6-dihydro-10H-imidazo[1,2-a]pyrido[2,1-c]pyrazin-10-one |
| 57 | 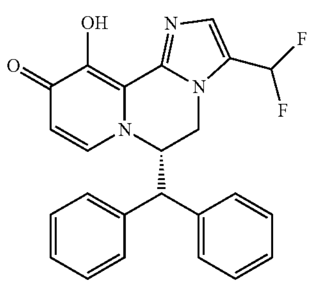 [SMILES: O=c1ccn2c(c1O)-c1ncc(C(F)F)n1C[C@@H]2C(c1ccccc1)c1ccccc1] | (S)-6-benzhydryl-3-(difluoromethyl)-11-hydroxy-5,6-dihydro-10H-imidazo[1,2-a]pyrido[2,1-c]pyrazin-10-one |
| 58 | 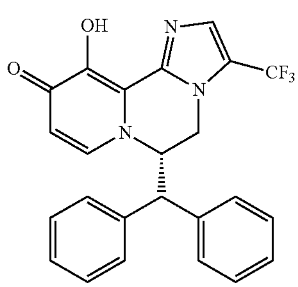 [SMILES: O=c1ccn2c(c1O)-c1ncc(C(F)(F)F)n1C[C@@H]2C(c1ccccc1)c1ccccc1] | (S)-6-benzhydryl-11-hydroxy-3-(trifluoromethyl)-5,6-dihydro-10H-imidazo[1,2-a]pyrido[2,1-c]pyrazin-10-one |
| 59 | 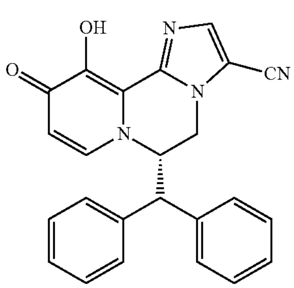 [SMILES: N#Cc1cnc2n1C[C@H](C(c1ccccc1)c1ccccc1)n1ccc(=O)c(O)c1-2] | (S)-6-benzhydryl-11-hydroxy-10-oxo-5,6-dihydro-10H-imidazo[1,2-a]pyrido[2,1-c]pyrazine-3-carbonitrile |

TABLE 1-continued

Compounds of the Examples.

| Example No. | Structure | Name |
|---|---|---|
| 60 | 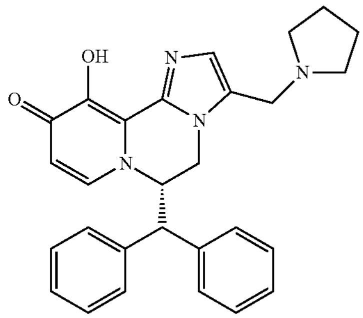 [SMILES: O=c1ccn2c(c1O)-c1ncc(CN3CCCC3)n1C[C@@H]2C(c1ccccc1)c1ccccc1] | (S)-6-benzhydryl-11-hydroxy-3-(pyrrolidin-1-ylmethyl)-5,6-dihydro-10H-imidazo[1,2-a]pyrido[2,1-c]pyrazin-10-one |
| 61 | 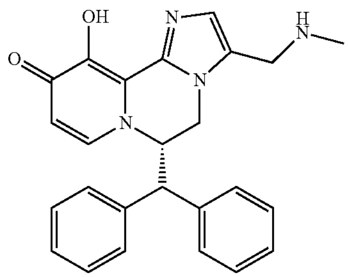 [SMILES: CNCc1cnc2n1C[C@H](C(c1ccccc1)c1ccccc1)n1ccc(=O)c(O)c1-2] | (S)-6-benzhydryl-11-hydroxy-3-((methylamino)methyl)-5,6-dihydro-10H-imidazo[1,2-a]pyrido[2,1-c]pyrazin-10-one |
| 62 | 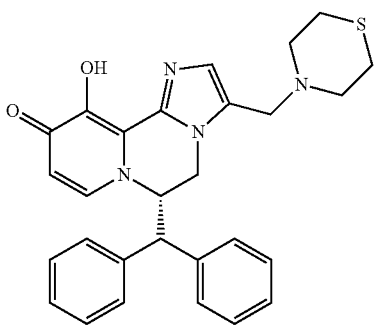 [SMILES: O=c1ccn2c(c1O)-c1ncc(CN3CCSCC3)n1C[C@@H]2C(c1ccccc1)c1ccccc1] | (S)-6-benzhydryl-11-hydroxy-3-(thiomorpholinomethyl)-5,6-dihydro-10H-imidazo[1,2-a]pyrido[2,1-c]pyrazin-10-one |
| 63 | 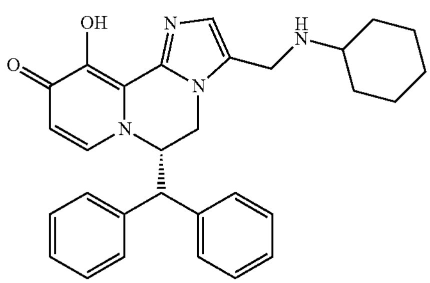 [SMILES: O=c1ccn2c(c1O)-c1ncc(CNC3CCCCC3)n1C[C@@H]2C(c1ccccc1)c1ccccc1] | (S)-6-benzhydryl-3-((cyclohexylamino)methyl)-11-hydroxy-5,6-dihydro-10H-imidazo[1,2-a]pyrido[2,1-c]pyrazin-10-one |
| 64 | 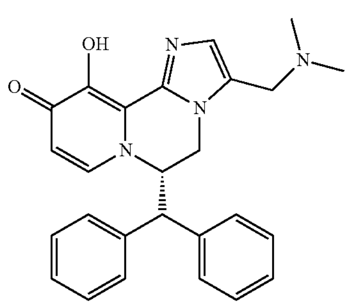 [SMILES: CN(C)Cc1cnc2n1C[C@H](C(c1ccccc1)c1ccccc1)n1ccc(=O)c(O)c1-2] | (S)-6-benzhydryl-3-((dimethylamino)methyl)-11-hydroxy-5,6-dihydro-10H-imidazo[1,2-a]pyrido[2,1-c]pyrazin-10-one |

TABLE 1-continued

Compounds of the Examples.

| Example No. | Structure | Name |
|---|---|---|
| 65 | 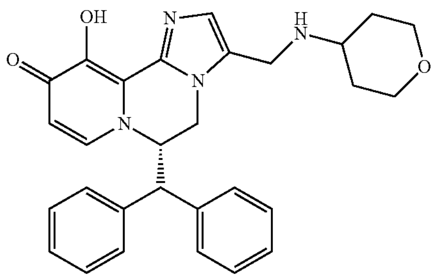 [SMILES: O=c1ccn2c(c1O)-c1ncc(CNC3CCOCC3)n1C[C@@H]2C(c1ccccc1)c1ccccc1] | (S)-6-benzhydryl-11-hydroxy-3-(((tetrahydro-2H-pyran-4-yl)amino)methyl)-5,6-dihydro-10H-imidazo[1,2-a]pyrido[2,1-c]pyrazin-10-one |
| 66 | 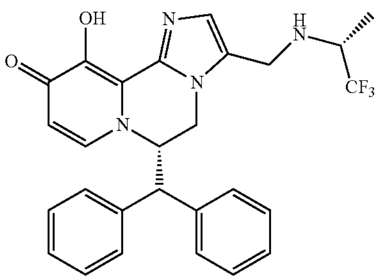 [SMILES: C[C@@H](NCc1cnc2n1C[C@H](C(c1ccccc1)c1ccccc1)n1ccc(=O)c(O)c1-2)C(F)(F)F] | (S)-6-benzhydryl-11-hydroxy-3-((((R)-1,1,1-trifluoropropan-2-yl)amino)methyl)-5,6-dihydro-10H-imidazo[1,2-a]pyrido[2,1-c]pyrazin-10-one |
| 67 | 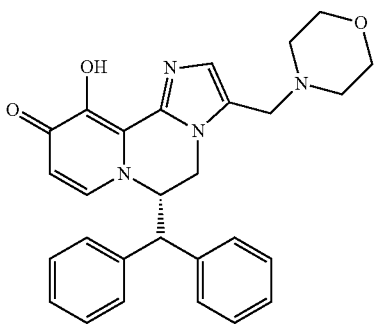 | (S)-6-benzhydryl-11-hydroxy-3-(morpholinomethyl)-5,6-dihydro-10H-imidazo[1,2-a]pyrido[2,1-c]pyrazin-10-one |
| 68 | 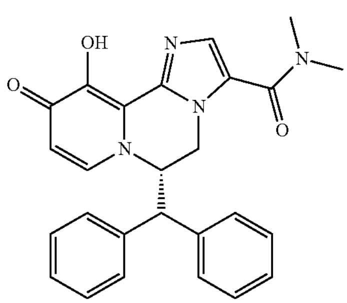 [SMILES: CN(C)C(=O)c1cnc2n1C[C@H](C(c1ccccc1)c1ccccc1)n1ccc(=O)c(O)c1-2] | (S)-6-benzhydryl-11-hydroxy-N,N-dimethyl-10-oxo-5,6-dihydro-10H-imidazo[1,2-a]pyrido[2,1-c]pyrazine-3-carboxamide |
| 69 | 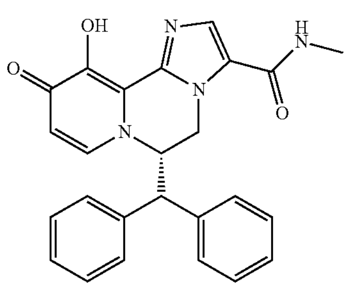 [SMILES: CNC(=O)c1cnc2n1C[C@H](C(c1ccccc1)c1ccccc1)n1ccc(=O)c(O)c1-2] | (S)-6-benzhydryl-11-hydroxy-N-methyl-10-oxo-5,6-dihydro-10H-imidazo[1,2-a]pyrido[2,1-c]pyrazine-3-carboxamide |

TABLE 1-continued

Compounds of the Examples.

| Example No. | Structure | Name |
|---|---|---|
| 70 | 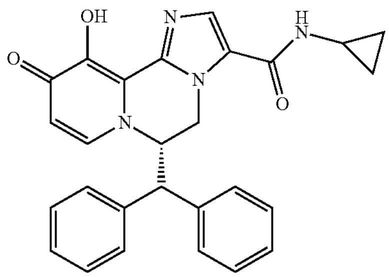 [SMILES: O=C(NC1CC1)c1cnc2n1C[C@H](C(c1ccccc1)c1ccccc1)n1ccc(=O)c(O)c1-2] | (S)-6-benzhydryl-N-cyclopropyl-11-hydroxy-10-oxo-5,6-dihydro-10H-imidazo[1,2-a]pyrido[2,1-c]pyrazine-3-carboxamide |
| 71 | 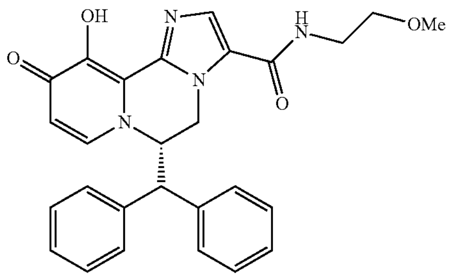 [SMILES: COCCNC(=O)c1cnc2n1C[C@H](C(c1ccccc1)c1ccccc1)n1ccc(=O)c(O)c1-2] | (S)-6-benzhydryl-11-hydroxy-N-(2-methoxyethyl)-10-oxo-5,6-dihydro-10H-imidazo[1,2-a]pyrido[2,1-c]pyrazine-3-carboxamide |
| 72 | 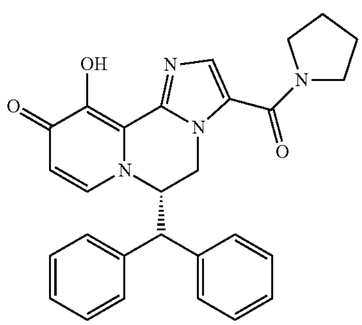 [SMILES: O=C(c1cnc2n1C[C@H](C(c1ccccc1)c1ccccc1)n1ccc(=O)c(O)c1-2)N1CCCC1] | (S)-6-benzhydryl-11-hydroxy-3-(pyrrolidine-1-carbonyl)-5,6-dihydro-10H-imidazo[1,2-a]pyrido[2,1-c]pyrazin-10-one |
| 73 | 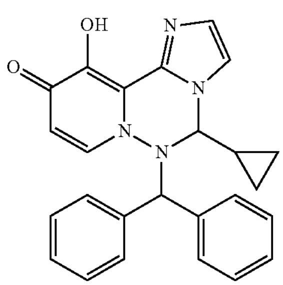 [SMILES: O=c1ccn2c(c1O)-c1nccn1C(C1CC1)N2C(c1ccccc1)c1ccccc1] | 6-benzhydryl-5-cyclopropyl-11-hydroxy-5,6-dihydro-10H-imidazo[1,2-d]pyrido[2,1-f][1,2,4]triazin-10-one |
| 74 | 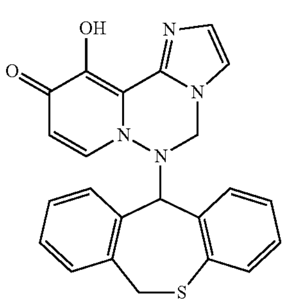 [SMILES: O=c1ccn2c(c1O)-c1nccn1CN2C1c2ccccc2CSc2ccccc21] | 6-(6,11-dihydrodibenzo[b,e]thiepin-11-yl)-11-hydroxy-5,6-dihydro-10H-imidazo[1,2-d]pyrido[2,1-f][1,2,4]triazin-10-one |

TABLE 1-continued

Compounds of the Examples.

| Example No. | Structure | Name |
|---|---|---|
| 75 | 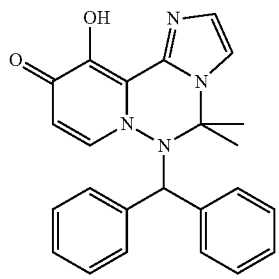 [SMILES: CC1(C)N(C(c2ccccc2)c2ccccc2)n2ccc(=O)c(O)c2-c2nccn21] | 6-benzhydryl-11-hydroxy-5,5-dimethyl-5,6-dihydro-10H-imidazo[1,2-d]pyrido[2,1-f][1,2,4]triazin-10-one |
| 76 | 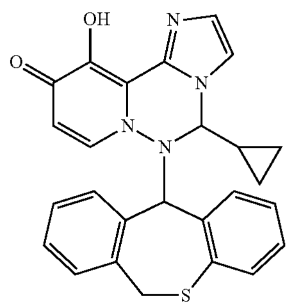 [SMILES: O=c1ccn2c(c1O)-c1nccn1C(C1CC1)N2C1c2ccccc2CSc2ccccc21] | 5-cyclopropyl-6-(6,11-dihydrodibenzo[b,e]thiepin-11-yl)-11-hydroxy-5,6-dihydro-10H-imidazo[1,2-d]pyrido[2,1-f][1,2,4]triazin-10-one |
| 77 | 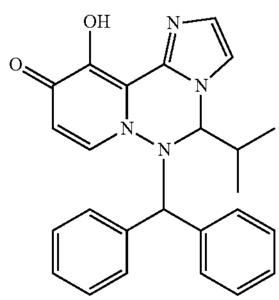 [SMILES: CC(C)C1N(C(c2ccccc2)c2ccccc2)n2ccc(=O)c(O)c2-c2nccn21] | 6-benzhydryl-11-hydroxy-5-isopropyl-5,6-dihydro-10H-imidazo[1,2-d]pyrido[2,1-f][1,2,4]triazin-10-one |
| 78 | 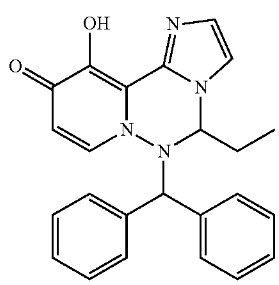 [SMILES: CCC1N(C(c2ccccc2)c2ccccc2)n2ccc(=O)c(O)c2-c2nccn21] | 6-benzhydryl-5-ethyl-11-hydroxy-5,6-dihydro-10H-imidazo[1,2-d]pyrido[2,1-f][1,2,4]triazin-10-one |
| 79 | 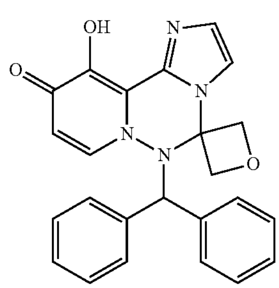 [SMILES: O=c1ccn2c(c1O)-c1nccn1C1(COC1)N2C(c1ccccc1)c1ccccc1] | 6-benzhydryl-11-hydroxy-6H,10H-spiro[imidazo[1,2-d]pyrido[2,1-f][1,2,4]triazine-5,3'-oxetan]-10-one |

TABLE 1-continued

Compounds of the Examples.

| Example No. | Structure | Name |
|---|---|---|
| 80 | 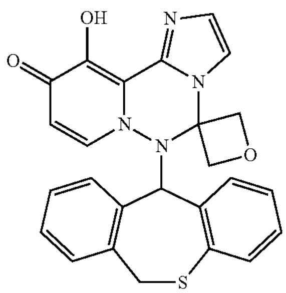 [SMILES: O=c1ccn2c(c1O)-c1nccn1C1(COC1)N2C1c2ccccc2CSc2ccccc21] | 6-(6,11-dihydrodibenzo[b,e]thiepin-11-yl)-11-hydroxy-6H,10H-spiro[imidazo[1,2-d]pyrido[2,1-f][1,2,4]triazine-5,3'-oxetan]-10-one |
| 81 | 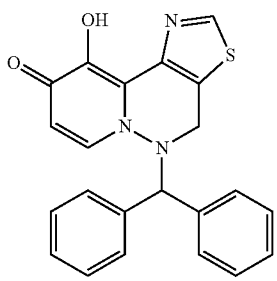 [SMILES: O=c1ccn2c(c1O)-c1ncsc1CN2C(c1ccccc1)c1ccccc1] | 5-benzhydryl-10-hydroxy-4,5-dihydro-9H-pyrido[1,2-b]thiazolo[4,5-d]pyridazin-9-one |
| 82 | 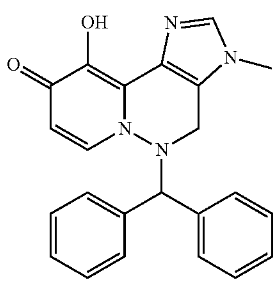 [SMILES: Cn1cnc2c1CN(C(c1ccccc1)c1ccccc1)n1ccc(=O)c(O)c1-2] | 5-benzhydryl-10-hydroxy-3-methyl-4,5-dihydroimidazo[4,5-d]pyrido[1,2-b]pyridazin-9(3H)-one |
| 83 | 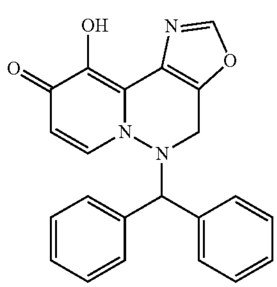 [SMILES: O=c1ccn2c(c1O)-c1ncoc1CN2C(c1ccccc1)c1ccccc1] | 5-benzhydryl-10-hydroxy-4,5-dihydro-9H-oxazolo[4,5-d]pyrido[1,2-b]pyridazin-9-one |
| 84 | 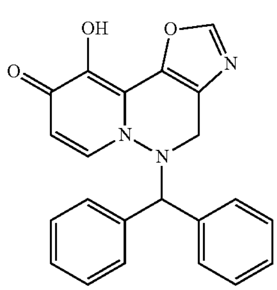 [SMILES: O=c1ccn2c(c1O)-c1ocnc1CN2C(c1ccccc1)c1ccccc1] | 5-benzhydryl-10-hydroxy-4,5-dihydro-9H-oxazolo[5,4-d]pyrido[1,2-b]pyridazin-9-one |

TABLE 1-continued

Compounds of the Examples.

| Example No. | Structure | Name |
|---|---|---|
| 85 | 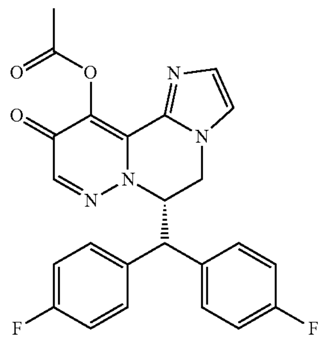 [SMILES: CC(=O)Oc1c2n(ncc1=O)[C@@H](C(c1ccc(F)cc1)c1ccc(F)cc1)Cn1ccnc1-2] | (S)-6-(bis(4-fluorophenyl)methyl)-10-oxo-5,6-dihydro-10H-imidazo[2',1':3,4]pyrazino[1,2-b]pyridazin-11-yl acetate |
| 86 | 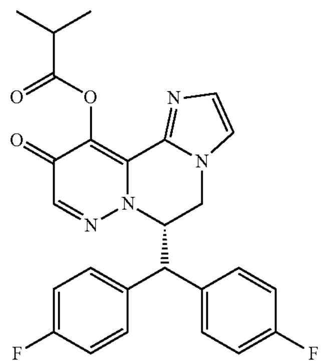 [SMILES: CC(C)C(=O)Oc1c2n(ncc1=O)[C@@H](C(c1ccc(F)cc1)c1ccc(F)cc1)Cn1ccnc1-2] | (S)-6-(bis(4-fluorophenyl)methyl)-10-oxo-5,6-dihydro-10H-imidazo[2',1':3,4]pyrazino[1,2-b]pyridazin-11-yl isobutyrate |
| 87 | 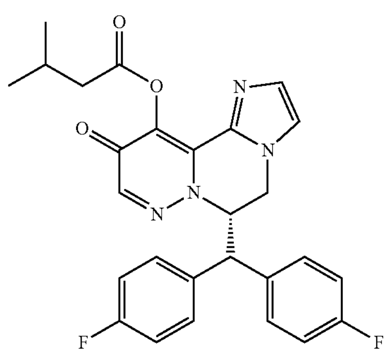 [SMILES: CC(C)CC(=O)Oc1c2n(ncc1=O)[C@@H](C(c1ccc(F)cc1)c1ccc(F)cc1)Cn1ccnc1-2] | (S)-6-(bis(4-fluorophenyl)methyl)-10-oxo-5,6-dihydro-10H-imidazo[2',1':3,4]pyrazino[1,2-b]pyridazin-11-yl 3-methylbutanoate |
| 88 | 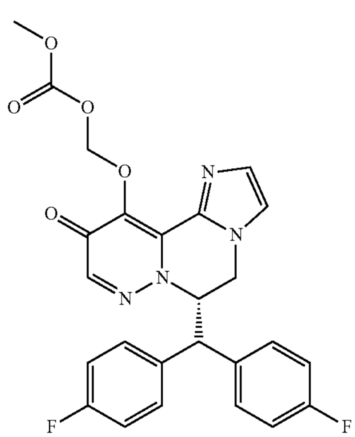 [SMILES: COC(=O)OCOc1c2n(ncc1=O)[C@@H](C(c1ccc(F)cc1)c1ccc(F)cc1)Cn1ccnc1-2] | (S)-((6-(bis(4-fluorophenyl)methyl)-10-oxo-5,6-dihydro-10H-imidazo[2',1':3,4]pyrazino[1,2-b]pyridazin-11-yl)oxy)methyl methyl carbonate |

Biological Assays and Data

The activity of a compound according to the present invention can be assessed by the following in vitro and in vivo methods. Using the test assay described herein, compounds of the invention exhibit inhibitory efficacy in accordance with Table 2.

Endonuclease Inhibition Assay (PA FP Assay)

Compounds were dissolved and serially diluted in 100% DMSO then 0.5 µl was transferred to 384-well plates. 50 nM truncated Influenza A/victoria/75 PA(1-209) was prepared in assay buffer (20 mM Tris, pH=7.5, 10 mM $MgCl_2$, 0.01% Tween 20, 100 mM NaCl and 1 mM DTT) and 20 ul was added to each well of assay plate with compounds, centrifuged for 1 min at 1000 rpm and incubated for 30 min at room temperature. 20 µl of 20 nM fluorescein-labeled probe [5-(4-(3-carboxy-3-oxopropanoyl)-4-(4-chlorobenzyl)piperidine-1-carbonyl)-2-(6-hydroxy-3-oxo-3H-xanthen-9-yl)benzoic acid] in assay buffer was then added, centrifuged for 1 min at 1000 rpm and incubated for 60 min at room temperature.

Fluorescence polarization was measured on Perkin Elmer Envision plate reader with excitation at 480 nm and emission at 535 nm and reported in millipolarization units (mP). $IC_{50}$ values were determined relative to wells containing 125 uM of a compound known to bind to the active site of PA and uninhibited wells containing 1.25% DMSO.

Influenza Virus Minigenome Assays (RNP Assay)

For influenza A virus minigenome reporter assays, 293T cells were transfected with expression vectors encoding PB2, PB1, PA, NP proteins and an influenza A Luciferase reporter plasmid. Cells were harvested in Dulbecco's modified Eagle's medium (DMEM) minus phenol red, supplemented with 10% heat inactivated FBS (fetal bovine serum), 1% sodium pyruvate and 1% L-glutamine (Cellgro, Manassas, Va.). The five plasmids were co-transfected with Fugene 6 transfection reagent (Promega, Madison, Wis.) with a 1:3 ratio DNA (µg):Fugene 6 (µl), in OptiMEM® (Gibco, Carlsbad, Calif.). Transfections were performed at cell densities of $1.8 \times 10^4$ cells/well in 384-well format. Compounds were added 2 hours post-transfection, and plates were incubated at 37° C., 5% $CO_2$ for 48 hours. Following incubation, cells were lysed and luciferase production quantified by addition of Britelite Plus® (Perkin-Elmer, Waltham, Mass.). For cell toxicity measurement, CellTiter-Glo® (Promega, Madison, Wis.) was added to treated cells following manufacturer's instructions.

Influenza Virus Neuraminidase Assay (NA Assay)

For influenza NA assays, MDCK cells were plated in Phenol Red-free DMEM (Gibco) supplemented with 2 mM L-Glutamine, 1% sodium pyruvate (Cellgro, Manassas, Va.) and 0.1% BSA at cell densities of $1.8 \times 104$ cells/well in 384-well format. Compounds were added to the cells 2 hours pre-infection. Infections were performed at MOI 0.005 and the plates were incubated at 37° C., 5% CO2 for 48 hours. Following incubation, neuraminidase activity was evaluated with the NA assay kit (ThermoFisher, Carlsbad, Calif.). For cell toxicity measurement, CellTiter-Glo® (Promega, Madison, Wis.) was added to treated cells according to manufacturer's instructions.

TABLE 2

Biological Activity of Selected Compounds

| Example # | PA FP $IC_{50}$ (µM) | RNP_Alaska $EC_{50}$ (µM) | RNP_CAL_$EC_{50}$ (µM) | RNP_Hubei $EC_{50}$ (µM) |
|---|---|---|---|---|
| 1 | 0.05 | 0.13 | 0.11 | 0.11 |
| 2 | 0.07 | 0.11 | 0.11 | 0.09 |
| 3 | 0.4 | 1.4 | 1.1 | 0.79 |
| 4 | 0.01 | 0.18 | 0.16 | 0.09 |
| 5 | 0.02 | 0.22 | 0.10 | 0.18 |
| 6 | 0.04 | 0.15 | 0.19 | 0.1 |
| 7 | 0.009 | 0.14 | 0.17 | 0.16 |
| 8 | 0.04 | 0.49 | 0.15 | 0.53 |
| 9 | | 0.85 | 0.58 | 0.59 |
| 10 | | 0.29 | 0.32 | 0.82 |
| 11 | | 0.16 | 0.08 | 0.09 |
| 12 | | 0.07 | 0.8 | 0.06 |
| 13 | | 0.57 | 0.31 | 0.30 |
| 14 | 0.1 | 6.7 | 4.2 | 5.5 |
| 15 | | 0.04 | 0.025 | 0.019 |
| 16 | | 0.96 | 0.82 | 0.95 |
| 17 | 0.02 | 0.03 | 0.01 | 0.07 |
| 18 | 0.02 | 0.13 | 0.13 | 0.16 |
| 19 | 0.04 | 0.23 | 0.26 | 0.49 |
| 20 | 0.3 | 0.69 | 0.72 | 0.74 |
| 21 | | 0.071 | 0.052 | 0.11 |
| 22 | | 0.027 | 0.082 | 0.01 |
| 23 | 0.05 | 0.023 | 0.039 | 0.036 |
| 24 | 0.009 | 0.052 | 0.036 | 0.059 |
| 25 | | 0.062 | 0.056 | 0.1 |
| 26 | | 0.027 | 0.038 | 0.051 |
| 27 | | 0.05 | 0.05 | 0.027 |
| 28 | | 0.072 | 0.081 | 0.078 |
| 29 | | 0.07 | 0.072 | 0.058 |
| 31 | | 0.034 | 0.037 | 0.064 |
| 32 | | 0.28 | 0.25 | 0.72 |
| 33 | 0.02 | 0.087 | 0.11 | 0.27 |
| 34 | | 0.033 | 0.025 | 0.034 |
| 35 | | 0.098 | 0.05 | 0.11 |
| 36 | | 0.021 | 0.027 | 0.063 |
| 38 | 0.04 | 0.043 | 0.049 | 0.097 |
| 39 | 0.01 | 0.025 | 0.033 | 0.053 |

TABLE 2-continued

Biological Activity of Selected Compounds

| Example # | PA FP IC$_{50}$ (μM) | RNP_Alaska EC$_{50}$ (μM) | RNP_CAL_EC$_{50}$ (μM) | RNP_Hubei EC$_{50}$ (μM) |
|---|---|---|---|---|
| 40 | 0.02 | 0.02 | 0.032 | 0.035 |
| 42 |  | 3.6 | 2.8 | 3.8 |
| 43 | 0.02 | 0.14 | 0.039 | 0.17 |
| 44 |  | 0.55 | 0.3 | 0.31 |
| 45 |  | 0.076 | 0.042 | 0.16 |
| 46 | 0.05 | 0.15 | 0.064 | 0.19 |
| 48 |  | 5.0 | 4.3 | 12 |
| 49 |  | 0.87 | 0.82 | 0.56 |
| 50 |  | 0.43 | 0.1 | 0.7 |
| 51 |  | 0.23 | 0.09 | 0.16 |
| 52 | 0.008 | 5.1 | 8.3 | 0.97 |
| 53 | 0.06 | 0.54 | 3 | 0.19 |
| 55 |  | 2.6 | 1.7 | 6.6 |
| 56 | 0.1 | 0.28 | 0.092 | 0.27 |
| 57 | 0.04 | 0.22 | 0.18 | 0.58 |
| 62 |  | 1.9 | 0.64 | 1.5 |
| 65 |  | 4.8 | 3.5 | 4.9 |
| 66 |  | 0.72 | 0.31 | 0.63 |
| 70 |  | 6.4 | 1.7 | 12.3 |
| 72 |  | 3 | 1.7 | 5.5 |
| 73 |  | 0.39 | 0.17 |  |
| 74 |  | 0.13 | 0.084 | 0.26 |
| 75 | 0.1 | 0.48 | 0.3 | 0.4 |
| 76 |  | 0.43 | 0.16 | 0.67 |
| 78 | 0.04 | 0.25 | 0.18 | 0.34 |
| 80 |  | 0.17 | 0.01 | 0.027 |
| 81 |  | 2.2 | 7 |  |
| 83 |  | 0.96 | 0.97 | 0.73 |
| 84 |  | 14 | 11 | 16 |
| 85 |  | 0.019 | 0.022 | 0.049 |
| 86 |  | 0.03 | 0.021 | 0.047 |
| 87 |  | 0.027 | 0.021 | 0.043 |
| 88 |  | 0.032 | 0.042 | 0.089 |

Inhibitory Activity of Selected Compounds on multiple flu strains (NA assay)

| Example # | PA FP IC$_{50}$ (μM) | NA_VIR_H1N1 EC$_{50}$ (μM) | NA_VIR_H3N2 EC$_{50}$ (μM) | NA_Hubei EC$_{50}$ (μM) |
|---|---|---|---|---|
| 30 | 0.01 | 0.045 | 0.19 | 0.065 |
| 47 |  | 0.29 | 0.84 | 0.56 |
| 54 | 0.1 | 2.6 | 4.6 | 1.6 |
| 58 |  | 0.2 | 1.8 | 0.82 |
| 59 |  | 1.4 | 5.7 | 1.2 |
| 61 |  | 2.3 | 5.7 | 3.4 |
| 63 |  | 3.2 | 6.1 | 3.9 |
| 64 |  | 1.7 | 4.3 | 2.4 |
| 67 |  | 4.1 | 10 | 3.8 |
| 68 |  | 6.3 | 32 | 17 |
| 69 |  | 15 | >50 | 14 |
| 71 |  | 19 | >50 | 27 |
| 79 |  | 0.61 | 1.5 | 0.39 |
| 82 |  | 1 | 4 | 1.4 |

The invention claimed is:

1. A method of treating or preventing a viral infection, comprising administering to a subject a therapeutically effective amount of a compound selected from the group consisting of:

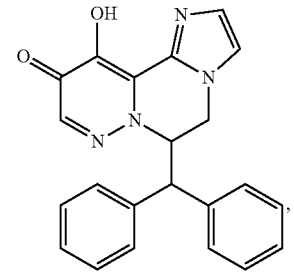

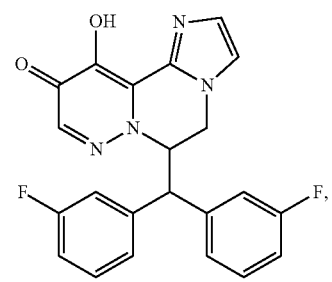

-continued
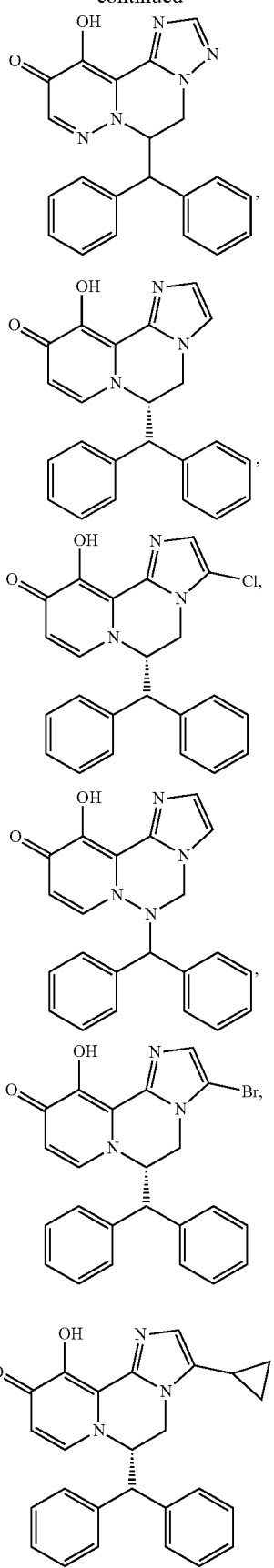
-continued
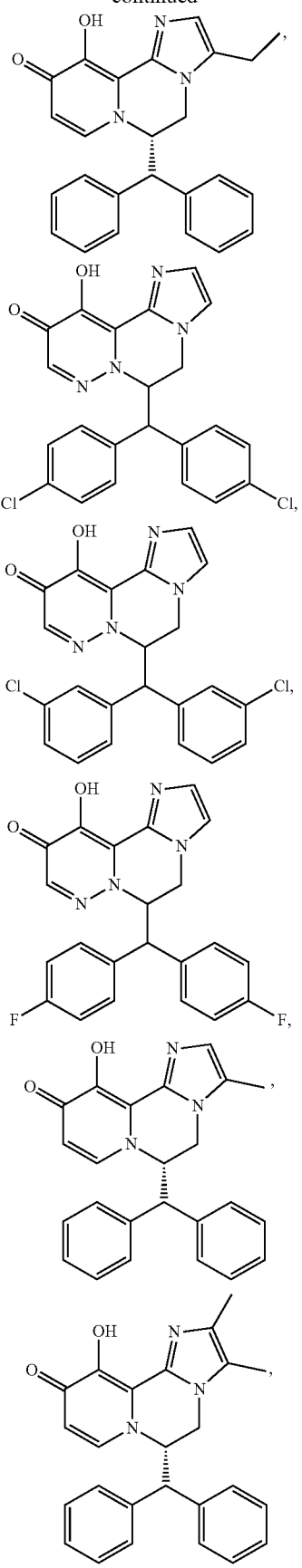

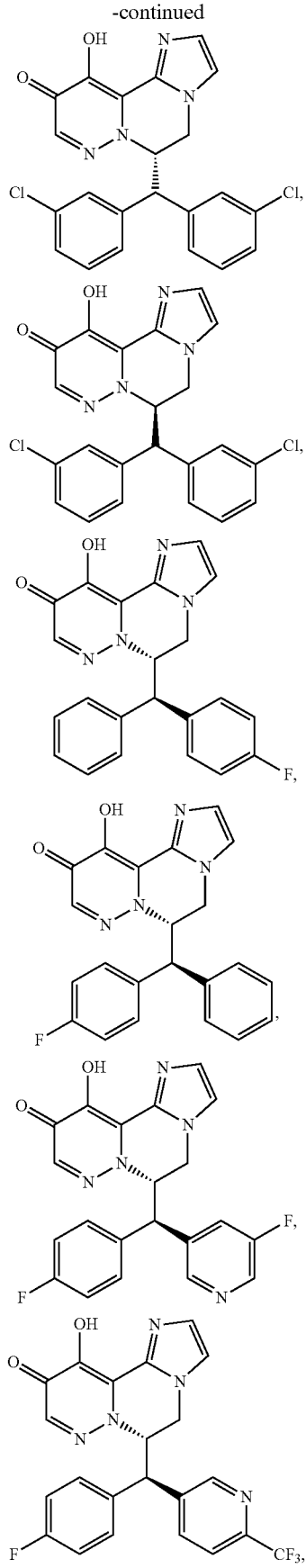
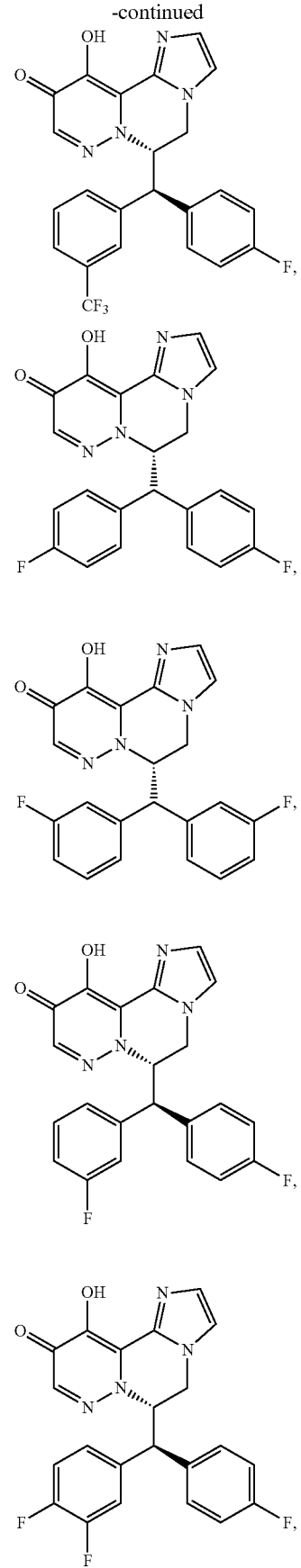

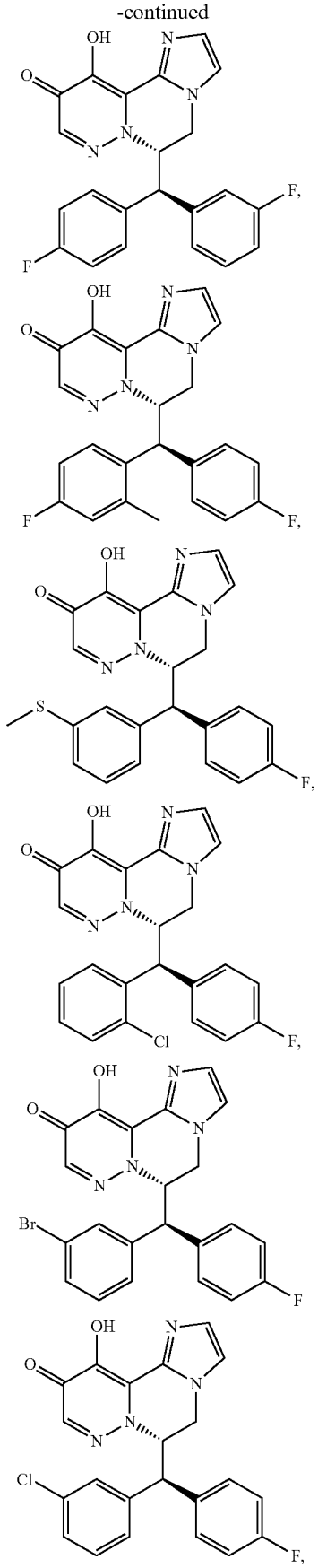
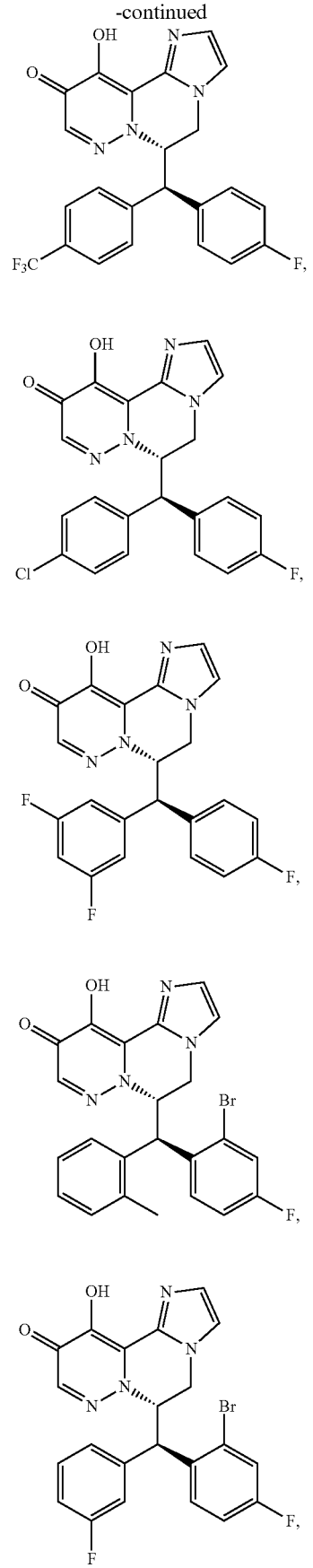

179
-continued
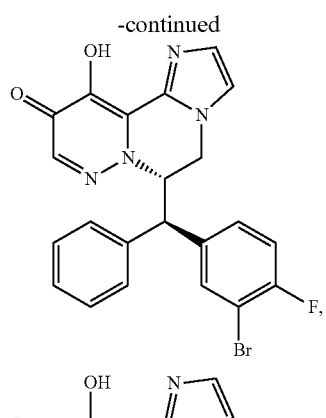
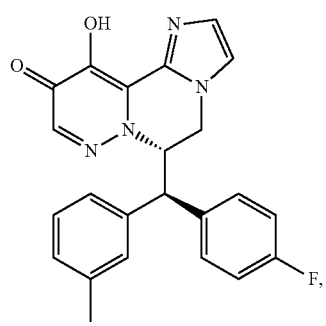
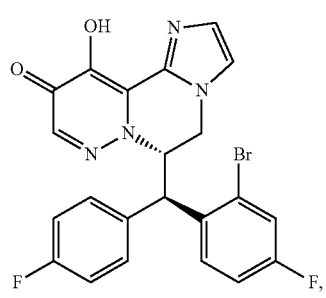
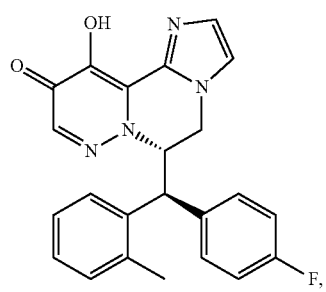
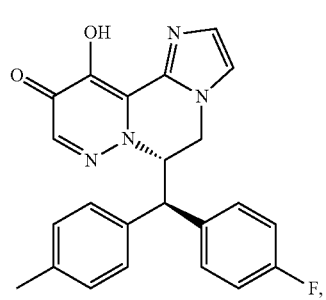
180
-continued
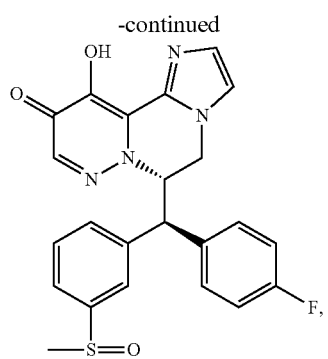
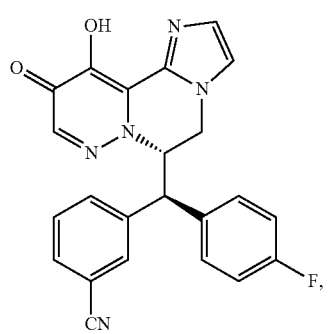
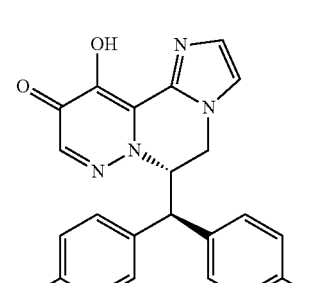
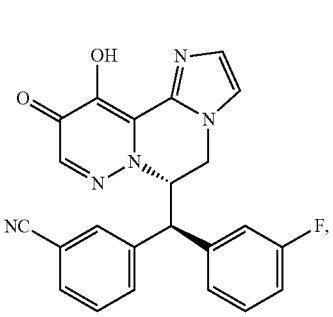

181
-continued
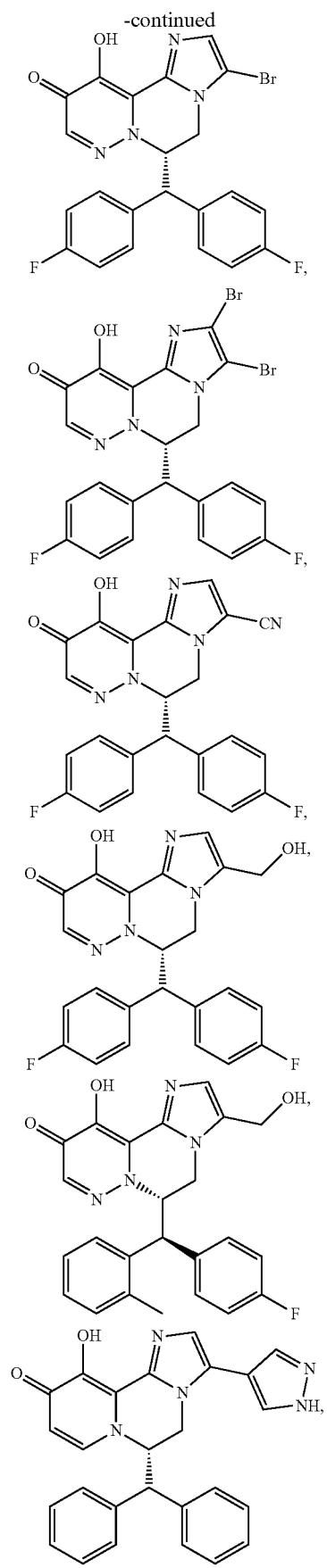
182
-continued
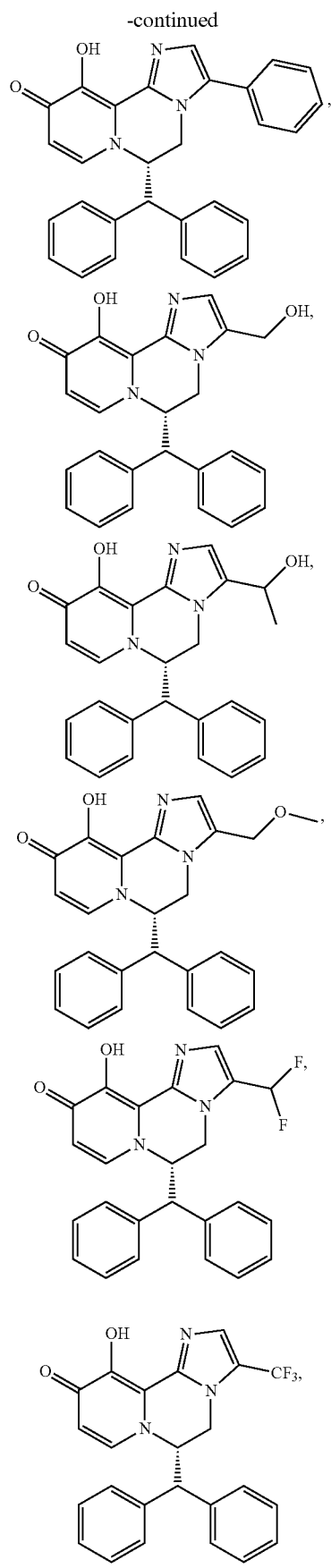

183
-continued
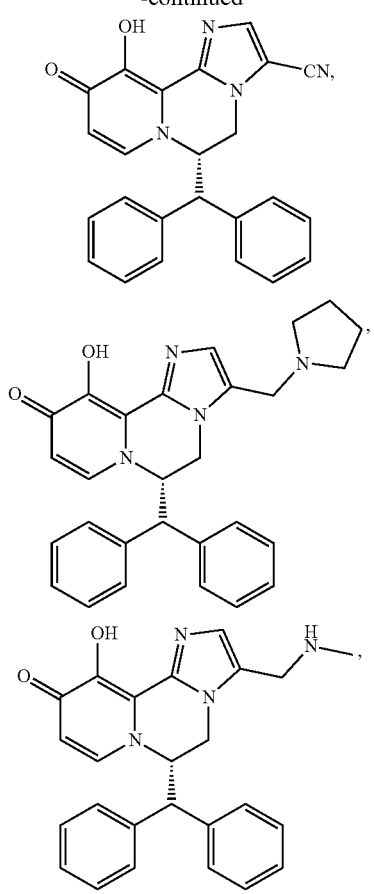
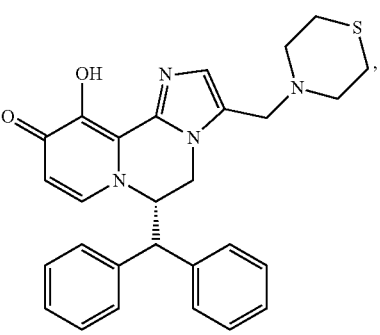
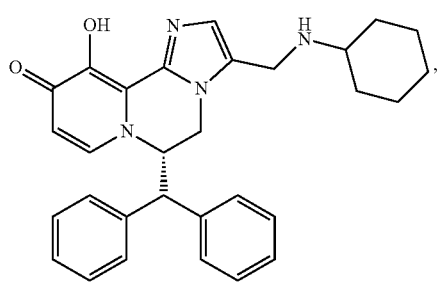
184
-continued
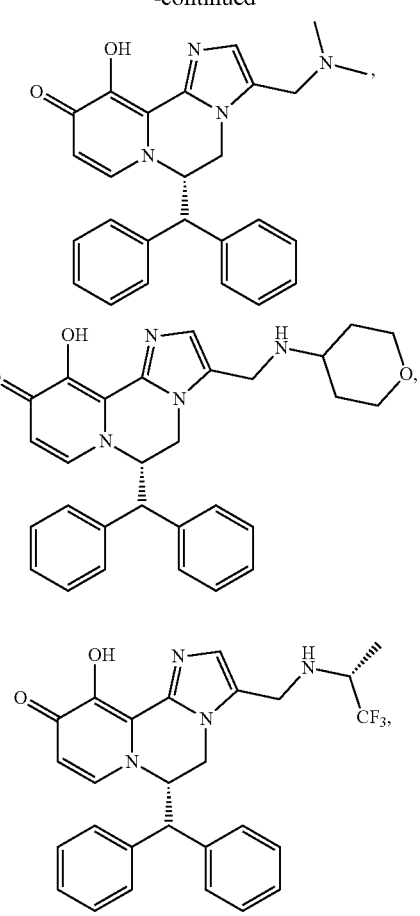
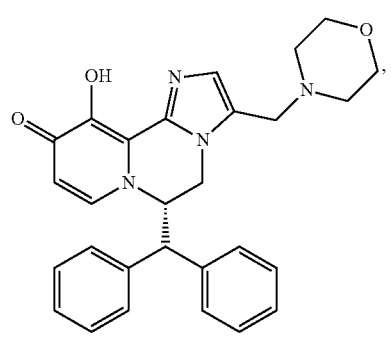
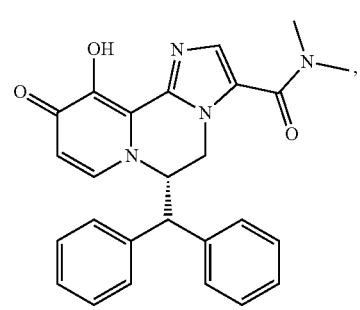

-continued
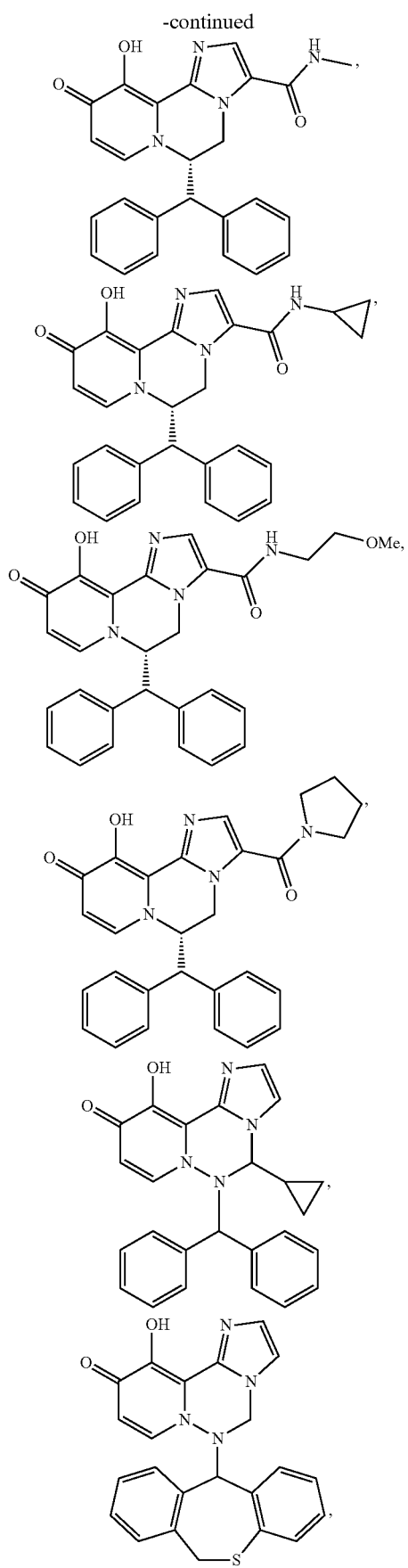
-continued
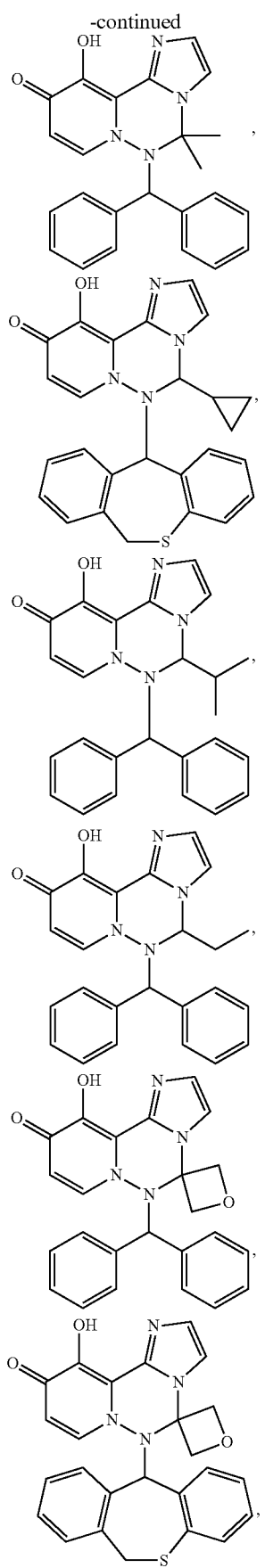

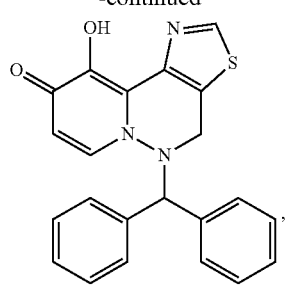

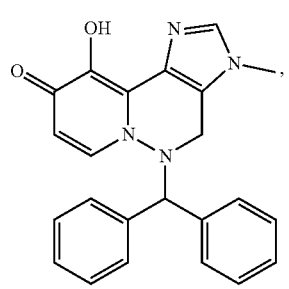

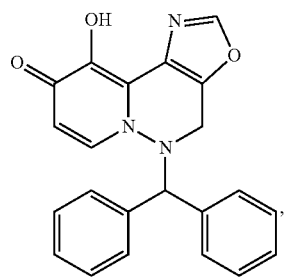

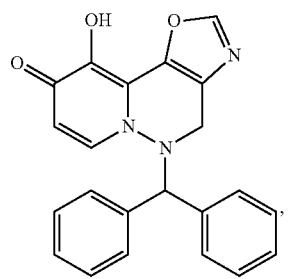

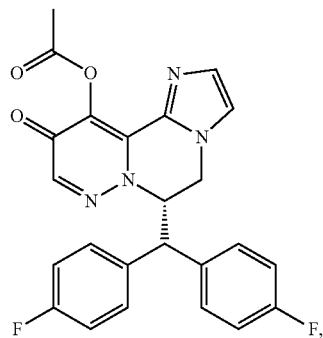

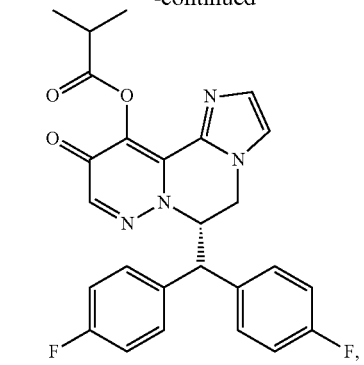

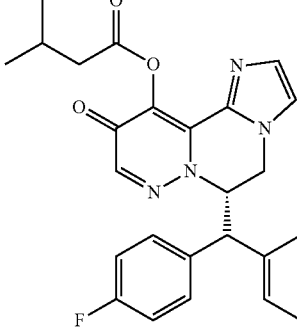

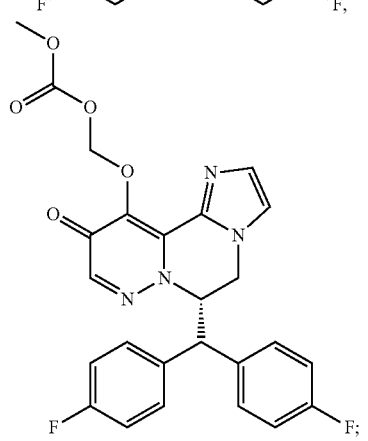

or a pharmaceutically acceptable salt thereof.

2. The method of claim 1, wherein the viral infection is an orthomyxovirus infection.

3. The method of claim 1, wherein the viral infection is an influenza virus infection.

4. The method of claim 1, wherein the viral infection is an influenza A virus infection.

5. The method of claim 1, wherein the viral infection is an influenza B virus infection.

6. The method of claim 1, wherein the viral infection is an influenza C virus infection.

7. The method of claim 1, wherein the compound inhibits a viral RNA polymerase.

8. The method of claim 7, wherein the compound inhibits an endonuclease function of the RNA polymerase.

9. The method of claim 1, wherein the subject is a human.

10. The method of claim 1, wherein the subject suffers from at least one of asthma and COPD.

11. The method of claim 1, further comprising administering an antiviral co-agent to the subject.

12. The method of claim 11, wherein the antiviral co-agent is selected from the group consisting of oseltamivir, peramivir, zanamivir, laninamivir, amantadine, and rimantadine.

13. The method of claim 1, wherein the compound is administered orally.

14. The method of claim 1, wherein the compound is administered parenterally.

* * * * *